US010709707B2

(12) United States Patent
Ackermann et al.

(10) Patent No.: US 10,709,707 B2
(45) Date of Patent: Jul. 14, 2020

(54) METHODS OF TREATING OCULAR CONDITIONS

(71) Applicant: Oyster Point Pharma, Inc., Princeton, NJ (US)

(72) Inventors: Douglas Michael Ackermann, Reno, NV (US); James Loudin, Houston, TX (US); Kenneth J. Mandell, Lexington, MA (US)

(73) Assignee: Oyster Point Pharma, Inc., Princeton, NJ (US)

( * ) Notice: Subject to any disclaimer, the term of this patent is extended or adjusted under 35 U.S.C. 154(b) by 0 days.

(21) Appl. No.: 16/091,830

(22) PCT Filed: Apr. 6, 2017

(86) PCT No.: PCT/US2017/026385
§ 371 (c)(1),
(2) Date: Oct. 5, 2018

(87) PCT Pub. No.: WO2017/177024
PCT Pub. Date: Oct. 12, 2017

(65) Prior Publication Data
US 2019/0201397 A1    Jul. 4, 2019

Related U.S. Application Data

(60) Provisional application No. 62/319,648, filed on Apr. 7, 2016.

(51) Int. Cl.
| *A61K 31/506* | (2006.01) |
| *A61K 9/00* | (2006.01) |
| *A61K 38/13* | (2006.01) |
| *A61K 31/436* | (2006.01) |
| *A61P 27/04* | (2006.01) |
| *A61K 45/06* | (2006.01) |

(52) U.S. Cl.
CPC .......... *A61K 31/506* (2013.01); *A61K 9/0043* (2013.01); *A61K 31/436* (2013.01); *A61K 38/13* (2013.01); *A61K 45/06* (2013.01); *A61P 27/04* (2018.01)

(58) Field of Classification Search
CPC ...... A61K 31/506; A61K 31/436; A61K 9/00; A61K 38/13; A61P 27/04
See application file for complete search history.

(56) References Cited

U.S. PATENT DOCUMENTS

| 6,277,855 | B1 * | 8/2001 | Yerxa ..................... A61K 31/44 514/256 |
| 7,098,331 | B2 | 8/2006 | Schmitt et al. |
| 7,714,001 | B2 | 5/2010 | Schmitt et al. |
| 8,063,068 | B2 | 11/2011 | Schmitt et al. |
| 8,067,443 | B2 | 11/2011 | Genevois-Borella et al. |
| 8,153,821 | B2 | 4/2012 | Akireddy et al. |
| 8,604,191 | B2 | 12/2013 | Akireddy et al. |
| 8,633,222 | B2 | 1/2014 | Schmitt et al. |
| 8,633,227 | B2 | 1/2014 | Akireddy et al. |
| 9,145,396 | B2 | 9/2015 | Akireddy et al. |
| 9,504,644 | B2 | 11/2016 | Ackermann, Jr. et al. |
| 9,504,645 | B2 | 11/2016 | Ackermann, Jr. et al. |
| 9,532,944 | B2 | 1/2017 | Ackermann, Jr. et al. |
| 9,597,284 | B2 | 3/2017 | Ackermann, Jr. et al. |
| 9,981,949 | B2 * | 5/2018 | Akireddy ............. C07C 59/265 |
| 10,456,396 | B2 | 10/2019 | Ackermann, Jr. et al. |
| 2006/0084656 | A1 | 4/2006 | Ziegler et al. |
| 2006/0094732 | A1 | 5/2006 | Schmitt et al. |
| 2008/0261890 | A1 | 10/2008 | Ousler et al. |
| 2009/0093446 | A1 | 4/2009 | Bernstein |
| 2011/0086086 | A1 | 4/2011 | Johnson et al. |
| 2011/0263629 | A1 | 10/2011 | Strachan et al. |
| 2011/0274628 | A1 | 11/2011 | Borschke |
| 2012/0059338 | A1 | 3/2012 | Beeley et al. |
| 2012/0095062 | A1 | 4/2012 | Cheng et al. |
| 2012/0289572 | A1 | 11/2012 | Mazurov et al. |
| 2014/0107163 | A1 | 4/2014 | Akireddy et al. |
| 2014/0107164 | A1 | 4/2014 | Schmitt et al. |
| 2014/0357971 | A1 | 12/2014 | Eilat et al. |
| 2015/0164894 | A1 | 6/2015 | Schmitt et al. |
| 2016/0046609 | A1 | 2/2016 | Akireddy et al. |
| 2017/0239244 | A1 | 8/2017 | Ackermann, Jr. et al. |

FOREIGN PATENT DOCUMENTS

| EP | 1214062 B1 | 11/2003 |
| JP | 2003-531168 A | 10/2003 |
| JP | 2011-504490 A | 2/2011 |
| WO | WO-2001/080844 A2 | 11/2001 |
| WO | WO-2003/005998 A2 | 1/2003 |
| WO | WO-2003/045394 A1 | 6/2003 |
| WO | WO-2004/39366 A1 | 5/2004 |
| WO | WO-2004/078752 A1 | 9/2004 |
| WO | WO2006/100075 A2 | 9/2006 |

(Continued)

OTHER PUBLICATIONS

Notice of Allowance dated Jun. 12, 2019 by the U.S. Patent and Trademark Office for U.S. Appl. No. 15/422,382, filed Feb. 1, 2017, 5 pages.

Final Office Action dated Feb. 25, 2019, by the U.S. Patent and Trademark Office for U.S. Appl. No. 15/422,382, filed Feb. 1, 2017, 13 pages.

Chatzidaki, A. et al. "Allosteric modulation of nicotinic acetylcholine receptors", Biochem Pharmacol.;97(4):408-417. (Oct. 15, 2015) Epub Jul. 29, 2015.

International Search Report and Written Opinion issued by the International Searching Authority for Application No. PCT/US2019/041013, dated Oct. 16, 2019, 16 pages.

International Search Report and Written Opinion issued by the International Searching Authority for Application No. PCT/US2019/040990, dated Oct. 9, 2019, 14 pages.

(Continued)

*Primary Examiner* — Yong L Chu
(74) *Attorney, Agent, or Firm* — Cooley LLP

(57) ABSTRACT

Described herein are methods and pharmaceutical formulations for treating ocular conditions.

72 Claims, 6 Drawing Sheets

(56) References Cited

FOREIGN PATENT DOCUMENTS

| WO | WO-2008/057938 A1 | 5/2008 |
|---|---|---|
| WO | WO-2009/069126 A1 | 6/2009 |
| WO | WO-2009/111550 A1 | 9/2009 |
| WO | WO-2010/028011 A1 | 3/2010 |
| WO | WO-2010/028033 A1 | 3/2010 |
| WO | WO-2010/065443 A1 | 6/2010 |
| WO | WO-2010/065447 A2 | 6/2010 |
| WO | WO-2010/065449 A1 | 6/2010 |
| WO | WO-2013/057687 A2 | 4/2013 |
| WO | WO-2016/064759 A1 | 4/2016 |
| WO | WO-2017/177024 A1 | 10/2017 |

OTHER PUBLICATIONS

Wang, J. et al. "Selective Activation of ($\alpha$4)3($\beta$2)2 nAChRs Reduces Ethanol Consumption Without Affecting Ethanol Intoxication", Neuropsychopharmacology, ACNP 55th Annual Meeting; 41:S626 (Dec. 7, 2016).

Wang, J. et al. "A Novel $\alpha$2/$\alpha$4 Subtype-selective Positive Allosteric Modulator of Nicotinic Acetylcholine Receptors Acting from the C-tail of an $\alpha$ Subunit", J Biol Chem.;290(48):28834-46. (Nov. 27, 2015) Epub Oct. 2, 2015.

Albietz et al., "Dry eye: an update on clinical diagnosis, management and promising new treatments," Clinical and Experimental Optometry 84(1):4-18 (2001).

Alimohammadi et al., "Evidence for nicotinic acetylcholine receptors on nasal trigeminal nerve endings of the rat," Chem Senses 25:61-66 (2000).

Beule, "Physiology and pathophysiology of respiratory mucosa of the nose and the paranasal sinuses," GMS Curr Top Otorhinolaryngol Head Neck Surg 9:1-24 (2010).

Bron, "Diagnosis of Dry Eye", Survey of Opthalmology vol. 45, supplement 2, Mar. 2001, pp. 221-226.

Extended European Search Report issued by the European Patent Office for Application No. 15852340.7, dated Apr. 24, 2018, 8 pages.

Fenster et al., "Regulation of $\alpha$4$\beta$2 Nicotinic Receptor Desensitization by Calcium and Protein Kinase C," Mol. Pharmacol. 55(3):432-443 (1999).

International Search Report and Written Opinion issued by the International Searching Authority for Application No. PCT/US2017/026385, dated Jul. 5, 2017, 9 pages.

International Search Report and Written Opinion dated Jan. 8, 2016, by the International Searching Authority for Application No. PCT/US2015/056273, filed Oct. 19, 2015, 8 pages.

Mazzanti, "Cyclosporine A inhibits acetylcholinesterase activity in rats experimentally demyelinated with ethidium bromide," Int. J. Devi Neuroscience 25(4):259-264 (2007).

Office Action dated Mar. 18, 2016, by the U.S. Patent and Trademark Office for U.S. Appl. No. 14/887,248, filed Oct. 19, 2015, 13 pages.

Office Action dated Mar. 21, 2016, by the U.S. Patent and Trademark Office for U.S. Appl. No. 14/887,259, filed Oct. 19, 2015, 14 pages.

Office Action dated Mar. 23, 2016, by the U.S. Patent and Trademark Office for U.S. Appl. No. 14/887,253, filed Oct. 19, 2015, 14 pages.

Office Action dated Mar. 24, 2016, by the U.S. Patent and Trademark Office for U.S. Appl. No. 14/887,243, filed Oct. 19, 2015, 14 pages.

Office Action dated Jun. 28, 2016, by the U.S. Patent and Trademark Office for U.S. Appl. No. 14/887,248, filed Oct. 15, 2015, 18 pages.

Office Action dated Jul. 13, 2018, by the U.S. Patent and Trademark Office for U.S. Appl. No. 15/422,382, filed Feb. 1, 2017, 29 pages.

Thuerauf et al., "Dose-dependent stereoselective activation of the trigeminal sensory system by nicotine in man," Psychopharmacology (Berl) 142(3):236-243 (1999).

U.S. Appl. No. 15/962,982, filed Apr. 25, 2018, for Akireddy et al.

* cited by examiner

FIG. 3

Ocular Surface Disease Index (OSDI)

Ask your patients the following 12 questions, and circle the number in the box that best represents each answer. Then, fill in boxes A, B, C, D, and E according to the instructions beside each.

| Have you experienced any of the following during the last week? | All of the time | Most of the time | Half of the time | Some of the time | None of the time |
|---|---|---|---|---|---|
| 1. Eyes that are sensitive to light? | 4 | 3 | 2 | 1 | 0 |
| 2. Eyes that feel gritty? | 4 | 3 | 2 | 1 | 0 |
| 3. Painful or sore eyes? | 4 | 3 | 2 | 1 | 0 |
| 4. Blurred vision? | 4 | 3 | 2 | 1 | 0 |
| 5. Poor vision? | 4 | 3 | 2 | 1 | 0 |

Subtotal score for answers 1 to 5 [A]

| Have problems with your eyes limited you in performing any of the following during the last week? | All of the time | Most of the time | Half of the time | Some of the time | None of the time | |
|---|---|---|---|---|---|---|
| 6. Reading? | 4 | 3 | 2 | 1 | 0 | N/A |
| 7. Driving at night? | 4 | 3 | 2 | 1 | 0 | N/A |
| 8. Working with a computer or bank machine (ATM)? | 4 | 3 | 2 | 1 | 0 | N/A |
| 9. Watching TV? | 4 | 3 | 2 | 1 | 0 | N/A |

Subtotal score for answers 6 to 9 [B]

| Have your eyes felt uncomfortable in any of the following situations during the last week? | All of the time | Most of the time | Half of the time | Some of the time | None of the time | |
|---|---|---|---|---|---|---|
| 10. Windy conditions? | 4 | 3 | 2 | 1 | 0 | N/A |
| 11. Places or areas with low humidity (very dry)? | 4 | 3 | 2 | 1 | 0 | N/A |
| 12. Areas that are air conditioned? | 4 | 3 | 2 | 1 | 0 | N/A |

Subtotal score for answers 10 to 12 [C]

Add subtotals A, B, and C to obtain D
(D = sum of scores for all questions answered) [D]

Total number of questions answered
(do not include questions answered N/A) [E]

Please turn over the questionnaire to calculate the patient's final OSDI score.

FIG. 3 (continued)

Evaluating the OSDI® Score[1]

The OSDI® is assessed on a scale of 0 to 100, with higher scores representing greater disability. The index demonstrates sensitivity and specificity in distinguishing between normal subjects and patients with dry eye disease. The OSDI® is a valid and reliable instrument for measuring dry eye disease (normal, mild to moderate, and severe) and effect on vision-related function.

Assessing Your Patient's Dry Eye Disease[1,2]

Use your answers D and E from side 1 to compare the sum of scores for all questions answered (D) and the number of questions answered (E) with the chart below.* Find where your patient's score would fall. Match the corresponding shade of red to the key below to determine whether your patient's score indicates normal, mild, moderate, or severe dry eye disease.

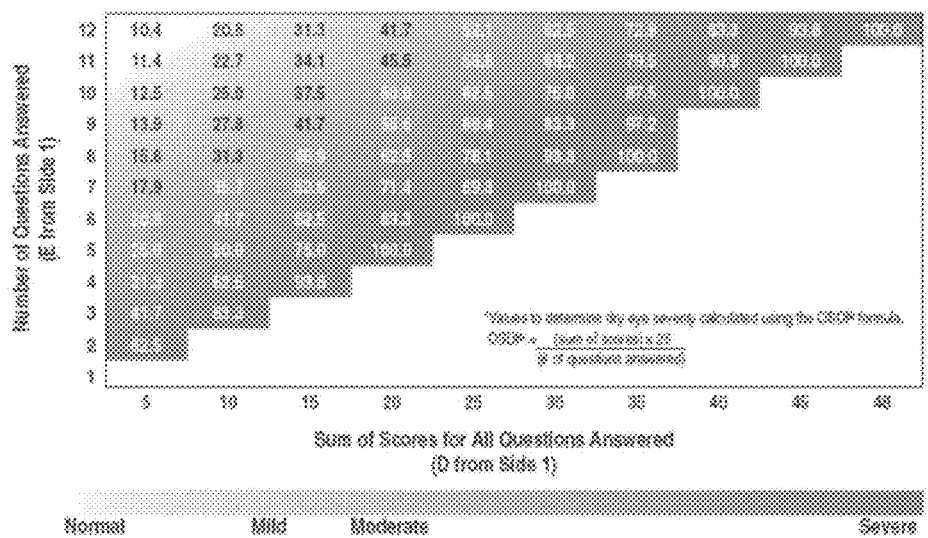

1. Data on file, Allergan, Inc.
2. Schiffman RM, Christianson MD, Jacobsen G, Hirsch JD, Reis BL. Reliability and validity of the Ocular Surface Disease Index. Arch Ophthalmol. 2000;118:615-621.

METHODS OF TREATING OCULAR CONDITIONS

CROSS REFERENCE TO RELATED APPLICATIONS

This application is a U.S. National Phase application under 35 U.S.C. § 371 of International Application No. PCT/US2017/026385, filed on Apr. 6, 2017, which designated the United States, and claims priority to U.S. Provisional Application No. 62/319,648, filed on Apr. 7, 2016, the contents of which are incorporated herein by reference in their entirety.

BACKGROUND OF THE INVENTION

Dry Eye Disease ("DED") is a condition that affects millions of people worldwide. Approximately 40 million people in North America have some form of dry eye, and many millions more suffer worldwide. DED results from the disruption of the natural tear film on the surface of the eye, and can result in ocular discomfort, visual disturbance and a reduction in vision-related quality of life. Patients with severe cases of DED are at risk for serious ocular health deficiencies such as corneal ulceration, and can experience a quality of life deficiency comparable to that of moderate-severe angina.

SUMMARY OF THE INVENTION

The present disclosure provides a method of increasing tear production, comprising the local administration of a therapeutically effective amount of (R)-5-((E)-2-pyrrolidin-3-ylvinyl)pyrimidine, or a pharmaceutically acceptable salt thereof, into the nasal cavity of an individual in need thereof.

The present disclosure provides a method of treating d y eye, comprising the local administration of a therapeutically effective amount of (R)-5-((E)-2-pyrrolidin-3-ylvinyl)pyrimidine, or a pharmaceutically acceptable salt thereof, into the nasal cavity of an individual in need thereof.

The present disclosure provides a method of improving ocular discomfort, comprising the local administration of a therapeutically effective amount of (R)-5-((E)-2-pyrrolidin-3-ylvinyl)pyrimidine, or a pharmaceutically acceptable salt thereof, into the nasal cavity of an individual in need thereof.

In certain embodiments, (R)-5-((E)-2-pyrrolidin-3-ylvinyl)pyrimidine is administered as a free base. In certain embodiments, (R)-5-((E)-2-pyrrolidin-3-ylvinyl)pyrimidine is administered as a pharmaceutically acceptable salt of (R)-5-((E)-2-pyrrolidin-3-ylvinyl)pyrimidine. In certain embodiments, the pharmaceutical acceptable salt is a galactarate or citrate salt. In certain embodiments, the pharmaceutical acceptable salt is a galactarate salt. In certain embodiments, the pharmaceutical acceptable salt is a citrate salt. In certain embodiments, the pharmaceutical acceptable salt is (R)-5-((E)-2-pyrrolidin-3-ylvinyl)pyrimidine monocitrate salt.

In certain embodiments, the dose of (R)-5-((E)-2-pyrrolidin-3-ylvinyl)pyrimidine, or a pharmaceutically acceptable salt thereof, is between 500 micrograms and 10 milligrams per dose.

In certain embodiments, the method further comprises the local administration of one or more substances that prevent the entry or reduce the entry of the nicotinic acetylcholine receptor into the desensitized state, or facilitate the recovery of a peripheral nicotinic acetylcholine receptor from the desensitized state. In certain embodiments, the one or more substances are selected from the group consisting of protein kinase C (PKC) or factors that upregulate or up-modulate PKC, cAMP-dependent protein kinase (PKA) or factors that upregulate or up-modulate PKA, and calcineurin inhibitors. In certain embodiments, the calcineurin inhibitor is selected from the group consisting of cyclosporine, pimecrolimus, and tacrolimus. In certain embodiments, (R)-5-((E)-2-pyrrolidin-3-ylvinyl)pyrimidine, or a pharmaceutically acceptable salt thereof, is administered without any form of nicotine.

In certain embodiments, between 500 micrograms and 5 milligrams of (R)-5-((E)-2-pyrrolidin-3-ylvinyl)pyrimidine, or a pharmaceutically acceptable salt thereof, is administered. In certain embodiments, less than 5 milligrams of (R)-5-((E)-2-pyrrolidin-3-ylvinyl)pyrimidine, or a pharmaceutically acceptable salt thereof, is administered. In certain embodiments, between 1 milligram and 3 milligrams of (R)-5-((E)-2-pyrrolidin-3-ylvinyl)pyrimidine, or a pharmaceutically acceptable salt thereof, is administered. In certain embodiments, between 500 micrograms and 5 milligrams of (R)-5-((E)-2-pyrrolidin-3-ylvinyl)pyrimidine, or a pharmaceutically acceptable salt thereof, is administered. In certain embodiments, between 1 milligram and 2 milligrams of (R)-5-((E)-2-pyrrolidin-3-ylvinyl)pyrimidine, or a pharmaceutically acceptable salt thereof, is administered. In certain embodiments, about 1 milligram of (R)-5-((E)-2-pyrrolidin-3-ylvinyl)pyrimidine, or a pharmaceutically acceptable salt thereof, is administered. In certain embodiments, about 1.5 milligrams of (R)-5-((E)-2-pyrrolidin-3-ylvinyl)pyrimidine, or a pharmaceutically acceptable salt thereof, is administered. In certain embodiments, about 2 milligrams of (R)-5-((E)-2-pyrrolidin-3-ylvinyl)pyrimidine, or a pharmaceutically acceptable salt thereof, is administered.

In certain embodiments, (R)-5-((E)-2-pyrrolidin-3-ylvinyl)pyrimidine, or a pharmaceutically acceptable salt thereof, is administered as needed in response to symptoms. In certain embodiments, (R)-5-((E)-2-pyrrolidin-3-ylvinyl)pyrimidine, or a pharmaceutically acceptable salt thereof, is administered at least once daily. In certain embodiments, (R)-5-((E)-2-pyrrolidin-3-ylvinyl)pyrimidine, or a pharmaceutically acceptable salt thereof, is administered at least twice daily. In certain embodiments, wherein (R)-5-((E)-2-pyrrolidin-3-ylvinyl)pyrimidine, or a pharmaceutically acceptable salt thereof, is administered at least once weekly.

In certain embodiments, (R)-5-((E)-2-pyrrolidin-3-ylvinyl)pyrimidine, or a pharmaceutically acceptable salt thereof, is administered into the nasal cavity as a liquid, suspension, aerosol, gel, ointment, dry powder, cream, paste, lotion, or balm. In certain embodiments, (R)-5-((E)-2-pyrrolidin-3-ylvinyl)pyrimidine, or a pharmaceutically acceptable salt thereof, is administered into the nasal cavity by a syringe, dropper, bottle nebulizer, atomization pump, inhaler, powder spray device, vaporizer, patch, medicated stick, pipette, or jet of liquid. In certain embodiments, the (R)-5-((E)-2-pyrrolidin-3-ylvinyl)pyrimidine, or a pharmaceutically acceptable salt thereof, is administered in a pharmaceutical formulation for nasal administration comprising between 5 mg/mL and 200 mg/mL of (R)-5-((E)-2-pyrrolidin-3-ylvinyl)pyrimidine, or a pharmaceutically acceptable salt thereof. In certain embodiments, the pharmaceutical formulation for nasal administration comprises between 10 mg/mL and 75 mg/mL of (R)-5-((E)-2-pyrrolidin-3-ylvinyl)pyrimidine, or a pharmaceutically acceptable salt thereof. In certain embodiments, the pharmaceutical formulation for nasal administration comprises between 10 mg/mL and 50 mg/mL of (R)-5-((E)-2-pyrrolidin-3-ylvinyl)pyrimidine, or a pharmaceutically acceptable salt thereof.

The present disclosure provides a pharmaceutical formulation for local administration into the nasal cavity of an individual comprising (R)-5-((E)-2-pyrrolidin-3-ylvinyl)pyrimidine, or a pharmaceutically acceptable salt thereof, formulated for nasal administration.

The present disclosure provides a pharmaceutical formulation for use in treatment of dry eye or ocular discomfort, the formulation comprising (R)-5-((E)-2-pyrrolidin-3-ylvinyl)pyrimidine, or a pharmaceutically acceptable salt thereof.

In certain embodiments, (R)-5-((E)-2-pyrrolidin-3-ylvinyl)pyrimidine is formulated as a free base. In certain embodiments, the pharmaceutically acceptable salt is a galactarate or citrate salt. In certain embodiments, the pharmaceutically acceptable salt is a galactarate salt. In certain embodiments, the pharmaceutically acceptable salt is a citrate salt. In certain embodiments, the citrate salt is (R)-5-((E)-2-pyrrolidin-3-ylvinyl)pyridine mono-citrate salt. In certain embodiments, the pharmaceutical formulation is formulated for administration of a dose between 500 micrograms and 10 milligrams per dose.

In certain embodiments, the pharmaceutical formulation further comprises one or more substances selected from the group consisting of protein kinase C (PKC) or factors that upregulate or up-modulate PKC, cAMP-dependent protein kinase (PKA) or factors that upregulate or up-modulate PKA, and calcineurin inhibitors. In certain embodiments, the calcineurin inhibitor is selected from the group consisting of cyclosporine, pimecrolimus, and tacrolimus. In certain embodiments, the pharmaceutical formulation does not contain nicotine in any form.

In certain embodiments, the pharmaceutical formulation comprises between 5 mg/mL and 200 mg/mL of (R)-5-((E)-2-pyrrolidin-3-ylvinyl)pyrimidine, or a pharmaceutically acceptable salt thereof. In certain embodiments, the pharmaceutical formulation comprises between 10 mg/ml, and 75 mg/mL, of (R)-5-((E)-2-pyrrolidin-3-ylvinyl)pyrimidine, or a pharmaceutically acceptable salt thereof. In certain embodiments, the pharmaceutical formulation comprises between 10 mg/mL and 50 mg/mL of (R)-5-((E)-2-pyrrolidin-3-ylvinyl)pyrimidine, or a pharmaceutically acceptable salt thereof. In certain embodiments, the pharmaceutical formulation comprises between 500 micrograms and 5 milligrams of (R)-5-((E)-2-pyrrolidin-3-ylvinyl)pyrimidine, or a pharmaceutically acceptable salt thereof, per dose. In certain embodiments, the pharmaceutical formulation comprises less than 5 milligrams of (R)-5-((E)-2-pyrrolidin-3-ylvinyl)pyrimidine, or a pharmaceutically acceptable salt thereof, per dose. In certain embodiments, the pharmaceutical formulation comprises between 1 milligram and 3 milligrams of (R)-5-((E)-2-pyrrolidin-3-ylvinyl)pyrimidine, or a pharmaceutically acceptable salt thereof, per dose. In certain embodiments, the pharmaceutical formulation comprises between 1 milligram and 2 milligrams of (R)-5-((E)-2-pyrrolidin-3-ylvinyl)pyrimidine, or a pharmaceutically acceptable salt thereof, per dose. In certain embodiments, the pharmaceutical formulation comprises about 1 milligram of (R)-5-((E)-2-pyrrolidin-3-ylvinyl)pyrimidine, or a pharmaceutically acceptable salt thereof, per dose. In certain embodiments, the pharmaceutical formulation comprises about 1.5 milligrams of (R)-5-((E)-2-pyrrolidin-3-ylvinyl)pyrimidine, or a pharmaceutically acceptable salt thereof, per dose. In certain embodiments, the pharmaceutical formulation comprises about 2 milligrams of (R)-5-((E)-2-pyrrolidin-3-ylvinyl)pyrimidine, or a pharmaceutically acceptable salt thereof, per dose.

In certain embodiments, the pharmaceutical formulation is formulated for administration as needed in response to symptoms. In certain embodiments, the pharmaceutical formulation is formulated for administration at least once daily. In certain embodiments, the pharmaceutical formulation is formulated for administration at least twice daily. In certain embodiments, the pharmaceutical formulation is formulated for administration at least once weekly.

In certain embodiments, the pharmaceutical formulation is formulated as a liquid, suspension, aerosol, gel, ointment, dry powder, cream, paste, lotion, or balm. In certain embodiments, the pharmaceutical formulation is formulated for local delivery into the nasal cavity via a syringe, dropper, bottle nebulizer, atomization pump, inhaler, powder spray device, vaporizer, patch, medicated stick, pipette, or jet of liquid.

The present disclosure provides the compound (R)-5-((E)-2-pyrrolidin-3-ylvinyl)pyrimidine, or a pharmaceutically acceptable salt thereof, for use in the treatment of dry eye or ocular discomfort, which is administered into the nasal cavity of an individual in need thereof.

The present disclosure provides the compound (R)-5-((E)-2-pyrrolidin-3-ylvinyl)pyrimidine, or a pharmaceutically acceptable salt thereof, for use in the treatment of dry eye or ocular discomfort, which is administered into the nasal cavity of an individual in need thereof, and wherein the ocular condition is a result from an ophthalmologic surgical procedure or an ophthalmologic treatment.

In certain embodiments, the dose of (R)-5-((E)-2-pyrrolidin-3-ylvinyl)pyrimidine, or a pharmaceutically acceptable salt thereof, is between 500 micrograms and 10 milligrams per dose.

The methods for treating ocular conditions described herein, comprise the local administration of a therapeutically effective amount of a compound of Formula (I), (II), (IIIa), or (IIIb) into the nasal cavity of an individual in need thereof, wherein the compound of Formula (I), (II), (IIIa), or (IIIb) binds to the peripheral nicotinic acetylcholine receptor to provide a local effect. Although a small amount of a compound of Formula (I), (II), (IIIa), or (IIIb) may enter the systemic circulation, the amount is insufficient to elicit a systemic pharmacological effect. Furthermore, the dose amounts of a compound of Formula (I), (II), (IIIa), or (IIIb), required to treat ocular conditions in an individual in need, are substantially lower than the amounts needed to produce systemic pharmacological effects in such an individual. Indeed, the amounts of a compound of Formula (I), (II), (IIIa), or (IIIb) that produce systemic pharmacological effects in an individual generally desensitize the peripheral nicotinic acetylcholine receptor in the nasal cavity of the individual, and thereby do not effectively treat the ocular conditions.

Provided herein, in some embodiments, is a method of increasing tear production, comprising the local administration of a therapeutically effective amount of a compound of Formula (I) into the nasal cavity of an individual in need thereof, wherein the compound of Formula (I) binds to the peripheral nicotinic acetylcholine receptor and the compound of Formula (I) has the structure:

Formula (I)

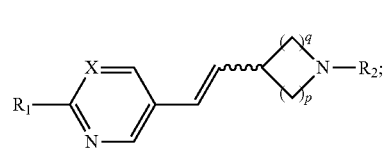

wherein:
the wavy line represents E or Z geometry about the double bond;
X is N or $CR_1$;
$R_1$ is hydrogen, $C_{1-6}$alkyl, halogen, —$OR_4$, —$SR_4$, or —$NR_5R_6$;
$R_2$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl;
$R_3$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), cycloalkyl, —$OR_7$, —$SR_7$, —$NR_8R_9$, —$SOR_7$, or —$SO_2R_7$, wherein the $C_{1-6}$alkyl, heterocycloalkyl, heteroaryl, and aryl groups are optionally substituted with one or more substituents selected from halogen, —CN, —$NO_2$, —$NH_2$, —OH, —$OR_7$, —$CO_2H$, —$C(O)OR_7$, —O—$C(O)R_7$, —$NR_8R_9$, —$NHC(O)R_7$, —$C(O)NR_8R_9$, —$SR_7$, —$S(O)R_7$, —$SO_2R_7$, —$NHSO_2R_7$, —$SO_2NR_8R_9$, —$C(S)NR_8R_9$, —$NHC(S)R_7$, and —O—$SO_2R_7$
$R_4$, $R_5$, and $R_6$ are independently hydrogen or $C_{1-6}$alkyl; and
$R_7$, $R_8$, and $R_9$ are hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl, wherein the $C_{1-6}$alkyl, heterocycloalkyl, heteroaryl, and aryl groups are optionally substituted one or more substituents selected from the group consisting of F, Cl, Br, I, $R_{10}$, —$NR_{10}R_{11}$, —$CF_3$, —CN, —$NO_2$, —$CR_{10}$, —$N_3$, —$SO_2CH_3$, —$OR_{10}$, —$SR_{10}$, —$C(O)NR_{10}R_{11}$, —$NR_{10}C(=O)R_{10}$, —$C(=O)R_{10}$, —$C(=O)OR_{10}$, —$(CH_2)OR_{10}$, —$(CH_2)_2OR_{10}$, —$OC(=O)R_{10}$, —$OC(=O)NR_{10}R_{11}$ and —$NR_{10}C(=O)OR_{10}$;
$R_{10}$ and $R_{11}$ are independently hydrogen, $C_{1-6}$alkyl, pyridyl, quinolinyl, pyrimidinyl, pyrimidinyl, phenyl, or benzyl; or
either $R_8$ and $R_9$ or $R_{10}$ and $R_{11}$ together with the nitrogen to which they are attached, optionally form a heterocycloalkyl ring;
p is 1, 2, 3, or 4; and
q is 1, 2, or 3;
or an enantiomer, diastereomer, tautomer, or pharmaceutically acceptable salt thereof.

In some embodiments, is a method of increasing tear production, comprising the local administration of a therapeutically effective amount of a compound of Formula (I) into the nasal cavity of an individual in need thereof, wherein X is N. In some embodiments, is a method of increasing tear production, comprising the local administration of a therapeutically effective amount of a compound of Formula (I) into the nasal cavity of an individual in need thereof, wherein $R_2$ is hydrogen. In some embodiments, is a method of increasing tear production, comprising the local administration of a therapeutically effective amount of a compound of Formula (I) into the nasal cavity of an individual in need thereof, wherein $R_1$ is hydrogen, $C_{1-6}$alkyl, —$OR_4$, or —$NR_5R_6$. In some embodiments, is a method of increasing tear production, comprising the local administration of a therapeutically effective amount of a compound of Formula (I) into the nasal cavity of an individual in need thereof, wherein $R_1$ is hydrogen. In some embodiments, is a method of increasing tear production, comprising the local administration of a therapeutically effective amount of a compound of Formula (I) into the nasal cavity of an individual in need thereof, wherein q is 1. In some embodiments, is a method of increasing tear production, comprising the local administration of a therapeutically effective amount of a compound of Formula (I) into the nasal cavity of an individual in need thereof, wherein p is 2. In some embodiments, is a method of increasing tear production, comprising the local administration of a therapeutically effective amount of a compound of Formula (I) into the nasal cavity of an individual in need thereof, wherein the wavy line represents E geometry about the double bond. In some embodiments, is a method of increasing tear production, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine. In some embodiments, is a method of increasing tear production, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine citrate salt. In some embodiments, is a method of increasing tear production, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine mono citrate salt. In some embodiments, is a method of increasing tear production, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine HCl salt. In some embodiments, is a method of increasing tear production, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine galactarate salt.

In some embodiments, is a method of increasing tear production, comprising the local administration of a therapeutically effective amount of a compound of Formula (I) into the nasal cavity of an individual in need thereof, wherein the compound of Formula (I) selectively binds to the peripheral nicotinic acetylcholine receptor and does not cross the blood-brain barrier in a pharmacologically relevant concentration. In some embodiments is method of increasing tear production, comprising the local administration of a therapeutically effective amount of a compound of Formula (I) into the nasal cavity of an individual in need thereof, wherein the compound of Formula (I) selectively binds to at least one of the peripheral nicotinic acetylcholine receptor subtypes selected from alpha3beta4, alpha4beta2, and alpha7. In some embodiments is a method of increasing tear production, comprising the local administration of a therapeutically effective amount of a compound of Formula (I) into the nasal cavity of an individual in need thereof, wherein the compound of Formula (I) selectively binds to the peripheral nicotinic acetylcholine receptor and is administered in an amount that is not systemically bioavailable. In some embodiments is a method of increasing tear production, comprising the local administration of a therapeutically effective amount of a compound of Formula (I) into the nasal cavity of an individual in need thereof, wherein the compound of Formula (I) selectively binds to the peripheral nicotinic acetylcholine receptor and in an amount that does not result in undesired psychoactive side effects. In some embodiments is a method of increasing tear production, comprising the local administration of a therapeutically effective amount of a compound of Formula (I) into the nasal cavity of an individual in need thereof, wherein the compound of Formula (I) selectively binds to the peripheral nicotinic acetylcholine receptor and in an amount that does not result in undesired systemic side effects. In some embodiments is a method of increasing tear production, comprising the local administration of a therapeutically effective amount of a compound of Formula (I) into the nasal cavity of an individual in need thereof, wherein the compound of Formula (I) selectively binds to the peripheral nicotinic acetylcholine receptor and in an amount that produces a local effect.

Further provided herein, in some embodiments, is a method of treating dry eye, comprising the local administration of a therapeutically effective amount of a compound of Formula (I) into the nasal cavity of an individual in need thereof, wherein the compound of Formula (I) binds to the peripheral nicotinic acetylcholine receptor and the compound of Formula (I) has the structure:

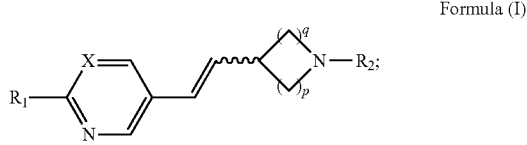

Formula (I)

wherein:
the wavy line represents E or Z geometry about the double bond;
X is N or $CR_3$;
$R_1$ is hydrogen, $C_{1-6}$alkyl, halogen, $-OR_4$, $-SR_4$, or $-NR_5R_6$;
$R_2$ is hydrogen, $C_{1-6}$alkyl, aryl, $-C_{1-6}$alkyl-(aryl), -aryl-($C_{1-6}$alkyl), heteroaryl, $-C_{1-6}$alkyl-(heteroaryl), -heteroaryl-($C_{1-6}$alkyl), heterocycloalkyl, $-C_{1-6}$alkyl(heterocycloalkyl), or cycloalkyl;
$R_3$ is hydrogen, $C_{1-6}$alkyl, aryl, $-C_{1-6}$alkyl-(aryl), -aryl-($C_{1-6}$alkyl), heteroaryl, $-C_{1-6}$alkyl-(heteroaryl), -heteroaryl-($C_{1-6}$alkyl), heterocycloalkyl, $-C_{1-6}$alkyl(heterocycloalkyl), cycloalkyl, $-OR_7$, $-SR_7$, $-NR_8R_9$, $-SOR_7$, or $-SO_2R_7$, wherein the $C_{1-6}$alkyl, heterocycloalkyl, heteroaryl, and aryl groups are optionally substituted with one or more substituents selected from halogen, $-CN$, $-NO_2$, $-NH_2$, $-OH$, $-OR_7$, $-CO_2H$, $-C(O)OR_7$, $-O-C(O)R_7$, $-NR_8R_9$, $-NHC(O)R_7$, $-C(O)NR_8R_9$, $-SR_7$, $-S(O)R_7$, $-SO_2R_7$, $-NHSO_2R_7$, $-SO_2NR_8R_9$, $-C(S)NR_8R_9$, $-NHC(S)R_7$, and $-O-SO_2R_7$;
$R_4$, $R_5$, and $R_6$ are independently hydrogen or $C_{1-6}$alkyl; and
$R_7$, $R_8$, and $R_9$ are hydrogen, $C_{1-6}$alkyl, aryl, $-C_{1-6}$alkyl-(aryl), -aryl-($C_{1-6}$alkyl), heteroaryl, $-C_{1-6}$alkyl-(heteroaryl), -heteroaryl-($C_{1-6}$alkyl), heterocycloalkyl, $-C_{1-6}$alkyl(heterocycloalkyl), or cycloalkyl wherein the $C_{1-6}$alkyl, heterocycloalkyl, heteroaryl, and aryl groups are optionally substituted one or more substituents selected from the group consisting of F, Cl, Br, I, $R_{10}$, $-NR_{10}R_{11}$, $-CF_3$, $-CN$, $-NO_2$, $-C_2R_{10}$, $-N_3$, $-SO_2CH_3$, $-OR_{10}$, $-SR_{10}$, $-C(O)NR_{10}R_{11}$, $-NR_{10}C(=O)R_{10}$, $-C(=O)R_{10}$, $-C(=O)OR_{10}$, $-(CH_2)OR_{10}$, $-(CH_2)_2OR_{10}$, $-OC(=O)R_{10}$, $-OC(=O)NR_{10}R_{11}$ and $-NR_{10}C(=O)OR_{10}$;
$R_{10}$ and $R_{11}$ are independently hydrogen, $C_{1-6}$alkyl, pyridyl, quinolinyl, pyrimidinyl, pyrimidinyl, phenyl, or benzyl; or
either $R_8$ and $R_9$ or $R_{10}$ and $R_{11}$ together with the nitrogen to which they are attached, optionally form a heterocycloalkyl ring;
p is 1, 2, 3, or 4; and
q is 1, 2, or 3;
or an enantiomer, diastereomer, tautomer, or pharmaceutically acceptable salt thereof.

In some embodiments, is a method of treating dry eye, comprising the local administration of a therapeutically effective amount of a compound of Formula (I) into the nasal cavity of an individual in need thereof, wherein X is N. In some embodiments, is a method of treating dry eye, comprising the local administration of a therapeutically effective amount of a compound of Formula (I) into the nasal cavity of an individual in need thereof, wherein $R_2$ is hydrogen. In some embodiments, is a method of treating dry eye, comprising the local administration of a therapeutically effective amount of a compound of Formula (I) into the nasal cavity of an individual in need thereof, wherein $R_1$ is hydrogen, $C_{1-6}$alkyl, $-OR_4$, or $-NR_5R_6$. In some embodiments, is a method of treating dry eye, comprising the local administration of a therapeutically effective amount of a compound of Formula (I) into the nasal cavity of an individual in need thereof, wherein $R_1$ is hydrogen. In some embodiments, is a method of treating dry eye, comprising the local administration of a therapeutically effective amount of a compound of Formula (I) into the nasal cavity of an individual in need thereof, wherein q is 1. In some embodiments, is a method of treating dry eye, comprising the local administration of a therapeutically effective amount of a compound of Formula (I) into the nasal cavity of an individual in need thereof, wherein p is 2. In some embodiments, is a method of treating dry eye, comprising the local administration of a therapeutically effective amount of a compound of Formula (I) into the nasal cavity of an individual in need thereof wherein the wavy line represents E geometry about the double bond. In some embodiments, is a method of treating dry eye, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine. In some embodiments, is a method of treating dry eye, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl) pyrimidine citrate salt. In some embodiments, is a method of treating dry eye, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine mono citrate salt. In some embodiments, is a method of treating dry eye, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine HCl salt. In some embodiments, is a method of treating dry eye, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl) pyrimidine galactarate salt.

In some embodiments, is a method of treating dry eye, comprising the local administration of a therapeutically effective amount of a compound of Formula (I) into the nasal cavity of an individual in need thereof, wherein the compound of Formula (I) selectively binds to the peripheral nicotinic acetylcholine receptor and does not cross the blood-brain barrier in a pharmacologically relevant concentration. In some embodiments is method of treating dry eye, comprising the local administration of a therapeutically effective amount of a compound of Formula (I) into the nasal cavity of an individual in need thereof, wherein the compound of Formula (I) selectively binds to at least one of the peripheral nicotinic acetylcholine receptor subtypes selected from alpha3beta4, alpha4beta2, and alpha7. In some embodiments is a method of treating dry eye, comprising the local administration of a therapeutically effective amount of a compound of Formula (I) into the nasal cavity of an individual in need thereof, wherein the compound of Formula (I) selectively binds to the peripheral nicotinic acetylcholine receptor and is administered in an amount that is not systemically bioavailable. In some embodiments is a method of treating dry eye, comprising the local administration of a therapeutically effective amount of a compound of Formula (I) into the nasal cavity of an individual in need thereof, wherein the compound of Formula (I) selectively binds to the peripheral nicotinic acetylcholine receptor and in an amount that does not result in undesired psychoactive side effects. In some embodiments is a method of treating dry eye, comprising the local administration of a therapeutically effective amount of a compound of Formula (I) into the nasal cavity of an individual in need thereof, wherein the compound of Formula (I) selectively binds to the peripheral nicotinic acetylcholine receptor and in an amount that does not result in undesired systemic side effects. In some embodiments is a method of treating dry eye, comprising the local administration of a therapeutically effective amount of a compound of Formula (I) into the nasal cavity of an individual in need thereof, wherein the compound of Formula (I) selectively binds to the peripheral nicotinic acetylcholine receptor and in an amount that produces a local effect.

Also provided herein, in some embodiments, is a method of improving ocular discomfort, comprising the local administration of a therapeutically effective amount of a compound of Formula (I) into the nasal cavity of an individual in need thereof, wherein the compound of Formula (I) binds to the peripheral nicotinic acetylcholine receptor and the compound of Formula (I) has the structure:

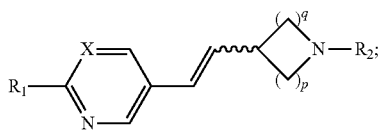

Formula (I)

wherein:
the wavy line represents E or Z geometry about the double bond;
X is N or $CR_3$;
$R_1$ is hydrogen, $C_{1-6}$alkyl, halogen, $-OR_4$, $-SR_4$, or $-NR_5R_6$;
$R_2$ is hydrogen, $C_{1-6}$alkyl, aryl, $-C_{1-6}$alkyl-(aryl), -aryl-($C_{1-6}$alkyl), heteroaryl, $-C_{1-6}$alkyl-(heteroaryl), -heteroaryl-($C_{1-6}$alkyl), heterocycloalkyl, $-C_{1-6}$alkyl(heterocycloalkyl), or cycloalkyl;
$R_3$ is hydrogen, $C_{1-6}$alkyl, aryl, $-C_{1-6}$alkyl-(aryl), -aryl-($C_{1-6}$alkyl), heteroaryl, $-C_{1-6}$alkyl-(heteroaryl), -heteroaryl-($C_{1-6}$alkyl), heterocycloalkyl, $-C_{1-6}$alkyl(heterocycloalkyl), cycloalkyl, $-OR_7$, $-SR_7$, $-NR_8R_9$, $-SOR_7$, or $-SO_2R_7$, wherein the $C_{1-6}$alkyl, heterocycloalkyl, heteroaryl, and aryl groups are optionally substituted with one or more substituents selected from halogen, $-CN$, $-NO_2$, $-NH_2$, $-OH$, $-OR_7$, $-CO_2H$, $-C(O)OR_7$, $-O-C(O)R_7$, $-NR_8R_9$, $-NHC(O)R_7$, $-C(O)NR_8R_9$, $-SR_7$, $-S(O)R_7$, $-SO_2R_7$, $-NHSO_2R_7$, $-SO_2NR_8R_9$, $-C(S)NR_8R_9$, $-NHC(S)R_7$, and $-O-SO_2R_7$;
$R_4$, $R_5$, and $R_6$ are independently hydrogen or $C_{1-6}$alkyl; and
$R_7$, $R_8$, and $R_9$ are hydrogen, $C_{1-6}$alkyl, aryl, $-C_{1-6}$alkyl-(aryl), -aryl-($C_{1-6}$alkyl), heteroaryl, $-C_{1-6}$ alkyl-(heteroaryl), -heteroaryl-($C_{1-6}$alkyl), heterocycloalkyl, $-C_{1-6}$ alkyl(heterocycloalkyl), or cycloalkyl, wherein the $C_{1-6}$alkyl, heterocycloalkyl, heteroaryl, and aryl groups are optionally substituted one or more substituents selected from the group consisting of F, Cl, Br, I, $R_{10}$, $-NR_{10}R_{11}$, $-CF_3$, $-CN$, $-NO_2$, $-C_2R_{10}$, $-N_3$, $-SO_2CH_3$, $-OR_{10}$, $-SR_{10}$, $-C(O)NR_{10}R_{11}$, $-NR_{10}C(=O)R_{10}$, $-C(=O)R_{10}$, $-C(=O)OR_{10}$, $-(CH_2)OR_{10}$, $-(CH_2)_2OR_{10}$, $-OC(=O)R_{10}$, $-OC(=O)NR_{10}R_{11}$ and $-NR_{10}C(=O)OR_{10}$;
$R_{10}$ and $R_{11}$ are independently hydrogen, $C_{1-6}$alkyl, pyridyl, quinolinyl, pyrimidinyl, pyrimidinyl, phenyl, or benzyl; or
either $R_8$ and $R_9$ or $R_{10}$ and $R_{11}$ together with the nitrogen to which they are attached, optionally form a heterocycloalkyl ring;
p is 1, 2, 3, or 4; and
q is 1, 2, or 3;
or an enantiomer, diastereomer, tautomer, or pharmaceutically acceptable salt thereof.

In some embodiments, is a method of improving ocular discomfort, comprising the local administration of a therapeutically effective amount of a compound of Formula (I) into the nasal cavity of an individual in need thereof, wherein X is N. In some embodiments, is a method of improving ocular discomfort, comprising the local administration of a therapeutically effective amount of a compound of Formula (I) into the nasal cavity of an individual in need thereof, wherein $R_2$ is hydrogen. In some embodiments, is a method of improving ocular discomfort, comprising the local administration of a therapeutically effective amount of a compound of Formula (I) into the nasal cavity of an individual in need thereof, wherein $R_1$ is hydrogen, $C_{1-6}$alkyl, $-OR_4$, or $-N_5R_6$. In some embodiments, is a method of improving ocular discomfort, comprising the local administration of a therapeutically effective amount of a compound of Formula (I) into the nasal cavity of an individual in need thereof, wherein $R_1$ is hydrogen. In some embodiments, is a method of improving ocular discomfort, comprising the local administration of a therapeutically effective amount of a compound of Formula (I) into the nasal cavity of an individual in need thereof, wherein q is 1. In some embodiments, is a method of improving ocular discomfort, comprising the local administration of a therapeutically effective amount of a compound of Formula (I) into the nasal cavity of an individual in need thereof, wherein p is 2. In some embodiments, is a method of improving ocular discomfort, comprising the local administration of a therapeutically effective amount of a compound of Formula (I) into the nasal cavity of an individual in need thereof, wherein the wavy line represents E geometry about the double bond. In some embodiments, is a method of improving ocular discomfort, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine. In some embodiments, is a method of improving ocular discomfort, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine citrate salt. In some embodiments, is a method of improving ocular discomfort, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine mono citrate salt. In some embodiments, is a method of improving ocular discomfort, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl) pyrimidine HCl salt. In some embodiments, is a method of improving ocular discomfort, comprising the local administration of a therapeutically effective amount of a compound of Formula (I) into the nasal cavity of an individual in need thereof, wherein the compound of Formula (I) is (R)-5-((E)-2-pyrrolidin-3-ylvinyl)pyrimidine galactarate salt.

In some embodiments, is a method of improving ocular discomfort, comprising the local administration of a therapeutically effective amount of a compound of Formula (I) into the nasal cavity of an individual in need thereof, wherein the compound of Formula (I) selectively binds to the peripheral nicotinic acetylcholine receptor and does not cross the blood-brain barrier in a pharmacologically relevant concentration. In some embodiments is method of improving ocular discomfort, comprising the local administration of a therapeutically effective amount of a compound of Formula (I) into the nasal cavity of an individual in need thereof, wherein the compound of Formula (I) selectively binds to at least one of the peripheral nicotinic acetylcholine receptor subtypes selected from alpha3beta4, alpha4beta2, and alpha7. In some embodiments is a method of improving ocular discomfort, comprising the local administration of a therapeutically effective amount of a compound of Formula (I) into the nasal cavity of an individual in need thereof, wherein the compound of Formula (I) selectively binds to the peripheral nicotinic acetylcholine receptor and is administered in an amount that is not systemically bioavailable. In some embodiments is a method of improving ocular discomfort, comprising the local administration of a therapeutically effective amount of a compound of Formula (I) into the nasal cavity of an individual in need thereof, wherein the compound of Formula (I) selectively binds to the peripheral nicotinic acetylcholine receptor and in an amount that does not result in undesired psychoactive side effects. In some embodiments is a method of improving ocular discomfort, comprising the local administration of a therapeutically effective amount of a compound of Formula (I) into the nasal cavity of an individual in need thereof, wherein the compound of Formula (I) selectively binds to the peripheral nicotinic acetylcholine receptor and in an amount that does not result in undesired systemic side effects. In some embodiments is a method of improving ocular discomfort, comprising the local administration of a therapeutically effective amount of a compound of Formula (I) into the nasal cavity of an individual in need thereof, wherein the compound of Formula (I) selectively binds to the peripheral nicotinic acetylcholine receptor and in an amount that produces a local effect.

Further provided herein, in some embodiments, is a method of increasing tear production, comprising the local administration of a therapeutically effective amount of a compound of Formula (II) into the nasal cavity of an individual in need thereof, wherein the compound of Formula (II) binds to the peripheral nicotinic acetylcholine receptor and the compound of Formula (II) has the structure:

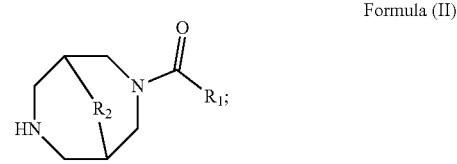

Formula (II)

wherein:
$R_1$ is $C_{1-6}$alkyl, $C_{2-6}$alkenyl, $C_{2-6}$alkynyl, $C_{3-8}$heterocycloalkyl, $C_{3-8}$cycloalkyl, or heteroaryl, optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —NO$_2$, —OR$_3$, —NR$_4$R$_5$, —CF$_3$, —C$_2$R$_3$, —SR$_3$, —N$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$;

$R_2$ is a bond or —CH$_2$—;

$R_3$ is hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; and $R_4$ and $R_5$ are independently hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; or $R_4$ and $R_5$ together with the nitrogen to which they are attached, form a heterocycloalkyl ring or a pharmaceutically acceptable salt thereof.

In some embodiments, is a method of increasing tear production, comprising the local administration of a therapeutically effective amount of a compound of Formula (II) into the nasal cavity of an individual in need thereof, wherein $R_1$ is heteroaryl optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —OR$_3$, —NR$_4$R$_5$, —CF$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$. In some embodiments, is a method of increasing tear production, comprising the local administration of a therapeutically effective amount of a compound of Formula (II) into the nasal cavity of an individual in need thereof, wherein $R_1$ is 2-furanyl, 3-furanyl, 2-oxazolyl, 4-oxazolyl, 5-oxazolyl, 3-isoxazolyl, 4-isoxazolyl, 5-isoxazolyl, 1,3,4-oxadiazol-2-yl, 1,2,4-oxadiazol-3-yl, 1,2,4-oxadiazol-5-yl, 2-thiazolyl, 4-thiazolyl, 5-thiazolyl, 3-isothiazolyl, 4-isothiazolyl, 5-isothiazolyl, 1,3,4-thiadiazol-2-yl, 1,2,4-thiadiazol-3-yl, 1,2,4-thiadiazol-5-yl or 4-pyridinyl. In some embodiments, is a method of increasing tear production, comprising the local administration of a therapeutically effective amount of a compound of Formula (II) into the nasal cavity of an individual in need thereof, wherein $R_2$ is a bond. In some embodiments, is a method of increasing tear production, comprising the local administration of a therapeutically effective amount of a compound of Formula (II) into the nasal cavity of an individual in need thereof, wherein $R_2$ is a —$CH_2$—. In some embodiments, is a method of increasing tear production, comprising the local administration of a therapeutically effective amount of a compound of Formula (II) into the nasal cavity of an individual in need thereof, wherein the compound of Formula (II) is N-(5-chlorofuran-2-ylcarbonyl)-3,7-diazabicyclo[3.3.0]octane.

In some embodiments, is a method of increasing tear production, comprising the local administration of a therapeutically effective amount of a compound of Formula (II) into the nasal cavity of an individual in need thereof, wherein the compound of Formula (II) selectively binds to the peripheral nicotinic acetylcholine receptor and does not cross the blood-brain barrier in a pharmacologically relevant concentration. In some embodiments is method of increasing tear production, comprising the local administration of a therapeutically effective amount of a compound of Formula (II) into the nasal cavity of an individual in need thereof, wherein the compound of Formula (II) selectively binds to at least one of the peripheral nicotinic acetylcholine receptor subtypes selected from alpha3beta4, alpha4beta2, and alpha7. In some embodiments is a method of increasing tear production, comprising the local administration of a therapeutically effective amount of a compound of Formula (II) into the nasal cavity of an individual in need thereof, wherein the compound of Formula (II) selectively binds to the peripheral nicotinic acetylcholine receptor and is administered in an amount that is not systemically bioavailable. In some embodiments is a method of increasing tear production, comprising the local administration of a therapeutically effective amount of a compound of Formula (II) into the nasal cavity of an individual in need thereof, wherein the compound of Formula (II) selectively binds to the peripheral nicotinic acetylcholine receptor and in an amount that does not result in undesired psychoactive side effects. In some embodiments is a method of increasing tear production, comprising the local administration of a therapeutically effective amount of a compound of Formula (II) into the nasal cavity of an individual in need thereof, wherein the compound of Formula (II) selectively binds to the peripheral nicotinic acetylcholine receptor and in an amount that does not result in undesired systemic side effects. In some embodiments is a method of increasing tear production, comprising the local administration of a therapeutically effective amount of a compound of Formula (II) into the nasal cavity of an individual in need thereof, wherein the compound of Formula (II) selectively binds to the peripheral nicotinic acetylcholine receptor and in an amount that produces a local effect.

Further provided herein, in some embodiments, is a method of treating dry eye, comprising the local administration of a therapeutically effective amount of a compound of Formula (II) into the nasal cavity of an individual in need thereof, wherein the compound of Formula (II) binds to the peripheral nicotinic acetylcholine receptor and the compound of Formula (II) has the structure:

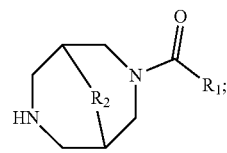

Formula (II)

wherein:

$R_1$ is $C_{1-6}$alkyl, $C_{2-6}$alkenyl, $C_{2-6}$alkynyl, $C_{3-8}$heterocycloalkyl, $C_{3-8}$cycloalkyl, or heteroaryl, optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$NO_2$, —$OR_3$, —$NR_4R_5$, —$CF_3$, —$C_2R_3$, —$SR_3$, —$N_3$, —C(O)$NR_4R_5$, —$NR_4$C(O)$R_1$, —C(O)$R_3$, —C(O)$OR_3$, —OC(O)$R_3$, —OC(O)$NR_4R_5$, —$NR_4$C(O)$OR_3$, —$SO_2R_3$, —$NR_4SO_2R_5$, and —$SO_2NR_4R_5$;

$R_2$ is a bond or —$CH_2$—;

$R_3$ is hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl), or heteroaryl and $R_4$ and $R_5$ are independently hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; or $R_4$ and $R_5$ together with the nitrogen to which they are attached, form a heterocycloalkyl ring;

or a pharmaceutically acceptable salt thereof.

In some embodiments, is a method of treating dry eye, comprising the local administration of a therapeutically effective amount of a compound of Formula (II) into the nasal cavity of an individual in need thereof, wherein $R_1$ is heteroaryl optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$OR_3$, —$NR_4R_5$, —$CF_3$, —C(O)$NR_4R_5$, —$NR_4$C(O)$R_3$, —C(O)$R_3$, —C(O)$OR_3$, —OC(O)$R_3$, —OC(O)$NR_4R_5$, —$NR_4$C(O)$OR_3$, —$SO_2R_3$, —$NR_4SO_2R_5$, and —$SO_2NR_4R_5$. In some embodiments, is a method of treating dry eye, comprising the local administration of a therapeutically effective amount of a compound of Formula (II) into the nasal cavity of an individual in need thereof, wherein $R_1$ is 2-furanyl, 3-furanyl, 2-oxazolyl, 4-oxazolyl, 5-oxazolyl, 3-isoxazolyl, 4-isoxazolyl, 5-isoxazolyl, 1,3,4-oxadiazol-2-yl, 1,2,4-oxadiazol-3-yl, 1,2,4-oxadiazol-5-yl, 2-thiazolyl, 4-thiazolyl, 5-thiazolyl, 3-isothiazolyl, 4-isothiazolyl, 5-isothiazolyl, 1,3,4-thiadiazol-2-yl, 1,2,4-thiadiazol-3-yl, 1,2,4-thiadiazol-5-yl or 4-pyridinyl. In some embodiments, is a method of treating dry eye, comprising the local administration of a therapeutically effective amount of a compound of Formula (II) into the nasal cavity of an individual in need thereof, wherein $R_2$ is a bond. In some embodiments, is a method of treating dry eye, comprising the local administration of a therapeutically effective amount of a compound of Formula (II) into the nasal cavity of an individual in need thereof, wherein $R_2$ is a —$CH_2$—. In some embodiments, is a method of treating dry eye, comprising the local administration of a therapeutically effective amount of a compound of Formula (II) into the nasal cavity of an individual in need thereof, wherein the compound of Formula (II) is N-(5-chlorofuran-2-ylcarbonyl)-3,7-diazabicyclo[3.3.0]octane.

In some embodiments, is a method of treating dry eye, comprising the local administration of a therapeutically effective amount of a compound of Formula (II) into the nasal cavity of an individual in need thereof, wherein the compound of Formula (II) selectively binds to the peripheral nicotinic acetylcholine receptor and does not cross the blood-brain barrier in a pharmacologically relevant concentration. In some embodiments is method of treating dry eye, comprising the local administration of a therapeutically effective amount of a compound of Formula (II) into the nasal cavity of an individual in need thereof wherein the compound of Formula (II) selectively binds to at least one of the peripheral nicotinic acetylcholine receptor subtypes selected from alpha3beta4, alpha4beta2, and alpha7. In some embodiments is a method of treating dry eye, comprising the local administration of a therapeutically effective amount of a compound of Formula (II) into the nasal cavity of an individual in need thereof, wherein the compound of Formula (II) selectively binds to the peripheral nicotinic acetylcholine receptor and is administered in an amount that is not systemically bioavailable. In some embodiments is a method of treating dry eye, comprising the local administration of a therapeutically effective amount of a compound of Formula (II) into the nasal cavity of an individual in need thereof, wherein the compound of Formula (II) selectively binds to the peripheral nicotinic acetylcholine receptor and in an amount that does not result in undesired psychoactive side effects. In some embodiments is a method of treating dry eye, comprising the local administration of a therapeutically effective amount of a compound of Formula (II) into the nasal cavity of an individual in need thereof, wherein the compound of Formula (II) selectively binds to the peripheral nicotinic acetylcholine receptor and in an amount that does not result in undesired systemic side effects. In some embodiments is a method of treating dry eye, comprising the local administration of a therapeutically effective amount of a compound of Formula (II) into the nasal cavity of an individual in need thereof, wherein the compound of Formula (II) selectively binds to the peripheral nicotinic acetylcholine receptor and in an amount that produces a local effect.

Further provided herein, in some embodiments, is a method of improving ocular discomfort, comprising the local administration of a therapeutically effective amount of a compound of Formula (II) into the nasal cavity of an individual in need thereof, wherein the compound of Formula (II) binds to the peripheral nicotinic acetylcholine receptor and the compound of Formula (II) has the structure:

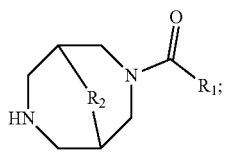

Formula (II)

wherein:
R$_1$ is C$_{1-6}$alkyl, C$_{2-6}$alkenyl, C$_{2-6}$alkynyl, C$_{3-8}$heterocycloalkyl, C$_{3-8}$cycloalkyl, or heteroaryl, optionally substituted with one to three non-hydrogen substituents independently selected from C$_{1-6}$alkyl, C$_{2-6}$alkenyl, C$_{2-6}$alkynyl, C$_{3-8}$heterocycloalkyl, C$_{3-8}$cycloalkyl, heteroaryl, aryl, —C$_{1-6}$alkyl-(aryl), -aryl-(C$_{1-6}$alkyl), heteroaryl, —C$_{1-6}$alkyl-(heteroaryl), -heteroaryl-(C$_{1-6}$alkyl), halogen, —CN, —NO$_2$, —OR$_3$, —NR$_4$R$_5$, —CF$_3$, —C$_2$R$_3$, —SR$_3$, —N$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)R$_5$, —NR$_4$C(O)OR$_3$, —SO$_2$R$_3$, —NR$_4$SO$_2$R$_5$, and —SO$_2$NR$_4$R$_5$;

R$_2$ is a bond or —CH$_2$—;

R$_3$ is hydrogen, C$_{1-6}$alkyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; and R$_4$ and R$_5$ are independently hydrogen, C$_{1-6}$alkyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; or R$_4$ and R$_5$ together with the nitrogen to which they are attached, form a heterocycloalkyl ring;

or a pharmaceutically acceptable salt thereof.

In some embodiments, is a method of improving ocular discomfort, comprising the local administration of a therapeutically effective amount of a compound of Formula (II) into the nasal cavity of an individual in need thereof, wherein R$_1$ is heteroaryl optionally substituted with one to three non-hydrogen substituents independently selected from C$_{1-6}$alkyl, C$_{2-6}$alkenyl, C$_{2-6}$alkynyl, C$_{3-8}$heterocycloalkyl, C$_{3-8}$cycloalkyl, heteroaryl, aryl, —C$_{1-6}$alkyl-(aryl), -aryl-(C$_{1-6}$alkyl), heteroaryl, —C$_{1-6}$alkyl-(heteroaryl), -heteroaryl-(C$_{1-6}$alkyl), halogen, —CN, —OR$_3$, —NR$_4$R$_5$, —CF$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$. In some embodiments, is a method of improving ocular discomfort, comprising the local administration of a therapeutically effective amount of a compound of Formula (II) into the nasal cavity of an individual in need thereof, wherein R$_1$ is 2-furanyl, 3-furanyl, 2-oxazolyl, 4-oxazolyl, 5-oxazolyl, 3-isoxazolyl, 4-isoxazolyl, 5-isoxazolyl, 1,3,4-oxadiazol-2-yl, 1,2,4-oxadiazol-3-yl, 1,2,4-oxadiazol-5-yl, 2-thiazolyl, 4-thiazolyl, 5-thiazolyl, 3-isothiazolyl, 4-isothiazolyl, 5-isothiazolyl, 1,3,4-thiadiazol-2-yl, 1,2,4-thiadiazol-3-yl, 1,2,4-thiadiazol-5-yl or 4-pyridinyl. In some embodiments, is a method of improving ocular discomfort, comprising the local administration of a therapeutically effective amount of a compound of Formula (II) into the nasal cavity of an individual in need thereof, wherein R$_2$ is a bond. In some embodiments, is a method of improving ocular discomfort, comprising the local administration of a therapeutically effective amount of a compound of Formula (II) into the nasal cavity of an individual in need thereof, wherein R$_2$ is a —CH$_2$—. In some embodiments, is a method of improving ocular discomfort, comprising the local administration of a therapeutically effective amount of a compound of Formula (II) into the nasal cavity of an individual in need thereof, wherein the compound of Formula (II) is N-(5-chlorofuran-2-ylcarbonyl)-3,7-diazabicyclo[3.3.0]octane.

In some embodiments, is a method of improving ocular discomfort, comprising the local administration of a therapeutically effective amount of a compound of Formula (II) into the nasal cavity of an individual in need thereof, wherein the compound of Formula (II) selectively binds to the peripheral nicotinic acetylcholine receptor and does not cross the blood-brain barrier in a pharmacologically relevant concentration. In some embodiments is method of improving ocular discomfort, comprising the local administration of a therapeutically effective amount of a compound of Formula (II) into the nasal cavity of an individual in need thereof, wherein the compound of Formula (II) selectively binds to at least one of the peripheral nicotinic acetylcholine receptor subtypes selected from alpha3beta4, alpha4beta2, and alpha7. In some embodiments is a method of improving ocular discomfort, comprising the local administration of a therapeutically effective amount of a compound of Formula (II) into the nasal cavity of an individual in need thereof, wherein the compound of Formula (II) selectively binds to the peripheral nicotinic acetylcholine receptor and is administered in an amount that is not systemically bioavailable. In some embodiments is a method of improving ocular discomfort, comprising the local administration of a therapeutically effective amount of a compound of Formula (II) into the nasal cavity of an individual in need thereof, wherein the compound of Formula (II) selectively binds to the peripheral nicotinic acetylcholine receptor and in an amount that does not result in undesired psychoactive side effects. In some embodiments is a method of improving ocular discomfort, comprising the local administration of a therapeutically effective amount of a compound of Formula (II) into the nasal cavity of an individual in need thereof, wherein the compound of Formula (II) selectively binds to the peripheral nicotinic acetylcholine receptor and in an amount that does not result in undesired systemic side effects. In some embodiments is a method of improving ocular discomfort, comprising the local administration of a therapeutically effective amount of a compound of Formula (II) into the nasal cavity of an individual in need thereof, wherein the compound of Formula (II) selectively binds to the peripheral nicotinic acetylcholine receptor and in an amount that produces a local effect.

Further provided herein, in some embodiments, is a method of increasing tear production, comprising the local administration of a therapeutically effective amount of a compound of Formula (IIIa) or (IIIb) into the nasal cavity of an individual in need thereof, wherein the compound of Formula (IIIa) or (IIIb) binds to the peripheral nicotinic acetylcholine receptor and the compound of Formula (IIIa) or (IIIb) has the structure:

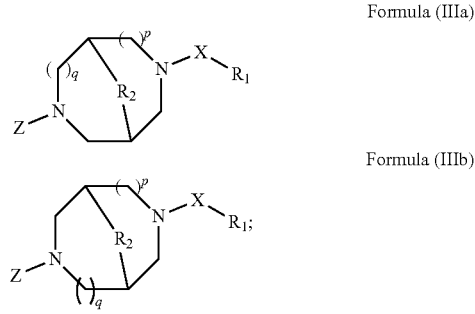

Formula (IIIa)

Formula (IIIb)

wherein:
X is C(O), C(S), or S(O)$_n$;
Z is hydrogen, $C_{1-6}$alkyl, or $C_{1-6}$haloalkyl;
n is 1 or 2;
p is 0 or 1;
q is 0 or 1;
when p is 1, then q is 0;
when q is 1, then p is 0;
$R_1$ is —$OR_3$, —$NR_4R_5$, $C_{1-6}$alkyl, $C_{2-6}$alkenyl, $C_{2-6}$alkynyl, $C_{3-8}$heterocycloalkyl, $C_{3-8}$cycloalkyl, aryl or heteroaryl, wherein $C_{1-6}$alkyl, $C_{2-6}$alkenyl, $C_{2-6}$alkynyl, $C_{3-8}$heterocycloalkyl, $C_{3-8}$cycloalkyl, aryl or heteroaryl are optionally substituted with one to three non-hydrogen substituents independently selected from $C_{1-6}$alkyl, $C_{2-6}$alkenyl, $C_{2-6}$alkynyl, $C_{3-8}$ heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$NO_2$, —$OR_3$, —$NR_4R_5$, —$CF_3$, —$C_2R_3$, —$SR_3$, —$N_3$, —$C(O)NR_4R_5$, —$NR_4C(O)R_3$, —$C(O)R_3$, —$C(O)OR_3$, —$OC(O)R_3$, —$OC(O)NR_4R_5$, —$NR_4C(O)OR_3$, —$SO_2R_3$, —$NR_4SO_2R_5$, and —$SO_2NR_4R_5$;
$R_2$ is —$CH_2$— or —$CH_2CH_2$—;
$R_3$ is hydrogen, $C_{1-6}$alkyl, $C_{2-6}$alkenyl, $C_{2-6}$alkynyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; and
$R_4$ and $R_5$ are independently hydrogen, $C_{1-6}$alkyl, $C_{2-6}$alkenyl, $C_{2-6}$alkynyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; or $R_4$ and $R_5$ together with the nitrogen to which they are attached, form a heterocycloalkyl ring;
or a pharmaceutically acceptable salt thereof.

In some embodiments, is a method of increasing tear production, comprising the local administration of a therapeutically effective amount of a compound of (IIIa) or (IIIb) into the nasal cavity of an individual in need thereof wherein p is 1 and q is 0. In some embodiments, is a method of increasing tear production, comprising the local administration of a therapeutically effective amount of a compound of (IIIa) or (IIIb) into the nasal cavity of an individual in need thereof, wherein p is 0 and q is 1. In some embodiments, is a method of increasing tear production, comprising the local administration of a therapeutically effective amount of a compound of Formula (IIIa) or (IIIb) into the nasal cavity of an individual in need thereof, wherein $R_2$ is —$CH_2$—. In some embodiments, is a method of increasing tear production, comprising the local administration of a therapeutically effective amount of a compound of Formula (IIIa) or (IIIb) into the nasal cavity of an individual in need thereof, wherein $R_2$ is —$CH_2CH_2$—. In some embodiments, is a method of increasing tear production, comprising the local administration of a therapeutically effective amount of a compound of Formula (IIIa) or (IIIb) into the nasal cavity of an individual in need thereof, wherein Z is hydrogen. In some embodiments, is a method of increasing tear production, comprising the local administration of a therapeutically effective amount of a compound of Formula (IIIa) or (IIIb) into the nasal cavity of an individual in need thereof, wherein Z is $C_{1-6}$alkyl. In some embodiments, is a method of increasing tear production, comprising the local administration of a therapeutically effective amount of a compound of Formula (IIIa) or (IIIb) into the nasal cavity of an individual in need thereof, wherein X is C(O).

In some embodiments, is a method of increasing tear production, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and does not cross the blood-brain barrier in a pharmacologically relevant concentration. In some embodiments is method of increasing tear production, comprising the local administration of a therapeutically effective amount of a compound of Formula (IIIa) or (IIIb) into the nasal cavity of an individual in need thereof, wherein the compound of Formula (IIIa) or (IIIb) selectively binds to at least one of the peripheral nicotinic acetylcholine receptor subtypes selected from alpha3beta4, alpha4beta2, and alpha7. In some embodiments is a method of increasing tear production, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and is administered in an amount that is not systemically bioavailable. In some embodiments is a method of increasing tear production, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and in an amount that does not result in undesired psychoactive side effects. In some embodiments is a method of increasing tear production, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and in an amount that does not result in undesired systemic side effects. In some embodiments is a method of increasing tear production, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and in an amount that produces a local effect.

Further provided herein, in some embodiments, is a method of treating dry eye, comprising the local administration of a therapeutically effective amount of a compound of Formula (IIIa) or (IIIb) into the nasal cavity of an individual in need thereof, wherein the compound of Formula (IIIa) or (IIIb) binds to the peripheral nicotinic acetylcholine receptor and the compound of Formula (IIIa) or (IIIb) has the structure:

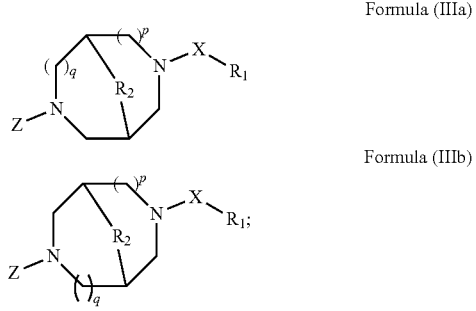

Formula (IIIa)

Formula (IIIb)

wherein:
X is C(O), C(S), or S(O);
Z is hydrogen, $C_{1-6}$alkyl, or $C_{1-6}$haloalkyl;
n is 1 or 2;
p is 0 or 1;
q is 0 or 1;
when p is 1, then q is 0;
when q is 1, then p is 0;
$R_1$ is —$OR_3$, —$NR_4R_5$, $C_{1-6}$alkyl, $C_{2-6}$alkenyl, $C_{2-6}$alkynyl, $C_{3-8}$heterocycloalkyl, $C_{3-8}$cycloalkyl, aryl or heteroaryl, wherein $C_{1-6}$alkyl, $C_{2-6}$alkenyl, $C_{2-6}$alkynyl, $C_{3-8}$heterocycloalkyl, $C_{3-8}$ cycloalkyl, aryl or heteroaryl are optionally substituted with one to three non-hydrogen substituents independently selected from $C_{1-6}$alkyl, $C_{2-6}$alkenyl, $C_{2-6}$alkynyl, $C_{3-8}$ heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$NO_2$, —$OR_3$, —$NR_4R_5$, —$CF_3$, —$C_2R_3$, —$SR_3$, —$N_3$, —$C(O)NR_4R_5$, —$NR_4C(O)R_3$, —$C(O)R_3$, —$C(O)OR_3$, —$OC(O)R_3$, —$OC(O)NR_4R_5$, —$NR_4C(O)OR_3$, —$SO_2R_3$, —$NR_4SO_2R_5$, and —$SO_2NR_4R_5$;
$R_2$ is —$CH_2$— or —$CH_2CH_2$—;
$R_3$ is hydrogen, $C_{1-6}$alkyl, $C_{2-6}$alkenyl, $C_{2-6}$alkynyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; and
$R_4$ and $R_5$ are independently hydrogen, $C_{1-6}$alkyl, $C_{2-6}$alkenyl, $C_{2-6}$alkynyl, $C_{3-8}$cycloalkyl, $C_{3-8}$-heterocycloalkyl, aryl, —$C_{1-6}$alkyl-(aryl), -aryl-($C_{1-6}$alkyl), or heteroaryl; or $R_4$ and $R_5$ together with the nitrogen to which they are attached, form a heterocycloalkyl ring;
or a pharmaceutically acceptable salt thereof.

In some embodiments, is a method of treating dry eye, comprising the local administration of a therapeutically effective amount of a compound of (IIIa) or (IIIb) into the nasal cavity of an individual in need thereof, wherein p is 1 and q is 0. In some embodiments, is a method of treating dry eye, comprising the local administration of a therapeutically effective amount of a compound of (IIIa) or (IIIb) into the nasal cavity of an individual in need thereof, wherein p is 0 and q is 1. In some embodiments, is a method of treating dry eye, comprising the local administration of a therapeutically effective amount of a compound of Formula (IIIa) or (IIIb) into the nasal cavity of an individual in need thereof, wherein $R_2$ is —$CH_2$—. In some embodiments, is a method of treating dry eye, comprising the local administration of a therapeutically effective amount of a compound of Formula (IIIa) or (IIIb) into the nasal cavity of an individual in need thereof, wherein R is —$CH_2CH_2$—. In some embodiments, is a method of treating dry eye, comprising the local administration of a therapeutically effective amount of a compound of Formula (IIIa) or (IIIb) into the nasal cavity of an individual in need thereof, wherein Z is hydrogen. In some embodiments, is a method of treating dry eye, comprising the local administration of a therapeutically effective amount of a compound of Formula (IIIa) or (IIIb) into the nasal cavity of an individual in need thereof, wherein Z is $C_{1-6}$alkyl. In some embodiments, is a method of treating dry eye, comprising the local administration of a therapeutically effective amount of a compound of Formula (IIIa) or (IIIb) into the nasal cavity of an individual in need thereof, wherein X is C(O).

In some embodiments, is a method of treating dry eye, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and does not cross the blood-brain barrier in a pharmacologically relevant concentration. In some embodiments is method of treating dry eye, comprising the local administration of a therapeutically effective amount of a compound of Formula (IIIa) or (IIIb) into the nasal cavity of an individual in need thereof, wherein the compound of Formula (IIIa) or (IIIb) selectively binds to at least one of the peripheral nicotinic acetylcholine receptor subtypes selected from alpha3beta4, alpha4beta2, and alpha7. In some embodiments is a method of treating dry eye, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and is administered in an amount that is not systemically bioavailable. In some embodiments is a method of treating dry eye, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and in an amount that does not result in undesired psychoactive side effects. In some embodiments is a method of treating dry eye, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and in an amount that does not result in undesired systemic side effects. In some embodiments is a method of treating dry eye, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and in an amount that produces a local effect.

Further provided herein, in some embodiments, is a method of improving ocular discomfort, comprising the local administration of a therapeutically effective amount of a compound of Formula (IIIa) or (IIIb) into the nasal cavity of an individual in need thereof, wherein the compound of Formula (IIIa) or (IIIb) binds to the peripheral nicotinic acetylcholine receptor and the compound of Formula (IIIa) or (IIIb) has the structure:

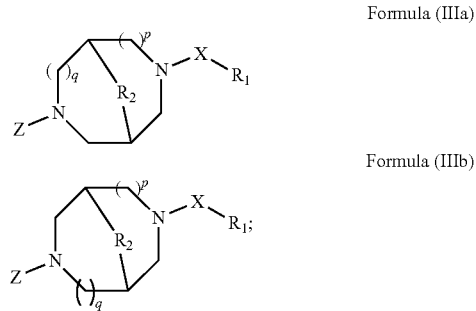

Formula (IIIa)

Formula (IIIb)

wherein:
X is C(O), C(S), or S(O)$_n$;
Z is hydrogen, $C_{1-6}$alkyl, or $C_{1-6}$haloalkyl;
n is 1 or 2;
p is 0 or 1;
q is 0 or 1;
when p is 1, then q is 0;
when q is 1, then p is 0.
$R_1$ is —$OR_3$, —$NR_4R_5$, $C_{1-6}$alkyl, $C_{2-6}$alkenyl, $C_{2-6}$alkynyl, $C_{3-8}$heterocycloalkyl, $C_{3-8}$cycloalkyl, aryl or heteroaryl, wherein $C_{1-6}$alkyl, $C_{2-6}$alkenyl, $C_{2-6}$alkynyl, $C_{3-8}$heterocycloalkyl, $C_{3-8}$cycloalkyl, aryl or heteroaryl are optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$NO_2$, —$OR_3$, —$NR_4R_5$, —$CF_3$, —$C_2R_3$, —$SR_3$, —$N_3$, —$C(O)NR_4R_5$, —$NR_4C(O)R_3$, —$C(O)R_3$, —$C(O)OR_3$, —$OC(O)R_3$, —$OC(O)NR_4R_5$, —$NR_4C(O)OR_3$, —$SO_2R_3$, —$NR_4SO_2R_5$, and —$SO_2NR_4R_5$;
$R_2$ is —$CH_2$— or —$CH_2CH_2$—;

$R_3$ is hydrogen, $C_{1-6}$alkyl, $C_{2-6}$alkenyl, $C_{2-6}$alkynyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; and
$R_4$ and $R_5$ are independently hydrogen, $C_{1-6}$alkyl, $C_{2-6}$alkenyl, $C_{2-6}$alkynyl, $C_{3-8}$cycloalkyl, $C_{3-8}$ heterocycloalkyl, aryl, —$C_{1-6}$alkyl-(aryl), -aryl-($C_{1-6}$alkyl), or heteroaryl; or $R_4$ and $R_5$ together with the nitrogen to which they are attached, form a heterocycloalkyl ring:
or a pharmaceutically acceptable salt thereof.

In some embodiments, is a method of improving ocular discomfort, comprising the local administration of a therapeutically effective amount of a compound of (IIIa) or (IIIb) into the nasal cavity of an individual in need thereof, wherein p is 1 and q is 0. In some embodiments, is a method of improving ocular discomfort, comprising the local administration of a therapeutically effective amount of a compound of (IIIa) or (IIIb) into the nasal cavity of an individual in need thereof, wherein p is 0 and q is 1. In some embodiments, is a method of improving ocular discomfort, comprising the local administration of a therapeutically effective amount of a compound of Formula (IIIa) or (IIIb) into the nasal cavity of an individual in need thereof, wherein $R_2$ is —$CH_2$—. In some embodiments, is a method of improving ocular discomfort, comprising the local administration of a therapeutically effective amount of a compound of Formula (IIIa) or (IIIb) into the nasal cavity of an individual in need thereof, wherein $R_2$ is —$CH_2CH_2$—. In some embodiments, is a method of improving ocular discomfort, comprising the local administration of a therapeutically effective amount of a compound of Formula (IIIa) or (IIIb) into the nasal cavity of an individual in need thereof; wherein Z is hydrogen. In some embodiments, is a method of improving ocular discomfort, comprising the local administration of a therapeutically effective amount of a compound of Formula (IIIa) or (IIIb) into the nasal cavity of an individual in need thereof, wherein Z is $C_{1-6}$alkyl. In some embodiments, is a method of improving ocular discomfort, comprising the local administration of a therapeutically effective amount of a compound of Formula (IIIa) or (IIIb) into the nasal cavity of an individual in need thereof, wherein X is C(O).

In some embodiments, is a method of improving ocular discomfort, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and does not cross the blood-brain barrier in a pharmacologically relevant concentration. In some embodiments is method of improving ocular discomfort, comprising the local administration of a therapeutically effective amount of a compound of Formula (IIIa) or (IIIb) into the nasal cavity of an individual in need thereof, wherein the compound of Formula (IIIa) or (IIIb) selectively binds to at least one of the peripheral nicotinic acetylcholine receptor subtypes selected from alpha3beta4, alpha4beta2, and alpha7. In some embodiments is a method of improving ocular discomfort, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and is administered in an amount that is not systemically bioavailable. In some embodiments is a method of improving ocular discomfort, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and in an amount that does not result in undesired psychoactive side effects. In some embodiments is a method of improving ocular discomfort, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and in an amount that does not result in undesired systemic side effects. In some embodiments is a method of improving ocular discomfort, comprising the local administration of a therapeutically effective amount of a compound of Formula (IIIa) or (IIIb) into the nasal cavity of an individual in need thereof, wherein the compound of Formula (IIIa) or (IIIb) selectively binds to the peripheral nicotinic acetylcholine receptor and in an amount that produces a local effect.

In a further embodiment of any of the aforementioned embodiments, the method further comprises the local administration of one or more substances that prevent or facilitate the recovery of the nicotinic acetylcholine receptor from the desensitized state. In a further embodiment of any of the aforementioned embodiments, the method further comprises the local administration of one or more substances that prevent the entry or reduce the entry of the nicotinic acetylcholine receptor into the desensitized state, or facilitate the recovery of the nicotinic acetylcholine receptor from the desensitized state. In some embodiments, the one or more substances are selected from protein kinase C (PKC) or factors that upregulate or up-modulate PKC, cAMP-dependent protein kinase (PKA) or factors that upregulate or up-modulate PKA, and calcineurin inhibitors. In some embodiments, the calcineurin inhibitor is selected from cyclosporine, pimecrolimus, and tacrolimus.

In another embodiment of any of the aforementioned embodiments, less than 5 milligrams of the compound of Formula (I), (II), (IIIa), or (IIIb) is administered into the nasal cavity. In another embodiment of any of the aforementioned embodiments, between 500 micrograms and 5 milligrams of the compound of Formula (I), (II), (IIIa), or (IIIb) is administered into the nasal cavity. In another embodiment of any of the aforementioned embodiments, between 1 milligram and 2 milligrams of the compound of Formula (I), (II), (IIIa), or (IIIb) is administered into the nasal cavity. In another embodiment of any of the aforementioned embodiments, about 1 milligram of the compound of Formula (I), (II), (IIIa), or (IIIb) is administered into the nasal cavity. In another embodiment of any of the aforementioned embodiments, about 1.5 milligrams of the compound of Formula (I), (II), (IIIa), or (IIIb) is administered into the nasal cavity. In another embodiment of any of the aforementioned embodiments, about 2 milligrams of the compound of Formula (I), (II), (IIIa), or (IIIb) is administered into the nasal cavity.

In a further embodiment of any of the aforementioned embodiments, the compound of Formula (I), (II), (IIIa), or (IIIb) is administered at least once daily. In another embodiment of any of the aforementioned embodiments, the compound of Formula (I), (II), (IIIa), or (IIIb) is administered at least twice daily. In another embodiment of any of the aforementioned embodiments, the compound of Formula (I), (II), (IIIa), or (IIIb) is administered for at least two days.

In a further embodiment of any of the aforementioned embodiments, the compound of Formula (I), (II), (IIIa), or (IIIb) is administered as needed. In another embodiment of any of the aforementioned embodiments, the compound of Formula (I), (II), (IIIa), or (IIIb) is administered as needed in response to symptoms. In another embodiment of any of the aforementioned embodiments, the timing or frequency of administration of the compound of Formula (I), (II), (IIIa), or (IIIb) is designed or adjusted to prevent desensitization of the nicotinic acetylcholine receptors.

In a further embodiment of any of the aforementioned embodiments, the compound of Formula (I), (II), (IIIa), or (IIIb) is administered into the nasal cavity as a liquid, suspension, aerosol, gel, ointment, dry powder, cream, paste, lotion, or balm. In a further embodiment of any of the aforementioned embodiments, the compound of Formula (I), (II), (IIIa), or (IIIb) is administered into the nasal cavity by a syringe, dropper, bottle nebulizer, atomization pump, inhaler, powder spray device, vaporizer, patch, medicated stick, pipette, or jet of liquid.

In a further embodiment of any of the aforementioned embodiments, the trigeminal nerve is activated. In a further embodiment, the anterior ethmoidal nerve is activated.

In a further embodiment of any of the aforementioned embodiments, the nasolacrimal reflex is activated.

Further provided herein, in some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein the compound of Formula (I) has the structure:

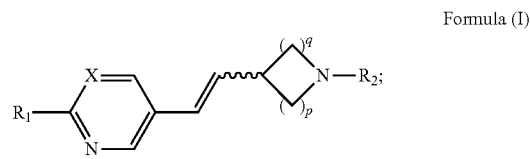

Formula (I)

wherein:
the wavy line represents E or Z geometry about the double bond;
X is N or $CR_3$;
$R_1$ is hydrogen, $C_{1-6}$alkyl, halogen, —$OR_4$—, —$SR_4$, or —$NR_5R_6$;
$R_2$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl;
$R_3$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), cycloalkyl, —$OR_7$, —$SR_7$, —$NR_8R_9$, —$SOR_7$, or —$SO_2R_7$, wherein the $C_{1-6}$alkyl heterocycloalkyl, heteroaryl, and aryl groups are optionally substituted with one or more substituents selected from halogen, —CN, —$NO_2$, —$NH_2$, —OH, —$OR_7$, —$CO_2H$, —$C(O)OR_7$, —O—$C(O)R_7$, —$NR_8R_9$, —$NHC(O)R_7$, —$C(O)NR_8R_9$, —$SR_7$, —$S(O)R_7$, —$SO_2R_7$, —$NHSO_2R_7$, —$SO_2NR_8R_9$, —$C(S)NR_8R_9$, —$NHC(S)R_7$, and —O—$SO_2R_7$;
$R_4$, $R_5$, and $R_6$ are independently hydrogen or $C_{1-6}$alkyl; and
$R_7$, $R_8$, and $R_9$ are hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl, wherein the $C_{1-6}$alkyl, heterocycloalkyl, heteroaryl, and aryl groups are optionally substituted one or more substituents selected from the group consisting of F, Cl, Br, I, $R_{10}$, —$NR_{10}R_{11}$, —$CF_3$, —CN, —$NO_2$, —$C_2R_{10}$, —$N_3$, —$SO_2CH_3$, —$OR_{10}$, —$SR_{10}$, —$C(O)NR_{10}R_{11}$, —$NR_{10}C(=O)R_{10}$, —$C(=O)R_{10}$, —$C(=O)OR_{10}$, —$(CH_2)OR_{10}$, —$(CH_2)_2OR_{10}$, —$OC(=O)R_{10}$, —$OC(=O)NR_{10}R_{11}$ and —$NR_{10}C(=O)OR_{10}$;

$R_{10}$ and $R_{11}$ are independently hydrogen, $C_{1-6}$alkyl, pyridyl, quinolinyl, pyrimidinyl, pyrimidinyl, phenyl, or benzyl; or either $R_8$ and $R_9$ or $R_{10}$ and $R_{11}$, together with the nitrogen to which they are attached, optionally form a heterocycloalkyl ring;

p is 1, 2, 3, or 4; and q is 1, 2, or 3;

or an enantiomer, diastereomer, tautomer or pharmaceutically acceptable salt thereof.

In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein X is N. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein $R_2$ is hydrogen. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein $R_1$ is hydrogen, $C_{1-6}$alkyl, —$OR_4$, or —$NR_5R_6$. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein $R_1$ is hydrogen. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein q is 1. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein p is 2. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein the wavy line represents E geometry about the double bond. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein the compound of Formula (I) is (R)-5-((E)-2-pyrrolidin-3-ylvinyl)pyrimidine. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein the compound of Formula (I) is (R)-5-((E)-2-pyrrolidin-3-ylvinyl)pyrimidine citrate salt. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein the compound of Formula (I) is (R)-5-((E)-2-pyrrolidin-3-ylvinyl)pyrimidine mono citrate salt. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein the compound of Formula (I) is (R)-5-((E)-2-pyrrolidin-3-ylvinyl)pyrimidine HCl salt. In some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors, wherein the compound of Formula (I) is (R)-5-((E)-2-pyrrolidin-3-ylvinyl)pyrimidine galactarate salt.

Further provided herein, in some embodiments, is a pharmaceutical formulation for local administration in the nasal cavity of an individual comprising a compound of Formula (I) formulated (a) for nasal administration and (b) to prevent desensitization of peripheral nicotinic acetylcholine receptors and in a dosage amount that is not systemically bioavailable. In some embodiments is a pharmaceutical formulation for local administration in the nasal cavity of an individual comprising a compound of Formula (I) formulated (a) for nasal administration and (b) to prevent desensitization of peripheral nicotinic acetylcholine receptors and in a dosage amount that does not result in undesired psychoactive side effects. In some embodiments is a pharmaceutical formulation for local administration in the nasal cavity of an individual comprising a compound of Formula (I) formulated (a) for nasal administration and (b) to prevent desensitization of peripheral nicotinic acetylcholine receptors and in a dosage amount that does not result in undesired systemic side effects. In some embodiments is a pharmaceutical formulation for local administration in the nasal cavity of an individual comprising a compound of Formula (I) formulated (a) for nasal administration and (b) to prevent desensitization of peripheral nicotinic acetylcholine receptors and in a dosage amount that produces a local effect.

Further provided herein, in some embodiments, is a pharmaceutical formulation for local administration in the nasal cavity of an individual comprising a compound of Formula (II) formulated (a) for nasal administration and (b) to prevent desensitization of peripheral nicotinic acetylcholine receptors, wherein the compound of Formula (II) has the structure:

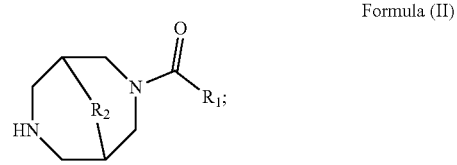

Formula (II)

wherein:

$R_1$ is $C_{1-6}$alkyl, $C_{2-6}$alkenyl, $C_{2-6}$alkynyl, $C_{3-8}$heterocycloalkyl, $C_{3-8}$cycloalkyl, or heteroaryl, optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —C$_{1-6}$alkyl-(aryl), -aryl-(C$_{1-6}$alkyl), heteroaryl, —C$_{1-6}$alkyl-(heteroaryl), -heteroaryl-(C$_{1-6}$alkyl), halogen, —CN, —NO$_2$, —OR$_3$, —NR$_4$R$_5$, —CF$_3$, —C$_2$R$_3$, —SR$_3$, —N$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$;

R$_2$ is a bond or —CH$_2$—;

R$_3$ is hydrogen, C$_{1-6}$alkyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; and R$_4$ and R$_5$ are independently hydrogen, C$_{1-6}$alkyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; or R$_4$ and R$_5$ together with the nitrogen to which they are attached, form a heterocycloalkyl ring;

or a pharmaceutically acceptable salt thereof.

In some embodiments, is a pharmaceutical formulation for local administration in the nasal cavity of an individual comprising a compound of Formula (II) formulated (a) for nasal administration and (b) to prevent desensitization of peripheral nicotinic acetylcholine receptors, wherein R$_1$ is heteroaryl optionally substituted with one to three non-hydrogen substituents independently selected from C$_{1-6}$alkyl, C$_{2-6}$alkenyl, C$_{2-6}$alkynyl, C$_{3-8}$heterocycloalkyl, C$_{3-8}$cycloalkyl, heteroaryl, aryl, —C$_{1-6}$alkyl-(aryl), -aryl-(C$_{1-6}$alkyl), heteroaryl, —C$_{1-6}$-alkyl-(heteroaryl), -heteroaryl-(C$_{1-6}$alkyl), halogen, —CN, —OR$_3$, —NR$_4$R$_5$, —CF$_3$, —C(O)NR$_4$R$_5$, —NR$_4$C(O)R$_3$, —C(O)R$_3$, —C(O)OR$_3$, —OC(O)R$_3$, —OC(O)NR$_4$AR, —NR$_4$C(O)OR$_3$, —SO$_2$R$_3$, —NR$_4$SO$_2$R$_5$, and —SO$_2$NR$_4$R$_5$. In some embodiments, is a pharmaceutical formulation for local administration in the nasal cavity of an individual comprising a compound of Formula (II) formulated (a) for nasal administration and (b) to prevent desensitization of peripheral nicotinic acetylcholine receptors, wherein R$_1$ is 2-furanyl, 3-furanyl, 2-oxazolyl, 4-oxazolyl, 5-oxazolyl, 3-isoxazolyl, 4-isoxazolyl, 5-isoxazolyl, 1,3,4-oxadiazol-2-yl, 1,2,4-oxadiazol-3-yl, 1,2,4-oxadiazol-5-yl, 2-thiazolyl, 4-thiazolyl, 5-thiazolyl, 3-isothiazolyl, 4-isothiazolyl, 5-isothiazolyl, 1,3,4-thiadiazol-2-yl, 1,2,4-thiadiazol-3-yl, 1,2,4-thiadiazol-5-yl or 4-pyridinyl. In some embodiments, is a pharmaceutical formulation for local administration in the nasal cavity of an individual comprising a compound of Formula (II) formulated (a) for nasal administration and (b) to prevent desensitization of peripheral nicotinic acetylcholine receptors, wherein R$_2$ is a bond. In some embodiments, is a pharmaceutical formulation for local administration in the nasal cavity of an individual comprising a compound of Formula (II) formulated (a) for nasal administration and (b) to prevent desensitization of peripheral nicotinic acetylcholine receptors, wherein R$_2$ is —CH$_2$—. In some embodiments, is a pharmaceutical formulation for local administration in the nasal cavity of an individual comprising a compound of Formula (II) formulated (a) for nasal administration and (b) to prevent desensitization of peripheral nicotinic acetylcholine receptors, wherein the compound of Formula (II) is N-(5-chlorofuran-2-ylcarbonyl)-3,7-diazabicyclo[3.3.0]octane.

Further provided herein, in some embodiments, is a pharmaceutical formulation for local administration in the nasal cavity of an individual comprising a compound of Formula (II) formulated (a) for nasal administration and (b) to prevent desensitization of peripheral nicotinic acetylcholine receptors and in a dosage amount that is not systemically bioavailable. In some embodiments is a pharmaceutical formulation for local administration in the nasal cavity of an individual comprising a compound of Formula (II) formulated (a) for nasal administration and (b) to prevent desensitization of peripheral nicotinic acetylcholine receptors and in a dosage amount that does not result in undesired psychoactive side effects. In some embodiments is a pharmaceutical formulation for local administration in the nasal cavity of an individual comprising a compound of Formula (II) formulated (a) for nasal administration and (b) to prevent desensitization of peripheral nicotinic acetylcholine receptors and in a dosage amount that does not result in undesired systemic side effects. In some embodiments is a pharmaceutical formulation for local administration in the nasal cavity of an individual comprising a compound of Formula (I) formulated (a) for nasal administration and (b) to prevent desensitization of peripheral nicotinic acetylcholine receptors and in a dosage amount that produces a local effect.

Further provided herein, in some embodiments, is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors, wherein the compound of Formula (IIIa) or (IIIb) has the structure:

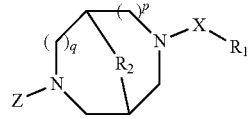

Formula (IIIa)

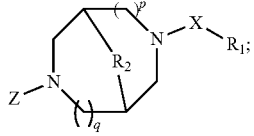

Formula (IIIb)

wherein:

X is C(O), C(S), or S(O)$_n$;

Z is hydrogen, C$_{1-6}$alkyl, or C$_{1-6}$haloalkyl;

n is 1 or 2;

p is 0 or 1;

q is 0 or 1;

when p is 1, then q is 0;

when q is 1, then p is 0;

R$_1$ is —OR$_3$, —NR$_4$R$_5$, C$_{1-6}$alkyl, C$_{2-6}$alkenyl, C$_{2-6}$alkynyl, C$_{3-8}$heterocycloalkyl, C$_{3-8}$cycloalkyl, aryl or heteroaryl, wherein C$_{1-6}$alkyl, C$_{2-6}$alkenyl, C$_{2-6}$alkynyl, C$_{3-8}$heterocycloalkyl, C$_{3-8}$cycloalkyl, aryl or heteroaryl are optionally substituted with one to three non-hydrogen substituents independently selected from C$_{1-6}$alkyl, C$_{2-6}$alkenyl, C$_{2-6}$alkynyl, C$_{3-8}$heterocycloalkyl, C$_{3-8}$cycloalkyl, heteroaryl, aryl, —C$_{1-6}$alkyl-(aryl), -aryl-(C$_{1-6}$alkyl), heteroaryl, —C$_{1-6}$alkyl-(heteroaryl), -heteroaryl-(C$_{1-6}$alkyl), halogen, —CN, —NO$_2$, —OR$_3$, —NR$_4$R$_5$, —CF$_3$, —C$_2$R$_3$, —SR$_3$, —N$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$;

R$_2$ is —CH$_2$— or —CH$_2$CH$_2$—;

R$_3$ is hydrogen, C$_{1-6}$alkyl, C$_{2-6}$alkenyl, C$_{2-6}$alkynyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; and $R_4$ and $R_5$ are independently hydrogen, $C_{1-6}$alkyl, $C_{2-6}$alkenyl, $C_{2-6}$alkynyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; or $R_4$ and $R_5$ together with the nitrogen to which they are attached, form a heterocycloalkyl ring; or a pharmaceutically acceptable salt thereof.

In some embodiments, is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors, wherein p is 1 and q is 0. In some embodiments, is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors, wherein p is 0 and q is 1. In some embodiments, is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors, wherein $R_2$ is —$CH_2$—. In some embodiments, is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors, wherein $R_2$ is —$CH_2CH_2$—. In some embodiments, is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors, wherein Z is hydrogen. In some embodiments, is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors, wherein Z is $C_{1-6}$alkyl. In some embodiments, is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors, wherein X is C(O). Further provided herein, in some embodiments, is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors and in a dosage amount that is not systemically bioavailable. In some embodiments is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors and in a dosage amount that does not result in undesired psychoactive side effects. In some embodiments is a pharmaceutical formulation for local administration in the nasal cavity of an individual comprising a compound of (IIIa) or (IIIb) formulated (a) for nasal administration and (b) to prevent desensitization of peripheral nicotinic acetylcholine receptors and in a dosage amount that does not result in undesired systemic side effects. In some embodiments is a pharmaceutical formulation for local administration in the nasal cavity of an individual comprising a compound of Formula (IIIa) or (IIIb) formulated (a) for nasal administration and (b) to prevent desensitization of peripheral nicotinic acetylcholine receptors and in a dosage amount that produces a local effect.

In some embodiments, the pharmaceutical formulation further comprises one or more substances selected from protein kinase C (PKC) or factors that upregulate or up-modulate PKC, cAMP-dependent protein kinase (PKA) or factors that upregulate or up-modulate PKA, and calcineurin inhibitors. In some embodiments, the calcineurin inhibitor is selected from cyclosporine, pimecrolimus, and tacrolimus.

In some embodiments is a pharmaceutical formulation for local administration in the nasal cavity of an individual comprising a compound of Formula (I), (II), (IIIa), or (IIIb) formulated (a) for nasal administration and (b) to prevent desensitization of peripheral nicotinic acetylcholine receptors, wherein the pharmaceutical formulation does not contain nicotine in any form. In some embodiments is a pharmaceutical formulation for local administration in the nasal cavity of an individual comprising a compound of Formula (I), (II), (IIIa), or (IIIb) formulated (a) for nasal administration and (b) to prevent desensitization of peripheral nicotinic acetylcholine receptors, wherein the pharmaceutical formulation does not contain nicotine free base, a nicotine salt, a nicotine complex, or a nicotine solvate. In some embodiments is a pharmaceutical formulation for local administration in the nasal cavity of an individual comprising a compound of Formula (I), (II), (IIIa), or (IIIb) formulated (a) for nasal administration and (b) to prevent desensitization of peripheral nicotinic acetylcholine receptors, wherein the compound of Formula (I), (II), (IIIa), or (IIIb) selectively binds to at least one of the peripheral nicotinic acetylcholine receptor subtypes selected from alpha3beta4, alpha4beta2, and alpha7. In some embodiments, the pharmaceutical formulation comprises about 1 mg/mL of a compound of Formula (I), (II), (IIIa), or (IIIb). In some embodiments, the pharmaceutical formulation comprises about 5 mg/mL of a compound of Formula (I), (II), (IIIa), or (IIIb). In some embodiments, the pharmaceutical formulation comprises less than 5 milligrams of a compound of Formula (I), (II), (IIIa), or (IIIb) per dose. In some embodiments, the pharmaceutical formulation comprises between 500 micrograms and 5 milligrams of a compound of Formula (I), (II), (IIIa), or (IIIb) per dose. In some embodiments, the pharmaceutical formulation comprises between 1 milligram and 2 milligrams of a compound of Formula (I), (II), (IIIa), or (IIIb) per dose. In some embodiments, the pharmaceutical formulation comprises about 1 milligram of a compound of Formula (I), (II), (IIIa), or (IIIb) per dose. In some embodiments, the pharmaceutical formulation comprises about 1.5 milligrams of a compound of Formula (I), (II), (IIIa), or (IIIb) per dose. In some embodiments, the pharmaceutical formulation comprises about 1 milligram of a compound of Formula (I), (II), (IIIa), or (IIIb) per dose. In some embodiments, the pharmaceutical formulation comprises about 2 milligrams of a compound of Formula (I), (II), (IIIa), or (IIIb) per dose. In some embodiments, the pharmaceutical formulation is administered at least once daily. In some embodiments, the pharmaceutical formulation is administered at least twice daily. In some embodiments, the pharmaceutical formulation is administered for at least two days. In some embodiments, the pharmaceutical formulation is administered into the nasal cavity as a liquid, suspension, aerosol, gel, ointment, dry powder, cream, paste, lotion, or balm. In some embodiments, the pharmaceutical formulation is administered into the nasal cavity by a syringe, dropper, bottle nebulizer, atomization pump, inhaler, powder spray device, vaporizer, patch, medicated stick, pipette, or jet of liquid.

The present disclosure provides, in some embodiments, a compound of Formula (I), (II), (IIIa), or (IIIb), (e.g., (R)-5-((E)-2-pyrrolidin-3-ylvinyl)pyrimidine), or a pharmaceutically acceptable salt thereof, for use in the treatment of dry eye or ocular discomfort or increasing tear production, which is administered into the nasal cavity of an individual in need thereof.

The present disclosure provides, in some embodiments, a compound of Formula (I), (II), (IIIa), or (IIIb), (e.g., (R)-5-((E)-2-pyrrolidin-3-ylvinyl)pyrimidine), or a pharmaceutically acceptable salt thereof, for the manufacture of a medicament for use in the treatment of dry eye or ocular discomfort or increasing tear production, which is administered into the nasal cavity of an individual in need thereof.

It is also appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Additional embodiments, features, and advantages of the invention will be apparent from the following detailed description and through practice of the invention.

For the sake of brevity, the disclosures of the publications cited in this specification, including patents, are herein incorporated by reference in their entirety.

BRIEF DESCRIPTION OF THE DRAWINGS

FIG. 3 shows an example of a questionnaire.

DETAILED DESCRIPTION OF THE INVENTION

Figure 1:
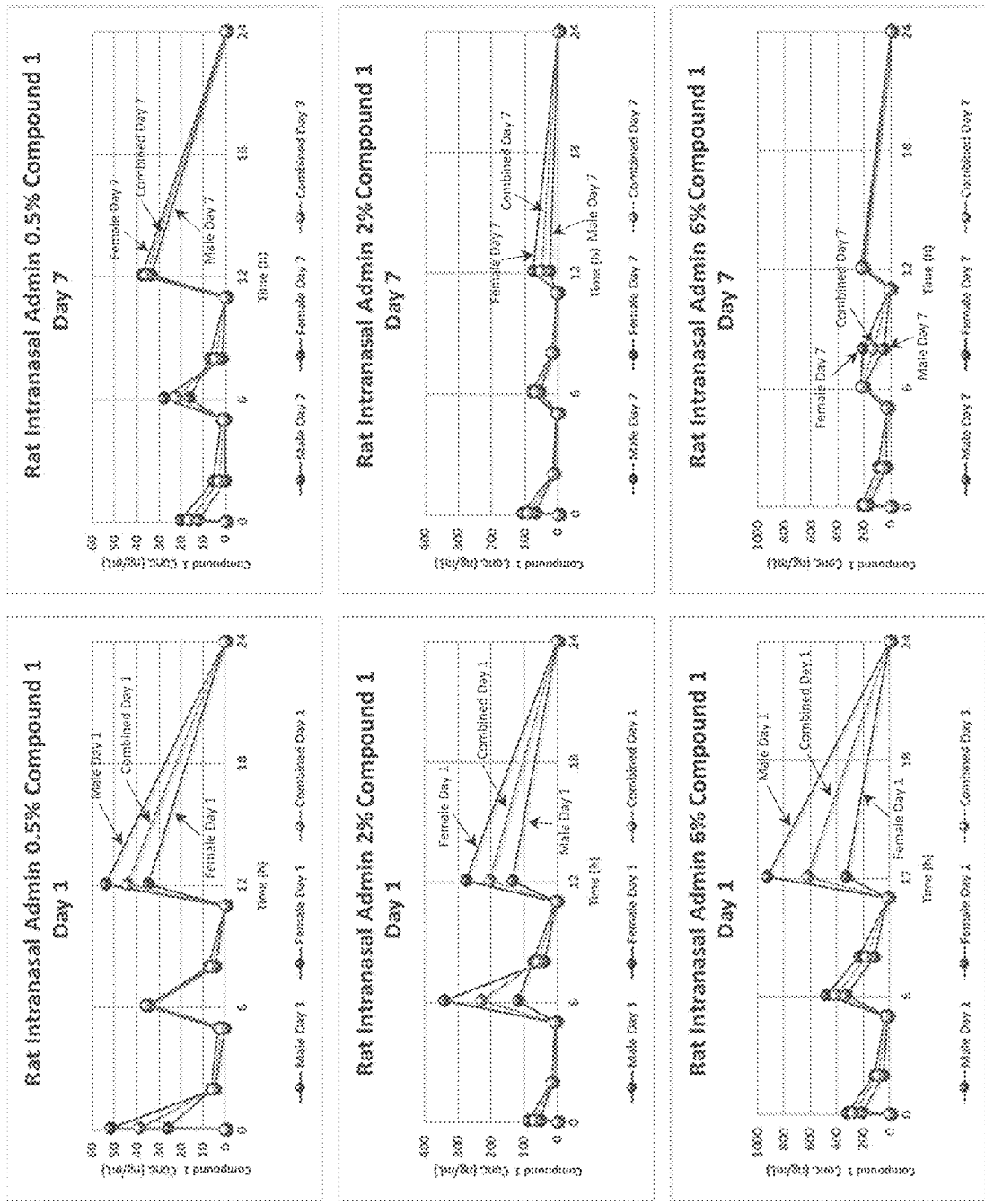
FIG. 1 shows toxicokinetic parameters of Compound 1 after TID administration in the rat on Day 1 and Day 7.

The methods for treating ocular conditions described herein, comprise the local administration of a therapeutically effective amount of a compound of Formula (I), (II), (IIIa), or (IIIb) into the nasal cavity of an individual in need thereof, wherein the compound of Formula (I), (II), (IIIa), or (IIIb) binds to the peripheral nicotinic acetylcholine receptor to provide a local effect. Although a small amount of a compound of Formula (I), (II), (IIIa), or (IIIb) may enter the systemic circulation, the amount is insufficient to elicit a systemic pharmacological effect. Furthermore, the dose amounts of a compound of Formula (I), (II), (IIIa), or (IIIb), required to treat ocular conditions in an individual in need, are substantially lower than the amounts needed to produce systemic pharmacological effects in such an individual. Indeed, the amounts of a compound of Formula (I), (II), (IIIa), or (IIIb) that produce systemic pharmacological effects in an individual generally desensitize the peripheral nicotinic acetylcholine receptor in the nasal cavity of the individual, and thereby do not effectively treat the ocular conditions. In some embodiments, the compound of Formula (I), (II), (IIIa), or (IIIb) is (R)-5-((E)-2-pyrrolidin-3-ylvinyl)pyrimidine, or a pharmaceutically acceptable salt thereof.

The etiology of DED is becoming increasingly well understood. DED is progressive in nature, and fundamentally results from insufficient tear coverage on the surface of the eye. This poor tear coverage prevents healthy gas exchange and nutrient transport for the ocular surface, promotes cellular desiccation and creates a poor refractive surface for vision. Poor tear coverage typically results from: 1) insufficient aqueous tear production from the lacrimal glands (e.g. secondary to post-menopausal hormonal deficiency, auto-immune disease, LASIK surgery, etc.), and/or 2) excessive evaporation of aqueous tear resulting from dysfunction of the meibomian glands. Low tear volume causes a hyperosmolar environment that induces an inflamed state of the ocular surface. This inflammatory response induces apoptosis of the surface cells which in turn prevents proper distribution of the tear film on the ocular surface so that any given tear volume is rendered less effective. This initiates a vicious cycle where more inflammation can ensue causing more surface cell damage, etc. Additionally, the neural control loop, which controls reflex tear activation, is disrupted because the sensory neurons in the surface of the eye are damaged. As a result, fewer tears are secreted and a second vicious cycle develops that results in further progression of the disease (fewer tears cause nerve cell loss, which results in fewer tears, etc.).

There is a wide spectrum of treatments for DED, however, none provides substantial efficacy for treatment of the condition. Treatment options include: artificial tear substitutes, ointments, gels, warm compresses, environmental modification, topical cyclosporine, omega-3 fatty acid supplements, punctal plugs and moisture chamber goggles. Patients with severe disease may further be treated with punctal cautery, systemic cholinergic agonists, systemic anti-inflammatory agents, mucolytic agents, autologous serum tears, PROSE scleral contact lenses and tarsorrhaphy. Despite these treatment options, DED continues to be considered one of the most poorly treated diseases in ophthalmology. Accordingly, it would be desirable to have a more effective treatment for dry eye.

Nicotinic acetylcholine receptors are cholinergic receptors found in the central nervous system (CNS), peripheral nervous systems (PNS) and skeletal muscles. These receptors are ligand-gated ion channels with binding sites for acetylcholine and other molecules. When a nicotinic acetylcholine receptor agonist binds to the receptor, it stabilizes the open state of the ion channel allowing influx of cations such as potassium, calcium and sodium ions.

Acting on the central nervous system, systemic nicotinic acetylcholine receptor agonists agonist are gaining attention as drug candidates for multiple disorders such as Alzheimer's disease, Parkinson's disease, schizophrenia, attention-deficit hyperactivity disorder (ADHD), and nicotine addiction. However, systemic exposure of these central nervous system agents has, been associated with a variety of undesired psychoactive side effects including anxiety, depression, and irritability.

Described herein are methods of treating ocular conditions and/or improving ocular surface health comprising the local administration of a therapeutically effective amount of a nicotinic acetylcholine receptor agonist into the nasal cavity of an individual in need thereof, wherein the agonist selectively binds to the peripheral nicotinic acetylcholine receptor and wherein the nicotinic acetylcholine receptor agonist is a compound of Formula (I), (II), (IIIa), or (IIIb).

In some embodiments the compound of Formula (I), (II), (IIIa), or (IIIb) binds to the peripheral nicotinic acetylcholine receptor and does not cross the blood-brain barrier in a pharmacologically relevant concentration. In some embodiments the compound of Formula (I). (II), (IIIa), or (IIIb) binds to the peripheral nicotinic acetylcholine receptor and does not cross the blood-brain barrier in a pharmacologically relevant concentration and is administered in an amount that is not systemically bioavailable. In some embodiments the compound of Formula (I), (II), (IIIa), or (IIIb) binds to the peripheral nicotinic acetylcholine receptor and does not cross the blood-brain barrier in a pharmacologically relevant concentration and is administered in an amount that does not result in undesired psychoactive side effects. In some embodiments the compound of Formula (I), (II), (IIIa), or (IIIb) binds to the peripheral nicotinic acetylcholine receptor and does not cross the blood-brain barrier in a pharmacologically relevant concentration and is administered in an amount that does not result in undesired systemic side effects. In some embodiments the compound of Formula (I), (II), (IIIa), or (IIIb) binds to the peripheral nicotinic acetylcholine receptor and does not cross the blood-brain barrier in a pharmacologically relevant concentration and is administered in an amount that produces a local effect. In some embodiments, the compound of Formula (I) is (R)-5-((E)-2-pyrrolidin-3-ylvinyl)pyrimidine, or a pharmaceutically acceptable salt thereof.

Prolonged or repeat exposure to a stimulus often results in decreased responsiveness of that receptor toward a stimulus, termed desensitization. It has been reported that, after prolonged nicotinic acetylcholine receptor exposure to an agonist, the agonist itself causes an agonist-induced conformational change in the receptor, resulting in receptor desensitization.

Described herein are methods of treating ocular conditions and/or improving ocular surface health comprising the local administration of a, therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor, further comprising the local administration of one or more substances that prevent or facilitate the recovery of the nicotinic acetylcholine receptor from the desensitized state. Also described herein are methods of treating ocular conditions and/or improving ocular surface health comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments, the one or more substances that prevent or facilitate the recovery of the nicotinic acetylcholine receptor from the desensitized state are selected from protein kinase C (PKC) or factors that upregulate or up-modulate PKC, cAMP-dependent protein kinase (PKA) or factors that upregulate or up-modulate PKA, and calcineurin inhibitors. In some embodiments, the compound of Formula (I) is (R)-5-((E)-2-pyrrolidin-3-ylvinyl)pyrimidine, or a pharmaceutically acceptable salt thereof.

Further described herein are pharmaceutical formulations for local administration into the nasal cavity of an individual comprising a compound of Formula (I), (II), (IIIa), or (IIIb) formulated to prevent desensitization. In some embodiments, the compound of Formula (I) is (R)-5-((E)-2-pyrrolidin-3-ylvinyl)pyrimidine, or a pharmaceutically acceptable salt thereof. Also described herein are pharmaceutical formulations for local administration into the nasal cavity of an individual, further comprising one or more substances that prevent or facilitate the recovery of the nicotinic acetylcholine receptor from the desensitized state. Also described herein are pharmaceutical formulations for local administration into the nasal cavity of an individual, further comprising one or more substances that prevent the entry or reduce the entry of the nicotinic acetylcholine receptor into the desensitized state, or facilitate the recovery of the nicotinic acetylcholine receptor from the desensitized state. Also described herein are pharmaceutical formulations for local administration into the nasal cavity of an individual, further comprising one or more substances that prevent or facilitate the recovery of the nicotinic acetylcholine receptor from the desensitized state, wherein the one or more substances are selected from protein kinase C (PKC) or factors that upregulate or up-modulate PKC, cAMP-dependent protein kinase (PKA) or factors that upregulate or up-modulate PKA, and calcineurin inhibitors. Also described herein are pharmaceutical formulations for local administration into the nasal cavity of an individual, further comprising one or more substances that prevent the entry or reduce the entry of the nicotinic acetylcholine receptor into the desensitized state, or facilitate the recovery of the nicotinic acetylcholine receptor from the desensitized state, wherein the one or more substances are selected from protein kinase C (PKC) or factors that upregulate or up-modulate PKC, cAMP-dependent protein kinase (PKA) or factors that upregulate or up-modulate PKA, and calcineurin inhibitors.

Increased Tear Production

Provided herein, in some embodiments, is a method of increasing tear production in a subject. In some embodiments, is a method of increasing tear production, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and does not cross the blood-brain barrier in a pharmacologically relevant concentration. In some embodiments, the compound of Formula (I) is (R)-5-((E)-2-pyrrolidin-3-ylvinyl)pyrimidine, or a pharmaceutically acceptable salt thereof. In some embodiments is method of increasing tear production, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of increasing tear production, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha3beta4. In some embodiments is method of increasing tear production, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha4beta2. In some embodiments is method of increasing tear production, comprising the local administration of a therapeutically effective amount of a compound of Formula (I), (II), (IIIa), or (IIIb) into the nasal cavity of an individual in need thereof; wherein the compound of Formula (I), (II), (IIIa), or (IIIb) does not cross the blood-brain barrier in a pharmacologically relevant concentration and selectively binds to the peripheral nicotinic acetylcholine receptor subtype alpha7. In some embodiments is a method of increasing tear production, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that is not systemically bioavailable. In some embodiments is a method of increasing tear production, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired psychoactive side effects. In some embodiments is a method of increasing tear production, comprising the local administration of a therapeutically effective amount of a compound of Formula (I), (II), (IIIa), or (IIIb) into the nasal cavity of an individual in need thereof wherein the compound of Formula (I), (II), (IIIa), or (IIIb) selectively binds to the peripheral nicotinic acetylcholine receptor and in an amount that does not result in undesired systemic side effects. In some embodiments is a method of increasing tear production, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that produces a local effect. In some embodiments is a method of increasing tear production, further comprising the local administration of one or more substances that prevent or facilitate the recovery of the nicotinic acetylcholine receptor from the desensitized state. In some embodiments is a method of increasing tear production, further comprising the local administration of one or more substances that prevent the entry or reduce the entry of the nicotinic acetylcholine receptor into the desensitized state, or facilitate the recovery of the nicotinic acetylcholine receptor from the desensitized state.

In some embodiments of the method of increasing tear production described herein, the compound of Formula (I), (II), (IIIa), or (IIIb) is (R)-5-((E)-2-pyrrolidin-3-ylvinyl) pyrimidine (or Compound 1). In some embodiments of the methods described herein, the compound of Formula (I), (II), (IIIa), or (IIIb) is (R)-5-((E)-2-pyrrolidin-3-ylvinyl) pyrimidine, or a pharmaceutically acceptable salt thereof. In some embodiments of the methods described herein, the compound of Formula (I), (II), (IIIa), or (IIIb) is (R)-5-((E)-2-pyrrolidin-3-ylvinyl)pyrimidine as a free base. In some embodiments of the method of increasing tear production described herein, the compound of Formula (I), (II), (IIIa), or (IIIb) is (R)-5-((E)-2-pyrrolidin-3-ylvinyl)pyrimidine citrate salt. In some embodiments of the method of increasing tear production described herein, the compound of Formula (I), (II), (IIIa), or (IIIb) is (R)-5-((E)-2-pyrrolidin-3-ylvinyl) pyrimidine mono citrate salt. In some embodiments of the method of increasing tear production described herein, the compound of Formula (I), (II), (IIIa), or (IIIb) is (R)-5-((E)-2-pyrrolidin-3-ylvinyl)pyrimidine HCl salt. In some embodiments of the method of increasing tear production described herein, the compound of Formula (I), (II), (IIIa), or (IIIb) is (R)-5-((E)-2-pyrrolidin-3-ylvinyl)pyrimidine galactarate salt. In some embodiments of the method of increasing tear production described herein, the compound of Formula (I), (II), (IIIa), or (IIIb) is (R)-5-((E)-2-pyrrolidin-3-ylvinyl)pyrimidine hemigalactarate salt. In some embodiments of the method of increasing tear production described herein, the compound of Formula (I), (II), (IIIa), or (IIIb) is (R)-5-((E)-2-pyrrolidin-3-ylvinyl)pyrimidine hemigalactarate monohydrate. In some embodiments of the method described herein, the compound of Formula (I), (II), (IIIa), or (IIIb) is (R)-5-((E)-2-pyrrolidin-3-ylvinyl)pyrimidine hemigalactarate dihydrate.

In some embodiments is a method of increasing tear production, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing tear production, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing tear production, further comprising the local administration of protein kinase C (PKC) or factors that upregulate or up-modulate PKC. In some embodiments is a method of increasing tear production, further comprising the local administration of cAMP-dependent protein kinase (PKA) or factors that upregulate or up-modulate PKA. In some embodiments is a method of increasing tear production, further comprising the local administration of a calcineurin inhibitor. In some embodiments is a method of increasing tear production, further comprising the local administration of a calcineurin inhibitor, wherein the calcineurin inhibitor is selected from cyclosporine, pimecrolimus, and tacrolimus. In some embodiments is a method of increasing tear production, further comprising the local administration of cyclosporine. In some embodiments is a method of increasing tear production, further comprising the local administration of pimecrolimus. In some embodiments is a method of increasing tear production, further comprising the local administration of tacrolimus.

In another embodiment of any of the aforementioned embodiments of increasing tear production, at least 1 microgram of the compound of Formula (I), (II), (IIIa), or (IIIb) is administered into the nasal cavity. In another embodiment of any of the aforementioned embodiments of increasing tear production, at least 5 micrograms of the compound of Formula (I), (II), (IIIa), or (IIIb) is administered into the nasal cavity. In another embodiment of any of the aforementioned embodiments of increasing tear production, at least 10 micrograms of the compound of Formula (I), (II), (IIIa), or (IIIb) is administered into the nasal cavity. In another embodiment of any of the aforementioned embodiments of increasing tear production, at least 25 micrograms of the compound of Formula (I), (II), (IIIa), or (IIIb) is administered into the nasal cavity. In another embodiment of any of the aforementioned embodiments of increasing tear production, at least 50 micrograms of the compound of Formula (I), (II), (IIIa), or (IIIb) is administered into the nasal cavity. In another embodiment of any of the aforementioned embodiments of increasing tear production, at least 100 micrograms of the compound of Formula (I), (II), (IIIa), or (IIIb) is administered into the nasal cavity. In another embodiment of any of the aforementioned embodiments of increasing tear production, at least 250 micrograms of the compound of Formula (I), (II), (IIIa), or (IIIb) is administered into the nasal cavity. In another embodiment of any of the aforementioned embodiments of increasing tear production, at least 500 micrograms of the compound of Formula (I), (II), (IIIa), or (IIIb) is administered into the nasal cavity. In another embodiment of any of the aforementioned embodiments of increasing tear production, at least 750 micrograms of the compound of Formula (I), (II), (IIIa), or (IIIb) is administered into the nasal cavity. In another embodiment of any of the aforementioned embodiments of increasing tear production, at least 1000 micrograms of the compound of Formula (I), (II), (IIIa), or (IIIb) is administered into the nasal cavity.

In another embodiment of any of the aforementioned embodiments of increasing tear production, between 1 microgram and 1000 micrograms of the compound of Formula (I), (II), (IIIa), or (IIIb) is administered into the nasal cavity. In another embodiment of any of the aforementioned embodiments of increasing tear production, between 5 micrograms and 1000 micrograms of the compound of Formula (I), (II), (IIIa), or (IIIb) is administered into the nasal cavity. In another embodiment of any of the aforementioned embodiments of increasing tear production, between 10 micrograms and 1000 micrograms of the compound of Formula (I), (II), (IIIa), or (IIIb) is administered into the nasal cavity. In another embodiment of any of the aforementioned embodiments of increasing tear production, between 5 micrograms and 100 micrograms of the compound of Formula (I), (II), (IIIa), or (IIIb) is administered into the nasal cavity. In another embodiment of any of the aforementioned embodiments of increasing tear production, between 5 micrograms and 50 micrograms of the compound of Formula (I), (II), (IIIa), or (IIIb) is administered into the nasal cavity. In another embodiment of any of the aforementioned embodiments of increasing tear production, between 10 micrograms and 50 micrograms of the compound of Formula (I), (II), (IIIa), or (IIIb) is administered into the nasal cavity. In another embodiment of any of the aforementioned embodiments of increasing tear production, between 25 micrograms and 1000 micrograms of the compound of Formula (I), (II), (IIIa), or (IIIb) is administered into the nasal cavity. In another embodiment of any of the aforementioned embodiments of increasing tear production, between 50 micrograms and 1000 micrograms of the compound of Formula (I), (II), (IIIa), or (IIIb) is administered into the nasal cavity. In another embodiment of any of the aforementioned embodiments of increasing tear production, between 100 micrograms and 1000 micrograms of the compound of Formula (I), (II), (IIIa), or (IIIb) is administered into the nasal cavity. In another embodiment of any of the aforementioned embodiments of increasing tear production, between 150 micrograms and 1000 micrograms of the compound of Formula (I), (II), (IIIa), or (IIIb) is administered into the nasal cavity. In another embodiment of any of the aforementioned embodiments of increasing tear production, between 100 micrograms and 750 micrograms of the compound of Formula (I), (II), (IIIa), or (IIIb) is administered into the nasal cavity. In another embodiment of any of the aforementioned embodiments of increasing tear production, between 150 micrograms and 750 micrograms of the compound of Formula (I), (II), (IIIa), or (IIIb) is administered into the nasal cavity. In another embodiment of any of the aforementioned embodiments of increasing tear production, between 150 micrograms and 600 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, less than 100 micrograms of a compound of Formula (I), (II), (IIIa), or (IIIb) is administered into the nasal cavity. In another embodiment of any of the aforementioned embodiments of increasing tear production, less than 75 micrograms of a compound of Formula (I), (II), (IIIa), or (IIIb) is administered into the nasal cavity. In another embodiment of any of the aforementioned embodiments of increasing tear production, less than 50 micrograms of a compound of Formula (I), (II), (IIIa), or (IIIb) is administered into the nasal cavity. In another embodiment of any of the aforementioned embodiments of increasing tear production, less than 25 micrograms of a compound of Formula (I), (II), (IIIa), or (IIIb) is administered into the nasal cavity. In another embodiment of any of the aforementioned embodiments of increasing tear production, less than 15 micrograms of a compound of Formula (I), (II), (IIIa), or (IIIb) is administered into the nasal cavity. In another embodiment of any of the aforementioned embodiments of increasing tear production, about 75 micrograms of a compound of Formula (I), (II), (IIIa), or (IIIb) is administered into the nasal cavity. In another embodiment of any of the aforementioned embodiments of increasing tear production, about 50 micrograms of a compound of Formula (I), (II), (IIIa), or (IIIb) is administered into the nasal cavity. In another embodiment of any of the aforementioned embodiments of increasing tear production, about 25 micrograms of a compound of Formula (I), (II), (IIIa), or (IIIb) is administered into the nasal cavity. In another embodiment of any of the aforementioned embodiments of increasing tear production, about 10 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, between 1 microgram and 100 micrograms of a compound of Formula (I), (II), (IIIa), or (IIIb) is administered into the nasal cavity. In another embodiment of any of the aforementioned embodiments of increasing tear production, between 1 microgram and 75 micrograms of a compound of Formula (I), (II), (IIIa), or (IIIb) is administered into the nasal cavity. In another embodiment of any of the aforementioned embodiments of increasing tear production, between 5 micrograms and 100 micrograms of a compound of Formula (I), (II), (IIIa), or (IIIb) is administered into the nasal cavity. In another embodiment of any of the aforementioned embodiments of increasing tear production, between 5 micrograms and 75 micrograms of a compound of Formula (I), (II), (IIIa), or (IIIb) is administered into the nasal cavity. In another embodiment of any of the aforementioned embodiments of increasing tear production, between 15 micrograms and 100 micrograms of a compound of Formula (I), (II), (IIIa), or (IIIb) is administered into the nasal cavity. In another embodiment of any of the aforementioned embodiments of increasing tear production, between 15 micrograms and 75 micrograms of a compound of Formula (I), (II), (IIIa), or (IIIb) is administered into the nasal cavity. In another embodiment of any of the aforementioned embodiments of increasing tear production, between 25 micrograms and 100 micrograms of a compound of Formula (I), (II), (IIIa), or (IIIb) is administered into the nasal cavity. In another embodiment of any of the aforementioned embodiments of increasing tear production, between 25 micrograms and 75 micrograms of a compound of Formula (I), (II), (IIIa), or (IIIb) is administered into the nasal cavity. In another embodiment of any of the aforementioned embodiments of increasing tear production, between 25 micrograms and 60 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, between 500 micrograms and 10 milligrams of a compound of Formula (I), (II), (IIIa), or (IIIb) is administered into the nasal cavity. In another embodiment of any of the aforementioned embodiments of increasing tear production, between 500 micrograms and 5 milligrams of a compound of Formula (I), (II), (IIIa), or (IIIb) is administered into the nasal cavity. In another embodiment of any of the aforementioned embodiments of increasing tear production, between 500 micrograms and 3 milligrams of a compound of Formula (I), (II), (IIIa), or (IIIb) is administered into the nasal cavity. In another embodiment of any of the aforementioned embodiments of increasing tear production, between 500 micrograms and 2 milligrams of a compound of Formula (I), (II), (IIIa), or (IIIb) is administered into the nasal cavity. In another embodiment of any of the aforementioned embodiments of increasing tear production, between 1 milligram and 10 milligrams of a compound of Formula (I), (II), (IIIa), or (IIIb) is administered into the nasal cavity. In another embodiment of any of the aforementioned embodiments of increasing tear production, between 1 milligram and 5 milligrams of a compound of Formula (I), (II), (IIIa), or (IIIb) is administered into the nasal cavity. In another embodiment of any of the aforementioned embodiments of increasing tear production, between 1 milligram and 3 milligrams of a compound of Formula (I), (II), (IIIa), or (IIIb) is administered into the nasal cavity. In another embodiment of any of the aforementioned embodiments of increasing tear production, between 1 milligram and 2 milligrams of a compound of Formula (I), (II), (IIIa), or (IIIb) is administered into the nasal cavity. In another embodiment of any of the aforementioned embodiments of increasing tear production, about 500 micrograms of a compound of Formula (I), (II), (IIIa), or (IIIb) is administered into the nasal cavity. In another embodiment of any of the aforementioned embodiments of increasing tear production, about 1 milligram of a compound of Formula (I), (II), (IIIa), or (IIIb) is administered into the nasal cavity. In another embodiment of any of the aforementioned embodiments of increasing tear production, about 1.5 milligrams of a compound of Formula (I), (II), (IIIa), or (IIIb) is administered into the nasal cavity. In another embodiment of any of the aforementioned embodiments of increasing tear production, about 2 milligrams of a compound of Formula (I), (II), (IIIa), or (IIIb) is administered into the nasal cavity. In another embodiment of any of the aforementioned embodiments of increasing tear production, about 2.5 milligrams of a compound of Formula (I), (II), (IIIa), or (IIIb) is administered into the nasal cavity. In another embodiment of any of the aforementioned embodiments of increasing tear production, about 3 milligrams of a compound of Formula (I), (II), (IIIa), or (IIIb) is administered into the nasal cavity. In another embodiment of any of the aforementioned embodiments of increasing tear production, about 4 milligrams of a compound of Formula (I), (II), (IIIa), or (IIIb) is administered into the nasal cavity. In another embodiment of any of the aforementioned embodiments of increasing tear production, about 5 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, between 1 microgram and 10 milligrams of a compound of Formula (I), (II), (IIIa), or (IIIb) is administered into the nasal cavity. In another embodiment of any of the aforementioned embodiments of increasing tear production, between 5 micrograms and 10 milligrams of a compound of Formula (I), (II), (IIIa), or (IIIb) is administered into the nasal cavity. In another embodiment of any of the aforementioned embodiments of increasing tear production, between 10 micrograms and 10 milligrams of a compound of Formula (I), (II), (IIIa), or (IIIb) is administered into the nasal cavity. In another embodiment of any of the aforementioned embodiments of increasing tear production, between 25 micrograms and 10 milligrams of a compound of Formula (I), (II), (IIIa), or (IIIb) is administered into the nasal cavity. In another embodiment of any of the aforementioned embodiments of increasing tear production, between 50 micrograms and 10 milligrams of a compound of Formula (I), (II), (IIIa), or (IIIb) is administered into the nasal cavity. In another embodiment of any of the aforementioned embodiments of increasing tear production, between 100 micrograms and 10 milligrams of a compound of Formula (I), (II), (IIIa), or (IIIb) is administered into the nasal cavity. In another embodiment of any of the aforementioned embodiments of increasing tear production, between 150 micrograms and 10 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, between 1 microgram and 10 milligrams of a compound of Formula (I), (II), (IIIa), or (IIIb) is administered into the nasal cavity. In another embodiment of any of the aforementioned embodiments of increasing tear production, between 1 microgram and 5 milligrams of a compound of Formula (I), (II), (IIIa), or (IIIb) is administered into the nasal cavity. In another embodiment of any of the aforementioned embodiments of increasing tear production, between 1 microgram and 4 milligrams of a compound of Formula (I), (II), (IIIa), or (IIIb) is administered into the nasal cavity. In another embodiment of any of the aforementioned embodiments of increasing tear production, between 1 microgram and 3 milligrams of a compound of Formula (I), (II), (IIIa), or (IIIb) is administered into the nasal cavity. In another embodiment of any of the aforementioned embodiments of increasing tear production, between 1 microgram and 2 milligrams of a compound of Formula (I), (II), (IIIa), or (IIIb) is administered into the nasal cavity. In another embodiment of any of the aforementioned embodiments of increasing tear production, between 1 microgram and 1 milligrams of a compound of Formula (I), (II), (IIIa), or (IIIb) is administered into the nasal cavity. In another embodiment of any of the aforementioned embodiments of increasing tear production, between 1 microgram and 750 micrograms of a compound of Formula (I), (II), (IIIa), or (IIIb) is administered into the nasal cavity. In another embodiment of any of the aforementioned embodiments of increasing tear production, between 1 microgram and 600 micrograms of a compound of Formula (I), (II), (IIIa), or (IIIb) is administered into the nasal cavity. In another embodiment of any of the aforementioned embodiments of increasing tear production, between 1 microgram and 100 micrograms of a compound of Formula (I), (II), (IIIa), or (IIIb) is administered into the nasal cavity. In another embodiment of any of the aforementioned embodiments of increasing tear production, between 1 microgram and 50 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method comprises about 0.1 mg/mL of a compound of Formula (I), (II), (IIIa), or (IIIb). In another embodiment, the pharmaceutical formulation for use in the method comprises about 0.2 mg/mL of a compound of Formula (I), (II), (IIIa), or (IIIb). In another embodiment, the pharmaceutical formulation for use in the method comprises about 0.5 mg/mL of a compound of Formula (I), (II), (IIIa), or (IIIb). In another embodiment, the pharmaceutical formulation for use in the method comprises about 1 mg/mL of a compound of Formula (I), (II), (IIIa), or (IIIb). In another embodiment, the pharmaceutical formulation for use in the method comprises about 2 mg/mL of a compound of Formula (I), (II), (IIIa), or (IIIb). In another embodiment, the pharmaceutical formulation for use in the method comprises about 3 mg/mL of a compound of Formula (I), (II), (IIIa), or (IIIb). In another embodiment, the pharmaceutical formulation for use in the method comprises about 4 mg/mL of a compound of Formula (I), (II), (IIIa), or (IIIb). In another embodiment, the pharmaceutical formulation for use in the method comprises about 5 mg/mL of a compound of Formula (I), (II), (IIIa), or (IIIb). In another embodiment, the pharmaceutical formulation for use in the method comprises about 6 mg/mL of a compound of Formula (I), (II), (IIIa), or (IIIb). In another embodiment, the pharmaceutical formulation for use in the method comprises about 7 mg/mL of a compound of Formula (I), (II), (IIIa), or (IIIb). In another embodiment, the pharmaceutical formulation for use in the method comprises about 8 mg/mL of a compound of Formula (I), (II), (IIIa), or (IIIb). In another embodiment, the pharmaceutical formulation for use in the method comprises about 9 mg/ml of a compound of Formula (I), (II), (IIIa), or (IIIb). In another embodiment, the pharmaceutical formulation for use in the method comprises about 10 mg/mL of a compound of Formula (I), (II), (IIIa), or (IIIb). In another embodiment, the pharmaceutical formulation for use in the method comprises about 12 mg/mL of a compound of Formula (I), (II), (IIIa), or (IIIb). In another embodiment, the pharmaceutical formulation for use in the method comprises about 15 mg/mL of a compound of Formula (I), (II), (IIIa), or (IIIb). In another embodiment, the pharmaceutical formulation for use in the method comprises about 20 mg/mL of a compound of Formula (I), (II), (IIIa), or (IIIb). In another embodiment, the pharmaceutical formulation for use in the method comprises about 25 mg/mL of a compound of Formula (I), (II), (IIIa), or (IIIb). In another embodiment, the pharmaceutical formulation for use in the method comprises about 30 mg/mL of a compound of Formula (I), (II), (IIIa), or (IIIb). In another embodiment, the pharmaceutical formulation for use in the method comprises about 40 mg/mL of a compound of Formula (I), (II), (IIIa), or (IIIb). In another embodiment, the pharmaceutical formulation for use in the method comprises about 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 5 mg/mL and 200 mg/mL of a compound of Formula (I), (II), (IIIa), or (IIIb). In another embodiment, the pharmaceutical formulation for use in the method comprises between 10 mg/mL and 200 mg/mL of a compound of Formula (I), (II), (IIIa), or (IIIb). In another embodiment, the pharmaceutical formulation for use in the method comprises between 5 mg/mL, and 100 mg/mL of a compound of Formula (I), (II), (IIIa), or (IIIb). In another embodiment, the pharmaceutical formulation for use in the method comprises between 10 mg/mL and 75 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 10 mg/mL and 30 mg/mL of a compound of Formula (I), (II), (IIIa), or (IIIb). In another embodiment, the pharmaceutical formulation for use in the method comprises between 5 mg/mL and 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 10 mg/mL and 25 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 20 mg/mL and 50 mg/mL of a compound of Formula (I), (II), (IIIa), or (IIIb). In another embodiment, the pharmaceutical formulation for use in the method comprises between 30 mg/mL and 75 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method is provided at about 10 to 200 µl. In another embodiment, the pharmaceutical formulation for use in the method is provided at about 10 to 150 µl. In another embodiment, the pharmaceutical formulation for use in the method is provided at about 10 to 100 µl. In another embodiment, the pharmaceutical formulation for use in the method is provided at about 50 to 200 µl. In another embodiment, the pharmaceutical formulation for use in the method is provided at about 100 to 200 µl. In another embodiment, the pharmaceutical formulation for use in the method is provided at about 50 to 100 µl. In another embodiment, the pharmaceutical formulation for use in the method is provided at about 10 to 150 µl. In another embodiment, the pharmaceutical formulation for use in the method is provided at about 10, 20, 30, 40, 50, 60, 70, 80, 90, 100, 110, 120, 130, 140, 150, 160, 170, 180, 190, or 200 µl. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, the compound of Formula (I), (II), (IIIa), or (IIIb) is administered once daily. In another embodiment of any of the aforementioned embodiments of increasing tear production, the compound of Formula (I), (II), (IIIa), or (IIIb) is administered at least once daily. In another embodiment of any of the aforementioned embodiments of increasing tear production, the compound of Formula (I), (II), (IIIa), or (IIIb) is administered twice daily. In another embodiment of any of the aforementioned embodiments of increasing tear production, the compound of Formula (I), (II), (IIIa), or (IIIb) is administered at least twice daily. In another embodiment of any of the aforementioned embodiments of increasing tear production, the compound of Formula (I), (II), (IIIa), or (IIIb) is administered three times daily. In another embodiment of any of the aforementioned embodiments of increasing tear production, the compound of Formula (I), (II), (IIIa), or (IIIb) is administered at least three times daily. In another embodiment of any of the aforementioned embodiments of increasing tear production, the compound of Formula (I), (II), (IIIa), or (IIIb) is administered for one day. In another embodiment of any of the aforementioned embodiments of increasing tear production, the compound of Formula (I), (II), (IIIa), or (IIIb) is administered for at least two days. In another embodiment of any of the aforementioned embodiments of increasing tear production, the compound of Formula (I), (II), (IIIa), or (IIIb) is administered for at least three days. In another embodiment of any of the aforementioned embodiments of increasing tear production, the compound of Formula (I), (II), (IIIa), or (IIIb) is administered for at least four days. In another embodiment of any of the aforementioned embodiments of increasing tear production, the compound of Formula (I), (II), (IIIa), or (IIIb) is administered for at least five days. In another embodiment of any of the aforementioned embodiments of increasing tear production, the compound of Formula (I), (II), (IIIa), or (IIIb) is administered for at least seven days. In another embodiment of any of the aforementioned embodiments of increasing tear production, the compound of Formula (I), (II), (IIIa), or (IIIb) is administered for at least ten days. In another embodiment of any of the aforementioned embodiments of increasing tear production, the compound of Formula (I), (II), (IIIa), or (IIIb) is administered for at least fourteen days. In another embodiment of any of the aforementioned embodiments of increasing tear production, the compound of Formula (I), (II), (IIIa), or (IIIb) is administered for at least twenty one days.

In another embodiment of any of the aforementioned embodiments of increasing tear production, the compound of Formula (I), (II), (IIIa), or (IIIb) is administered for at least thirty days. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, the compound of Formula (I), (II), (IIIa), or (IIIb) is administered in alternating nostrils. For example, the compound of Formula (I), (II), (IIIa), or (IIIb) is administered in one nostril and then the other nostril after a pre-determined amount of time. In another embodiment, the compound of Formula (I), (II), (IIIa), or (IIIb) is administered in both nostrils. For example, the compound of Formula (I), (II), (IIIa), or (IIIb) is administered in one nostril and then the other nostril at the same time or immediately after the first nostril. In another embodiment, the compound of Formula (I), (II), (IIIa), or (IIIb) is administered in one nostril. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, the compound of Formula (I), (II), (IIIa), or (IIIb) is administered into the nasal cavity as a liquid, suspension, aerosol, gel, ointment, dry powder, cream, paste, lotion, or balm. In another embodiment of any of the aforementioned embodiments of increasing tear production, the compound of Formula (I), (II), (IIIa), or (IIIb) is administered into the nasal cavity as a liquid. In another embodiment of any of the aforementioned embodiments of increasing tear production, the compound of Formula (I), (II), (IIIa), or (IIIb) is administered into the nasal cavity as a suspension. In another embodiment of any of the aforementioned embodiments of increasing tear production, the compound of Formula (I), (II), (IIIa), or (IIIb) is administered into the nasal cavity as an aerosol. In another embodiment of any of the aforementioned embodiments of increasing tear production, the compound of Formula (I), (II), (IIIa), or (IIIb) is administered into the nasal cavity as a gel. In another embodiment of any of the aforementioned embodiments of increasing tear production, the compound of Formula (I), (II), (IIIa), or (IIIb) is administered into the nasal cavity as an ointment. In another embodiment of any of the aforementioned embodiments of increasing tear production, the compound of Formula (I), (II), (IIIa), or (IIIb) is administered into the nasal cavity as a dry powder. In another embodiment of any of the aforementioned embodiments of increasing tear production, the compound of Formula (I), (II), (IIIa), or (IIIb) is administered into the nasal cavity as a cream. In another embodiment of any of the aforementioned embodiments of increasing tear production, the compound of Formula (I), (II), (IIIa), or (IIIb) is administered into the nasal cavity as a paste. In another embodiment of any of the aforementioned embodiments of increasing tear production, the compound of Formula (I), (II), (IIIa), or (IIIb) is administered into the nasal cavity as a lotion. In another embodiment of any of the aforementioned embodiments of increasing tear production, the compound of Formula (I), (II), (IIIa), or (IIIb) is administered into the nasal cavity as a balm. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, the compound of Formula (I), (II), (IIIa), or (IIIb) is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of increasing tear production, the compound of Formula (I), (II), (IIIa), or (IIIb) is administered into the nasal cavity by a syringe. In another embodiment of the aforementioned embodiments of increasing tear production, the compound of Formula (I), (II), (IIIa), or (IIIb) is administered into the nasal cavity by a dropper. In another embodiment of any of the aforementioned embodiments of increasing tear production, the compound of Formula (I), (II), (IIIa), or (IIIb) is administered into the nasal cavity by a bottle nebulizer. In another embodiment of any of the aforementioned embodiments of increasing tear production, the compound of Formula (I), (II), (IIIa), or (IIIb) is administered into the nasal cavity by an atomization pump. In another embodiment of any of the aforementioned embodiments of increasing tear production, the compound of Formula (I), (II), (IIIa), or (IIIb) is administered into the nasal cavity by an inhaler. In another embodiment of any of the aforementioned embodiments of increasing tear production, the compound of Formula (I), (II), (IIIa), or (IIIb) is administered into the nasal cavity by a powder spray device. In another embodiment of any of the aforementioned embodiments of increasing tear production, the compound of Formula (I), (II), (IIIa), or (IIIb) is administered into the nasal cavity by a vaporizer. In another embodiment of any of the aforementioned embodiments of increasing tear production, the compound of Formula (I), (II), (IIIa), or (IIIb) is administered into the nasal cavity by a patch. In another embodiment of any of the aforementioned embodiments of increasing tear production, the compound of Formula (I), (II), (IIIa), or (IIIb) is administered into the nasal cavity by a medicated stick. In another embodiment of any of the aforementioned embodiments of increasing tear production, the compound of Formula (I), (II), (IIIa), or (IIIb) is administered into the nasal cavity by a pipette. In another embodiment of any of the aforementioned embodiments of increasing tear production, the compound of Formula (I), (II), (IIIa), or (IIIb) is administered into the nasal cavity by a jet of liquid. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, the trigeminal nerve is activated. In a further embodiment of increasing tear production, the anterior ethmoidal nerve is activated. In another embodiment of any of the aforementioned embodiments of increasing tear production, the nasolacrimal reflex is activated. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing tear production, the condition relieved by increasing tear production is an acute condition. An acute condition refers to a condition with a rapid onset of a health effect that is considered brief, not prolonged. Acute conditions can result from ophthalmologic surgical procedures or other ophthalmologic treatment. In some embodiments, the ophthalmologic surgical procedure is cataract surgery (cataract extraction and lens replacement), refractive lens exchange, glaucoma surgery, lasik surgery (laser eye surgery), vitrectomy, retinal photocoagulation, retinal detachment repair, macular hole repair, retroiris tumor or mass removal, posterior sclerotomy, optic neurotomy, or other treatments that decrease the function of the lacrimal gland. In some embodiments, the ophthalmologic treatment comprises radiation therapy. In some embodiments, the radiation therapy is directed to orbital area, for example, in connection to cancers of head and/or neck. In some embodiments, the compound of Formula (I) is (R)-5-((E)-2-pyrrolidin-3-ylvinyl)pyrimidine, or a pharmaceutically acceptable salt thereof.

Treating Dry Eye

Provided herein, in some embodiments, is a method of treating dry eye in a subject. In some embodiments, is a method of treating dry eye, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and does not cross the blood-brain barrier in a pharmacologically relevant concentration. In some embodiments is method of treating dry eye, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of treating dry eye, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha3beta4. In some embodiments is method of treating dry eye, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha4beta2. In some embodiments is method of treating dry eye, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha7. In some embodiments is a method of treating dry eye, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that is not systemically bioavailable. In some embodiments is a method of treating dry eye, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired psychoactive side effects. In some embodiments is a method of treating dry eye, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired systemic side effects. In some embodiments is a method of treating dry eye, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that produces a local effect. In some embodiments is a method of treating dry eye, further comprising the local administration of one or more substances that prevent or facilitate the recovery of the nicotinic acetylcholine receptor from the desensitized state. In some embodiments is a method of treating dry eye, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments, the compound of Formula (I) is (R)-5-((E)-2-pyrrolidin-3-ylvinyl)pyrimidine, or a pharmaceutically acceptable salt thereof.

In some embodiments of the method of treating dry eye described herein, the compound of Formula (I), (II), (IIIa), or (IIIb) is (R)-5-((E)-2-pyrrolidin-3-ylvinyl)pyrimidine (or Compound 1). In some embodiments of the methods described herein, the compound of Formula (I), (II), (IIIa), or (IIIb) is (R)-5-((E)-2-pyrrolidin-3-ylvinyl)pyrimidine, or a pharmaceutically acceptable salt thereof. In some embodiments of the methods described herein, the compound of Formula (I), (II), (IIIa), or (IIIb) is (R)-5-((E)-2-pyrrolidin-3-ylvinyl)pyrimidine as a free base. In some embodiments of the method of treating dry eye described herein, the compound of Formula (I), (II), (IIIa), or (IIIb) is (R)-5-((E)-2-pyrrolidin-3-ylvinyl)pyrimidine citrate salt. In some embodiments of the method of treating dry eye described herein, the compound of Formula (I), (II), (IIIa), or (IIIb) is (R)-5-((E)-2-pyrrolidin-3-ylvinyl)pyrimidine mono citrate salt. In some embodiments of the method of treating dry eye described herein, the compound of Formula (I), (II), (IIIa), or (IIIb) is (R)-5-((E)-2-pyrrolidin-3-ylvinyl)pyrimidine HCl salt. In some embodiments of the method of treating dry eye described herein, the compound of Formula (I), (II), (IIIa), or (IIIb) is (R)-5-((E)-2-pyrrolidin-3-ylvinyl)pyrimidine galactarate salt. In some embodiments of the method of treating dry eye described herein, the compound of Formula (I), (II), (IIIa), or (IIIb) is (R)-5-((E)-2-pyrrolidin-3-ylvinyl) pyrimidine hemigalactarate salt. In some embodiments of the method of treating dry eye described herein, the compound of Formula (I), (II), (IIIa), or (IIIb) is (R)-5-((E)-2-pyrrolidin-3-ylvinyl)pyrimidine hemigalactarate monohydrate. In some embodiments of the method described herein, the compound of Formula (I), (II), (IIIa), or (IIIb) is (R)-5-((E)-2-pyrrolidin-3-ylvinyl)pyrimidine hemigalactarate dihydrate.

In some embodiments is a method of treating dry eye, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of treating dry eye, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of treating dry eye, further comprising the local administration of protein kinase C (PKC) or factors that upregulate or up-modulate PKC. In some embodiments is a method of treating dry eye, further comprising the local administration of cAMP-dependent protein kinase (PKA) or factors that upregulate or up-modulate PKA. In some embodiments is a method of treating dry eye, further comprising the local administration of a calcineurin inhibitor. In some embodiments is a method of treating dry eye, further comprising the local administration of a calcineurin inhibitor, wherein the calcineurin inhibitor is selected from cyclosporine, pimecrolimus, and tacrolimus. In some embodiments is a method of treating dry eye, further comprising the local administration of cyclosporine. In some embodiments is a method of treating dry eye, further comprising the local administration of pimecrolimus. In some embodiments is a method of treating dry eye, further comprising the local administration of tacrolimus.

In another embodiment of any of the aforementioned embodiments of treating dry eye, at least 1 microgram of the compound of Formula (I), (II), (IIIa), or (IIIb) is administered into the nasal cavity. In another embodiment of any of the aforementioned embodiments of treating dry eye, at least 5 micrograms of the compound of Formula (I), (II), (IIIa), or (IIIb) is administered into the nasal cavity. In another embodiment of any of the aforementioned embodiments of treating dry eye, at least 10 micrograms of the compound of Formula (I), (II), (IIIa), or (IIIb) is administered into the nasal cavity. In another embodiment of any of the aforementioned embodiments of treating dry eye, at least 25 micrograms of the compound of Formula (I), (II), (IIIa), or (IIIb) is administered into the nasal cavity. In another embodiment of any of the aforementioned embodiments of treating dry eye, at least 50 micrograms of the compound of Formula (I), (II), (IIIa), or (IIIb) is administered into the nasal cavity. In another embodiment of any of the aforementioned embodiments of treating dry eye, at least 100 micrograms of the compound of Formula (I), (II), (IIIa), or (IIIb) is administered into the nasal cavity. In another embodiment of any of the aforementioned embodiments of treating dry eye, at least 250 micrograms of the compound of Formula (I), (II), (IIIa), or (IIIb) is administered into the nasal cavity. In another embodiment of any of the aforementioned embodiments of treating dry eye, at least 500 micrograms of the compound of Formula (I), (II), (IIIa), or (IIIb) is administered into the nasal cavity. In another embodiment of any of the aforementioned embodiments of treating dry eye, at least 750 micrograms of the compound of Formula (I), (II), (IIIa), or (IIIb) is administered into the nasal cavity. In another embodiment of any of the aforementioned embodiments of treating dry eye, at least 1000 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, between 1 microgram and 1000 micrograms of the compound of Formula (I), (II), (IIIa), or (IIIb) is administered into the nasal cavity. In another embodiment of any of the aforementioned embodiments of treating dry eye, between 5 micrograms and 1000 micrograms of the compound of Formula (I), (II), (IIIa), or (IIIb) is administered into the nasal cavity. In another embodiment of any of the aforementioned embodiments of treating dry eye, between 10 micrograms and 1000 micrograms of the compound of Formula (I), (II), (IIIa), or (IIIb) is administered into the nasal cavity. In another embodiment of any of the aforementioned embodiments of treating dry eye, between 5 micrograms and 100 micrograms of the compound of Formula (I), (II), (IIIa), or (IIIb) is administered into the nasal cavity. In another embodiment of any of the aforementioned embodiments of treating dry eye, between 5 micrograms and 50 micrograms of the compound of Formula (I), (II), (IIIa), or (IIIb) is administered into the nasal cavity. In another embodiment of any of the aforementioned embodiments of treating dry eye, between 10 micrograms and 50 micrograms of the compound of Formula (I), (II), (IIIa), or (IIIb) is administered into the nasal cavity. In another embodiment of any of the aforementioned embodiments of treating dry eye, between 25 micrograms and 1000 micrograms of the compound of Formula (I), (II), (IIIa), or (IIIb) is administered into the nasal cavity. In another embodiment of any of the aforementioned embodiments of treating dry eye, between 50 micrograms and 1000 micrograms of the compound of Formula (I), (II), (IIIa), or (IIIb) is administered into the nasal cavity. In another embodiment of any of the aforementioned embodiments of treating dry eye, between 100 micrograms and 1000 micrograms of the compound of Formula (I), (II), (IIIa), or (IIIb) is administered into the nasal cavity. In another embodiment of any of the aforementioned embodiments of treating dry eye, between 150 micrograms and 1000 micrograms of the compound of Formula (I), (II), (IIIa), or (IIIb) is administered into the nasal cavity. In another embodiment of any of the aforementioned embodiments of treating dry eye, between 100 micrograms and 750 micrograms of the compound of Formula (I), (II), (IIIa), or (IIIb) is administered into the nasal cavity. In another embodiment of any of the aforementioned embodiments of treating dry eye, between 150 micrograms and 750 micrograms of the compound of Formula (I), (II), (IIIa), or (IIIb) is administered into the nasal cavity. In another embodiment of any of the aforementioned embodiments of treating dry eye, between 150 micrograms and 600 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, less than 100 micrograms of a compound of Formula (I), (II), (IIIa), or (IIIb) is administered into the nasal cavity. In another embodiment of any of the aforementioned embodiments of treating dry eye, less than 75 micrograms of a compound of Formula (I), (II), (IIIa), or (IIIb) is administered into the nasal cavity. In another embodiment of any of the aforementioned embodiments of treating dry eye, less than 50 micrograms of a compound of Formula (I), (II), (IIIa), or (IIIb) is administered into the nasal cavity. In another embodiment of any of the aforementioned embodiments of treating dry eye, less than 25 micrograms of a compound of Formula (I), (II), (IIIa), or (IIIb) is administered into the nasal cavity. In another embodiment of any of the aforementioned embodiments of treating dry eye, less than 15 micrograms of a compound of Formula (I), (II), (IIIa), or (IIIb) is administered into the nasal cavity. In another embodiment of any of the aforementioned embodiments of treating dry eye, about 75 micrograms of a compound of Formula (I), (II), (IIIa), or (IIIb) is administered into the nasal cavity. In another embodiment of any of the aforementioned embodiments of treating dry eye, about 50 micrograms of a compound of Formula (I), (II), (IIIa), or (IIIb) is administered into the nasal cavity. In another embodiment of any of the aforementioned embodiments of treating dry eye, about 25 micrograms of a compound of Formula (I), (II), (IIIa), or (IIIb) is administered into the nasal cavity. In another embodiment of any of the aforementioned embodiments of treating dry eye, about 10 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, between 1 microgram and 100 micrograms of a compound of Formula (I), (II), (IIIa), or (IIIb) is administered into the nasal cavity. In another embodiment of any of the aforementioned embodiments of treating dry eye, between 1 microgram and 75 micrograms of a compound of Formula (I), (II), (IIIa), or (IIIb) is administered into the nasal cavity. In another embodiment of any of the aforementioned embodiments of treating dry eye, between 5 micrograms and 100 micrograms of a compound of Formula (I), (II), (IIIa), or (IIIb) is administered into the nasal cavity. In another embodiment of any of the aforementioned embodiments of treating dry eye, between 5 micrograms and 75 micrograms of a compound of Formula (I), (II), (IIIa), or (IIIb) is administered into the nasal cavity. In another embodiment of any of the aforementioned embodiments of treating dry eye, between 15 micrograms and 100 micrograms of a compound of Formula (I), (II), (IIIa), or (IIIb) is administered into the nasal cavity. In another embodiment of any of the aforementioned embodiments of treating dry eye, between 15 micrograms and 75 micrograms of a compound of Formula (I), (II), (IIIa), or (IIIb) is administered into the nasal cavity. In another embodiment of any of the aforementioned embodiments of treating dry eye, between 25 micrograms and 100 micrograms of a compound of Formula (I), (II), (IIIa), or (IIIb) is administered into the nasal cavity. In another embodiment of any of the aforementioned embodiments of treating dry eye, between 25 micrograms and 75 micrograms of a compound of Formula (I), (II), (IIIa), or (IIIb) is administered into the nasal cavity. In another embodiment of any of the aforementioned embodiments of treating dry eye, between 25 micrograms and 60 micrograms of a compound of Formula (I), (II), (IIIa), or (IIIb) is administered into the nasal cavity.

In another embodiment of any of the aforementioned embodiments of treating dry eye, between 500 micrograms and 10 milligrams of a compound of Formula (I), (II), (IIIa), or (IIIb) is administered into the nasal cavity. In another embodiment of any of the aforementioned embodiments of treating dry eye, between 500 micrograms and 5 milligrams of a compound of Formula (I), (II), (IIIa), or (IIIb) is administered into the nasal cavity. In another embodiment of any of the aforementioned embodiments of treating dry eye, between 500 micrograms and 3 milligrams of a compound of Formula (I), (II), (IIIa), or (IIIb) is administered into the nasal cavity. In another embodiment of any of the aforementioned embodiments of treating dry ee, between 500 micrograms and 2 milligrams of a compound of Formula (I), (II), (IIIa), or (IIIb) is administered into the nasal cavity. In another embodiment of any of the aforementioned embodiments of treating dry eye, between 1 milligram and 10 milligrams of a compound of Formula (I), (II), (IIIa), or (IIIb) is administered into the nasal cavity. In another embodiment of any of the aforementioned embodiments of treating dry eye, between 1 milligram and 5 milligrams of a compound of Formula (I), (II), (IIIa), or (IIIb) is administered into the nasal cavity. In another embodiment of any of the aforementioned embodiments of treating dry eye, between 1 milligram and 3 milligrams of a compound of Formula (I), (II), (IIIa), or (IIIb) is administered into the nasal cavity. In another embodiment of any of the aforementioned embodiments of treating dry eye, between 1 milligram and 2 milligrams of a compound of Formula (I), (II), (IIIa), or (IIIb) is administered into the nasal cavity. In another embodiment of any of the aforementioned embodiments of treating dry eye, about 500 micrograms of a compound of Formula (I), (II), (IIIa), or (IIIb) is administered into the nasal cavity. In another embodiment of any of the aforementioned embodiments of treating dry eye, about 1 milligram of a compound of Formula (I), (II), (IIIa), or (IIIb) is administered into the nasal cavity. In another embodiment of any of the aforementioned embodiments of treating dry eye, about 1.5 milligrams of a compound of Formula (I), (II), (IIIa), or (IIIb) is administered into the nasal cavity. In another embodiment of any of the aforementioned embodiments of treating dry eye, about 2 milligrams of a compound of Formula (I), (II), (IIIa), or (IIIb) is administered into the nasal cavity. In another embodiment of any of the aforementioned embodiments of treating dry eye, about 2.5 milligrams of a compound of Formula (I), (II), (IIIa), or (IIIb) is administered into the nasal cavity. In another embodiment of any of the aforementioned embodiments of treating dry eye, about 3 milligrams of a compound of Formula (I), (II), (IIIa), or (IIIb) is administered into the nasal cavity. In another embodiment of any of the aforementioned embodiments of treating dry eye, about 4 milligrams of a compound of Formula (I), (II), (IIIa), or (IIIb) is administered into the nasal cavity. In another embodiment of any of the aforementioned embodiments of treating dry eye, about 5 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, between 1 microgram and 10 milligrams of a compound of Formula (I), (II), (IIIa), or (IIIb) is administered into the nasal cavity. In another embodiment of any of the aforementioned embodiments of treating dry eye, between 5 micrograms and 10 milligrams of a compound of Formula (I), (II), (IIIa), or (IIIb) is administered into the nasal cavity. In another embodiment of any of the aforementioned embodiments of treating dry eye, between 10 micrograms and 10 milligrams of a compound of Formula (I), (II), (IIIa), or (IIIb) is administered into the nasal cavity. In another embodiment of any of the aforementioned embodiments of treating dry eye, between 25 micrograms and 10 milligrams of a compound of Formula (I), (II), (IIIa), or (IIIb) is administered into the nasal cavity. In another embodiment of any of the aforementioned embodiments of treating dry eye, between 50 micrograms and 10 milligrams of a compound of Formula (I), (II), (IIIa), or (IIIb) is administered into the nasal cavity. In another embodiment of any of the aforementioned embodiments of treating dry eye, between 100 micrograms and 10 milligrams of a compound of Formula (I), (II), (IIIa), or (IIIb) is administered into the nasal cavity. In another embodiment of any of the aforementioned embodiments of treating dry eye, between 150 micrograms and 10 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, between 1 microgram and 10 milligrams of a compound of Formula (I), (II), (IIIa), or (IIIb) is administered into the nasal cavity. In another embodiment of any of the aforementioned embodiments of treating dry eye, between 1 microgram and 5 milligrams of a compound of Formula (I), (II), (IIIa), or (IIIb) is administered into the nasal cavity. In another embodiment of any of the aforementioned embodiments of treating dry eye, between 1 microgram and 4 milligrams of a compound of Formula (I), (II), (IIIa), or (IIIb) is administered into the nasal cavity. In another embodiment of any of the aforementioned embodiments of treating dry eye, between 1 microgram and 3 milligrams of a compound of Formula (I), (II), (IIIa), or (IIIb) is administered into the nasal cavity. In another embodiment of any of the aforementioned embodiments of treating dry eye, between 1 microgram and 2 milligrams of a compound of Formula (I), (II), (IIIa), or (IIIb) is administered into the nasal cavity. In another embodiment of any of the aforementioned embodiments of treating dry eye, between 1 microgram and 1 milligrams of a compound of Formula (I), (II), (IIIa), or (IIIb) is administered into the nasal cavity. In another embodiment of any of the aforementioned embodiments of treating dry eye, between 1 microgram and 750 micrograms of a compound of Formula (I), (II), (IIIa), or (IIIb) is administered into the nasal cavity. In another embodiment of any of the aforementioned embodiments of treating dry eye, between 1 microgram and 600 micrograms of a compound of Formula (I), (II), (IIIa), or (IIIb) is administered into the nasal cavity. In another embodiment of any of the aforementioned embodiments of treating dry eye, between 1 microgram and 100 micrograms of a compound of Formula (I), (II), (IIIa), or (IIIb) is administered into the nasal cavity. In another embodiment of any of the aforementioned embodiments of treating dry eye, between 1 microgram and 50 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method comprises about 0.1 mg/mL of a compound of Formula (I), (II), (IIIa), or (IIIb). In another embodiment, the pharmaceutical formulation for use in the method comprises about 0.2 mg/mL of a compound of Formula (I), (II), (IIIa), or (IIIb). In another embodiment, the pharmaceutical formulation for use in the method comprises about 0.5 mg/mL of a compound of Formula (I), (II), (IIIa), or (IIIb). In another embodiment, the pharmaceutical formulation for use in the method comprises about 1 mg/mL of a compound of Formula (I), (II), (IIIa), or (IIIb). In another embodiment, the pharmaceutical formulation for use in the method comprises about 2 mg/ml, of a compound of Formula (I), (II), (IIIa), or (IIIb). In another embodiment, the pharmaceutical formulation for use in the method comprises about 3 mg/mL of a compound of Formula (I), (II), (IIIa), or (IIIb). In another embodiment, the pharmaceutical formulation for use in the method comprises about 4 mg/mL of a compound of Formula (I), (II), (IIIa), or (IIIb). In another embodiment, the pharmaceutical formulation for use in the method comprises about 5 mg/mL of a compound of Formula (I), (II), (IIIa), or (IIIb). In another embodiment, the pharmaceutical formulation for use in the method comprises about 6 mg/mL of a compound of Formula (I), (II), (IIIa), or (IIIb). In another embodiment, the pharmaceutical formulation for use in the method comprises about 7 mg/mL of a compound of Formula (I), (II), (IIIa), or (IIIb). In another embodiment, the pharmaceutical formulation for use in the method comprises about 8 mg/mL of a compound of Formula (I), (II), (IIIa), or (IIIb). In another embodiment, the pharmaceutical formulation for use in the method comprises about 9 mg/mL of a compound of Formula (I), (II), (IIIa), or (IIIb). In another embodiment, the pharmaceutical formulation for use in the method comprises about 10 mg/mL of a compound of Formula (I), (II), (IIIa), or (IIIb). In another embodiment, the pharmaceutical formulation for use in the method comprises about 12 mg/mL of a compound of Formula (I), (II), (IIIa), or (IIIb). In another embodiment, the pharmaceutical formulation for use in the method comprises about 15 mg/mL of a compound of Formula (I), (II), (IIIa), or (IIIb). In another embodiment, the pharmaceutical formulation for use in the method comprises about 20 mg/m L of a compound of Formula (I), (II), (IIIa), or (IIIb). In another embodiment, the pharmaceutical formulation for use in the method comprises about 25 mg/mL of a compound of Formula (I), (II), (IIIa), or (IIIb). In another embodiment, the pharmaceutical formulation for use in the method comprises about 30 mg/mL of a compound of Formula (I), (II), (IIIa), or (IIIb). In another embodiment, the pharmaceutical formulation for use in the method comprises about 40 mg/mL of a compound of Formula (I), (II), (IIIa), or (IIIb). In another embodiment, the pharmaceutical formulation for use in the method comprises about 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 5 mg/mL and 200 mg/mL of a compound of Formula (I), (II), (IIIa), or (IIIb). In another embodiment, the pharmaceutical formulation for use in the method comprises between 10 mg/mL and 200 mg/mL of a compound of Formula (I), (II), (IIIa), or (IIIb). In another embodiment, the pharmaceutical formulation for use in the method comprises between 5 mg/mL, and 100 mg/mL of a compound of Formula (I), (II), (IIIa), or (IIIb). In another embodiment, the pharmaceutical formulation for use in the method comprises between 10 mg/mL and 75 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 10 mg/mL and 30 mg/mL of a compound of Formula (I), (II), (IIIa), or (IIIb). In another embodiment, the pharmaceutical formulation for use in the method comprises between 5 mg/mL and 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 10 mg/mL and 25 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 20 mg/mL and 50 mg/mL of a compound of Formula (I), (II), (IIIa), or (IIIb). In another embodiment, the pharmaceutical formulation for use in the method comprises between 30 mg/mL and 75 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method is provided at about 10 to 200 µl. In another embodiment, the pharmaceutical formulation for use in the method is provided at about 10 to 150 µl. In another embodiment, the pharmaceutical formulation for use in the method is provided at about 10 to 100 µl. In another embodiment, the pharmaceutical formulation for use in the method is provided at about 50 to 200 µl. In another embodiment, the pharmaceutical formulation for use in the method is provided at about 100 to 200 µl. In another embodiment, the pharmaceutical formulation for use in the method is provided at about 50 to 100 µl. In another embodiment, the pharmaceutical formulation for use in the method is provided at about 10 to 150 µl. In another embodiment, the pharmaceutical formulation for use in the method is provided at about 10, 20, 30, 40, 50, 60, 70, 80, 90, 100, 110, 120, 130, 140, 150, 160, 170, 180, 190, or 200 µl. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, the compound of Formula (I), (II), (IIIa), or (IIIb) is administered once daily. In another embodiment of any of the aforementioned embodiments of treating dry eye, the compound of Formula (I), (II), (IIIa), or (IIIb) is administered at least once daily. In another embodiment of any of the aforementioned embodiments of treating dry eye, the compound of Formula (I), (II), (IIIa), or (IIIb) is administered twice daily. In another embodiment of any of the aforementioned embodiments of treating dry eye, the compound of Formula (I), (II), (IIIa), or (IIIb) is administered at least twice daily. In another embodiment of any of the aforementioned embodiments of treating dry eye, the compound of Formula (I), (II), (IIIa), or (IIIb) is administered three times daily. In another embodiment of any of the aforementioned embodiments of treating dry eye, the compound of Formula (I), (II), (IIIa), or (IIIb) is administered at least three times daily. In another embodiment of any of the aforementioned embodiments of treating dry eye, the compound of Formula (I), (II), (IIIa), or (IIIb) is administered for one day. In another embodiment of any of the aforementioned embodiments of treating dry eye, the compound of Formula (I), (II), (IIIa), or (IIIb) is administered for at least two days. In another embodiment of any of the aforementioned embodiments of treating dry eye, the compound of Formula (I), (II), (IIIa), or (IIIb) is administered for at least three days. In another embodiment of any of the aforementioned embodiments of treating dry eye, the compound of Formula (I), (II), (IIIa), or (IIIb) is administered for at least four days. In another embodiment of any of the aforementioned embodiments of treating dry eye, the compound of Formula (I), (II), (IIIa), or (IIIb) is administered for at least five days. In another embodiment of any of the aforementioned embodiments of treating dry eye, the compound of Formula (I), (II), (IIIa), or (IIIb) is administered for at least seven days. In another embodiment of any of the aforementioned embodiments of treating dry eye, the compound of Formula (I), (II), (IIIa), or (IIIb) is administered for at least ten days. In another embodiment of any of the aforementioned embodiments of treating dry eye, the compound of Formula (I), (II), (IIIa), or (IIIb) is administered for at least fourteen days. In another embodiment of any of the aforementioned embodiments of treating dry eye, the compound of Formula (I), (II), (IIIa), or (IIIb) is administered for at least twenty one days. In another embodiment of any of the aforementioned embodiments of treating dry eye, the compound of Formula (I), (II), (IIIa), or (IIIb) is administered for at least thirty days. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, the compound of Formula (I), (II), (IIIa), or (IIIb) is administered in alternating nostrils. For example, the compound of Formula (I), (II), (IIIa), or (IIIb) is administered in one nostril and then the other nostril after a pre-determined amount of time. In another embodiment, the compound of Formula (I), (II), (IIIa), or (IIIb) is administered in both nostrils. For example, the compound of Formula (I), (II), (IIIa), or (IIIb) is administered in one nostril and then the other nostril at the same time or immediately after the first nostril. In another embodiment, the compound of Formula (I), (II), (IIIa), or (IIIb) is administered in one nostril. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, the compound of Formula (I), (II), (IIIa), or (IIIb) is administered into the nasal cavity as a liquid, suspension, aerosol, gel, ointment, dry powder, cream, paste, lotion, or balm. In another embodiment of any of the aforementioned embodiments of treating dry eye, the compound of Formula (I), (II), (IIIa), or (IIIb) is administered into the nasal cavity as a liquid. In another embodiment of any of the aforementioned embodiments of treating dry eye, the compound of Formula (I), (II), (IIIa), or (IIIb) is administered into the nasal cavity as a suspension. In another embodiment of any of the aforementioned embodiments of treating dry eye, the compound of Formula (I), (II), (IIIa), or (IIIb) is administered into the nasal cavity as an aerosol. In another embodiment of any of the aforementioned embodiments of treating dry eye, the compound of Formula (I), (II), (IIIa), or (IIIb) is administered into the nasal cavity as a gel. In another embodiment of any of the aforementioned embodiments of treating dry eye, the compound of Formula (I), (II), (IIIa), or (IIIb) is administered into the nasal cavity as an ointment. In another embodiment of any of the aforementioned embodiments of treating dry eye, the compound of Formula (I), (II), (IIIa), or (IIIb) is administered into the nasal cavity as a dry powder. In another embodiment of any of the aforementioned embodiments of treating dry eye, the compound of Formula (I), (II), (IIIa), or (IIIb) is administered into the nasal cavity as a cream. In another embodiment of any of the aforementioned embodiments of treating dry eye, the compound of Formula (I), (II), (IIIa), or (IIIb) is administered into the nasal cavity as a paste. In another embodiment of any of the aforementioned embodiments of treating dry eye, the compound of Formula (I), (II), (IIIa), or (IIIb) is administered into the nasal cavity as a lotion. In another embodiment of any of the aforementioned embodiments of treating dry eye, the compound of Formula (I), (II), (IIIa), or (IIIb) is administered into the nasal cavity as a balm. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, the compound of Formula (I), (II), (IIIa), or (IIIb) is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of treating dry eye, the compound of Formula (I), (II), (IIIa), or (IIIb) is administered into the nasal cavity by a syringe. In another embodiment of any of the aforementioned embodiments of treating dry eye, the compound of Formula (I), (II), (IIIa), or (IIIb) is administered into the nasal cavity by a dropper. In another embodiment of any of the aforementioned embodiments of treating dry eye, the compound of Formula (I), (II), (IIIa), or (IIIb) is administered into the nasal cavity by a bottle nebulizer. In another embodiment of any of the aforementioned embodiments of treating dry eye, the compound of Formula (I), (II), (IIIa), or (IIIb) is administered into the nasal cavity by an atomization pump. In another embodiment of any of the aforementioned embodiments of treating dry eye, the compound of Formula (I), (II), (IIIa), or (IIIb) is administered into the nasal cavity by an inhaler. In another embodiment of any of the aforementioned embodiments of treating dry eye, the compound of Formula (I), (II), (IIIa), or (IIIb) is administered into the nasal cavity by a powder spray device. In another embodiment of any of the aforementioned embodiments of treating dry eye, the compound of Formula (I), (II), (IIIa), or (IIIb) is administered into the nasal cavity by a vaporizer. In another embodiment of any of the aforementioned embodiments of treating dry eye, the compound of Formula (I), (II), (IIIa), or (IIIb) is administered into the nasal cavity by a patch. In another embodiment of any of the aforementioned embodiments of treating dry eye, the compound of Formula (I), (II), (IIIa), or (IIIb) is administered into the nasal cavity by a medicated stick. In another embodiment of any of the aforementioned embodiments of treating dry eye, the compound of Formula (I), (II), (IIIa), or (IIIb) is administered into the nasal cavity by a pipette. In another embodiment of any of the aforementioned embodiments of treating dry eye, the compound of Formula (I), (II), (IIIa), or (IIIb) is administered into the nasal cavity by a jet of liquid. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, the trigeminal nerve is activated. In a further embodiment of treating dry eye, the anterior ethmoidal nerve is activated. In another embodiment of any of the aforementioned embodiments of treating dry eye, the nasolacrimal reflex is activated. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of treating dry eye, the condition relieved by treating dry eye is an acute condition. An acute condition refers to a condition with a rapid onset of a health effect that is considered brief, not prolonged. Acute conditions can result from ophthalmologic surgical procedures or other ophthalmologic treatment. In some embodiments, the ophthalmologic surgical procedure is cataract surgery (cataract extraction and lens replacement), refractive lens exchange, glaucoma, surgery, lasik surgery (laser eye surgery), vitrectomy, retinal photocoagulation, retinal detachment repair, macular hole repair, retroiris tumor or mass removal, posterior sclerotomy, optic neurotomy, or other treatments that decrease the function of the lacrimal gland. In some embodiments, the ophthalmologic treatment comprises radiation therapy. In some embodiments, the radiation therapy is directed to orbital area, for example, in connection to cancers of head and/or neck. In some embodiments, the compound of Formula (I) is (R)-5-((E)-2-pyrrolidin-3-ylvinyl)pyrimidine, or a pharmaceutically acceptable salt thereof.

Improved Ocular Discomfort

Provided herein, in some embodiments, is a method of improving ocular discomfort in a subject. In some embodiments, is a method of improving ocular discomfort, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and does not cross the blood-brain barrier in a pharmacologically relevant concentration. In some embodiments is method of improving ocular discomfort, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of improving ocular discomfort, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha3beta4. In some embodiments is method of improving ocular discomfort, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha4beta2. In some embodiments is method of improving ocular discomfort, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha7. In some embodiments is a method of improving ocular discomfort, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that is not systemically bioavailable, hi some embodiments is a method of improving ocular discomfort, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired psychoactive side effects. In some embodiments is a method of improving ocular discomfort, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired systemic side effects. In some embodiments is a method of improving ocular discomfort, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that produces a local effect. In some embodiments is a method of improving ocular discomfort, further comprising the local administration of one or more substances that prevent or facilitate the recovery of the nicotinic acetylcholine receptor from the desensitized state. In some embodiments is a method of improving ocular discomfort, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments, the compound of Formula (I) is (R)-5-((E)-2-pyrrolidin-3-ylvinyl)pyrimidine, or a pharmaceutically acceptable salt thereof.

In some embodiments of the method of improving ocular discomfort described herein, the compound of Formula (I), (II), (IIIa), or (IIIb) is (R)-5-((E)-2-pyrrolidin-3-ylvinyl)pyrimidine (or Compound 1). In some embodiments of the methods described herein, the compound of Formula (I), (II), (IIIa), or (IIIb) is (R)-5-((E)-2-pyrrolidin-3-ylvinyl)pyrimidine, or a pharmaceutically acceptable salt thereof. In some embodiments of the method of improving ocular discomfort described herein, the compound of Formula (I), (II), (IIIa), or (IIIb) is (R)-5-((E)-2-pyrrolidin-3-ylvinyl)pyrimidine as a free base. In some embodiments of the method of improving ocular discomfort described herein, the compound of Formula (I), (II), (IIIa), or (IIIb) is (R)-5-((E)-2-pyrrolidin-3-ylvinyl)pyrimidine citrate salt. In some embodiments of the method of improving ocular discomfort described herein, the compound of Formula (I), (II), (IIIa), or (IIIb) is (R)-5-((E)-2-pyrrolidin-3-ylvinyl)pyrimidine mono citrate salt. In some embodiments of the method of improving ocular discomfort described herein, the compound of Formula (I), (II), (IIIa), or (IIIb) is (R)-5-((E)-2-pyrrolidin-3-ylvinyl)pyrimidine HCl salt. In some embodiments of the method of improving ocular discomfort described herein, the compound of Formula (I), (II), (IIIa), or (IIIb) is (R)-5-((E)-2-pyrrolidin-3-ylvinyl)pyrimidine galactarate salt. In some embodiments of the method of improving ocular discomfort described herein, the compound of Formula (I), (II), (IIIa), or (IIIb) is (R)-5-((E)-2-pyrrolidin-3-ylvinyl)pyrimidine hemigalactarate salt. In some embodiments of the method of improving ocular discomfort described herein, the compound of Formula (I), (II), (IIIa), or (IIIb) is (R)-5-((E)-2-pyrrolidin-3-ylvinyl)pyrimidine hemigalactarate monohydrate. In some embodiments of the method described herein, the compound of Formula (I), (II), (IIIa), or (IIIb) is (R)-5-((E)-2-pyrrolidin-3-ylvinyl)pyrimidine hemigalactarate dihydrate.

In some embodiments is a method of improving ocular discomfort, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of improving ocular discomfort, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of improving ocular discomfort, further comprising the local administration of protein kinase C (PKC) or factors that upregulate or up-modulate PKC. In some embodiments is a method of improving ocular discomfort, further comprising the local administration of cAMP-dependent protein kinase (PKA) or factors that upregulate or up-modulate PKA. In some embodiments is a method of improving ocular discomfort, further comprising the local administration of a calcineurin inhibitor. In some embodiments is a method of improving ocular discomfort, further comprising the local administration of a calcineurin inhibitor, wherein the calcineurin inhibitor is selected from cyclosporine, pimecrolimus, and tacrolimus. In some embodiments is a method of improving ocular discomfort, further comprising the local administration of cyclosporine. In some embodiments is a method of improving ocular discomfort, further comprising the local administration of pimecrolimus. In some embodiments is a method of improving ocular discomfort, further comprising the local administration of tacrolimus.

In another embodiment of any of the aforementioned embodiments of improving ocular discomfort, the ocular discomfort is associated with dry eye disease. In another embodiment of any of the aforementioned embodiments of improving ocular discomfort, the ocular discomfort is associated with the symptoms of dry eye disease. In another embodiment of any of the aforementioned embodiments of improving ocular discomfort, the ocular discomfort is associated with the symptoms of dry eye disease, wherein the symptoms are selected from itchiness, dryness, photophobia, blurriness, pain, sticky feeling, burning, stinging, and foreign body sensation. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, the ocular discomfort is associated with blepharitis. In another embodiment of any of the aforementioned embodiments of improving ocular discomfort, the ocular discomfort is associated with meibomian gland dysfunction. In another embodiment of any of the aforementioned embodiments of improving ocular discomfort, the ocular discomfort is associated with allergic conjunctivitis. In another embodiment of any of the aforementioned embodiments of improving ocular discomfort, the ocular discomfort is associated with ocular surface toxicity and irritation. In another embodiment of any of the aforementioned embodiments of improving ocular discomfort, the ocular discomfort is associated with lacrimal drainage problems. In another embodiment of any of the aforementioned embodiments of improving ocular discomfort, the ocular discomfort is associated with eyelid disorders. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, the ocular discomfort is associated with an acute condition. An acute condition refers to a condition with a rapid onset of a health effect that is considered brief, not prolonged. Acute conditions can result from ophthalmologic surgical procedures or other ophthalmologic treatment, hi some embodiments, the ophthalmologic surgical procedure is cataract surgery (cataract extraction and lens replacement), refractive lens exchange, glaucoma surgery, lasik surgery (laser eye surgery), vitrectomy, retinal photocoagulation, retinal detachment repair, macular hole repair, retroiris tumor or mass removal, posterior sclerotomy, optic neurotomy, or other treatments that decrease the function of the lacrimal gland. In some embodiments, the ophthalmologic treatment comprises radiation therapy. In some embodiments, the radiation therapy is directed to orbital area, for example, in connection to cancers of head and/or neck. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, at least 1 microgram of the compound of Formula (I), (II), (IIIa), or (IIIb) is administered into the nasal cavity. In another embodiment of any of the aforementioned embodiments of improving ocular discomfort, at least 5 micrograms of the compound of Formula (I), (II), (IIIa), or (IIIb) is administered into the nasal cavity. In another embodiment of any of the aforementioned embodiments of improving ocular discomfort, at least 10 micrograms of the compound of Formula (I), (II), (IIIa), or (IIIb) is administered into the nasal cavity. In another embodiment of any of the aforementioned embodiments of improving ocular discomfort, at least 25 micrograms of the compound of Formula (I), (II), (IIIa), or (IIIb) is administered into the nasal cavity. In another embodiment of any of the aforementioned embodiments of improving ocular discomfort, at least 50 micrograms of the compound of Formula (I), (II), (IIIa), or (IIIb) is administered into the nasal cavity. In another embodiment of any of the aforementioned embodiments of improving ocular discomfort, at least 100 micrograms of the compound of Formula (I), (II), (IIIa), or (IIIb) is administered into the nasal cavity. In another embodiment of any of the aforementioned embodiments of improving ocular discomfort, at least 250 micrograms of the compound of Formula (I), (II), (IIIa), or (IIIb) is administered into the nasal cavity. In another embodiment of any of the aforementioned embodiments of improving ocular discomfort, at least 500 micrograms of the compound of Formula (I), (II), (IIIa), or (IIIb) is administered into the nasal cavity. In another embodiment of any of the aforementioned embodiments of improving ocular discomfort, at least 750 micrograms of the compound of Formula (I), (II), (IIIa), or (IIIb) is administered into the nasal cavity. In another embodiment of any of the aforementioned embodiments of improving ocular discomfort, at least 1000 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, between 1 microgram and 1000 micrograms of the compound of Formula (I), (II), (IIIa), or (IIIb) is administered into the nasal cavity. In another embodiment of any of the aforementioned embodiments of improving ocular discomfort, between 5 micrograms and 1000 micrograms of the compound of Formula (I), (II), (IIIa), or (IIIb) is administered into the nasal cavity. In another embodiment of any of the aforementioned embodiments of improving ocular discomfort, between 10 micrograms and 1000 micrograms of the compound of Formula (I), (II), (IIIa), or (IIIb) is administered into the nasal cavity. In another embodiment of any of the aforementioned embodiments of improving ocular discomfort, between 5 micrograms and 100 micrograms of the compound of Formula (I), (II), (IIIa), or (IIIb) is administered into the nasal cavity. In another embodiment of any of the aforementioned embodiments of improving ocular discomfort, between 5 micrograms and 50 micrograms of the compound of Formula (I), (II), (IIIa), or (IIIb) is administered into the nasal cavity. In another embodiment of any of the aforementioned embodiments of improving ocular discomfort, between 10 micrograms and 50 micrograms of the compound of Formula (I), (II), (IIIa), or (IIIb) is administered into the nasal cavity. In another embodiment of any of the aforementioned embodiments of improving ocular discomfort, between 25 micrograms and 1000 micrograms of the compound of Formula (I), (II), (IIIa), or (IIIb) is administered into the nasal cavity. In another embodiment of any of the aforementioned embodiments of improving ocular discomfort, between 50 micrograms and 1000 micrograms of the compound of Formula (I), (II), (IIIa), or (IIIb) is administered into the nasal cavity. In another embodiment of any of the aforementioned embodiments of improving ocular discomfort, between 100 micrograms and 1000 micrograms of the compound of Formula (I), (II), (IIIa), or (IIIb) is administered into the nasal cavity. In another embodiment of any of the aforementioned embodiments of improving ocular discomfort, between 150 micrograms and 1000 micrograms of the compound of Formula (I), (II), (IIIa), or (IIIb) is administered into the nasal cavity. In another embodiment of any of the aforementioned embodiments of improving ocular discomfort, between 100 micrograms and 750 micrograms of the compound of Formula (I), (II), (IIIa), or (IIIb) is administered into the nasal cavity. In another embodiment of any of the aforementioned embodiments of improving ocular discomfort, between 150 micrograms and 750 micrograms of the compound of Formula (I), (II), (IIIa), or (IIIb) is administered into the nasal cavity. In another embodiment of any of the aforementioned embodiments of improving ocular discomfort, between 150 micrograms and 600 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, less than 100 micrograms of a compound of Formula (I), (II), (IIIa), or (IIIb) is administered into the nasal cavity. In another embodiment of any of the aforementioned embodiments of improving ocular discomfort, less than 75 micrograms of a compound of Formula (I), (II), (IIIa), or (IIIb) is administered into the nasal cavity. In another embodiment of any of the aforementioned embodiments of improving ocular discomfort, less than 50 micrograms of a compound of Formula (I), (II), (IIIa), or (IIIb) is administered into the nasal cavity. In another embodiment of any of the aforementioned embodiments of improving ocular discomfort, less than 25 micrograms of a compound of Formula (I), (II), (IIIa), or (IIIb) is administered into the nasal cavity. In another embodiment of any of the aforementioned embodiments of improving ocular discomfort, less than 15 micrograms of a compound of Formula (I), (II), (IIIa), or (IIIb) is administered into the nasal cavity. In another embodiment of any of the aforementioned embodiments of improving ocular discomfort, about 75 micrograms of a compound of Formula (I), (II), (IIIa), or (IIIb) is administered into the nasal cavity. In another embodiment of any of the aforementioned embodiments of improving ocular discomfort, about 50 micrograms of a compound of Formula (I), (II), (IIIa), or (IIIb) is administered into the nasal cavity. In another embodiment of any of the aforementioned embodiments of improving ocular discomfort, about 25 micrograms of a compound of Formula (I), (II), (IIIa), or (IIIb) is administered into the nasal cavity. In another embodiment of any of the aforementioned embodiments of improving ocular discomfort, about 10 micrograms of a compound of Formula (I), (II), (IIIa), or (IIIb) is administered into the nasal cavity.

In another embodiment of any of the aforementioned embodiments of improving ocular discomfort, between 1 microgram and 100 micrograms of a compound of Formula (I), (II), (IIIa), or (IIIb) is administered into the nasal cavity. In another embodiment of any of the aforementioned embodiments of improving ocular discomfort, between 1 microgram and 75 micrograms of a compound of Formula (I), (II), (IIIa), or (IIIb) is administered into the nasal cavity. In another embodiment of any of the aforementioned embodiments of improving ocular discomfort, between 5 micrograms and 100 micrograms of a compound of Formula (I), (II), (IIIa), or (IIIb) is administered into the nasal cavity. In another embodiment of any of the aforementioned embodiments of improving ocular discomfort, between 5 micrograms and 75 micrograms of a compound of Formula (I), (II), (IIIa), or (IIIb) is administered into the nasal cavity. In another embodiment of any of the aforementioned embodiments of improving ocular discomfort, between 15 micrograms and 100 micrograms of a compound of Formula (I), (II), (IIIa), or (IIIb) is administered into the nasal cavity. In another embodiment of any of the aforementioned embodiments of improving ocular discomfort, between 15 micrograms and 75 micrograms of a compound of Formula (I), (II), (IIIa), or (IIIb) is administered into the nasal cavity. In another embodiment of any of the aforementioned embodiments of improving ocular discomfort, between 25 micrograms and 100 micrograms of a compound of Formula (I), (II), (IIIa), or (IIIb) is administered into the nasal cavity. In another embodiment of any of the aforementioned embodiments of improving ocular discomfort, between 25 micrograms and 75 micrograms of a compound of Formula (I), (II), (IIIa), or (IIIb) is administered into the nasal cavity. In another embodiment of any of the aforementioned embodiments of improving ocular discomfort, between 25 micrograms and 60 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, between 500 micrograms and 10 milligrams of a compound of Formula (I), (II), (IIIa), or (IIIb) is administered into the nasal cavity. In another embodiment of any of the aforementioned embodiments of improving ocular discomfort, between 500 micrograms and 5 milligrams of a compound of Formula (I), (II), (IIIa), or (IIIb) is administered into the nasal cavity. In another embodiment of any of the aforementioned embodiments of improving ocular discomfort, between 500 micrograms and 3 milligrams of a compound of Formula (I), (II), (IIIa), or (IIIb) is administered into the nasal cavity. In another embodiment of any of the aforementioned embodiments of improving ocular discomfort, between 500 micrograms and 2 milligrams of a compound of Formula (I), (II), (IIIa), or (IIIb) is administered into the nasal cavity. In another embodiment of any of the aforementioned embodiments of improving ocular discomfort, between 1 milligram and 10 milligrams of a compound of Formula (I), (II), (IIIa), or (IIIb) is administered into the nasal cavity. In another embodiment of any of the aforementioned embodiments of improving ocular discomfort, between 1 milligram and 5 milligrams of a compound of Formula (I), (II), (IIIa), or (IIIb) is administered into the nasal cavity. In another embodiment of any of the aforementioned embodiments of improving ocular discomfort, between 1 milligram and 3 milligrams of a compound of Formula (I), (II), (IIIa), or (IIIb) is administered into the nasal cavity. In another embodiment of any of the aforementioned embodiments of improving ocular discomfort, between 1 milligram and 2 milligrams of a compound of Formula (I), (II), (IIIa), or (IIIb) is administered into the nasal cavity. In another embodiment of any of the aforementioned embodiments of improving ocular discomfort, about 500 micrograms of a compound of Formula (I), (II), (IIIa), or (IIIb) is administered into the nasal cavity. In another embodiment of any of the aforementioned embodiments of improving ocular discomfort, about 1 milligram of a compound of Formula (I), (II), (IIIa), or (IIIb) is administered into the nasal cavity. In another embodiment of any of the aforementioned embodiments of improving ocular discomfort, about 1.5 milligrams of a compound of Formula (I), (II), (IIIa), or (IIIb) is administered into the nasal cavity. In another embodiment of any of the aforementioned embodiments of improving ocular discomfort, about 2 milligrams of a compound of Formula (I), (II), (IIIa), or (IIIb) is administered into the nasal cavity. In another embodiment of any of the aforementioned embodiments of improving ocular discomfort, about 2.5 milligrams of a compound of Formula (I), (II), (IIIa), or (IIIb) is administered into the nasal cavity. In another embodiment of any of the aforementioned embodiments of improving ocular discomfort, about 3 milligrams of a compound of Formula (I), (II), (IIIa), or (IIIb) is administered into the nasal cavity. In another embodiment of any of the aforementioned embodiments of improving ocular discomfort, about 4 milligrams of a compound of Formula (I), (II), (IIIa), or (IIIb) is administered into the nasal cavity. In another embodiment of any of the aforementioned embodiments of improving ocular discomfort, about 5 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, between 1 microgram and 10 milligrams of a compound of Formula (I), (II), (IIIa), or (IIIb) is administered into the nasal cavity. In another embodiment of any of the aforementioned embodiments of improving ocular discomfort, between 5 micrograms and 10 milligrams of a compound of Formula (I), (II), (IIIa), or (IIIb) is administered into the nasal cavity. In another embodiment of any of the aforementioned embodiments of improving ocular discomfort, between 10 micrograms and 10 milligrams of a compound of Formula (I), (II), (IIIa), or (IIIb) is administered into the nasal cavity. In another embodiment of any of the aforementioned embodiments of improving ocular discomfort, between 25 micrograms and 10 milligrams of a compound of Formula (I), (II), (IIIa), or (IIIb) is administered into the nasal cavity. In another embodiment of any of the aforementioned embodiments of improving ocular discomfort, between 50 micrograms and 10 milligrams of a compound of Formula (I), (II), (IIIa), or (IIIb) is administered into the nasal cavity. In another embodiment of any of the aforementioned embodiments of improving ocular discomfort, between 100 micrograms and 10 milligrams of a compound of Formula (I), (II), (IIIa), or (IIIb) is administered into the nasal cavity. In another embodiment of any of the aforementioned embodiments of improving ocular discomfort, between 150 micrograms and 10 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, between 1 microgram and 10 milligrams of a compound of Formula (I), (II), (IIIa), or (IIIb) is administered into the nasal cavity. In another embodiment of any of the aforementioned embodiments of improving ocular discomfort, between 1 microgram and 5 milligrams of a compound of Formula (I), (II), (IIIa), or (IIIb) is administered into the nasal cavity. In another embodiment of any of the aforementioned embodiments of improving ocular discomfort, between 1 microgram and 4 milligrams of a compound of Formula (I), (I), (IIIa), or (IIIb) is administered into the nasal cavity. In another embodiment of any of the aforementioned embodiments of improving ocular discomfort, between 1 microgram and 3 milligrams of a compound of Formula (I), (II), (IIIa), or (IIIb) is administered into the nasal cavity. In another embodiment of any of the aforementioned embodiments of improving ocular discomfort, between 1 microgram and 2 milligrams of a compound of Formula (I), (II), (IIIa), or (IIIb) is administered into the nasal cavity. In another embodiment of any of the aforementioned embodiments of improving ocular discomfort, between 1 microgram and 1 milligrams of a compound of Formula (I), (II), (IIIa), or (IIIb) is administered into the nasal cavity. In another embodiment of any of the aforementioned embodiments of improving ocular discomfort, between 1 microgram and 750 micrograms of a compound of Formula (I), (II), (IIIa), or (IIIb) is administered into the nasal cavity. In another embodiment of any of the aforementioned embodiments of improving ocular discomfort, between 1 microgram and 600 micrograms of a compound of Formula (I), (II), (IIIa), or (IIIb) is administered into the nasal cavity. In another embodiment of any of the aforementioned embodiments of improving ocular discomfort, between 1 microgram and 100 micrograms of a compound of Formula (I), (II), (IIIa), or (IIIb) is administered into the nasal cavity. In another embodiment of any of the aforementioned embodiments of improving ocular discomfort, between 1 microgram and 50 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method comprises about 0.1 mg/mL of a compound of Formula (I), (II), (IIIa), or (IIIb). In another embodiment, the pharmaceutical formulation for use in the method comprises about 0.2 mg/mL of a compound of Formula (I), (II), (IIIa), or (IIIb). In another embodiment, the pharmaceutical formulation for use in the method comprises about 0.5 mg/mL of a compound of Formula (I), (II), (IIIa), or (IIIb). In another embodiment, the pharmaceutical formulation for use in the method comprises about 1 mg/mL of a compound of Formula (I), (II), (IIIa), or (IIIb). In another embodiment, the pharmaceutical formulation for use in the method comprises about 2 mg/mL of a compound of Formula (I), (II), (IIIa), or (IIIb). In another embodiment, the pharmaceutical formulation for use in the method comprises about 3 mg/mL of a compound of Formula (I), (II), (IIIa), or (IIIb). In another embodiment, the pharmaceutical formulation for use in the method comprises about 4 mg/mL of a compound of Formula (I), (II), (IIIa), or (IIIb). In another embodiment, the pharmaceutical formulation for use in the method comprises about 5 mg/m L of a compound of Formula (I), (II), (IIIa), or (IIIb). In another embodiment, the pharmaceutical formulation for use in the method comprises about 6 mg/mL of a compound of Formula (I), (II), (IIIa), or (IIIb). In another embodiment, the pharmaceutical formulation for use in the method comprises about 7 mg/mL of a compound of Formula (I), (II), (IIIa), or (IIIb). In another embodiment, the pharmaceutical formulation for use in the method comprises about 8 mg/mL of a compound of Formula (I), (II), (IIIa), or (IIIb). In another embodiment, the pharmaceutical formulation for use in the method comprises about 9 mg/mL of a compound of Formula (I), (II), (IIIa), or (IIIb). In another embodiment, the pharmaceutical formulation for use in the method comprises about 10 mg/mL of a compound of Formula (I), (II), (IIIa), or (IIIb). In another embodiment, the pharmaceutical formulation for use in the method comprises about 12 mg/ml, of a compound of Formula (I), (II), (IIIa), or (IIIb). In another embodiment, the pharmaceutical formulation for use in the method comprises about 15 mg/mL of a compound of Formula (I), (II), (IIIa), or (IIIb). In another embodiment, the pharmaceutical formulation for use in the method comprises about 20 mg/mL of a compound of Formula (I), (II), (IIIa), or (IIIb). In another embodiment, the pharmaceutical formulation for use in the method comprises about 25 mg/mL of a compound of Formula (I), (II), (IIIa), or (IIIb). In another embodiment, the pharmaceutical formulation for use in the method comprises about 30 mg/mL of a compound of Formula (I), (II), (IIIa), or (IIIb). In another embodiment, the pharmaceutical formulation for use in the method comprises about 40 mg/mL of a compound of Formula (I), (II), (IIIa), or (IIIb). In another embodiment, the pharmaceutical formulation for use in the method comprises about 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 5 mg/mL and 200 mg/mL of a compound of Formula (I), (II), (IIIa), or (IIIb). In another embodiment, the pharmaceutical formulation for use in the method comprises between 10 mg/mL and 200 mg/mL of a compound of Formula (I), (II), (IIIa), or (IIIb). In another embodiment, the pharmaceutical formulation for use in the method comprises between 5 mg/mL and 100 mg/mL of a compound of Formula (I), (II), (IIIa), or (IIIb). In another embodiment, the pharmaceutical formulation for use in the method comprises between 10 mg/mL and 75 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 10 mg/mL and 30 mg/mL of a compound of Formula (I), (II), (IIIa), or (IIIb). In another embodiment, the pharmaceutical formulation for use in the method comprises between 5 mg/mL and 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 10 mg/mL and 25 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 20 mg/mL and 50 mg/mL of a compound of Formula (I), (II), (IIIa), or (IIIb). In another embodiment, the pharmaceutical formulation for use in the method comprises between 30 mg/mL and 75 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method is provided at about 10 to 200 µl. In another embodiment, the pharmaceutical formulation for use in the method is provided at about 10 to 150 µl. In another embodiment, the pharmaceutical formulation for use in the method is provided at about 10 to 100 µl. In another embodiment, the pharmaceutical formulation for use in the method is provided at about 50 to 200 µl. In another embodiment, the pharmaceutical formulation for use in the method is provided at about 100 to 200 µl. In another embodiment, the pharmaceutical formulation for use in the method is provided at about 50 to 100 µl. In another embodiment, the pharmaceutical formulation for use in the method is provided at about 10 to 150 µl. In another embodiment, the pharmaceutical formulation for use in the method is provided at about 10, 20, 30, 40, 50, 60, 70, 80, 90, 100, 110, 120, 130, 140, 150, 160, 170, 180, 190, or 200 µl. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, the compound of Formula (I), (II), (IIIa), or (IIIb) is administered once daily. In another embodiment of any of the aforementioned embodiments of improving ocular discomfort, the compound of Formula (I), (II), (IIIa), or (IIIb) is administered at least once daily. In another embodiment of any of the aforementioned embodiments of improving ocular discomfort, the compound of Formula (I), (II), (IIIa), or (IIIb) is administered twice daily. In another embodiment of any of the aforementioned embodiments of improving ocular discomfort, the compound of Formula (I), (II), (IIIa), or (IIIb) is administered at least twice daily. In another embodiment of any of the aforementioned embodiments of improving ocular discomfort, the compound of Formula (I), (II), (IIIa), or (IIIb) is administered three times daily. In another embodiment of any of the aforementioned embodiments of improving ocular discomfort, the compound of Formula (I), (II), (IIIa), or (IIIb) is administered at least three times daily. In another embodiment of any of the aforementioned embodiments of improving ocular discomfort, the compound of Formula (I), (II), (IIIa), or (IIIb) is administered for one day. In another embodiment of any of the aforementioned embodiments of improving ocular discomfort, the compound of Formula (I), (II), (IIIa), or (IIIb) is administered for at least two days. In another embodiment of any of the aforementioned embodiments of improving ocular discomfort, the compound of Formula (I), (II), (IIIa), or (IIIb) is administered for at least three days. In another embodiment of any of the aforementioned embodiments of improving ocular discomfort, the compound of Formula (I), (II), (IIIa), or (IIIb) is administered for at least four days. In another embodiment of any of the aforementioned embodiments of improving ocular discomfort, the compound of Formula (I), (II), (IIIa), or (IIIb) is administered for at least five days. In another embodiment of any of the aforementioned embodiments of improving ocular discomfort, the compound of Formula (I), (II), (IIIa), or (IIIb) is administered for at least seven days. In another embodiment of any of the aforementioned embodiments of improving ocular discomfort, the compound of Formula (I), (II), (IIIa), or (IIIb) is administered for at least ten days. In another embodiment of any of the aforementioned embodiments of improving ocular discomfort, the compound of Formula (I), (II), (IIIa), or (IIIb) is administered for at least fourteen days In another embodiment of any of the aforementioned embodiments of improving ocular discomfort, the compound of Formula (I), (II), (IIIa), or (IIIb) is administered for at least twenty one days. In another embodiment of any of the aforementioned embodiments of improving ocular discomfort, the compound of Formula (I), (II), (IIIa), or (IIIb) is administered for at least thirty days. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, the compound of Formula (I), (II), (IIIa), or (IIIb) is administered in alternating nostrils. For example, the compound of Formula (I), (II), (IIIa), or (IIIb) is administered in one nostril and then the other nostril after a pre-determined amount of time. In another embodiment, the compound of Formula (I), (II), (IIIa), or (IIIb) is administered in both nostrils. For example, the compound of Formula (I), (II), (IIIa), or (IIIb) is administered in one nostril and then the other nostril at the same time or immediately after the first nostril. In another embodiment, the compound of Formula (I), (II), (IIIa), or (IIIb) is administered in one nostril. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, the compound of Formula (I), (II), (IIIa), or (IIIb) is administered into the nasal cavity as a liquid, suspension, aerosol, gel, ointment, dry powder, cream, paste, lotion, or balm. In another embodiment of any of the aforementioned embodiments of improving ocular discomfort, the compound of Formula (I), (II), (IIIa), or (IIIb) is administered into the nasal cavity as a liquid. In another embodiment of any of the aforementioned embodiments of improving ocular discomfort, the compound of Formula (I), (II), (IIIa), or (IIIb) is administered into the nasal cavity as a suspension. In another embodiment of any of the aforementioned embodiments of improving ocular discomfort, the compound of Formula (I), (II), (IIIa), or (IIIb) is administered into the nasal cavity as an aerosol. In another embodiment of any of the aforementioned embodiments of improving ocular discomfort, the compound of Formula (I), (II), (IIIa), or (IIIb) is administered into the nasal cavity as a gel. In another embodiment of any of the aforementioned embodiments of improving ocular discomfort, the compound of Formula (I), (II), (IIIa), or (IIIb) is administered into the nasal cavity as an ointment. In another embodiment of any of the aforementioned embodiments of improving ocular discomfort, the compound of Formula (I), (II), (IIIa), or (IIIb) is administered into the nasal cavity as a dry powder. In another embodiment of any of the aforementioned embodiments of improving ocular discomfort, the compound of Formula (I), (II), (IIIa), or (IIIb) is administered into the nasal cavity as a cream. In another embodiment of any of the aforementioned embodiments of improving ocular discomfort, the compound of Formula (I), (II), (IIIa), or (IIIb) is administered into the nasal cavity as a paste. In another embodiment of any of the aforementioned embodiments of improving ocular discomfort, the compound of Formula (I), (II), (IIIa), or (IIIb) is administered into the nasal cavity as a lotion. In another embodiment of any of the aforementioned embodiments of improving ocular discomfort, the compound of Formula (I), (II), (IIIa), or (IIIb) is administered into the nasal cavity as a balm. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, the compound of Formula (I), (II), (IIIa), or (IIIb) is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of improving ocular discomfort, the compound of Formula (I), (II), (IIIa), or (IIIb) is administered into the nasal cavity by a syringe. In another embodiment of any of the aforementioned embodiments of improving ocular discomfort, the compound of Formula (I), (II), (IIIa), or (IIIb) is administered into the nasal cavity by a dropper. In another embodiment of any of the aforementioned embodiments of improving ocular discomfort, the compound of Formula (I), (II), (IIIa), or (IIIb) is administered into the nasal cavity by a bottle nebulizer. In another embodiment of any of the aforementioned embodiments of improving ocular discomfort, the compound of Formula (I), (II), (IIIa), or (IIIb) is administered into the nasal cavity by an atomization pump. In another embodiment of any of the aforementioned embodiments of improving ocular discomfort, the compound of Formula (I), (II), (IIIa), or (IIIb) is administered into the nasal cavity by an inhaler. In another embodiment of any of the aforementioned embodiments of improving ocular discomfort, the compound of Formula (I), (II), (IIIa), or (IIIb) is administered into the nasal cavity by a powder spray device.

In another embodiment of any of the aforementioned embodiments of improving ocular discomfort, the compound of Formula (I), (II), (IIIa), or (IIIb) is administered into the nasal cavity by a vaporizer. In another embodiment of any of the aforementioned embodiments of improving ocular discomfort, the compound of Formula (I), (II), (IIIa), or (IIIb) is administered into the nasal cavity by a patch. In another embodiment of any of the aforementioned embodiments of improving ocular discomfort, the compound of Formula (I), (II), (IIIa), or (IIIb) is administered into the nasal cavity by a medicated stick. In another embodiment of any of the aforementioned embodiments of improving ocular discomfort, the compound of Formula (I), (II), (IIIa), or (IIIb) is administered into the nasal cavity by a pipette. In another embodiment of any of the aforementioned embodiments of improving ocular discomfort, the compound of Formula (I), (II), (IIIa), or (IIIb) is administered into the nasal cavity by a jet of liquid. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular discomfort, the trigeminal nerve is activated. In a further embodiment of improving ocular discomfort, the anterior ethmoidal nerve is activated. In another embodiment of any of the aforementioned embodiments of improving ocular discomfort, the nasolacrimal reflex is activated. In some embodiments, the compound of Formula (I) is (R)-5-((E)-2-pyrrolidin-3-ylvinyl)pyrimidine, or a pharmaceutically acceptable salt thereof.

Improved Ocular Surface Health

Provided herein, in some embodiments, is a method of improving ocular surface health in a subject. In some embodiments, is a method of improving ocular surface health, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and does not cross the blood-brain barrier in a pharmacologically relevant concentration. In some embodiments is method of improving ocular surface health, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of improving ocular surface health, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha3beta4. In some embodiments is method of improving ocular surface health, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha4beta2. In some embodiments is method of improving ocular surface health, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha7. In some embodiments is a method of improving ocular surface health, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that is not systemically bioavailable. In some embodiments is a method of improving ocular surface health, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired psychoactive side effects. In some embodiments is a method of improving ocular surface health, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired systemic side effects. In some embodiments is a method of improving ocular surface health, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that produces a local effect. In some embodiments is a method of improving ocular surface health, further comprising the local administration of one or more substances that prevent or facilitate the recovery of the nicotinic acetylcholine receptor from the desensitized state. In some embodiments is a method of improving ocular surface health, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments, the compound of Formula (I) is (R)-5-((E)-2-pyrrolidin-3-ylvinyl)pyrimidine, or a pharmaceutically acceptable salt thereof.

In some embodiments of the method of improving ocular surface health described herein, the compound of Formula (I), (II), (IIIa), or (IIIb) is (R)-5-((E)-2-pyrrolidin-3-ylvinyl)pyrimidine (or Compound 1). In some embodiments of the methods described herein, the compound of Formula (I), (II), (IIIa), or (IIIb) is (R)-5-((E)-2-pyrrolidin-3-ylvinyl)pyrimidine, or a pharmaceutically acceptable salt thereof. In some embodiments of the method of improving ocular surface health described herein, the compound of Formula (I), (II), (IIIa), or (IIIb) is (R)-5-((E)-2-pyrrolidin-3-ylvinyl)pyrimidine as a free base. In some embodiments of the method of improving ocular surface health described herein, the compound of Formula (I), (II), (IIIa), or (IIIb) is (R)-5-((E)-2-pyrrolidin-3-ylvinyl)pyrimidine citrate salt. In some embodiments of the method of improving ocular surface health described herein, the compound of Formula (I), (II), (IIIa), or (IIIb) is (R)-5-((E)-2-pyrrolidin-3-ylvinyl)pyrimidine mono citrate salt. In some embodiments of the method of improving ocular surface health described herein, the compound of Formula (I), (II), (IIIa), or (IIIb) is (R)-5-((E)-2-pyrrolidin-3-ylvinyl)pyrimidine HCl salt. In some embodiments of the method of improving ocular surface health described herein, the compound of Formula (I), (II), (IIIa), or (IIIb) is (R)-5-((E)-2-pyrrolidin-3-ylvinyl)pyrimidine galactarate salt. In some embodiments of the method of improving ocular surface health described herein, the compound of Formula (I), (II), (IIIa), or (IIIb) is (R)-5-((E)-2-pyrrolidin-3-ylvinyl)pyrimidine hemigalactarate salt. In some embodiments of the method of improving ocular surface health described herein, the compound of Formula (I), (II), (IIIa), or (IIIb) is (R)-5-((E)-2-pyrrolidin-3-ylvinyl)pyrimidine hemigalactarate monohydrate. In some embodiments, the compound of Formula (I) is (R)-5-((E)-2-pyrrolidin-3-ylvinyl)pyrimidine, or a pharmaceutically acceptable salt thereof. In some embodiments of the method described herein, the compound of Formula (I), (II), (IIIa), or (IIIb) is (R)-5-((E)-2-pyrrolidin-3-ylvinyl)pyrimidine hemigalactarate dihydrate.

In some embodiments is a method of improving ocular surface health, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of improving ocular surface health, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of improving ocular surface health, further comprising the local administration of protein kinase C (PKC) or factors that upregulate or up-modulate PKC. In some embodiments is a method of improving ocular surface health, further comprising the local administration of cAMP-dependent protein kinase (PKA) or factors that upregulate or up-modulate PKA. In some embodiments is a method of improving ocular surface health, further comprising the local administration of a calcineurin inhibitor. In some embodiments is a method of improving ocular surface health, further comprising the local administration of a calcineurin inhibitor, wherein the calcineurin inhibitor is selected from cyclosporine, pimecrolimus, and tacrolimus. In some embodiments is a method of improving ocular surface health, further comprising the local administration of cyclosporine. In some embodiments is a method of improving ocular surface health, further comprising the local administration of pimecrolimus. In some embodiments is a method of improving ocular surface health, further comprising the local administration of tacrolimus. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, at least 1 microgram of the compound of Formula (I), (II), (IIIa), or (IIIb) is administered into the nasal cavity. In another embodiment of any of the aforementioned embodiments of improving ocular surface health, at least 5 micrograms of the compound of Formula (I), (II), (IIIa), or (IIIb) is administered into the nasal cavity. In another embodiment of any of the aforementioned embodiments of improving ocular surface health, at least 10 micrograms of the compound of Formula (I), (II), (IIIa), or (IIIb) is administered into the nasal cavity. In another embodiment of any of the aforementioned embodiments of improving ocular surface health, at least 25 micrograms of the compound of Formula (I), (II), (IIIa), or (IIIb) is administered into the nasal cavity. In another embodiment of any of the aforementioned embodiments of improving ocular surface health, at least 50 micrograms of the compound of Formula (I), (II), (IIIa), or (IIIb) is administered into the nasal cavity. In another embodiment of any of the aforementioned embodiments of improving ocular surface health, at least 100 micrograms of the compound of Formula (I), (II), (IIIa), or (IIIb) is administered into the nasal cavity. In another embodiment of any of the aforementioned embodiments of improving ocular surface health, at least 250 micrograms of the compound of Formula (I), (II), (IIIa), or (IIIb) is administered into the nasal cavity. In another embodiment of any of the aforementioned embodiments of improving ocular surface health, at least 500 micrograms of the compound of Formula (I), (II), (IIIa), or (IIIb) is administered into the nasal cavity. In another embodiment of any of the aforementioned embodiments of improving ocular surface health, at least 750 micrograms of the compound of Formula (I), (II), (IIIa), or (IIIb) is administered into the nasal cavity. In another embodiment of any of the aforementioned embodiments of improving ocular surface health, at least 1000 micrograms of the compound of Formula (I), (II), (IIIa), or (IIIb) is administered into the nasal cavity. In some embodiments, the compound of Formula (I) is (R)-5-((E)-2-pyrolidin-3-ylvinyl)pyrimidine, or a pharmaceutically acceptable salt thereof.

In another embodiment of any of the aforementioned embodiments of improving ocular surface health, between 1 microgram and 1000 micrograms of the compound of Formula (I), (II), (IIIa), or (IIIb) is administered into the nasal cavity. In another embodiment of any of the aforementioned embodiments of improving ocular surface health, between 5 micrograms and 1000 micrograms of the compound of Formula (I), (II), (IIIa), or (IIIb) is administered into the nasal cavity. In another embodiment of any of the aforementioned embodiments of improving ocular surface health, between 10 micrograms and 1000 micrograms of the compound of Formula (I), (II), (IIIa), or (IIIb) is administered into the nasal cavity. In another embodiment of any of the aforementioned embodiments of improving ocular surface health, between 5 micrograms and 100 micrograms of the compound of Formula (I), (II), (IIIa), or (IIIb) is administered into the nasal cavity. In another embodiment of any of the aforementioned embodiments of improving ocular surface health, between 5 micrograms and 50 micrograms of the compound of Formula (I), (II), (IIIa), or (IIIb) is administered into the nasal cavity. In another embodiment of any of the aforementioned embodiments of improving ocular surface health, between 10 micrograms and 50 micrograms of the compound of Formula (I), (II), (IIIa), or (IIIb) is administered into the nasal cavity. In another embodiment of any of the aforementioned embodiments of improving ocular surface health, between 25 micrograms and 1000 micrograms of the compound of Formula (I), (II), (IIIa), or (IIIb) is administered into the nasal cavity. In another embodiment of any of the aforementioned embodiments of improving ocular surface health, between 50 micrograms and 1000 micrograms of the compound of Formula (I), (II), (IIIa), or (IIIb) is administered into the nasal cavity. In another embodiment of any of the aforementioned embodiments of improving ocular surface health, between 100 micrograms and 1000 micrograms of the compound of Formula (I), (II), (IIIa), or (IIIb) is administered into the nasal cavity. In another embodiment of any of the aforementioned embodiments of improving ocular surface health, between 150 micrograms and 1000 micrograms of the compound of Formula (I), (II), (IIIa), or (IIIb) is administered into the nasal cavity. In another embodiment of any of the aforementioned embodiments of improving ocular surface health, between 100 micrograms and 750 micrograms of the compound of Formula (I), (II), (IIIa), or (IIIb) is administered into the nasal cavity. In another embodiment of any of the aforementioned embodiments of improving ocular surface health, between 150 micrograms and 750 micrograms of the compound of Formula (I), (II), (IIIa), or (IIIb) is administered into the nasal cavity. In another embodiment of any of the aforementioned embodiments of improving ocular surface health, between 150 micrograms and 600 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, less than 100 micrograms of a compound of Formula (I), (II), (IIIa), or (IIIb) is administered into the nasal cavity. In another embodiment of any of the aforementioned embodiments of improving ocular surface health, less than 75 micrograms of a compound of Formula (I), (II), (IIIa), or (IIIb) is administered into the nasal cavity. In another embodiment of any of the aforementioned embodiments of improving ocular surface health, less than 50 micrograms of a compound of Formula (I), (II), (IIIa), or (IIIb) is administered into the nasal cavity. In another embodiment of any of the aforementioned embodiments of improving ocular surface health, less than 25 micrograms of a compound of Formula (I), (II), (IIIa), or (IIIb) is administered into the nasal cavity. In another embodiment of any of the aforementioned embodiments of improving ocular surface health, less than 15 micrograms of a compound of Formula (I), (II), (IIIa), or (IIIb) is administered into the nasal cavity. In another embodiment of any of the aforementioned embodiments of improving ocular surface health, about 75 micrograms of a compound of Formula (I), (II), (IIIa), or (IIIb) is administered into the nasal cavity. In another embodiment of any of the aforementioned embodiments of improving ocular surface health, about 50 micrograms of a compound of Formula (I), (II), (IIIa), or (IIIb) is administered into the nasal cavity. In another embodiment of any of the aforementioned embodiments of improving ocular surface health, about 25 micrograms of a compound of Formula (I), (II), (IIIa), or (IIIb) is administered into the nasal cavity. In another embodiment of any of the aforementioned embodiments of improving ocular surface health, about 10 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, between 1 microgram and 100 micrograms of a compound of Formula (II) (II), (IIIa), or (IIIb) is administered into the nasal cavity. In another embodiment of any of the aforementioned embodiments of improving ocular surface health, between 1 microgram and 75 micrograms of a compound of Formula (I), (II), (IIIa), or (IIIb) is administered into the nasal cavity. In another embodiment of any of the aforementioned embodiments of improving ocular surface health, between 5 micrograms and 100 micrograms of a compound of Formula (I), (II), (IIIa), or (IIIb) is administered into the nasal cavity. In another embodiment of any of the aforementioned embodiments of improving ocular surface health, between 5 micrograms and 75 micrograms of a compound of Formula (I), (II), (IIIa), or (IIIb) is administered into the nasal cavity. In another embodiment of any of the aforementioned embodiments of improving ocular surface health, between 15 micrograms and 100 micrograms of a compound of Formula (I), (II), (IIIa), or (IIIb) is administered into the nasal cavity. In another embodiment of any of the aforementioned embodiments of improving ocular surface health, between 15 micrograms and 75 micrograms of a compound of Formula (I), (II), (IIIa), or (IIIb) is administered into the nasal cavity. In another embodiment of any of the aforementioned embodiments of improving ocular surface health, between 25 micrograms and 100 micrograms of a compound of Formula (I), (II), (IIIa), or (IIIb) is administered into the nasal cavity. In another embodiment of any of the aforementioned embodiments of improving ocular surface health, between 25 micrograms and 75 micrograms of a compound of Formula (I), (II), (IIIa), or (IIIb) is administered into the nasal cavity. In another embodiment of any of the aforementioned embodiments of improving ocular surface health, between 25 micrograms and 60 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, between 500 micrograms and 10 milligrams of a compound of Formula (I), (II), (IIIa), or (IIIb) is administered into the nasal cavity. In another embodiment of any of the aforementioned embodiments of improving ocular surface health, between 500 micrograms and 5 milligrams of a compound of Formula (I), (II), (IIIa), or (IIIb) is administered into the nasal cavity. In another embodiment of any of the aforementioned embodiments of improving ocular surface health, between 500 micrograms and 3 milligrams of a compound of Formula (I), (II), (IIIa), or (IIIb) is administered into the nasal cavity. In another embodiment of any of the aforementioned embodiments of improving ocular surface health, between 500 micrograms and 2 milligrams of a compound of Formula (I), (II), (IIIa), or (IIIb) is administered into the nasal cavity. In another embodiment of any of the aforementioned embodiments of improving ocular surface health, between 1 milligram and 10 milligrams of a compound of Formula (I), (II), (IIIa), or (IIIb) is administered into the nasal cavity. In another embodiment of any of the aforementioned embodiments of improving ocular surface health, between 1 milligram and 5 milligrams of a compound of Formula (I), (II), (IIIa), or (IIIb) is administered into the nasal cavity. In another embodiment of any of the aforementioned embodiments of improving ocular surface health, between 1 milligram and 3 milligrams of a compound of Formula (I), (II), (IIIa), or (IIIb) is administered into the nasal cavity. In another embodiment of any of the aforementioned embodiments of improving ocular surface health, between 1 milligram and 2 milligrams of a compound of Formula (I), (II), (IIIa), or (IIIb) is administered into the nasal cavity. In another embodiment of any of the aforementioned embodiments of improving ocular surface health, about 500 micrograms of a compound of Formula (I), (II), (IIIa), or (IIIb) is administered into the nasal cavity. In another embodiment of any of the aforementioned embodiments of improving ocular surface health, about 1 milligram of a compound of Formula (I), (II), (IIIa), or (Iib) is administered into the nasal cavity. In another embodiment of any of the aforementioned embodiments of improving ocular surface health, about 1.5 milligrams of a compound of Formula (I), (II), (IIIa), or (IIIb) is administered into the nasal cavity. In another embodiment of any of the aforementioned embodiments of improving ocular surface health, about 2 milligrams of a compound of Formula (I), (II), (IIIa), or (IIIb) is administered into the nasal cavity. In another embodiment of any of the aforementioned embodiments of improving ocular surface health, about 2.5 milligrams of a compound of Formula (I), (II), (IIIa), or (IIIb) is administered into the nasal cavity. In another embodiment of any of the aforementioned embodiments of improving ocular surface health, about 3 milligrams of a compound of Formula (I), (II), (IIIa), or (IIIb) is administered into the nasal cavity. In another embodiment of any of the aforementioned embodiments of improving ocular surface health, about 4 milligrams of a compound of Formula (I), (II), (IIIa), or (IIIb) is administered into the nasal cavity. In another embodiment of any of the aforementioned embodiments of improving ocular surface health, about 5 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, between 1 microgram and 10 milligrams of a compound of Formula (I), (II), (IIIa), or (IIIb) is administered into the nasal cavity. In another embodiment of any of the aforementioned embodiments of improving ocular surface health, between 5 micrograms and 10 milligrams of a compound of Formula (I), (II), (IIIa), or (IIIb) is administered into the nasal cavity. In another embodiment of any of the aforementioned embodiments of improving ocular surface health, between 10 micrograms and 10 milligrams of a compound of Formula (I), (II), (IIIa), or (IIIb) is administered into the nasal cavity. In another embodiment of any of the aforementioned embodiments of improving ocular surface health, between 25 micrograms and 10 milligrams of a compound of Formula (I), (II), (IIIa), or (IIIb) is administered into the nasal cavity. In another embodiment of any of the aforementioned embodiments of improving ocular surface health, between 50 micrograms and 10 milligrams of a compound of Formula (I), (II), (IIIa), or (IIIb) is administered into the nasal cavity. In another embodiment of any of the aforementioned embodiments of improving ocular surface health, between 100 micrograms and 10 milligrams of a compound of Formula (I), (II), (IIIa), or (IIIb) is administered into the nasal cavity. In another embodiment of any of the aforementioned embodiments of improving ocular surface health, between 150 micrograms and 10 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, between 1 microgram and 10 milligrams of a compound of Formula (I), (II), (IIIa), or (IIIb) is administered into the nasal cavity. In another embodiment of any of the aforementioned embodiments of improving ocular surface health, between 1 microgram and 5 milligrams of a compound of Formula (I), (II), (IIIa), or (IIIb) is administered into the nasal cavity. In another embodiment of any of the aforementioned embodiments of improving ocular surface health, between 1 microgram and 4 milligrams of a compound of Formula (I), (II), (IIIa), or (IIIb) is administered into the nasal cavity. In another embodiment of any of the aforementioned embodiments of improving ocular surface health, between 1 microgram and 3 milligrams of a compound of Formula (I), (II), (IIIa), or (IIIb) is administered into the nasal cavity. In another embodiment of any of the aforementioned embodiments of improving ocular surface health, between 1 microgram and 2 milligrams of a compound of Formula (I), (II), (IIIa), or (IIIb) is administered into the nasal cavity. In another embodiment of any of the aforementioned embodiments of improving ocular surface health, between 1 microgram and 1 milligrams of a compound of Formula (I), (II), (IIIa), or (IIIb) is administered into the nasal cavity. In another embodiment of any of the aforementioned embodiments of improving ocular surface health, between 1 microgram and 750 micrograms of a compound of Formula (I), (II), (IIIa), or (IIIb) is administered into the nasal cavity. In another embodiment of any of the aforementioned embodiments of improving ocular surface health, between 1 microgram and 600 micrograms of a compound of Formula (I), (II), (IIIa), or (IIIb) is administered into the nasal cavity. In another embodiment of any of the aforementioned embodiments of improving ocular surface health, between 1 microgram and 100 micrograms of a compound of Formula (I), (II), (IIIa), or (IIIb) is administered into the nasal cavity. In another embodiment of any of the aforementioned embodiments of improving ocular surface health, between 1 microgram and 50 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method comprises about 0.1 mg/mL of a compound of Formula (I), (II), (IIIa), or (IIIb). In another embodiment, the pharmaceutical formulation for use in the method comprises about 0.2 mg/mL of a compound of Formula (I), (II), (IIIa), or (IIIb). In another embodiment, the pharmaceutical formulation for use in the method comprises about 0.5 mg/mL of a compound of Formula (I), (II), (IIIa), or (IIIb). In another embodiment, the pharmaceutical formulation for use in the method comprises about 1 mg/mL of a compound of Formula (I), (II), (IIIa), or (IIIb). In another embodiment, the pharmaceutical formulation for use in the method comprises about 2 mg/m L of a compound of Formula (I), (II), (IIIa), or (IIIb). In another embodiment, the pharmaceutical formulation for use in the method comprises about 3 mg/mL of a compound of Formula (I), (II), (IIIa), or (IIIb). In another embodiment, the pharmaceutical formulation for use in the method comprises about 4 mg/mL of a compound of Formula (I), (II), (IIIa), or (IIIb). In another embodiment, the pharmaceutical formulation for use in the method comprises about 5 mg/mL of a compound of Formula (I), (II), (IIIa), or (IIIb). In another embodiment, the pharmaceutical formulation for use in the method comprises about 6 mg/mL of a compound of Formula (I), (II), (IIIa), or (IIIb). In another embodiment, the pharmaceutical formulation for use in the method comprises about 7 mg/mL of a compound of Formula (I), (II), (IIIa), or (IIIb). In another embodiment, the pharmaceutical formulation for use in the method comprises about 8 mg/mL of a compound of Formula (I), (II), (IIIa), or (IIIb). In another embodiment, the pharmaceutical formulation for use in the method comprises about 9 mg/mL of a compound of Formula (I), (II), (IIIa), or (IIIb). In another embodiment, the pharmaceutical formulation for use in the method comprises about 10 mg/mL of a compound of Formula (I), (II), (IIIa), or (IIIb). In another embodiment, the pharmaceutical formulation for use in the method comprises about 12 mg/mL of a compound of Formula (I), (II), (IIIa), or (IIIb). In another embodiment, the pharmaceutical formulation for use in the method comprises about 15 mg/mL of a compound of Formula (I), (II), (IIIa), or (IIIb). In another embodiment, the pharmaceutical formulation for use in the method comprises about 20 mg/mL of a compound of Formula (I), (II), (IIIa), or (IIIb). In another embodiment, the pharmaceutical formulation for use in the method comprises about 25 mg/mL of a compound of Formula (I), (II), (IIIa), or (IIIb). In another embodiment, the pharmaceutical formulation for use in the method comprises about 30 mg/mL of a compound of Formula (I), (II), (IIIa), or (IIIb). In another embodiment, the pharmaceutical formulation for use in the method comprises about 40 mg/mL of a compound of Formula (I), (II), (IIIa), or (IIIb). In another embodiment, the pharmaceutical formulation for use in the method comprises about 50 mg/mL of a compound of Formula (I), (II), (IIIa), or (IIIb). In some embodiments, the compound of Formula (I) is (R)-5-((E)-2-pyrolidin-3-ylvinyl)pyrimidine, or a pharmaceutically acceptable salt thereof.

In another embodiment, the pharmaceutical formulation for use in the method comprises between 5 mg/mL and 200 mg/mL of a compound of Formula (I), (II), (IIIa), or (IIIb). In another embodiment, the pharmaceutical formulation for use in the method comprises between 10 mg/mL and 200 mg/mL of a compound of Formula (I), (II), (IIIa), or (IIIb). In another embodiment, the pharmaceutical formulation for use in the method comprises between 5 mg/mL and 100 mg/mL of a compound of Formula (I), (II), (IIIa), or (IIIb). In another embodiment, the pharmaceutical formulation for use in the method comprises between 10 mg/mL and 75 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 10 mg/mL and 30 mg/mL of a compound of Formula (I), (II), (IIIa), or (IIIb). In another embodiment, the pharmaceutical formulation for use in the method comprises between 5 mg/mL and 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 10 mg/mL and 25 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 20 mg/mL and 50 mg/mL of a compound of Formula (I), (II), (IIIa), or (IIIb). In another embodiment, the pharmaceutical formulation for use in the method comprises between 30 mg/mL and 75 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method is provided at about 10 to 200 µl. In another embodiment, the pharmaceutical formulation for use in the method is provided at about 10 to 150 µl. In another embodiment, the pharmaceutical formulation for use in the method is provided at about 10 to 100 µl. In another embodiment, the pharmaceutical formulation for use in the method is provided at about 50 to 200 µl. In another embodiment, the pharmaceutical formulation for use in the method is provided at about 100 to 200 µl. In another embodiment, the pharmaceutical formulation for use in the method is provided at about 50 to 100 µl. In another embodiment, the pharmaceutical formulation for use in the method is provided at about 10 to 150. In another embodiment, the pharmaceutical formulation for use in the method is provided at about 10, 20, 30, 40, 50, 60, 70, 80, 90, 100, 110, 120, 130, 140, 150, 160, 170, 180, 190, or 200 µl. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, the compound of Formula (I), (II), (IIIa), or (IIIb) is administered once daily. In another embodiment of any of the aforementioned embodiments of improving ocular surface health, the compound of Formula (I), (II), (IIIa), or (IIIb) is administered at least once daily. In another embodiment of any of the aforementioned embodiments of improving ocular surface health, the compound of Formula (I), (II), (IIIa), or (IIIb) is administered twice daily. In another embodiment of any of the aforementioned embodiments of improving ocular surface health, the compound of Formula (I), (II), (IIIa), or (IIIb) is administered at least twice daily. In another embodiment of any of the aforementioned embodiments of improving ocular surface health, the compound of Formula (I), (II), (IIIa), or (IIIb) is administered three times daily. In another embodiment of any of the aforementioned embodiments of improving ocular surface health, the compound of Formula (I), (II), (IIIa), or (IIIb) is administered at least three times daily. In another embodiment of any of the aforementioned embodiments of improving ocular surface health, the compound of Formula (I), (II), (IIIa), or (IIIb) is administered for one day. In another embodiment of any of the aforementioned embodiments of improving ocular surface health, the compound of Formula (I), (II), (IIIa), or (IIIb) is administered for at least two days. In another embodiment of any of the aforementioned embodiments of improving ocular surface health, the compound of Formula (I), (II), (IIIa), or (IIIb) is administered for at least three days. In another embodiment of any of the aforementioned embodiments of improving ocular surface health, the compound of Formula (I), (II), (IIIa), or (IIIb) is administered for at least four days. In another embodiment of any of the aforementioned embodiments of improving ocular surface health, the compound of Formula (I), (II), (IIIa), or (IIIb) is administered for at least five days. In another embodiment of any of the aforementioned embodiments of improving ocular surface health, the compound of Formula (I), (II), (IIIa), or (IIIb) is administered for at least seven days. In another embodiment of any of the aforementioned embodiments of improving ocular surface health, the compound of Formula (I), (II), (IIIa), or (IIIb) is administered for at least ten days. In another embodiment of any of the aforementioned embodiments of improving ocular surface health, the compound of Formula (I), (II), (IIIa), or (IIIb) is administered for at least fourteen days. In another embodiment of any of the aforementioned embodiments of improving ocular surface health, the compound of Formula (I), (II), (IIIa), or (IIIb) is administered for at least twenty one days. In another embodiment of any of the aforementioned embodiments of improving ocular surface health, the compound of Formula (I), (II), (IIIa), or (IIIb) is administered for at least thirty days, in some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, the compound of Formula (I), (II), (IIIa), or (IIIb) is administered in alternating nostrils. For example, the compound of Formula (I), (II), (IIIa), or (IIIb) is administered in one nostril and then the other nostril after a pre-determined amount of time. In another embodiment, the compound of Formula (I), (II), (IIIa), or (IIIb) is administered in both nostrils. For example, the compound of Formula (I), (II), (IIIa), or (IIIb) is administered in one nostril and then the other nostril at the same time or immediately after the first nostril. In another embodiment, the compound of Formula (I), (II), (IIIa), or (IIIb) is administered in one nostril. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, the compound of Formula (I), (II), (IIIa), or (IIIb) is administered into the nasal cavity as a liquid, suspension, aerosol, gel, ointment, dry powder, cream, paste, lotion, or balm. In another embodiment of any of the aforementioned embodiments of improving ocular surface health, the compound of Formula (I), (II), (IIIa), or (IIIb) is administered into the nasal cavity as a liquid. In another embodiment of any of the aforementioned embodiments of improving ocular surface health, the compound of Formula (I), (II), (IIIa), or (IIIb) is administered into the nasal cavity as a suspension. In another embodiment of any of the aforementioned embodiments of improving ocular surface health, the compound of Formula (I), (II), (IIIa), or (IIIb) is administered into the nasal cavity as an aerosol. In another embodiment of any of the aforementioned embodiments of improving ocular surface health, the compound of Formula (I), (II), (IIIa), or (IIIb) is administered into the nasal cavity as a gel. In another embodiment of any of the aforementioned embodiments of improving ocular surface health, the compound of Formula (I), (II), (IIIa), or (IIIb) is administered into the nasal cavity as an ointment. In another embodiment of any of the aforementioned embodiments of improving ocular surface health, the compound of Formula (I), (II), (IIIa), or (IIIb) is administered into the nasal cavity as a dry powder. In another embodiment of any of the aforementioned embodiments of improving ocular surface health, the compound of Formula (I), (II), (IIIa), or (IIIb) is administered into the nasal cavity as a cream. In another embodiment of any of the aforementioned embodiments of improving ocular surface health, the compound of Formula (I), (II), (IIIa), or (IIIb) is administered into the nasal cavity as a paste. In another embodiment of any of the aforementioned embodiments of improving ocular surface health, the compound of Formula (I), (II), (IIIa), or (IIIb) is administered into the nasal cavity as a lotion. In another embodiment of any of the aforementioned embodiments of improving ocular surface health, the compound of Formula (I), (II), (IIIa), or (IIIb) is administered into the nasal cavity as a balm. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, the compound of Formula (I), (II), (IIIa), or (IIIb) is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of improving ocular surface health, the compound of Formula (I), (II), (IIIa), or (IIIb) is administered into the nasal cavity by a syringe. In another embodiment of any of the aforementioned embodiments of improving ocular surface health, the compound of Formula (I), (II), (IIIa), or (IIIb) is administered into the nasal cavity by a dropper. In another embodiment of any of the aforementioned embodiments of improving ocular surface health, the compound of Formula (I), (II), (IIIa), or (IIIb) is administered into the nasal cavity by a bottle nebulizer. In another embodiment of any of the aforementioned embodiments of improving ocular surface health, the compound of Formula (I), (II), (IIIa), or (IIIb) is administered into the nasal cavity by an atomization pump. In another embodiment of any of the aforementioned embodiments of improving ocular surface health, the compound of Formula (I), (II), (IIIa), or (IIIb) is administered into the nasal cavity by an inhaler. In another embodiment of any of the aforementioned embodiments of improving ocular surface health, the compound of Formula (I), (II), (IIIa), or (IIIb) is administered into the nasal cavity by a powder spray device. In another embodiment of any of the aforementioned embodiments of improving ocular surface health, the compound of Formula (I), (II), (IIIa), or (IIIb) is administered into the nasal cavity by a vaporizer. In another embodiment of any of the aforementioned embodiments of improving ocular surface health, the compound of Formula (I), (II), (IIIa), or (IIIb) is administered into the nasal cavity by a patch. In another embodiment of any of the aforementioned embodiments of improving ocular surface health, the compound of Formula (I), (II), (IIIa), or (IIIb) is administered into the nasal cavity by a medicated stick. In another embodiment of any of the aforementioned embodiments of improving ocular surface health, the compound of Formula (I), (II), (IIIa), or (IIIb) is administered into the nasal cavity by a pipette. In another embodiment of any of the aforementioned embodiments of improving ocular surface health, the compound of Formula (I), (II), (IIIa), or (IIIb) is administered into the nasal cavity by a jet of liquid. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, the trigeminal nerve is activated. In a further embodiment of improving ocular surface health, the anterior ethmoidal nerve is activated. In another embodiment of any of the aforementioned embodiments of improving ocular surface health, the nasolacrimal reflex is activated, hi some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of improving ocular surface health, the condition relieved by improving ocular surface health is an acute condition. An acute condition refers to a condition with a rapid onset of a health effect that is considered brief, not prolonged. Acute conditions can result from ophthalmologic surgical procedures or other ophthalmologic treatment. In some embodiments, the ophthalmologic surgical procedure is cataract surgery (cataract extraction and lens replacement), refractive lens exchange, glaucoma surgery, lasik surgery (laser eye surgery), vitrectomy, retinal photocoagulation, retinal detachment repair, macular hole repair, retroiris tumor or mass removal, posterior sclerotomy, optic neurotomy, or other treatments that decrease the function of the lacrimal gland. In some embodiments, the ophthalmologic treatment comprises radiation therapy. In some embodiments, the radiation therapy is directed to orbital area, for example, in connection to cancers of head and/or neck. In some embodiments, the compound of Formula (I) is (R)-5-((E)-2-pyrrolidin-3-ylvinyl)pyrimidine, or a pharmaceutically acceptable salt thereof.

Protecting the Ocular Surface During Environmentally Challenging Conditions

Provided herein, in some embodiments, is a method of protecting the ocular surface during environmentally challenging conditions in a subject. In some embodiments, is a method of protecting the ocular surface during environmentally challenging conditions, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and does not cross the blood-brain barrier in a pharmacologically relevant concentration. In some embodiments is method of protecting the ocular surface during environmentally challenging conditions, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of protecting the ocular surface during environmentally challenging conditions, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha3beta4. In some embodiments is method of protecting the ocular surface during environmentally challenging conditions, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha4beta2. In some embodiments is method of protecting the ocular surface during environmentally challenging conditions, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha7. In some embodiments is a method of protecting the ocular surface during environmentally challenging conditions, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that is not systemically bioavailable. In some embodiments is a method of protecting the ocular surface during environmentally challenging conditions, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired psychoactive side effects. In some embodiments is a method of protecting the ocular surface during environmentally challenging conditions, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired systemic side effects. In some embodiments is a method of protecting the ocular surface during environmentally challenging conditions, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that produces a local effect. In some embodiments is a method of protecting the ocular surface during environmentally challenging conditions, further comprising the local administration of one or more substances that prevent or facilitate the recovery of the nicotinic acetylcholine receptor from the desensitized state. In some embodiments, the compound of Formula (I) is (R)-5-((E)-2-pyrrolidin-3-ylvinyl)pyrimidine, or a pharmaceutically acceptable salt thereof.

In some embodiments of the method of protecting the ocular surface during environmentally challenging conditions described herein, the compound of Formula (I), (II), (IIIa), or (IIIb) is (R)-5-((E)-2-pyrrolidin-3-ylvinyl)pyrimidine (or Compound 1). In some embodiments of the methods described herein, the compound of Formula (I), (II), (IIIa), or (IIIb) is (R)-5-((E)-2-pyrrolidin-3-ylvinyl)pyrimidine, or a pharmaceutically acceptable salt thereof. In some embodiments of the methods described herein, the compound of Formula (I), (II), (IIIa), or (IIIb) is (R)-5-((E)-2-pyrrolidin-3-ylvinyl)pyrimidine as a free base. In some embodiments of the method of protecting the ocular surface during environmentally challenging conditions described herein, the compound of Formula (I), (II), (IIIa), or (IIIb) is (R)-5-((E)-2-pyrrolidin-3-ylvinyl)pyrimidine citrate salt. In some embodiments of the method of protecting the ocular surface during environmentally challenging conditions described herein, the compound of Formula (I), (II), (IIIa), or (IIIb) is (R)-5-((E)-2-pyrrolidin-3-ylvinyl)pyrimidine mono citrate salt. In some embodiments of the method of protecting the ocular surface during environmentally challenging conditions described herein, the compound of Formula (I), (II), (IIIa), or (IIIb) is (R)-5-((E)-2-pyrrolidin-3-ylvinyl)pyrimidine HCl salt. In some embodiments of the method of protecting the ocular surface during environmentally challenging conditions described herein, the compound of Formula (I), (II), (IIIa), or (IIIb) is (R)-5-((E)-2-pyrrolidin-3-ylvinyl)pyrimidine galactarate salt. In some embodiments of the method of protecting the ocular surface during environmentally challenging conditions described herein, the compound of Formula (I), (II), (IIIa), or (IIIb) is (R)-5-((E)-2-pyrrolidin-3-ylvinyl)pyrimidine hemigalactarate salt. In some embodiments of the method of protecting the ocular surface during environmentally challenging conditions described herein, the compound of Formula (I), (II), (IIIa), or (IIIb) is (R)-5-((E)-2-pyrrolidin-3-ylvinyl)pyrimidine hemigalactarate monohydrate. In some embodiments of the method described herein, the compound of Formula (I), (II), (IIIa), or (IIIb) is (R)-5-((E)-2-pyrrolidin-3-ylvinyl)pyrimidine hemigalactarate dihydrate.

In some embodiments is a method of protecting the ocular surface during environmentally challenging conditions, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments is a method of protecting the ocular surface during environmentally challenging conditions, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of protecting the ocular surface during environmentally challenging conditions, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of protecting the ocular surface during environmentally challenging conditions, further comprising the local administration of protein kinase C (PKC) or factors that upregulate or up-modulate PKC. In some embodiments is a method of protecting the ocular surface during environmentally challenging conditions, further comprising the local administration of cAMP-dependent protein kinase (PKA) or factors that upregulate or up-modulate PKA. In some embodiments is a method of protecting the ocular surface during environmentally challenging conditions, further comprising the local administration of a calcineurin inhibitor. In some embodiments is a method of protecting the ocular surface during environmentally challenging conditions, further comprising the local administration of a calcineurin inhibitor, wherein the calcineurin inhibitor is selected from cyclosporine, pimecrolimus, and tacrolimus. In some embodiments is a method of protecting the ocular surface during environmentally challenging conditions, further comprising the local administration of cyclosporine. In some embodiments is a method of protecting the ocular surface during environmentally challenging conditions, further comprising the local administration of pimecrolimus. In some embodiments is a method of protecting the ocular surface during environmentally challenging conditions, further comprising the local administration of tacrolimus.

In another embodiment of any of the aforementioned embodiments of protecting the ocular surface during environmentally challenging conditions, at least 1 microgram of the compound of Formula (I), (II), (IIIa), or (IIIb) is administered into the nasal cavity. In another embodiment of any of the aforementioned embodiments of protecting the ocular surface during environmentally challenging conditions, at least 5 micrograms of the compound of Formula (I), (II), (IIIa), or (IIIb) is administered into the nasal cavity. In another embodiment of any of the aforementioned embodiments of protecting the ocular surface during environmentally challenging conditions, at least 10 micrograms of the compound of Formula (I), (II), (IIIa), or (IIIb) is administered into the nasal cavity. In another embodiment of any of the aforementioned embodiments of protecting the ocular surface during environmentally challenging conditions, at least 25 micrograms of the compound of Formula (I), (II), (IIIa), or (IIIb) is administered into the nasal cavity. In another embodiment of any of the aforementioned embodiments of protecting the ocular surface during environmentally challenging conditions, at least 50 micrograms of the compound of Formula (I), (II), (IIIa), or (IIIb) is administered into the nasal cavity. In another embodiment of any of the aforementioned embodiments of protecting the ocular surface during environmentally challenging conditions, at least 100 micrograms of the compound of Formula (I), (II), (IIIa), or (IIIb) is administered into the nasal cavity. In another embodiment of any of the aforementioned embodiments of protecting the ocular surface during environmentally challenging conditions, at least 250 micrograms of the compound of Formula (I), (II), (IIIa), or (IIIb) is administered into the nasal cavity. In another embodiment of any of the aforementioned embodiments of protecting the ocular surface during environmentally challenging conditions, at least 500 micrograms of the compound of Formula (I), (II), (IIIa), or (IIIb) is administered into the nasal cavity. In another embodiment of any of the aforementioned embodiments of protecting the ocular surface during environmentally challenging conditions, at least 750 micrograms of the compound of Formula (I), (II), (IIIa), or (IIIb) is administered into the nasal cavity. In another embodiment of any of the aforementioned embodiments of protecting the ocular surface during environmentally challenging conditions, at least 1000 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, between 1 microgram and 1000 micrograms of the compound of Formula (I), (II), (IIIa), or (IIIb) is administered into the nasal cavity. In another embodiment of any of the aforementioned embodiments of protecting the ocular surface during environmentally challenging conditions, between 5 micrograms and 1000 micrograms of the compound of Formula (I), (II), (IIIa), or (IIIb) is administered into the nasal cavity. In another embodiment of any of the aforementioned embodiments of protecting the ocular surface during environmentally challenging conditions, between 10 micrograms and 1000 micrograms of the compound of Formula (I), (II), (IIIa), or (IIIb) is administered into the nasal cavity. In another embodiment of any of the aforementioned embodiments of protecting the ocular surface during environmentally challenging conditions, between 5 micrograms and 100 micrograms of the compound of Formula (I), (II), (IIIa), or (IIIb) is administered into the nasal cavity. In another embodiment of any of the aforementioned embodiments of protecting the ocular surface during environmentally challenging conditions, between 5 micrograms and 50 micrograms of the compound of Formula (I), (II), (IIIa), or (IIIb) is administered into the nasal cavity. In another embodiment of any of the aforementioned embodiments of protecting the ocular surface during environmentally challenging conditions, between 10 micrograms and 50 micrograms of the compound of Formula (I), (II), (IIIa), or (IIIb) is administered into the nasal cavity. In another embodiment of any of the aforementioned embodiments of protecting the ocular surface during environmentally challenging conditions, between 25 micrograms and 1000 micrograms of the compound of Formula (I), (II), (IIIa), or (IIIb) is administered into the nasal cavity. In another embodiment of any of the aforementioned embodiments of protecting the ocular surface during environmentally challenging conditions, between 50 micrograms and 1000 micrograms of the compound of Formula (I), (II), (IIIa), or (IIIb) is administered into the nasal cavity. In another embodiment of any of the aforementioned embodiments of protecting the ocular surface during environmentally challenging conditions, between 100 micrograms and 1000 micrograms of the compound of Formula (I), (II), (IIIa), or (IIIb) is administered into the nasal cavity. In another embodiment of any of the aforementioned embodiments of protecting the ocular surface during environmentally challenging conditions, between 150 micrograms and 1000 micrograms of the compound of Formula (I), (II), (IIIa), or (IIIb) is administered into the nasal cavity. In another embodiment of any of the aforementioned embodiments of protecting the ocular surface during environmentally challenging conditions, between 100 micrograms and 750 micrograms of the compound of Formula (I), (II), (IIIa), or (IIIb) is administered into the nasal cavity. In another embodiment of any of the aforementioned embodiments of protecting the ocular surface during environmentally challenging conditions, between 150 micrograms and 750 micrograms of the compound of Formula (I), (II), (IIIa), or (IIIb) is administered into the nasal cavity. In another embodiment of any of the aforementioned embodiments of protecting the ocular surface during environmentally challenging conditions, between 150 micrograms and 600 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, less than 100 micrograms of a compound of Formula (I), (II), (IIIa), or (IIIb) is administered into the nasal cavity. In another embodiment of any of the aforementioned embodiments of protecting the ocular surface during environmentally challenging conditions, less than 75 micrograms of a compound of Formula (I). (II), (IIIa), or (IIIb) is administered into the nasal cavity. In another embodiment of any of the aforementioned embodiments of protecting the ocular surface during environmentally challenging conditions, less than 50 micrograms of a compound of Formula (I), (II), (IIIa), or (IIIb) is administered into the nasal cavity. In another embodiment of any of the aforementioned embodiments of protecting the ocular surface during environmentally challenging conditions, less than 25 micrograms of a compound of Formula (I), (II), (IIIa), or (IIIb) is administered into the nasal cavity. In another embodiment of any of the aforementioned embodiments of protecting the ocular surface during environmentally challenging conditions, less than 15 micrograms of a compound of Formula (I), (II), (IIIa), or (IIIb) is administered into the nasal cavity. In another embodiment of any of the aforementioned embodiments of protecting the ocular surface during environmentally challenging conditions, about 75 micrograms of a compound of Formula (I), (II), (IIIa), or (IIIb) is administered into the nasal cavity. In another embodiment of any of the aforementioned embodiments of protecting the ocular surface during environmentally challenging conditions, about 50 micrograms of a compound of Formula (I), (II), (IIIa), or (IIIb) is administered into the nasal cavity. In another embodiment of any of the aforementioned embodiments of protecting the ocular surface during environmentally challenging conditions, about 25 micrograms of a compound of Formula (I), (II), (IIIa), or (IIIb) is administered into the nasal cavity. In another embodiment of any of the aforementioned embodiments of protecting the ocular surface during environmentally challenging conditions, about 0 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, between 1 microgram and 100 micrograms of a compound of Formula (I), (II), (IIIa), or (IIIb) is administered into the nasal cavity. In another embodiment of any of the aforementioned embodiments of protecting the ocular surface during environmentally challenging conditions, between 1 microgram and 75 micrograms of a compound of Formula (I), (II), (IIIa), or (IIIb) is administered into the nasal cavity. In another embodiment of any of the aforementioned embodiments of protecting the ocular surface during environmentally challenging conditions, between 5 micrograms and 100 micrograms of a compound of Formula (I), (II), (IIIa), or (IIIb) is administered into the nasal cavity. In another embodiment of any of the aforementioned embodiments of protecting the ocular surface during environmentally challenging conditions, between 5 micrograms and 75 micrograms of a compound of Formula (I), (II), (IIIa), or (IIIb) is administered into the nasal cavity. In another embodiment of any of the aforementioned embodiments of protecting the ocular surface during environmentally challenging conditions, between 15 micrograms and 100 micrograms of a compound of Formula (I), (II), (IIIa), or (IIIb) is administered into the nasal cavity. In another embodiment of any of the aforementioned embodiments of protecting the ocular surface during environmentally challenging conditions, between 15 micrograms and 75 micrograms of a compound of Formula (I), (II), (IIIa), or (IIIb) is administered into the nasal cavity. In another embodiment of any of the aforementioned embodiments of protecting the ocular surface during environmentally challenging conditions, between 25 micrograms and 100 micrograms of a compound of Formula (I), (II), (IIIa), or (IIIb) is administered into the nasal cavity. In another embodiment of any of the aforementioned embodiments of protecting the ocular surface during environmentally challenging conditions, between 25 micrograms and 75 micrograms of a compound of Formula (I), (II), (IIIa), or (IIIb) is administered into the nasal cavity. In another embodiment of any of the aforementioned embodiments of protecting the ocular surface during environmentally challenging conditions, between 25 micrograms and 60 micrograms of a compound of Formula (I), (II), (IIIa), or (IIIb) is administered into the nasal cavity.

In another embodiment of any of the aforementioned embodiments of protecting the ocular surface during environmentally challenging conditions, between 500 micrograms and 10 milligrams of a compound of Formula (I), (II), (IIIa), or (IIIb) is administered into the nasal cavity. In another embodiment of any of the aforementioned embodiments of protecting the ocular surface during environmentally challenging conditions, between 500 micrograms and 5 milligrams of a compound of Formula (I), (II), (IIIa), or (IIIb) is administered into the nasal cavity. In another embodiment of any of the aforementioned embodiments of protecting the ocular surface during environmentally challenging conditions, between 500 micrograms and 3 milligrams of a compound of Formula (I), (II), (IIIa), or (IIIb) is administered into the nasal cavity. In another embodiment of any of the aforementioned embodiments of protecting the ocular surface during environmentally challenging conditions, between 500 micrograms and 2 milligrams of a compound of Formula (I), (II), (IIIa), or (IIIb) is administered into the nasal cavity. In another embodiment of any of the aforementioned embodiments of protecting the ocular surface during environmentally challenging conditions, between 1 milligram and 10 milligrams of a compound of Formula (I), (II), (IIIa), or (IIIb) is administered into the nasal cavity. In another embodiment of any of the aforementioned embodiments of protecting the ocular surface during environmentally challenging conditions, between 1 milligram and 5 milligrams of a compound of Formula (I), (II), (IIIa), or (IIIb) is administered into the nasal cavity. In another embodiment of any of the aforementioned embodiments of protecting the ocular surface during environmentally challenging conditions, between 1 milligram and 3 milligrams of a compound of Formula (I), (II), (IIIa), or (IIIb) is administered into the nasal cavity. In another embodiment of any of the aforementioned embodiments of protecting the ocular surface during environmentally challenging conditions, between 1 milligram and 2 milligrams of a compound of Formula (I), (II), (IIIa), or (IIIb) is administered into the nasal cavity. In another embodiment of any of the aforementioned embodiments of protecting the ocular surface during environmentally challenging conditions, about 500 micrograms of a compound of Formula (I), (II), (IIIa), or (IIIb) is administered into the nasal cavity. In another embodiment of any of the aforementioned embodiments of protecting the ocular surface during environmentally challenging conditions, about 1 milligram of a compound of Formula (I), (II), (IIIa), or (IIIb) is administered into the nasal cavity. In another embodiment of any of the aforementioned embodiments of protecting the ocular surface during environmentally challenging conditions, about 1.5 milligrams of a compound of Formula (I), (II), (IIIa), or (IIIb) is administered into the nasal cavity. In another embodiment of any of the aforementioned embodiments of protecting the ocular surface during environmentally challenging conditions, about 2 milligrams of a compound of Formula (I), (II), (IIIa), or (IIIb) is administered into the nasal cavity. In another embodiment of any of the aforementioned embodiments of protecting the ocular surface during environmentally challenging conditions, about 2.5 milligrams of a compound of Formula (I), (II), (IIIa), or (IIIb) is administered into the nasal cavity. In another embodiment of any of the aforementioned embodiments of protecting the ocular surface during environmentally challenging conditions, about 3 milligrams of a compound of Formula (I), (II), (IIIa), or (IIIb) is administered into the nasal cavity. In another embodiment of any of the aforementioned embodiments of protecting the ocular surface during environmentally challenging conditions, about 4 milligrams of a compound of Formula (I), (II), (IIIa), or (IIIb) is administered into the nasal cavity. In another embodiment of any of the aforementioned embodiments of protecting the ocular surface during environmentally challenging conditions, about 5 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, between 1 microgram and 10 milligrams of a compound of Formula (I), (II), (IIIa), or (IIIb) is administered into the nasal cavity. In another embodiment of any of the aforementioned embodiments of protecting the ocular surface during environmentally challenging conditions, between 5 micrograms and 10 milligrams of a compound of Formula (I), (II), (IIIa), or (IIIb) is administered into the nasal cavity. In another embodiment of any of the aforementioned embodiments of protecting the ocular surface during environmentally challenging conditions, between 10 micrograms and 10 milligrams of a compound of Formula (I), (II), (IIIa), or (IIIb) is administered into the nasal cavity. In another embodiment of any of the aforementioned embodiments of protecting the ocular surface during environmentally challenging conditions, between 25 micrograms and 10 milligrams of a compound of Formula (I), (II), (IIIa), or (IIIb) is administered into the nasal cavity. In another embodiment of any of the aforementioned embodiments of protecting the ocular surface during environmentally challenging conditions, between 50 micrograms and 10 milligrams of a compound of Formula (I), (II), (IIIa), or (IIIb) is administered into the nasal cavity. In another embodiment of any of the aforementioned embodiments of protecting the ocular surface during environmentally challenging conditions, between 100 micrograms and 10 milligrams of a compound of Formula (I), (II), (IIIa), or (Tub) is administered into the nasal cavity. In another embodiment of any of the aforementioned embodiments of protecting the ocular surface during environmentally challenging conditions, between 150 micrograms and 10 milligrams of a compound of Formula (I), (I), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, between 1 microgram and 10 milligrams of a compound of Formula (I), (II), (IIIa), or (IIIb) is administered into the nasal cavity. In another embodiment of any of the aforementioned embodiments of protecting the ocular surface during environmentally challenging conditions, between 1 microgram and 5 milligrams of a compound of Formula (I), (II), (IIIa), or (IIIb) is administered into the nasal cavity. In another embodiment of any of the aforementioned embodiments of protecting the ocular surface during environmentally challenging conditions, between 1 microgram and 4 milligrams of a compound of Formula (I), (II), (IIIa), or (IIIb) is administered into the nasal cavity. In another embodiment of any of the aforementioned embodiments of protecting the ocular surface during environmentally challenging conditions, between 1 microgram and 3 milligrams of a compound of Formula (I), (II), (IIIa), or (IIIb) is administered into the nasal cavity. In another embodiment of any of the aforementioned embodiments of protecting the ocular surface during environmentally challenging conditions, between 1 microgram and 2 milligrams of a compound of Formula (I), (II), (IIIa), or (IIIb) is administered into the nasal cavity. In another embodiment of any of the aforementioned embodiments of protecting the ocular surface during environmentally challenging conditions, between 1 microgram and 1 milligrams of a compound of Formula (I), (II), (IIIa), or (IIIb) is administered into the nasal cavity. In another embodiment of any of the aforementioned embodiments of protecting the ocular surface during environmentally challenging conditions, between 1 microgram and 750 micrograms of a compound of Formula (I), (II), (IIIa), or (IIIb) is administered into the nasal cavity. In another embodiment of any of the aforementioned embodiments of protecting the ocular surface during environmentally challenging conditions, between 1 microgram and 600 micrograms of a compound of Formula (I), (II), (IIIa), or (IIIb) is administered into the nasal cavity. In another embodiment of any of the aforementioned embodiments of protecting the ocular surface during environmentally challenging conditions, between 1 microgram and 100 micrograms of a compound of Formula (I), (II), (IIIa), or (IIIb) is administered into the nasal cavity. In another embodiment of any of the aforementioned embodiments of protecting the ocular surface during environmentally challenging conditions, between 1 microgram and 50 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method comprises about 0.1 mg/mL of a compound of Formula (I), (II), (IIIa), or (IIIb). In another embodiment, the pharmaceutical formulation for use in the method comprises about 0.2 mg/mL of a compound of Formula (I), (II), (IIIa), or (IIIb). In another embodiment, the pharmaceutical formulation for use in the method comprises about 0.5 mg/mL of a compound of Formula (I), (II), (IIIa), or (IIIb). In another embodiment, the pharmaceutical formulation for use in the method comprises about 1 mg/mL of a compound of Formula (I), (II), (IIIa), or (IIIb). In another embodiment, the pharmaceutical formulation for use in the method comprises about 2 mg/mL of a compound of Formula (I), (II), (IIIa), or (IIIb). In another embodiment, the pharmaceutical formulation for use in the method comprises about 3 mg/mL of a compound of Formula (I), (II), (IIIa), or (IIIb). In another embodiment, the pharmaceutical formulation for use in the method comprises about 4 mg/mL of a compound of Formula (I), (II), (IIIa), or (IIIb). In another embodiment, the pharmaceutical formulation for use in the method comprises about 5 mg/mL of a compound of Formula (I), (II), (IIIa), or (IIIb). In another embodiment, the pharmaceutical formulation for use in the method comprises about 6 mg/mL of a compound of Formula (I), (II), (IIIa), or (IIIb). In another embodiment, the pharmaceutical formulation for use in the method comprises about 7 mg/mL of a compound of Formula (I), (II), (IIIa), or (IIIb). In another embodiment, the pharmaceutical formulation for use in the method comprises about 8 mg/mL of a compound of Formula (I), (II), (IIIa), or (IIIb). In another embodiment, the pharmaceutical formulation for use in the method comprises about 9 mg/mL of a compound of Formula (I), (II), (IIIa), or (IIIb). In another embodiment, the pharmaceutical formulation for use in the method comprises about 10 mg/mL of a compound of Formula (I), (II), (IIIa), or (IIIb). In another embodiment, the pharmaceutical formulation for use in the method comprises about 12 mg/mL of a compound of Formula (I), (II), (IIIa), or (IIIb). In another embodiment, the pharmaceutical formulation for use in the method comprises about 15 mg/mL of a compound of Formula (I), (II), (IIIa), or (IIIb). In another embodiment, the pharmaceutical formulation for use in the method comprises about 20 mg/mL of a compound of Formula (I), (II), (IIIa), or (IIIb). In another embodiment, the pharmaceutical formulation for use in the method comprises about 25 mg/mL of a compound of Formula (I), (II), (IIIa), or (IIIb). In another embodiment, the pharmaceutical formulation for use in the method comprises about 30 mg/mL of a compound of Formula (I), (II), (IIIa), or (IIIb). In another embodiment, the pharmaceutical formulation for use in the method comprises about 40 mg/mL of a compound of Formula (I), (II), (IIIa), or (IIIb). In another embodiment, the pharmaceutical formulation for use in the method comprises about 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 5 mg/mL and 200 mg/mL of a compound of Formula (I), (II), (IIIa), or (IIIb). In another embodiment, the pharmaceutical formulation for use in the method comprises between 10 mg/mL, and 200 mg/mL of a compound of Formula (I), (II), (IIIa), or (IIIb). In another embodiment, the pharmaceutical formulation for use in the method comprises between 5 mg/mL, and 100 mg/mL of a compound of Formula (I), (II), (IIIa), or (IIIb). In another embodiment, the pharmaceutical formulation for use in the method comprises between 10 mg/mL and 75 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 10 mg/mL and 30 mg/mL of a compound of Formula (I), (II), (IIIa), or (IIIb). In another embodiment, the pharmaceutical formulation for use in the method comprises between 5 mg/mL and 50 mg/mL of a compound of Formula (I), (II), (IIIa), or (IIIb). In some embodiments, the compound of Formula (I) is (R)-5-((E)-2-pyrrolidin-3-ylvinyl-3-ylvinyl)pyrimidine, or a pharmaceutically acceptable salt thereof.

In another embodiment, the pharmaceutical formulation for use in the method comprises between 10 mg/mL and 25 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 20 mg/mL and 50 mg/mL of a compound of Formula (I), (II), (IIIa), or (IIIb). In another embodiment, the pharmaceutical formulation for use in the method comprises between 30 mg/mL and 75 mg/mL, of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method is provided at about 10 to 200 µl. In another embodiment, the pharmaceutical formulation for use in the method is provided at about 10 to 150 µl. In another embodiment, the pharmaceutical formulation for use in the method is provided at about 10 to 100 µl. In another embodiment, the pharmaceutical formulation for use in the method is provided at about 50 to 200 µl. In another embodiment, the pharmaceutical formulation for use in the method is provided at about 100 to 200 µl. In another embodiment, the pharmaceutical formulation for use in the method is provided at about 50 to 100 µl. In another embodiment, the pharmaceutical formulation for use in the method is provided at about 10 to 150 µl. In another embodiment, the pharmaceutical formulation for use in the method is provided at about 10, 20, 30, 40, 50, 60, 70, 80, 90, 100, 110, 120, 130, 140, 150, 160, 170, 180, 190, or 200 µl. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, the compound of Formula (I), (II), (IIIa), or (IIIb) is administered once daily. In another embodiment of any of the aforementioned embodiments of protecting the ocular surface during environmentally challenging conditions, the compound of Formula (I), (II), (IIIa), or (IIIb) is administered at least once daily. In another embodiment of any of the aforementioned embodiments of protecting the ocular surface during environmentally challenging conditions, the compound of Formula (I), (II), (IIIa), or (IIIb) is administered twice daily. In another embodiment of any of the aforementioned embodiments of protecting the ocular surface during environmentally challenging conditions, the compound of Formula (I), (II), (IIIa), or (IIIb) is administered at least twice daily. In another embodiment of any of the aforementioned embodiments of protecting the ocular surface during environmentally challenging conditions, the compound of Formula (I), (II), (IIIa), or (IIIb) is administered three times daily. In another embodiment of any of the aforementioned embodiments of protecting the ocular surface during environmentally challenging conditions, the compound of Formula (I), (II), (IIIa), or (IIIb) is administered at least three times daily. In another embodiment of any of the aforementioned embodiments of protecting the ocular surface during environmentally challenging conditions, the compound of Formula (I), (II), (IIIa), or (IIIb) is administered for one day. In another embodiment of any of the aforementioned embodiments of protecting the ocular surface during environmentally challenging conditions, the compound of Formula (I), (II), (IIIa), or (IIIb) is administered for at least two days. In another embodiment of any of the aforementioned embodiments of protecting the ocular surface during environmentally challenging conditions, the compound of Formula (I), (II), (IIIa), or (IIIb) is administered for at least three days. In another embodiment of any of the aforementioned embodiments of protecting the ocular surface during environmentally challenging conditions, the compound of Formula (I), (II), (IIIa), or (IIIb) is administered for at least four days. In another embodiment of any of the aforementioned embodiments of protecting the ocular surface during environmentally challenging conditions, the compound of Formula (I). (II), (IIIa), or (IIIb) is administered for at least five days. In another embodiment of any of the aforementioned embodiments of protecting the ocular surface during environmentally challenging conditions, the compound of Formula (I), (II), (IIIa), or (IIIb) is administered for at least seven days. In another embodiment of any of the aforementioned embodiments of protecting the ocular surface during environmentally challenging conditions, the compound of Formula (I), (II), (IIIa), or (IIIb) is administered for at least ten days. In another embodiment of any of the aforementioned embodiments of protecting the ocular surface during environmentally challenging conditions, the compound of Formula (I), (II), (IIIa), or (IIIb) is administered for at least fourteen days. In another embodiment of any of the aforementioned embodiments of protecting the ocular surface during environmentally challenging conditions, the compound of Formula (I), (II), (IIIa), or (IIIb) is administered for at least twenty one days. In another embodiment of any of the aforementioned embodiments of protecting the ocular surface during environmentally challenging conditions, the compound of Formula (I), (II), (IIIa), or (IIIb) is administered for at least thirty days. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, the compound of Formula (I). (II), (IIIa), or (IIIb) is administered in alternating nostrils. For example, the compound of Formula (I), (II), (IIIa), or (IIIb) is administered in one nostril and then the other nostril after a pre-determined amount of time. In another embodiment, the compound of Formula (I), (II), (IIIa), or (IIIb) is administered in both nostrils. For example, the compound of Formula (I), (II), (IIIa), or (IIIb) is administered in one nostril and then the other nostril at the same time or immediately after the first nostril. In another embodiment, the compound of Formula (I), (II), (IIIa), or (IIIb) is administered in one nostril. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, the compound of Formula (I), (II), (IIIa), or (IIIb) is administered into the nasal cavity as a liquid, suspension, aerosol, gel, ointment, dry powder, cream, paste, lotion, or balm. In another embodiment of any of the aforementioned embodiments of protecting the ocular surface during environmentally challenging conditions, the compound of Formula (I), (II), (IIIa), or (IIIb) is administered into the nasal cavity as a liquid. In another embodiment of any of the aforementioned embodiments of protecting the ocular surface during environmentally challenging conditions, the compound of Formula (I), (II), (IIIa), or (IIIb) is administered into the nasal cavity as a suspension. In another embodiment of any of the aforementioned embodiments of protecting the ocular surface during environmentally challenging conditions, the compound of Formula (I), (II), (IIIa), or (IIIb) is administered into the nasal cavity as an aerosol. In another embodiment of any of the aforementioned embodiments of protecting the ocular surface during environmentally challenging conditions, the compound of Formula (I), (II), (IIIa), or (IIIb) is administered into the nasal cavity as a gel. In another embodiment of any of the aforementioned embodiments of protecting the ocular surface during environmentally challenging conditions, the compound of Formula (I), (II), (IIIa), or (IIIb) is administered into the nasal cavity as an ointment. In another embodiment of any of the aforementioned embodiments of protecting the ocular surface during environmentally challenging conditions, the compound of Formula (I), (II), (IIIa), or (IIIb) is administered into the nasal cavity as a dry powder. In another embodiment of any of the aforementioned embodiments of protecting the ocular surface during environmentally challenging conditions, the compound of Formula (I), (II), (IIIa), or (IIIb) is administered into the nasal cavity as a cream. In another embodiment of any of the aforementioned embodiments of protecting the ocular surface during environmentally challenging conditions, the compound of Formula (I), (II), (IIIa), or (IIIb) is administered into the nasal cavity as a paste. In another embodiment of any of the aforementioned embodiments of protecting the ocular surface during environmentally challenging conditions, the compound of Formula (I), (II), (IIIa), or (IIIb) is administered into the nasal cavity as a lotion. In another embodiment of any of the aforementioned embodiments of protecting the ocular surface during environmentally challenging conditions, the compound of Formula (I), (II), (IIIa), or (IIIb) is administered into the nasal cavity as a balm. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, the compound of Formula (I). (II), (IIIa), or (IIIb) is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of protecting the ocular surface during environmentally challenging conditions, the compound of Formula (I), (II), (IIIa), or (IIIb) is administered into the nasal cavity by a syringe. In another embodiment of any of the aforementioned embodiments of protecting the ocular surface during environmentally challenging conditions, the compound of Formula (I), (II), (IIIa), or (IIIb) is administered into the nasal cavity by a dropper. In another embodiment of any of the aforementioned embodiments of protecting the ocular surface during environmentally challenging conditions, the compound of Formula (I), (II), (IIIa), or (IIIb) is administered into the nasal cavity by a bottle nebulizer. In another embodiment of any of the aforementioned embodiments of protecting the ocular surface during environmentally challenging conditions, the compound of Formula (I), (II), (IIIa), or (IIIb) is administered into the nasal cavity by an atomization pump. In another embodiment of any of the aforementioned embodiments of protecting the ocular surface during environmentally challenging conditions, the compound of Formula (I), (II), (IIIa), or (IIIb) is administered into the nasal cavity by an inhaler. In another embodiment of any of the aforementioned embodiments of protecting the ocular surface during environmentally challenging conditions, the compound of Formula (I), (II), (IIIa), or (IIIb) is administered into the nasal cavity by a powder spray device. In another embodiment of any of the aforementioned embodiments of protecting the ocular surface during environmentally challenging conditions, the compound of Formula (I), (II), (IIIa), or (IIIb) is administered into the nasal cavity by a vaporizer. In another embodiment of any of the aforementioned embodiments of protecting the ocular surface during environmentally challenging conditions, the compound of Formula (I), (II), (IIIa), or (IIIb) is administered into the nasal cavity by a patch. In another embodiment of any of the aforementioned embodiments of protecting the ocular surface during environmentally challenging conditions, the compound of Formula (I), (II), (IIIa), or (IIIb) is administered into the nasal cavity by a medicated stick. In another embodiment of any of the aforementioned embodiments of protecting the ocular surface during environmentally challenging conditions, the compound of Formula (I), (II), (IIIa), or (IIIb) is administered into the nasal cavity by a pipette. In another embodiment of any of the aforementioned embodiments of protecting the ocular surface during environmentally challenging conditions, the compound of Formula (I), (II), (IIIa), or (IIIb) is administered into the nasal cavity by a jet of liquid. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of protecting the ocular surface during environmentally challenging conditions, the trigeminal nerve is activated. In a further embodiment of protecting the ocular surface during environmentally challenging conditions, the anterior ethmoidal nerve is activated. In another embodiment of any of the aforementioned embodiments of protecting the ocular surface during environmentally challenging conditions, the nasolacrimal reflex is activated. In some embodiments, the compound of Formula (I) is (R)-5-((E)-2-pyrrolidin-3-ylvinyl)pyrimidine, or a pharmaceutically acceptable salt thereof.

Increasing Mucin Content on the Ocular Surface

Provided herein, in some embodiments, is a method of increasing mucin content on the ocular surface in a subject. In some embodiments, is a method of increasing mucin content on the ocular surface, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and does not cross the blood-brain barrier in a pharmacologically relevant concentration. In some embodiments is method of increasing mucin content on the ocular surface, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of increasing mucin content on the ocular surface, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha3beta4. In some embodiments is method of increasing mucin content on the ocular surface, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha4beta2. In some embodiments is method of increasing mucin content on the ocular surface, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha7. In some embodiments is a method of increasing mucin content on the ocular surface, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that is not systemically bioavailable. In some embodiments is a method of increasing mucin content on the ocular surface, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired psychoactive side effects. In some embodiments is a method of increasing mucin content on the ocular surface, comprising the local administration of a therapeutically effective amount of a compound of Formula (I), (II). (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired systemic side effects. In some embodiments is a method of increasing mucin content on the ocular surface, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that produces a local effect. In some embodiments is a method of increasing mucin content on the ocular surface, further comprising the local administration of one or more substances that prevent or facilitate the recovery of the nicotinic acetylcholine receptor from the desensitized state. In some embodiments, the compound of Formula (I) is (R)-5-((E)-2-pyrrolidin-3-ylvinyl)pyrimidine, or a pharmaceutically acceptable salt thereof.

In some embodiments of the method of increasing mucin content on the ocular surface described herein, the compound of Formula (I), (II), (IIIa), or (IIIb) is (R)-5-((E)-2-pyrrolidin-3-ylvinyl)pyrimidine (or Compound 1). In some embodiments of the methods described herein, the compound of Formula (I), (II), (IIIa), or (IIIb) is (R)-5-((E)-2-pyrrolidin-3-ylvinyl)pyrimidine, or a pharmaceutically acceptable salt thereof. In some embodiments of the method of increasing mucin content on the ocular surface described herein, the compound of Formula (I), (II), (IIIa), or (IIIb) is (R)-5-((E)-2-pyrrolidin-3-ylvinyl)pyrimidine as a free base. In some embodiments of the method of increasing mucin content on the ocular surface described herein, the compound of Formula (I), (II), (IIIa), or (IIIb) is (R)-5-((E)-2-pyrrolidin-3-ylvinyl)pyrimidine citrate salt. In some embodiments of the method of increasing mucin content on the ocular surface described herein, the compound of Formula (I), (II), (IIIa), or (IIIb) is (R)-5-((E)-2-pyrrolidin-3-ylvinyl)pyrimidine mono citrate salt. In some embodiments of the method of increasing mucin content on the ocular surface described herein, the compound of Formula (I), (II), (IIIa), or (IIIb) is (R)-5-((E)-2-pyrrolidin-3-ylvinyl)pyrimidine HCl salt. In some embodiments of the method of increasing mucin content on the ocular surface described herein, the compound of Formula (I), (II), (IIIa), or (IIIb) is (R)-5-((E)-2-pyrrolidin-3-ylvinyl)pyrimidine galactarate salt. In some embodiments of the method of increasing mucin content on the ocular surface described herein, the compound of Formula (I), (II), (IIIa), or (IIIb) is (R)-5-((E)-2-pyrrolidin-3-ylvinyl)pyrimidine hemigalactarate salt. In some embodiments of the method of increasing mucin content on the ocular surface described herein, the compound of Formula (I), (II), (IIIa), or (IIIb) is (R)-5-((E)-2-pyrrolidin-3-ylvinyl)pyrimidine hemigalactarate monohydrate. In some embodiments of the method described herein, the compound of Formula (I), (II), (IIIa), or (IIIb) is (R)-5-((E)-2-pyrrolidin-3-ylvinyl)pyrimidine hemigalactarate dihydrate.

In some embodiments is a method of increasing mucin content on the ocular surface, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments is a method of increasing mucin content on the ocular surface, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing mucin content on the ocular surface, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing mucin content on the ocular surface, further comprising the local administration of protein kinase C (PKC) or factors that upregulate or up-modulate PKC. In some embodiments is a method of increasing mucin content on the ocular surface, further comprising the local administration of cAMP-dependent protein kinase (PKA) or factors that upregulate or up-modulate PKA. In some embodiments is a method of increasing mucin content on the ocular surface, further comprising the local administration of a calcineurin inhibitor. In some embodiments is a method of increasing mucin content on the ocular surface, further comprising the local administration of a calcineurin inhibitor, wherein the calcineurin inhibitor is selected from cyclosporine, pimecrolimus, and tacrolimus. In some embodiments is a method of increasing mucin content on the ocular surface, further comprising the local administration of cyclosporine. In some embodiments is a method of increasing mucin content on the ocular surface, further comprising the local administration of pimecrolimus. In some embodiments is a method of increasing mucin content on the ocular surface, further comprising the local administration of tacrolimus.

In another embodiment of any of the aforementioned embodiments of increasing mucin content on the ocular surface, at least 1 microgram of the compound of Formula (I), (II), (IIIa), or (IIIb) is administered into the nasal cavity. In another embodiment of any of the aforementioned embodiments of increasing mucin content on the ocular surface, at least 5 micrograms of the compound of Formula (I), (II), (IIIa), or (IIIb) is administered into the nasal cavity. In another embodiment of any of the aforementioned embodiments of increasing mucin content on the ocular surface, at least 10 micrograms of the compound of Formula (I), (II), (IIIa), or (IIIb) is administered into the nasal cavity. In another embodiment of any of the aforementioned embodiments of increasing mucin content on the ocular surface, at least 25 micrograms of the compound of Formula (I), (II), (IIIa), or (IIIb) is administered into the nasal cavity. In another embodiment of any of the aforementioned embodiments of increasing mucin content on the ocular surface, at least 50 micrograms of the compound of Formula (I), (II), (IIIa), or (IIIb) is administered into the nasal cavity. In another embodiment of any of the aforementioned embodiments of increasing mucin content on the ocular surface, at least 100 micrograms of the compound of Formula (I), (II), (IIIa), or (IIIb) is administered into the nasal cavity. In another embodiment of any of the aforementioned embodiments of increasing mucin content on the ocular surface, at least 250 micrograms of the compound of Formula (I), (II), (IIIa), or (IIIb) is administered into the nasal cavity. In another embodiment of any of the aforementioned embodiments of increasing mucin content on the ocular surface, at least 500 micrograms of the compound of Formula (I), (II), (IIIa), or (IIIb) is administered into the nasal cavity. In another embodiment of any of the aforementioned embodiments of increasing mucin content on the ocular surface, at least 750 micrograms of the compound of Formula (I), (II), (IIIa), or (IIIb) is administered into the nasal cavity. In another embodiment of any of the aforementioned embodiments of increasing mucin content on the ocular surface, at least 1000 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, between 1 microgram and 1000 micrograms of the compound of Formula (I), (II), (IIIa), or (IIIb) is administered into the nasal cavity. In another embodiment of any of the aforementioned embodiments of increasing mucin content on the ocular surface, between 5 micrograms and 1000 micrograms of the compound of Formula (I), (II), (IIIa), or (IIIb) is administered into the nasal cavity. In another embodiment of any of the aforementioned embodiments of increasing mucin content on the ocular surface, between 10 micrograms and 1000 micrograms of the compound of Formula (I), (II), (IIIa), or (IIIb) is administered into the nasal cavity. In another embodiment of any of the aforementioned embodiments of increasing mucin content on the ocular surface, between 5 micrograms and 100 micrograms of the compound of Formula (I), (II), (IIIa), or (IIIb) is administered into the nasal cavity. In another embodiment of any of the aforementioned embodiments of increasing mucin content on the ocular surface, between 5 micrograms and 50 micrograms of the compound of Formula (I), (II), (IIIa), or (IIIb) is administered into the nasal cavity. In another embodiment of any of the aforementioned embodiments of increasing mucin content on the ocular surface, between 10 micrograms and 50 micrograms of the compound of Formula (I), (II), (IIIa), or (IIIb) is administered into the nasal cavity. In another embodiment of any of the aforementioned embodiments of increasing mucin content on the ocular surface, between 25 micrograms and 1000 micrograms of the compound of Formula (I), (II), (IIIa), or (IIIb) is administered into the nasal cavity. In another embodiment of any of the aforementioned embodiments of increasing mucin content on the ocular surface, between 50 micrograms and 1000 micrograms of the compound of Formula (I), (II), (IIIa), or (IIIb) is administered into the nasal cavity. In another embodiment of any of the aforementioned embodiments of increasing mucin content on the ocular surface, between 100 micrograms and 1000 micrograms of the compound of Formula (I), (II), (IIIa), or (IIIb) is administered into the nasal cavity. In another embodiment of any of the aforementioned embodiments of increasing mucin content on the ocular surface, between 150 micrograms and 1000 micrograms of the compound of Formula (I), (II), (IIIa), or (IIIb) is administered into the nasal cavity. In another embodiment of any of the aforementioned embodiments of increasing mucin content on the ocular surface, between 100 micrograms and 750 micrograms of the compound of Formula (I), (II), (IIIa), or (IIIb) is administered into the nasal cavity. In another embodiment of any of the aforementioned embodiments of increasing mucin content on the ocular surface, between 150 micrograms and 750 micrograms of the compound of Formula (I), (II), (IIIa), or (IIIb) is administered into the nasal cavity. In another embodiment of any of the aforementioned embodiments of increasing mucin content on the ocular surface, between 150 micrograms and 600 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, less than 100 micrograms of a compound of Formula (I), (II), (IIIa), or (IIIb) is administered into the nasal cavity. In another embodiment of any of the aforementioned embodiments of increasing mucin content on the ocular surface, less than 75 micrograms of a compound of Formula (I), (II), (IIIa), or (IIIb) is administered into the nasal cavity. In another embodiment of any of the aforementioned embodiments of increasing mucin content on the ocular surface, less than 50 micrograms of a compound of Formula (I), (II), (IIIa), or (IIIb) is administered into the nasal cavity. In another embodiment of any of the aforementioned embodiments of increasing mucin content on the ocular surface, less than 25 micrograms of a compound of Formula (I), (II), (IIIa), or (IIIb) is administered into the nasal cavity. In another embodiment of any of the aforementioned embodiments of increasing mucin content on the ocular surface, less than 15 micrograms of a compound of Formula (I), (II), (IIIa), or (IIIb) is administered into the nasal cavity. In another embodiment of any of the aforementioned embodiments of increasing mucin content on the ocular surface, about 75 micrograms of a compound of Formula (I), (II), (IIIa), or (IIIb) is administered into the nasal cavity. In another embodiment of any of the aforementioned embodiments of increasing mucin content on the ocular surface, about 50 micrograms of a compound of Formula (I), (II), (IIIa), or (IIIb) is administered into the nasal cavity. In another embodiment of any of the aforementioned embodiments of increasing mucin content on the ocular surface, about 25 micrograms of a compound of Formula (I), (II), (IIIa), or (IIIb) is administered into the nasal cavity. In another embodiment of any of the aforementioned embodiments of increasing mucin content on the ocular surface, about 10 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, between 1 microgram and 100 micrograms of a compound of Formula (I), (II), (IIIa), or (IIIb) is administered into the nasal cavity. In another embodiment of any of the aforementioned embodiments of increasing mucin content on the ocular surface, between 1 microgram and 75 micrograms of a compound of Formula (I), (II), (IIIa), or (IIIb) is administered into the nasal cavity. In another embodiment of any of the aforementioned embodiments of increasing mucin content on the ocular surface, between 5 micrograms and 100 micrograms of a compound of Formula (I), (II), (IIIa), or (IIIb) is administered into the nasal cavity. In another embodiment of any of the aforementioned embodiments of increasing mucin content on the ocular surface, between 5 micrograms and 75 micrograms of a compound of Formula (I), (II), (IIIa), or (IIIb) is administered into the nasal cavity. In another embodiment of any of the aforementioned embodiments of increasing mucin content on the ocular surface, between 15 micrograms and 100 micrograms of a compound of Formula (I), (II), (IIIa), or (IIIb) is administered into the nasal cavity. In another embodiment of any of the aforementioned embodiments of increasing mucin content on the ocular surface, between 15 micrograms and 75 micrograms of a compound of Formula (I), (II), (IIIa), or (IIIb) is administered into the nasal cavity. In another embodiment of any of the aforementioned embodiments of increasing mucin content on the ocular surface, between 25 micrograms and 100 micrograms of a compound of Formula (I), (II), (IIIa), or (IIIb) is administered into the nasal cavity. In another embodiment of any of the aforementioned embodiments of increasing mucin content on the ocular surface, between 25 micrograms and 75 micrograms of a compound of Formula (I), (II), (IIIa), or (IIIb) is administered into the nasal cavity. In another embodiment of any of the aforementioned embodiments of increasing mucin content on the ocular surface, between 25 micrograms and 60 micrograms of a compound of Formula (I), (II), (IIIa), or (IIIb) is administered into the nasal cavity.

In another embodiment of any of the aforementioned embodiments of increasing mucin content on the ocular surface, between 500 micrograms and 10 milligrams of a compound of Formula (I), (II), (IIIa), or (IIIb) is administered into the nasal cavity. In another embodiment of any of the aforementioned embodiments of increasing mucin content on the ocular surface, between 500 micrograms and 5 milligrams of a compound of Formula (I), (II), (IIIa), or (IIIb) is administered into the nasal cavity. In another embodiment of any of the aforementioned embodiments of increasing mucin content on the ocular surface, between 500 micrograms and 3 milligrams of a compound of Formula (I), (II), (IIIa), or (IIIb) is administered into the nasal cavity. In another embodiment of any of the aforementioned embodiments of increasing mucin content on the ocular surface, between 500 micrograms and 2 milligrams of a compound of Formula (I), (II), (IIIa), or (IIIb) is administered into the nasal cavity. In another embodiment of any of the aforementioned embodiments of increasing mucin content on the ocular surface, between 1 milligram and 10 milligrams of a compound of Formula (I), (II), (IIIa), or (IIIb) is administered into the nasal cavity. In another embodiment of any of the aforementioned embodiments of increasing mucin content on the ocular surface, between 1 milligram and 5 milligrams of a compound of Formula (I), (II), (IIIa), or (IIIb) is administered into the nasal cavity. In another embodiment of any of the aforementioned embodiments of increasing mucin content on the ocular surface, between 1 milligram and 3 milligrams of a compound of Formula (I), (II), (IIIa), or (IIIb) is administered into the nasal cavity. In another embodiment of any of the aforementioned embodiments of increasing mucin content on the ocular surface, between 1 milligram and 2 milligrams of a compound of Formula (I), (II), (IIIa), or (IIIb) is administered into the nasal cavity. In another embodiment of any of the aforementioned embodiments of increasing mucin content on the ocular surface, about 500 micrograms of a compound of Formula (I), (II), (IIIa), or (IIIb) is administered into the nasal cavity. In another embodiment of any of the aforementioned embodiments of increasing mucin content on the ocular surface, about 1 milligram of a compound of Formula (I), (II), (IIIa), or (IIIb) is administered into the nasal cavity. In another embodiment of any of the aforementioned embodiments of increasing mucin content on the ocular surface, about 1.5 milligrams of a compound of Formula (I), (II), (IIIa), or (IIIb) is administered into the nasal cavity. In another embodiment of any of the aforementioned embodiments of increasing mucin content on the ocular surface, about 2 milligrams of a compound of Formula (I), (II), (IIIa), or (IIIb) is administered into the nasal cavity. In another embodiment of any of the aforementioned embodiments of increasing mucin content on the ocular surface, about 2.5 milligrams of a compound of Formula (I), (II), (IIIa), or (IIIb) is administered into the nasal cavity. In another embodiment of any of the aforementioned embodiments of increasing mucin content on the ocular surface, about 3 milligrams of a compound of Formula (I), (II), (IIIa), or (IIIb) is administered into the nasal cavity. In another embodiment of any of the aforementioned embodiments of increasing mucin content on the ocular surface, about 4 milligrams of a compound of Formula (I), (II), (IIIa), or (IIIb) is administered into the nasal cavity. In another embodiment of any of the aforementioned embodiments of increasing mucin content on the ocular surface, about 5 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, between 1 microgram and 10 milligrams of a compound of Formula (I), (II), (IIIa), or (IIIb) is administered into the nasal cavity. In another embodiment of any of the aforementioned embodiments of increasing mucin content on the ocular surface, between 5 micrograms and 10 milligrams of a compound of Formula (I), (II), (IIIa), or (IIIb) is administered into the nasal cavity. In another embodiment of any of the aforementioned embodiments of increasing mucin content on the ocular surface, between 10 micrograms and 10 milligrams of a compound of Formula (I), (II), (IIIa), or (IIIb) is administered into the nasal cavity. In another embodiment of any of the aforementioned embodiments of increasing mucin content on the ocular surface, between 25 micrograms and 10 milligrams of a compound of Formula (I), (II), (IIIa), or (IIIb) is administered into the nasal cavity. In another embodiment of any of the aforementioned embodiments of increasing mucin content on the ocular surface, between 50 micrograms and 10 milligrams of a compound of Formula (I), (II), (Ia), or (IIIb) is administered into the nasal cavity. In another embodiment of any of the aforementioned embodiments of increasing mucin content on the ocular surface, between 100 micrograms and 10 milligrams of a compound of Formula (I), (II), (IIIa), or (IIIb) is administered into the nasal cavity. In another embodiment of any of the aforementioned embodiments of increasing mucin content on the ocular surface, between 150 micrograms and 10 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, between 1 microgram and 10 milligrams of a compound of Formula (I), (II), (IIIa), or (IIIb) is administered into the nasal cavity. In another embodiment of any of the aforementioned embodiments of increasing mucin content on the ocular surface, between 1 microgram and 5 milligrams of a compound of Formula (I), (II), (IIIa), or (IIIb) is administered into the nasal cavity. In another embodiment of any of the aforementioned embodiments of increasing mucin content on the ocular surface, between 1 microgram and 4 milligrams of a compound of Formula (I), (II), (IIIa), or (IIIb) is administered into the nasal cavity. In another embodiment of any of the aforementioned embodiments of increasing mucin content on the ocular surface, between 1 microgram and 3 milligrams of a compound of Formula (I), (II), (IIIa), or (IIIb) is administered into the nasal cavity. In another embodiment of any of the aforementioned embodiments of increasing mucin content on the ocular surface, between 1 microgram and 2 milligrams of a compound of Formula (I), (II), (IIIa), or (IIIb) is administered into the nasal cavity. In another embodiment of any of the aforementioned embodiments of increasing mucin content on the ocular surface, between 1 microgram and 1 milligrams of a compound of Formula (I), (II), (IIIa), or (IIIb) is administered into the nasal cavity. In another embodiment of any of the aforementioned embodiments of increasing mucin content on the ocular surface, between 1 microgram and 750 micrograms of a compound of Formula (I), (II), (IIIa), or (IIIb) is administered into the nasal cavity. In another embodiment of any of the aforementioned embodiments of increasing mucin content on the ocular surface, between 1 microgram and 600 micrograms of a compound of Formula (I), (II), (IIIa), or (IIIb) is administered into the nasal cavity. In another embodiment of any of the aforementioned embodiments of increasing mucin content on the ocular surface, between 1 microgram and 100 micrograms of a compound of Formula (I), (II), (IIIa), or (IIIb) is administered into the nasal cavity. In another embodiment of any of the aforementioned embodiments of increasing mucin content on the ocular surface, between 1 microgram and 50 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method comprises about 0.1 mg/mL of a compound of Formula (I), (II), (IIIa), or (IIIb). In another embodiment, the pharmaceutical formulation for use in the method comprises about 0.2 mg/mL of a compound of Formula (I), (II), (IIIa), or (IIIb). In another embodiment, the pharmaceutical formulation for use in the method comprises about 0.5 mg/mL of a compound of Formula (I), (II), (IIIa), or (IIIb). In another embodiment, the pharmaceutical formulation for use in the method comprises about 1 mg/mL of a compound of Formula (I), (II), (IIIa), or (IIIb). In another embodiment, the pharmaceutical formulation for use in the method comprises about 2 mg/mL of a compound of Formula (I), (II), (IIIa), or (IIIb). In another embodiment, the pharmaceutical formulation for use in the method comprises about 3 mg/mL, of a compound of Formula (I), (II), (IIIa), or (IIIb). In another embodiment, the pharmaceutical formulation for use in the method comprises about 4 mg/mL of a compound of Formula (I), (II), (IIIa), or (IIIb). In another embodiment, the pharmaceutical formulation for use in the method comprises about 5 mg/mL of a compound of Formula (I), (II), (IIIa), or (IIIb). In another embodiment, the pharmaceutical formulation for use in the method comprises about 6 mg/mL of a compound of Formula (I), (II), (IIIa), or (IIIb). In another embodiment, the pharmaceutical formulation for use in the method comprises about 7 mg/mL of a compound of Formula (I), (II), (IIIa), or (IIIb). In another embodiment, the pharmaceutical formulation for use in the method comprises about 8 mg/mL of a compound of Formula (I), (II), (IIIa), or (IIIb). In another embodiment, the pharmaceutical formulation for use in the method comprises about 9 mg/ml, of a compound of Formula (I), (II), (IIIa), or (IIIb). In another embodiment, the pharmaceutical formulation for use in the method comprises about 10 mg/mL of a compound of Formula (I), (II), (IIIa), or (IIIb). In another embodiment, the pharmaceutical formulation for use in the method comprises about 12 mg/mL of a compound of Formula (I), (II), (IIIa), or (IIIb). In another embodiment, the pharmaceutical formulation for use in the method comprises about 15 mg/mL of a compound of Formula (I), (II), (IIIa), or (IIIb). In another embodiment, the pharmaceutical formulation for use in the method comprises about 20 mg/mL of a compound of Formula (I), (II), (IIIa), or (IIIb). In another embodiment, the pharmaceutical formulation for use in the method comprises about 25 mg/mL of a compound of Formula (I), (II), (IIIa), or (IIIb). In another embodiment, the pharmaceutical formulation for use in the method comprises about 30 mg/mL of a compound of Formula (I), (II), (IIIa), or (IIIb). In another embodiment, the pharmaceutical formulation for use in the method comprises about 40 mg/mL of a compound of Formula (I), (II), (IIIa), or (IIIb). In another embodiment, the pharmaceutical formulation for use in the method comprises about 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 5 mg/mL, and 200 mg/mL of a compound of Formula (I), (II), (IIIa), or (IIIb). In another embodiment, the pharmaceutical formulation for use in the method comprises between 10 mg/mL and 200 mg/mL of a compound of Formula (I), (II), (IIIa), or (IIIb). In another embodiment, the pharmaceutical formulation for use in the method comprises between 5 mg/mL and 100 mg/mL of a compound of Formula (I), (II), (IIIa), or (IIIb). In another embodiment, the pharmaceutical formulation for use in the method comprises between 10 mg/mL and 75 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 10 mg/mL and 30 mg/mL of a compound of Formula (I), (II), (IIIa), or (IIIb). In another embodiment, the pharmaceutical formulation for use in the method comprises between 5 mg/mL and 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 10 mg/mL and 25 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 20 mg/mL and 50 mg/mL of a compound of Formula (I), (II), (IIIa), or (IIIb). In another embodiment, the pharmaceutical formulation for use in the method comprises between 30 mg/mL and 75 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method is provided at about 10 to 200 μl. In another embodiment, the pharmaceutical formulation for use in the method is provided at about 10 to 150 μl. In another embodiment, the pharmaceutical formulation for use in the method is provided at about 10 to 100 μl. In another embodiment, the pharmaceutical formulation for use in the method is provided at about 50 to 200 μl. In another embodiment, the pharmaceutical formulation for use in the method is provided at about 100 to 200 μl. In another embodiment, the pharmaceutical formulation for use in the method is provided at about 50 to 100 μl. In another embodiment, the pharmaceutical formulation for use in the method is provided at about 10 to 150 μl. In another embodiment, the pharmaceutical formulation for use in the method is provided at about 10, 20, 30, 40, 50, 60, 70, 80, 90, 100, 110, 120, 130, 140, 150, 160, 170, 180, 190, or 200 μl. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, the compound of Formula (I), (II), (IIIa), or (IIIb) is administered once daily. In another embodiment of any of the aforementioned embodiments of increasing mucin content on the ocular surface, the compound of Formula (I), (II), (IIIa), or (IIIb) is administered at least once daily. In another embodiment of any of the aforementioned embodiments of increasing mucin content on the ocular surface, the compound of Formula (I), (II), (IIIa), or (IIIb) is administered twice daily. In another embodiment of any of the aforementioned embodiments of increasing mucin content on the ocular surface, the compound of Formula (I), (II), (IIIa), or (IIIb) is administered at least twice daily. In another embodiment of any of the aforementioned embodiments of increasing mucin content on the ocular surface, the compound of Formula (I), (II), (IIIa), or (IIIb) is administered three times daily. In another embodiment of any of the aforementioned embodiments of increasing mucin content on the ocular surface, the compound of Formula (I), (II), (IIIa), or (IIIb) is administered at least three times daily. In another embodiment of any of the aforementioned embodiments of increasing mucin content on the ocular surface, the compound of Formula (I), (II), (IIIa), or (IIIb) is administered for one day. In another embodiment of any of the aforementioned embodiments of increasing mucin content on the ocular surface, the compound of Formula (I), (II), (IIIa), or (IIIb) is administered for at least two days. In another embodiment of any of the aforementioned embodiments of increasing mucin content on the ocular surface, the compound of Formula (I), (II), (IIIa), or (IIIb) is administered for at least three days. In another embodiment of any of the aforementioned embodiments of increasing mucin content on the ocular surface, the compound of Formula (I), (II), (IIIa), or (IIIb) is administered for at least four days. In another embodiment of any of the aforementioned embodiments of increasing mucin content on the ocular surface, the compound of Formula (I), (II), (IIIa), or (IIIb) is administered for at least five days. In another embodiment of any of the aforementioned embodiments of increasing mucin content on the ocular surface, the compound of Formula (I), (II), (IIIa), or (IIIb) is administered for at least seven days. In another embodiment of any of the aforementioned embodiments of increasing mucin content on the ocular surface, the compound of Formula (I), (II), (IIIa), or (IIIb) is administered for at least ten days. In another embodiment of any of the aforementioned embodiments of increasing mucin content on the ocular surface, the compound of Formula (I), (II), (IIIa), or (IIIb) is administered for at least fourteen days. In another embodiment of any of the aforementioned embodiments of increasing mucin content on the ocular surface, the compound of Formula (I), (II), (IIIa), or (IIIb) is administered for at least twenty one days. In another embodiment of any of the aforementioned embodiments of increasing mucin content on the ocular surface, the compound of Formula (I), (II), (IIIa), or (IIIb) is administered for at least thirty days. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, the compound of Formula (I), (II), (IIIa), or (IIIb) is administered in alternating nostrils. For example, the compound of Formula (I), (II), (IIIa), or (IIIb) is administered in one nostril and then the other nostril after a pre-determined amount of time. In another embodiment, the compound of Formula (I), (II), (IIIa), or (IIIb) is administered in both nostrils. For example, the compound of Formula (I), (II), (IIIa), or (IIIb) is administered in one nostril and then the other nostril at the same time or immediately after the first nostril. In another embodiment, the compound of Formula (I), (II), (IIIa), or (IIIb) is administered in one nostril. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, the compound of Formula (I), (II), (IIIa), or (IIIb) is administered into the nasal cavity as a liquid, suspension, aerosol, gel, ointment dry powder, cream, paste, lotion, or balm. In another embodiment of any of the aforementioned embodiments of increasing mucin content on the ocular surface, the compound of Formula (I), (II), (IIIa), or (IIIb) is administered into the nasal cavity as a liquid. In another embodiment of any of the aforementioned embodiments of increasing mucin content on the ocular surface, the compound of Formula (I), (II), (IIIa), or (IIIb) is administered into the nasal cavity as a suspension. In another embodiment of any of the aforementioned embodiments of increasing mucin content on the ocular surface, the compound of Formula (I), (II), (IIIa), or (IIIb) is administered into the nasal cavity as an acrosol. In another embodiment of any of the aforementioned embodiments of increasing mucin content on the ocular surface, the compound of Formula (I), (II), (IIIa), or (IIIb) is administered into the nasal cavity as a gel. In another embodiment of any of the aforementioned embodiments of increasing mucin content on the ocular surface, the compound of Formula (I), (II), (IIIa), or (IIIb) is administered into the nasal cavity as an ointment. In another embodiment of any of the aforementioned embodiments of increasing mucin content on the ocular surface, the compound of Formula (I), (II), (IIIa), or (IIIb) is administered into the nasal cavity as a dry powder. In another embodiment of any of the aforementioned embodiments of increasing mucin content on the ocular surface, the compound of Formula (I), (II), (IIIa), or (IIIb) is administered into the nasal cavity as a cream. In another embodiment of any of the aforementioned embodiments of increasing mucin content on the ocular surface, the compound of Formula (I), (II), (IIIa), or (IIIb) is administered into the nasal cavity as a paste. In another embodiment of any of the aforementioned embodiments of increasing mucin content on the ocular surface, the compound of Formula (I), (II), (IIIa), or (IIIb) is administered into the nasal cavity as a lotion. In another embodiment of any of the aforementioned embodiments of increasing mucin content on the ocular surface, the compound of Formula (I), (II), (IIIa), or (IIIb) is administered into the nasal cavity as a balm. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, the compound of Formula (I), (II), (IIIa), or (IIIb) is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of increasing mucin content on the ocular surface, the compound of Formula (I), (II), (IIIa), or (IIIb) is administered into the nasal cavity by a syringe. In another embodiment of any of the aforementioned embodiments of increasing mucin content on the ocular surface, the compound of Formula (I), (II), (IIIa), or (IIIb) is administered into the nasal cavity by a dropper. In another embodiment of any of the aforementioned embodiments of increasing mucin content on the ocular surface, the compound of Formula (I), (II), (IIIa), or (IIIb) is administered into the nasal cavity by a bottle nebulizer. In another embodiment of any of the aforementioned embodiments of increasing mucin content on the ocular surface, the compound of Formula (I), (II), (IIIa), or (IIIb) is administered into the nasal cavity by an atomization pump. In another embodiment of any of the aforementioned embodiments of increasing mucin content on the ocular surface, the compound of Formula (I), (II), (IIIa), or (IIIb) is administered into the nasal cavity by an inhaler. In another embodiment of any of the aforementioned embodiments of increasing mucin content on the ocular surface, the compound of Formula (I), (II), (IIIa), or (IIIb) is administered into the nasal cavity by a powder spray device. In another embodiment of any of the aforementioned embodiments of increasing mucin content on the ocular surface, the compound of Formula (I), (II), (IIIa), or (IIIb) is administered into the nasal cavity by a vaporizer. In another embodiment of any of the aforementioned embodiments of increasing mucin content on the ocular surface, the compound of Formula (I), (II), (IIIa), or (IIIb) is administered into the nasal cavity by a patch. In another embodiment of any of the aforementioned embodiments of increasing mucin content on the ocular surface, the compound of Formula (I), (II), (IIIa), or (IIIb) is administered into the nasal cavity by a medicated stick. In another embodiment of any of the aforementioned embodiments of increasing mucin content on the ocular surface, the compound of Formula (I), (II), (IIIa), or (IIIb) is administered into the nasal cavity by a pipette. In another embodiment of any of the aforementioned embodiments of increasing mucin content on the ocular surface, the compound of Formula (I), (II), (IIIa), or (IIIb) is administered into the nasal cavity by a jet of liquid. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, the trigeminal nerve is activated. In a further embodiment of increasing mucin content on the ocular surface, the anterior ethmoidal nerve is activated. In another embodiment of any of the aforementioned embodiments of increasing mucin content on the ocular surface, the nasolacrimal reflex is activated. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing mucin content on the ocular surface, the mucin content on the ocular surface is associated with an acute condition. An acute condition refers to a condition with a rapid onset of a health effect that is considered brief, not prolonged. Acute conditions can result from ophthalmologic surgical procedures or other ophthalmologic treatment. In some embodiments, the ophthalmologic surgical procedure is cataract surgery (cataract extraction and lens replacement), refractive lens exchange, glaucoma surgery, lasik surgery (laser eye surgery), vitrectomy, retinal photocoagulation, retinal detachment repair, macular hole repair, retroiris tumor or mass removal, posterior sclerotomy, optic neurotomy, or other treatments that decrease the function of the lacrimal gland. In some embodiments, the ophthalmologic treatment comprises radiation therapy. In some embodiments, the radiation therapy is directed to orbital area, for example, in connection to cancers of head and/or neck. In some embodiments, the compound of Formula (I) is (R)-5-((E)-2-pyrrolidin-3-ylvinyl)pyrimidine, or a pharmaceutically acceptable salt thereof.

Increasing the Amount or Concentration of One or More Lacrimal Proteins

Provided herein, in some embodiments, is a method of increasing the amount or concentration of one or more lacrimal proteins in a subject. In some embodiments, is a method of increasing the amount or concentration of one or more lacrimal proteins, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and does not cross the blood-brain barrier in a pharmacologically relevant concentration. In some embodiments is method of increasing the amount or concentration of one or more lacrimal proteins, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of increasing the amount or concentration of one or more lacrimal proteins, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha3beta4. In some embodiments is method of increasing the amount or concentration of one or more lacrimal proteins, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha4beta2. In some embodiments is method of increasing the amount or concentration of one or more lacrimal proteins, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha7. In some embodiments is a method of increasing the amount or concentration of one or more lacrimal proteins, comprising the local administration of a therapeutically effective amount of a compound of Formula (I), (II), (IIIa), or (IIIb) into the nasal cavity of an individual in need thereof wherein the compound of Formula (I), (II), (IIIa), or (IIIb) selectively binds to the peripheral nicotinic acetylcholine receptor and is administered in an amount that is not systemically bioavailable. In some embodiments is a method of increasing the amount or concentration of one or more lacrimal proteins, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired psychoactive side effects. In some embodiments is a method of increasing the amount or concentration of one or more lacrimal proteins, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired systemic side effects. In some embodiments is a method of increasing the amount or concentration of one or more lacrimal proteins, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that produces a local effect. In some embodiments is a method of increasing the amount or concentration of one or more lacrimal proteins, wherein the lacrimal protein is epithelial growth factor, lactoferin, lacritin, prolactin, adrenocorticotropic, leucine enkephalin, ALS2CL, ARHGEF19, KIAA 1109, PLXNA1, POLG, WIPI1, ZMIZ2 or other proteins of the tear proteome. In some embodiments is a method of increasing the amount or concentration of one or more lacrimal proteins, wherein at least one lacrimal protein is epithelial growth factor. In some embodiments is a method of increasing the amount or concentration of one or more lacrimal proteins, wherein at least one lacrimal protein is lactoferin. In some embodiments is a method of increasing the amount or concentration of one or more lacrimal proteins, wherein at least one lacrimal protein is lacritin. In some embodiments is a method of increasing the amount or concentration of one or more lacrimal proteins, wherein at least one lacrimal protein is prolactin. In some embodiments is a method of increasing the amount or concentration of one or more lacrimal proteins, wherein at least one lacrimal protein is adrenocorticotropic. In some embodiments is a method of increasing the amount or concentration of one or more lacrimal proteins, wherein at least one lacrimal protein is leucine enkephalin. In some embodiments is a method of increasing the amount or concentration of one or more lacrimal proteins, wherein at least one lacrimal protein is ALS2CL. In some embodiments is a method of increasing the amount or concentration of one or more lacrimal proteins, wherein at least one lacrimal protein is ARHGEF19. In some embodiments is a method of increasing the amount or concentration of one or more lacrimal proteins, wherein at least one lacrimal protein is KIAA 1109. In some embodiments is a method of increasing the amount or concentration of one or more lacrimal proteins, wherein at least one lacrimal protein is PLXNA1. In some embodiments is a method of increasing the amount or concentration of one or more lacrimal proteins, wherein at least one lacrimal protein is POLG. In some embodiments is a method of increasing the amount or concentration of one or more lacrimal proteins, wherein at least one lacrimal protein is WIP11. In some embodiments is a method of increasing the amount or concentration of one or more lacrimal proteins, wherein at least one lacrimal protein is ZMIZ2. In some embodiments is a method of increasing the amount or concentration of one or more lacrimal proteins, further comprising the local administration of one or more substances that prevent or facilitate the recovery of the nicotinic acetylcholine receptor from the desensitized state. In some embodiments is a method of increasing the amount or concentration of one or more lacrimal proteins, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments, the compound of Formula (I) is (R)-5-((E)-2-pyrrolidin-3-ylvinyl)pyrimidine, or a pharmaceutically acceptable salt thereof.

In some embodiments of the method of increasing the amount or concentration of one or more lacrimal proteins described herein, the compound of Formula (I), (II), (IIIa), or (IIIb) is (R)-5-((E)-2-pyrrolidin-3-ylvinyl)pyrimidine (or Compound 1). In some embodiments of the methods described herein, the compound of Formula (I), (II), (IIIa), or (IIIb) is (R)-5-((E)-2-pyrrolidin-3-ylvinyl)pyrimidine, or a pharmaceutically acceptable salt thereof. In some embodiments of the method of increasing the amount or concentration of one or more lacrimal proteins described herein, the compound of Formula (I), (II), (IIIa), or (IIIb) is (R)-5-((E)-2-pyrrolidin-3-ylvinyl)pyrimidine as a free base. In some embodiments of the method of increasing the amount or concentration of one or more lacrimal proteins described herein, the compound of Formula (I), (II), (IIIa), or (IIIb) is (R)-5-((E)-2-pyrrolidin-3-ylvinyl)pyrimidine citrate salt. In some embodiments of the method of increasing the amount or concentration of one or more lacrimal proteins described herein, the compound of Formula (I), (II), (IIIa), or (IIIb) is (R)-5-((E)-2-pyrrolidin-3-ylvinyl)pyrimidine mono citrate salt. In some embodiments of the method of increasing the amount or concentration of one or more lacrimal proteins described herein, the compound of Formula (I), (II), (IIIa), or (IIIb) is (R)-5-((E)-2-pyrrolidin-3-ylvinyl)pyrimidine HCl salt. In some embodiments of the method of increasing the amount or concentration of one or more lacrimal proteins described herein, the compound of Formula (I), (II), (IIIa), or (IIIb) is (R)-5-((E)-2-pyrrolidin-3-ylvinyl)pyrimidine galactarate salt. In some embodiments of the method of increasing the amount or concentration of one or more lacrimal proteins described herein, the compound of Formula (I), (II), (IIIa), or (IIIb) is (R)-5-((E)-2-pyrrolidin-3-ylvinyl)pyrimidine hemigalactarate salt. In some embodiments of the method of increasing the amount or concentration of one or more lacrimal proteins described herein, the compound of Formula (I), (II), (IIIa), or (IIIb) is (R)-5-((E)-2-pyrrolidin-3-ylvinyl)pyrimidine hemigalactarate monohydrate. In some embodiments of the method described herein, the compound of Formula (I), (II), (IIIa), or (IIIb) is (R)-5-((E)-2-pyrrolidin-3-ylvinyl)pyrimidine hemigalactarate dihydrate.

In some embodiments is a method of increasing the amount or concentration of one or more lacrimal proteins, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing the amount or concentration of one or more lacrimal proteins, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing the amount or concentration of one or more lacrimal proteins, further comprising the local administration of protein kinase C (PKC) or factors that upregulate or up-modulate PKC. In some embodiments is a method of increasing the amount or concentration of one or more lacrimal proteins, further comprising the local administration of cAMP-dependent protein kinase (PKA) or factors that upregulate or up-modulate PKA. In some embodiments is a method of increasing the amount or concentration of one or more lacrimal proteins, further comprising the local administration of a calcineurin inhibitor. In some embodiments is a method of increasing the amount or concentration of one or more lacrimal proteins, further comprising the local administration of a calcineurin inhibitor, wherein the calcineurin inhibitor is selected from cyclosporine, pimecrolimus, and tacrolimus. In some embodiments is a method of increasing the amount or concentration of one or more lacrimal proteins, further comprising the local administration of cyclosporine. In some embodiments is a method of increasing the amount or concentration of one or more lacrimal proteins, further comprising the local administration of pimecrolimus. In some embodiments is a method of increasing the amount or concentration of one or more lacrimal proteins, further comprising the local administration of tacrolimus.

In another embodiment of any of the aforementioned embodiments of increasing the amount or concentration of one or more lacrimal proteins, at least 1 microgram of the compound of Formula (I), (II), (IIIa), or (IIIb) is administered into the nasal cavity. In another embodiment of any of the aforementioned embodiments of increasing the amount or concentration of one or more lacrimal proteins, at least 5 micrograms of the compound of Formula (I), (II), (IIIa), or (IIIb) is administered into the nasal cavity. In another embodiment of any of the aforementioned embodiments of increasing the amount or concentration of one or more lacrimal proteins, at least 10 micrograms of the compound of Formula (I), (II), (IIIa), or (IIIb) is administered into the nasal cavity. In another embodiment of any of the aforementioned embodiments of increasing the amount or concentration of one or more lacrimal proteins, at least 25 micrograms of the compound of Formula (I), (II), (IIIa), or (IIIb) is administered into the nasal cavity. In another embodiment of any of the aforementioned embodiments of increasing the amount or concentration of one or more lacrimal proteins, at least 50 micrograms of the compound of Formula (I), (II), (IIIa), or (IIIb) is administered into the nasal cavity. In another embodiment of any of the aforementioned embodiments of increasing the amount or concentration of one or more lacrimal proteins, at least 100 micrograms of the compound of Formula (I), (II), (IIIa), or (IIIb) is administered into the nasal cavity. In another embodiment of any of the aforementioned embodiments of increasing the amount or concentration of one or more lacrimal proteins, at least 250 micrograms of the compound of Formula (I), (II), (II), (IIIa), or (IIIb) is administered into the nasal cavity. In another embodiment of any of the aforementioned embodiments of increasing the amount or concentration of one or more lacrimal proteins, at least 500 micrograms of the compound of Formula (I), (II), (IIIa), or (IIIb) is administered into the nasal cavity. In another embodiment of any of the aforementioned embodiments of increasing the amount or concentration of one or more lacrimal proteins, at least 750 micrograms of the compound of Formula (I), (II), (IIIa), or (IIIb) is administered into the nasal cavity. In another embodiment of any of the aforementioned embodiments of increasing the amount or concentration of one or more lacrimal proteins, at least 1000 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, between 1 microgram and 1000 micrograms of the compound of Formula (I), (II), (IIIa), or (IIIb) is administered into the nasal cavity. In another embodiment of any of the aforementioned embodiments of increasing the amount or concentration of one or more lacrimal proteins, between 5 micrograms and 1000 micrograms of the compound of Formula (I), (II), (IIIa), or (IIIb) is administered into the nasal cavity. In another embodiment of any of the aforementioned embodiments of increasing the amount or concentration of one or more lacrimal proteins, between 10 micrograms and 1000 micrograms of the compound of Formula (I), (II), (IIIa), or (IIIb) is administered into the nasal cavity. In another embodiment of any of the aforementioned embodiments of increasing the amount or concentration of one or more lacrimal proteins, between 5 micrograms and 100 micrograms of the compound of Formula (I), (II), (IIIa), or (IIIb) is administered into the nasal cavity. In another embodiment of any of the aforementioned embodiments of increasing the amount or concentration of one or more lacrimal proteins, between 5 micrograms and 50 micrograms of the compound of Formula (I), (II), (IIIa), or (IIIb) is administered into the nasal cavity. In another embodiment of any of the aforementioned embodiments of increasing the amount or concentration of one or more lacrimal proteins, between 10 micrograms and 50 micrograms of the compound of Formula (I), (II), (IIIa), or (IIIb) is administered into the nasal cavity. In another embodiment of any of the aforementioned embodiments of increasing the amount or concentration of one or more lacrimal proteins, between 25 micrograms and 1000 micrograms of the compound of Formula (I), (II), (IIIa), or (IIIb) is administered into the nasal cavity. In another embodiment of any of the aforementioned embodiments of increasing the amount or concentration of one or more lacrimal proteins, between 50 micrograms and 1000 micrograms of the compound of Formula (I), (II), (IIIa), or (IIIb) is administered into the nasal cavity. In another embodiment of any of the aforementioned embodiments of increasing the amount or concentration of one or more lacrimal proteins, between 100 micrograms and 1000 micrograms of the compound of Formula (I), (II), (IIIa), or (IIIb) is administered into the nasal cavity. In another embodiment of any of the aforementioned embodiments of increasing the amount or concentration of one or more lacrimal proteins, between 150 micrograms and 1000 micrograms of the compound of Formula (I), (II), (IIIa), or (IIIb) is administered into the nasal cavity. In another embodiment of any of the aforementioned embodiments of increasing the amount or concentration of one or more lacrimal proteins, between 100 micrograms and 750 micrograms of the compound of Formula (I), (II), (IIIa), or (IIIb) is administered into the nasal cavity. In another embodiment of any of the aforementioned embodiments of increasing the amount or concentration of one or more lacrimal proteins, between 150 micrograms and 750 micrograms of the compound of Formula (I), (II), (IIIa), or (IIIb) is administered into the nasal cavity. In another embodiment of any of the aforementioned embodiments of increasing the amount or concentration of one or more lacrimal proteins, between 150 micrograms and 600 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, less than 100 micrograms of a compound of Formula (I), (II), (IIIa), or (IIIb) is administered into the nasal cavity. In another embodiment of any of the aforementioned embodiments of increasing the amount or concentration of one or more lacrimal proteins, less than 75 micrograms of a compound of Formula (I), (I), (IIIa), or (IIIb) is administered into the nasal cavity. In another embodiment of any of the aforementioned embodiments of increasing the amount or concentration of one or more lacrimal proteins, less than 50 micrograms of a compound of Formula (I), (II), (IIIa), or (IIIb) is administered into the nasal cavity. In another embodiment of any of the aforementioned embodiments of increasing the amount or concentration of one or more lacrimal proteins, less than 25 micrograms of a compound of Formula (I), (II), (IIIa), or (IIIb) is administered into the nasal cavity. In another embodiment of any of the aforementioned embodiments of increasing the amount or concentration of one or more lacrimal proteins, less than 15 micrograms of a compound of Formula (I), (II), (IIIa), or (IIIb) is administered into the nasal cavity. In another embodiment of any of the aforementioned embodiments of increasing the amount or concentration of one or more lacrimal proteins, about 75 micrograms of a compound of Formula (I), (II), (IIIa), or (IIIb) is administered into the nasal cavity. In another embodiment of any of the aforementioned embodiments of increasing the amount or concentration of one or more lacrimal proteins, about 50 micrograms of a compound of Formula (I), (II), (IIIa), or (IIIb) is administered into the nasal cavity. In another embodiment of any of the aforementioned embodiments of increasing the amount or concentration of one or more lacrimal proteins, about 25 micrograms of a compound of Formula (I), (II), (IIIa), or (IIIb) is administered into the nasal cavity. In another embodiment of any of the aforementioned embodiments of increasing the amount or concentration of one or more lacrimal proteins, about 10 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, between 1 microgram and 100 micrograms of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 75 micrograms of a compound of Formula (I), (II), (IIIa), or (IIIb) is administered into the nasal cavity. In another embodiment of any of the aforementioned embodiments of increasing the amount or concentration of one or more lacrimal proteins, between 5 micrograms and 100 micrograms of a compound of Formula (I), (II), (IIIa), or (IIIb) is administered into the nasal cavity. In another embodiment of any of the aforementioned embodiments of increasing the amount or concentration of one or more lacrimal proteins, between 5 micrograms and 75 micrograms of a compound of Formula (I), (II), (IIIa), or (IIIb) is administered into the nasal cavity. In another embodiment of any of the aforementioned embodiments of increasing the amount or concentration of one or more lacrimal proteins, between 15 micrograms and 100 micrograms of a compound of Formula (I), (II), (IIIa), or (IIIb) is administered into the nasal cavity. In another embodiment of any of the aforementioned embodiments of increasing the amount or concentration of one or more lacrimal proteins, between 15 micrograms and 75 micrograms of a compound of Formula (I), (II), (IIIa), or (IIIb) is administered into the nasal cavity. In another embodiment of any of the aforementioned embodiments of increasing the amount or concentration of one or more lacrimal proteins, between 25 micrograms and 100 micrograms of a compound of Formula (I), (II), (IIIa), or (IIIb) is administered into the nasal cavity. In another embodiment of any of the aforementioned embodiments of increasing the amount or concentration of one or more lacrimal proteins, between 25 micrograms and 75 micrograms of a compound of Formula (I), (II), (IIIa), or (IIIb) is administered into the nasal cavity. In another embodiment of any of the aforementioned embodiments of increasing the amount or concentration of one or more lacrimal proteins, between 25 micrograms and 60 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, between 500 micrograms and 10 milligrams of a compound of Formula (I), (II), (IIIa), or (IIIb) is administered into the nasal cavity. In another embodiment of any of the aforementioned embodiments of increasing the amount or concentration of one or more lacrimal proteins, between 500 micrograms and 5 milligrams of a compound of Formula (I), (II), (IIIa), or (IIIb) is administered into the nasal cavity. In another embodiment of any of the aforementioned embodiments of increasing the amount or concentration of one or more lacrimal proteins, between 500 micrograms and 3 milligrams of a compound of Formula (I), (II), (IIIa), or (IIIb) is administered into the nasal cavity. In another embodiment of any of the aforementioned embodiments of increasing the amount or concentration of one or more lacrimal proteins, between 500 micrograms and 2 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 milligram and 10 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 milligram and 5 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 milligram and 3 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 milligram and 2 milligrams of a compound of Formula (I), (II), (IIIa), or (IIIb) is administered into the nasal cavity. In another embodiment of any of the aforementioned embodiments of increasing the amount or concentration of one or more lacrimal proteins, about 500 micrograms of a compound of Formula (I), (II), (IIIa), or (IIIb) is administered into the nasal cavity. In another embodiment of any of the aforementioned embodiments of increasing the amount or concentration of one or more lacrimal proteins, about 1 milligram of a compound of Formula (I), (II), (IIIa), or (IIIb) is administered into the nasal cavity. In another embodiment of any of the aforementioned embodiments of increasing the amount or concentration of one or more lacrimal proteins, about 1.5 milligrams of a compound of Formula. (I), (II), (IIIa), or (IIIb) is administered into the nasal cavity. In another embodiment of any of the aforementioned embodiments of increasing the amount or concentration of one or more lacrimal proteins, about 2 milligrams of a compound of Formula (I), (II), (IIIa), or (IIIb) is administered into the nasal cavity. In another embodiment of any of the aforementioned embodiments of increasing the amount or concentration of one or more lacrimal proteins, about 2.5 milligrams of a compound of Formula (I), (II), (IIIa), or (IIIb) is administered into the nasal cavity. In another embodiment of any of the aforementioned embodiments of increasing the amount or concentration of one or more lacrimal proteins, about 3 milligrams of a compound of Formula (I), (II), (IIIa), or (IIIb) is administered into the nasal cavity. In another embodiment of any of the aforementioned embodiments of increasing the amount or concentration of one or more lacrimal proteins, about 4 milligrams of a compound of Formula (I), (II), (IIIa), or (IIIb) is administered into the nasal cavity. In another embodiment of any of the aforementioned embodiments of increasing the amount or concentration of one or more lacrimal proteins, about 5 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, between 1 microgram and 10 milligrams of a compound of Formula (I), (II), (IIIa), or (IIIb) is administered into the nasal cavity. In another embodiment of any of the aforementioned embodiments of increasing the amount or concentration of one or more lacrimal proteins, between 5 micrograms and 10 milligrams of a compound of Formula (I), (II), (IIIa), or (IIIb) is administered into the nasal cavity. In another embodiment of any of the aforementioned embodiments of increasing the amount or concentration of one or more lacrimal proteins, between 10 micrograms and 10 milligrams of a compound of Formula (I), (II), (IIIa), or (IIIb) is administered into the nasal cavity. In another embodiment of any of the aforementioned embodiments of increasing the amount or concentration of one or more lacrimal proteins, between 25 micrograms and 10 milligrams of a compound of Formula (I), (II), (IIIa), or (IIIb) is administered into the nasal cavity. In another embodiment of any of the aforementioned embodiments of increasing the amount or concentration of one or more lacrimal proteins, between 50 micrograms and 10 milligrams of a compound of Formula (I), (II), (IIIa), or (IIIb) is administered into the nasal cavity. In another embodiment of any of the aforementioned embodiments of increasing the amount or concentration of one or more lacrimal proteins, between 100 micrograms and 10 milligrams of a compound of Formula (I), (II), (IIIa), or (IIIb) is administered into the nasal cavity. In another embodiment of any of the aforementioned embodiments of increasing the amount or concentration of one or more lacrimal proteins, between 150 micrograms and 10 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, between 1 microgram and 10 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 5 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 4 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 3 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 2 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 1 milligrams of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 750 micrograms of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 600 micrograms of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 100 micrograms of a compound of Formula (I), (II), (IIIa), or (IIIb) is administered into the nasal cavity. In another embodiment of any of the aforementioned embodiments of increasing the amount or concentration of one or more lacrimal proteins, between 1 microgram and 50 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method comprises about 0.1 mg/mL of a compound of Formula (I), (II), (IIIa), or (IIIb). In another embodiment, the pharmaceutical formulation for use in the method comprises about 0.2 mg/mL of a compound of Formula (I), (II), (IIIa), or (IIIb). In another embodiment, the pharmaceutical formulation for use in the method comprises about 0.5 mg/mL of a compound of Formula (I), (II), (IIIa), or (IIIb). In another embodiment, the pharmaceutical formulation for use in the method comprises about 1 mg/mL of a compound of Formula (I), (II), (IIIa), or (IIIb). In another embodiment, the pharmaceutical formulation for use in the method comprises about 2 mg/mL of a compound of Formula (I), (II), (IIIa), or (IIIb). In another embodiment, the pharmaceutical formulation for use in the method comprises about 3 mg/mL of a compound of Formula (I), (II), (IIIa), or (IIIb). In another embodiment, the pharmaceutical formulation for use in the method comprises about 4 mg/mL of a compound of Formula (I), (II), (IIIa), or (IIIb). In another embodiment, the pharmaceutical formulation for use in the method comprises about 5 mg/mL of a compound of Formula (I), (II), (IIIa), or (IIIb). In another embodiment, the pharmaceutical formulation for use in the method comprises about 6 mg/mL of a compound of Formula (I), (II), (IIIa), or (IIIb). In another embodiment, the pharmaceutical formulation for use in the method comprises about 7 mg/mL, of a compound of Formula (I), (II), (IIIa), or (IIIb). In another embodiment, the pharmaceutical formulation for use in the method comprises about 8 mg/mL of a compound of Formula (I), (II), (IIIa), or (IIIb). In another embodiment, the pharmaceutical formulation for use in the method comprises about 9 mg/mL of a compound of Formula (I), (II), (IIIa), or (IIIb). In another embodiment, the pharmaceutical formulation for use in the method comprises about 10 mg/mL of a compound of Formula (I), (II), (IIIa), or (IIIb). In another embodiment, the pharmaceutical formulation for use in the method comprises about 12 mg/ml, of a compound of Formula (I), (II), (IIIa), or (IIIb). In another embodiment, the pharmaceutical formulation for use in the method comprises about 15 mg/mL of a compound of Formula (I), (II), (IIIa), or (IIIb). In another embodiment, the pharmaceutical formulation for use in the method comprises about 20 mg/mL of a compound of Formula (I), (II), (IIIa), or (IIIb). In another embodiment, the pharmaceutical formulation for use in the method comprises about 25 mg/mL of a compound of Formula (I), (II), (IIIa), or (IIIb). In another embodiment, the pharmaceutical formulation for use in the method comprises about 30 mg/mL of a compound of Formula (I), (II), (IIIa), or (IIIb). In another embodiment, the pharmaceutical formulation for use in the method comprises about 40 mg/mL of a compound of Formula (I), (II), (IIIa), or (IIIb). In another embodiment, the pharmaceutical formulation for use in the method comprises about 50 mg/mL, of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 5 mg/mL and 200 mg/mL of a compound of Formula (I), (II), (IIIa), or (IIIb). In another embodiment, the pharmaceutical formulation for use in the method comprises between 10 mg/mL and 200 mg/mL of a compound of Formula (I), (II), (IIIa), or (IIIb). In another embodiment, the pharmaceutical formulation for use in the method comprises between 5 mg/mL, and 100 mg/mL of a compound of Formula (I), (II), (IIIa), or (IIIb). In another embodiment, the pharmaceutical formulation for use in the method comprises between 10 mg/mL and 75 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 10 mg/mL and 30 mg/mL, of a compound of Formula (I), (II), (IIIa), or (IIIb). In another embodiment, the pharmaceutical formulation for use in the method comprises between 5 mg/mL and 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 10 mg/mL and 25 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 20 mg/mL and 50 mg/mL of a compound of Formula (I), (II), (IIIa), or (IIIb). In another embodiment, the pharmaceutical formulation for use in the method comprises between 30 mg/mL and 75 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method is provided at about 10 to 200 µl. In another embodiment, the pharmaceutical formulation for use in the method is provided at about 10 to 150 µl. In another embodiment, the pharmaceutical formulation for use in the method is provided at about 10 to 100 µl. In another embodiment, the pharmaceutical formulation for use in the method is provided at about 50 to 200 µl. In another embodiment, the pharmaceutical formulation for use in the method is provided at about 100 to 200 µl. In another embodiment, the pharmaceutical formulation for use in the method is provided at about 50 to 100 µl. In another embodiment, the pharmaceutical formulation for use in the method is provided at about 10 to 150 µl. In another embodiment, the pharmaceutical formulation for use in the method is provided at about 10, 20, 30, 40, 50, 60, 70, 80, 90, 100, 110, 120, 130, 140, 150, 160, 170, 180, 190, or 200 µl. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, the compound of Formula (I), (II), (IIIa), or (IIIb) is administered once daily. In another embodiment of any of the aforementioned embodiments of increasing the amount or concentration of one or more lacrimal proteins, the compound of Formula (I), (II), (IIIa), or (IIIb) is administered at least once daily. In another embodiment of any of the aforementioned embodiments of increasing the amount or concentration of one or more lacrimal proteins, the compound of Formula (I), (II), (IIIa), or (IIIb) is administered twice daily. In another embodiment of any of the aforementioned embodiments of increasing the amount or concentration of one or more lacrimal proteins, the compound of Formula (I), (II), (IIIa), or (IIIb) is administered at least twice daily. In another embodiment of any of the aforementioned embodiments of increasing the amount or concentration of one or more lacrimal proteins, the compound of Formula (I), (II), (IIIa), or (IIIb) is administered three times daily. In another embodiment of any of the aforementioned embodiments of increasing the amount or concentration of one or more lacrimal proteins, the compound of Formula (I), (II), (IIIa), or (IIIb) is administered at least three times daily. In another embodiment of any of the aforementioned embodiments of increasing the amount or concentration of one or more lacrimal proteins, the compound of Formula (I), (II), (IIIa), or (IIIb) is administered for one day. In another embodiment of any of the aforementioned embodiments of increasing the amount or concentration of one or more lacrimal proteins, the compound of Formula (I), (II), (IIIa), or (IIIb) is administered for at least two days. In another embodiment of any of the aforementioned embodiments of increasing the amount or concentration of one or more lacrimal proteins, the compound of Formula (I), (II), (IIIa), or (IIIb) is administered for at least three days. In another embodiment of any of the aforementioned embodiments of increasing the amount or concentration of one or more lacrimal proteins, the compound of Formula (I), (II), (IIIa), or (IIIb) is administered for at least four days. In another embodiment of any of the aforementioned embodiments of increasing the amount or concentration of one or more lacrimal proteins, the compound of Formula (I), (II), (IIIa), or (IIIb) is administered for at least five days. In another embodiment of any of the aforementioned embodiments of increasing the amount or concentration of one or more lacrimal proteins, the compound of Formula (I), (II), (IIIa), or (IIIb) is administered for at least seven days. In another embodiment of any of the aforementioned embodiments of increasing the amount or concentration of one or more lacrimal proteins, the compound of Formula (I), (II), (IIIa), or (IIIb) is administered for at least ten days. In another embodiment of any of the aforementioned embodiments of increasing the amount or concentration of one or more lacrimal proteins, the compound of Formula (I), (II), (IIIa), or (IIIb) is administered for at least fourteen days. In another embodiment of any of the aforementioned embodiments of increasing the amount or concentration of one or more lacrimal proteins, the compound of Formula (I), (I), (IIIa), or (IIIb) is administered for at least twenty one days. In another embodiment of any of the aforementioned embodiments of increasing the amount or concentration of one or more lacrimal proteins, the compound of Formula (I), (II), (IIIa), or (IIIb) is administered for at least thirty days. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, the compound of Formula (I), (II), (IIIa), or (IIIb) is administered in alternating nostrils. For example, the compound of Formula (IL) (II), (IIIa), or (IIIb) is administered in one nostril and then the other nostril after a pre-determined amount of time. In another embodiment, the compound of Formula (I), (II), (IIIa), or (IIIb) is administered in both nostrils. For example, the compound of Formula (I), (II), (IIIa), or (IIIb) is administered in one nostril and then the other nostril at the same time or immediately after the first nostril. In another embodiment, the compound of Formula (I), (II), (IIIa), or (IIIb) is administered in one nostril. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, the compound of Formula (I), (II), (IIIa), or (IIIb) is administered into the nasal cavity as a liquid, suspension aerosol, gel, ointment, dry powder, cream, paste, lotion, or balm. In another embodiment of any of the aforementioned embodiments of increasing the amount or concentration of one or more lacrimal proteins, the compound of Formula (I), (I), (IIIa), or (IIIb) is administered into the nasal cavity as a liquid. In another embodiment of any of the aforementioned embodiments of increasing the amount or concentration of one or more lacrimal proteins, the compound of Formula (I), (II), (IIIa), or (IIIb) is administered into the nasal cavity as a suspension. In another embodiment of any of the aforementioned embodiments of increasing the amount or concentration of one or more lacrimal proteins, the compound of Formula (I), (II), (IIIa), or (IIIb) is administered into the nasal cavity as an aerosol. In another embodiment of any of the aforementioned embodiments of increasing the amount or concentration of one or more lacrimal proteins, the compound of Formula (I), (II), (IIIa), or (IIIb) is administered into the nasal cavity as a gel. In another embodiment of any of the aforementioned embodiments of increasing the amount or concentration of one or more lacrimal proteins, the compound of Formula (I), (II), (IIIa), or (IIIb) is administered into the nasal cavity as an ointment. In another embodiment of any of the aforementioned embodiments of increasing the amount or concentration of one or more lacrimal proteins, the compound of Formula (I), (II), (IIIa), or (IIIb) is administered into the nasal cavity as a dry powder. In another embodiment of any of the aforementioned embodiments of increasing the amount or concentration of one or more lacrimal proteins, the compound of Formula (I), (II), (IIIa), or (IIIb) is administered into the nasal cavity as a cream. In another embodiment of any of the aforementioned embodiments of increasing the amount or concentration of one or more lacrimal proteins, the compound of Formula (I), (II), (IIIa), or (IIIb) is administered into the nasal cavity as a paste. In another embodiment of any of the aforementioned embodiments of increasing the amount or concentration of one or more lacrimal proteins, the compound of Formula (I), (II), (IIIa), or (IIIb) is administered into the nasal cavity as a lotion. In another embodiment of any of the aforementioned embodiments of increasing the amount or concentration of one or more lacrimal proteins, the compound of Formula (I), (II), (IIIa), or (IIIb) is administered into the nasal cavity as a balm. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, the compound of Formula (I), (II), (IIIa), or (IIIb) is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of increasing the amount or concentration of one or more lacrimal proteins, the compound of Formula (I), (II), (IIIa), or (IIIb) is administered into the nasal cavity by a syringe. In another embodiment of any of the aforementioned embodiments of increasing the amount or concentration of one or more lacrimal proteins, the compound of Formula (I), (II), (IIIa), or (IIIb) is administered into the nasal cavity by a dropper. In another embodiment of any of the aforementioned embodiments of increasing the amount or concentration of one or more lacrimal proteins, the compound of Formula (I), (II), (IIIa), or (IIIb) is administered into the nasal cavity by a bottle nebulizer. In another embodiment of any of the aforementioned embodiments of increasing the amount or concentration of one or more lacrimal proteins, the compound of Formula (I), (II), (IIIa), or (IIIb) is administered into the nasal cavity by an atomization pump. In another embodiment of any of the aforementioned embodiments of increasing the amount or concentration of one or more lacrimal proteins, the compound of Formula (I), (II), (IIIa), or (IIIb) is administered into the nasal cavity by an inhaler. In another embodiment of any of the aforementioned embodiments of increasing the amount or concentration of one or more lacrimal proteins, the compound of Formula (I), (II), (IIIa), or (IIIb) is administered into the nasal cavity by a powder spray device. In another embodiment of any of the aforementioned embodiments of increasing the amount or concentration of one or more lacrimal proteins, the compound of Formula (I), (II), (IIIa), or (IIIb) is administered into the nasal cavity by a vaporizer. In another embodiment of any of the aforementioned embodiments of increasing the amount or concentration of one or more lacrimal proteins, the compound of Formula (I), (II), (IIIa), or (IIIb) is administered into the nasal cavity by a patch. In another embodiment of any of the aforementioned embodiments of increasing the amount or concentration of one or more lacrimal proteins, the compound of Formula (I), (II), (IIIa), or (IIIb) is administered into the nasal cavity by a medicated stick. In another embodiment of any of the aforementioned embodiments of increasing the amount or concentration of one or more lacrimal proteins, the compound of Formula (I), (II), (IIIa), or (IIIb) is administered into the nasal cavity by a pipette. In another embodiment of any of the aforementioned embodiments of increasing the amount or concentration of one or more lacrimal proteins, the compound of Formula (I), (II), (IIIa), or (IIIb) is administered into the nasal cavity by a jet of liquid. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, the trigeminal nerve is activated. In a further embodiment of increasing the amount or concentration of one or more lacrimal proteins, the anterior ethmoidal nerve is activated, in another embodiment of any of the aforementioned embodiments of increasing the amount or concentration of one or more lacrimal proteins, the nasolacrimal reflex is activated. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of increasing the amount or concentration of one or more lacrimal proteins, the amount or concentration of one or more lacrimal proteins is associated with an acute condition. An acute condition refers to a condition with a rapid onset of a health effect that is considered brief, not prolonged. Acute conditions can result from ophthalmologic surgical procedures or other ophthalmologic treatment. In some embodiments, the ophthalmologic surgical procedure is cataract surgery (cataract extraction and lens replacement), refractive lens exchange, glaucoma surgery, lasik surgery (laser eye surgery), vitrectomy, retinal photocoagulation, retinal detachment repair, macular hole repair, retroiris tumor or mass removal, posterior sclerotomy, optic neurotomy, or other treatments that decrease the function of the lacrimal gland. In some embodiments, the ophthalmologic treatment comprises radiation therapy. In some embodiments, the radiation therapy is directed to orbital area, for example, in connection to cancers of head and/or neck. In some embodiments, the compound of Formula (I) is (R)-5-((E)-2-pyrrolidin-3-ylvinyl)pyrimidine, or a pharmaceutically acceptable salt thereof.

Enhancing Tear Clearance

Provided herein, in some embodiments, is a method of enhancing tear clearance in a subject. In some embodiments, is a method of enhancing tear clearance, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and does not cross the blood-brain barrier in a pharmacologically relevant concentration. In some embodiments is method of enhancing tear clearance, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of enhancing tear clearance, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha3beta4. In some embodiments is method of enhancing tear clearance, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha4beta2. In some embodiments is method of enhancing tear clearance, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) does not cross the blood-brain barrier in a pharmacologically relevant concentration and selectively binds to the peripheral nicotinic acetylcholine receptor subtype alpha7. In some embodiments is a method of enhancing tear clearance, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that is not systemically bioavailable. In some embodiments is a method of enhancing tear clearance, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and in an amount that does not result in undesired psychoactive side effects. In some embodiments is a method of enhancing tear clearance, comprising the local administration of a therapeutically effective amount of a compound of Formula (I), (II), (IIIa), or (IIIb) into the nasal cavity of an individual in need thereof, wherein the compound of Formula (I), (II), (IIIa) or (IIIb) selectively binds to the peripheral nicotinic acetylcholine receptor and in an amount that does not result in undesired systemic side effects. In some embodiments is a method of enhancing tear clearance, comprising the local administration of a therapeutically effective amount of a compound of Formula (I), (II), (IIIa), or (IIIb) into the nasal cavity of an individual in need thereof, wherein the compound of Formula (I), (II), (IIIa), or (IIIb) selectively binds to the peripheral nicotinic acetylcholine receptor and is administered in an amount that produces a local effect. In some embodiments is a method of enhancing tear clearance, further comprising the local administration of one or more substances that prevent or facilitate the recovery of the nicotinic acetylcholine receptor from the desensitized state. In some embodiments is a method of enhancing tear clearance, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments, the compound of Formula (I) is (R)-5-((E)-2-pyrrolidin-3-ylvinyl)pyrimidine, or a pharmaceutically acceptable salt thereof.

In some embodiments of the method of enhancing tear clearance described herein, the compound of Formula (I), (II), (IIIa), or (IIIb) is (R)-5-((E)-2-pyrrolidin-3-ylvinyl)pyrimidine (or Compound 1). In some embodiments of the methods described herein, the compound of Formula (I), (II), (IIIa), or (IIIb) is (R)-5-((E)-2-pyrrolidin-3-ylvinyl)pyrimidine, or a pharmaceutically acceptable salt thereof, in some embodiments of the method of enhancing tear clearance described herein, the compound of Formula (I), (II), (IIIa), or (IIIb) is (R)-5-((E)-2-pyrrolidin-3-ylvinyl)pyrimidine as a free base. In some embodiments of the method of enhancing tear clearance described herein, the compound of Formula (I), (II), (IIIa), or (IIIb) is (R)-5-((E)-2-pyrrolidin-3-ylvinyl)pyrimidine citrate salt. In some embodiments of the method of enhancing tear clearance described herein, the compound of Formula (I), (II), (IIIa), or (IIIb) is (R)-5-((E)-2-pyrrolidin-3-ylvinyl)pyrimidine mono citrate salt. In some embodiments of the method of enhancing tear clearance described herein, the compound of Formula (I), (II), (IIIa), or (IIIb) is (R)-5-((E)-2-pyrrolidin-3-ylvinyl)pyrimidine HCl salt. In some embodiments of the method of enhancing tear clearance described herein, the compound of Formula (I), (II), (IIIa), or (IIIb) is (R)-5-((E)-2-pyrrolidin-3-ylvinyl)pyrimidine galactarate salt. In some embodiments of the method of enhancing tear clearance described herein, the compound of Formula (I), (II), (IIIa), or (IIIb) is (R)-5-((E)-2-pyrrolidin-3-ylvinyl)pyrimidine hemigalactarate salt. In some embodiments of the method of enhancing tear clearance described herein, the compound of Formula (I), (II), (IIIa), or (IIIb) is (R)-5-((E)-2-pyrrolidin-3-ylvinyl)pyrimidine hemigalactarate monohydrate. In some embodiments of the method described herein, the compound of Formula (I), (II), (IIIa), or (IIIb) is (R)-5-((E)-2-pyrrolidin-3-ylvinyl)pyrimidine hemigalactarate dihydrate.

In some embodiments is a method of enhancing tear clearance, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of enhancing tear clearance, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of enhancing tear clearance, further comprising the local administration of protein kinase C (PKC) or factors that upregulate or up-modulate PKC. In some embodiments is a method of enhancing tear clearance, further comprising the local administration of cAMP-dependent protein kinase (PKA) or factors that upregulate or up-modulate PKA. In some embodiments is a method of enhancing tear clearance, further comprising the local administration of a calcineurin inhibitor. In some embodiments is a method of enhancing tear clearance, further comprising the local administration of a calcineurin inhibitor, wherein the calcineurin inhibitor is selected from cyclosporine, pimecrolimus, and tacrolimus. In some embodiments is a method of enhancing tear clearance, further comprising the local administration of cyclosporine. In some embodiments is a method of enhancing tear clearance, further comprising the local administration of pimecrolimus. In some embodiments is a method of enhancing tear clearance, further comprising the local administration of tacrolimus.

In another embodiment of any of the aforementioned embodiments of enhancing tear clearance, at least 1 microgram of the compound of Formula (I), (II), (IIIa), or (IIIb) is administered into the nasal cavity. In another embodiment of any of the aforementioned embodiments of enhancing tear clearance, at least 5 micrograms of the compound of Formula (I), (II), (IIIa), or (IIIb) is administered into the nasal cavity. In another embodiment of any of the aforementioned embodiments of enhancing tear clearance, at least 10 micrograms of the compound of Formula (I), (II), (IIIa), or (IIIb) is administered into the nasal cavity. In another embodiment of any of the aforementioned embodiments of enhancing tear clearance, at least 25 micrograms of the compound of Formula (I), (II), (IIIa), or (IIIb) is administered into the nasal cavity. In another embodiment of any of the aforementioned embodiments of enhancing tear clearance, at least 50 micrograms of the compound of Formula (I), (II), (IIIa), or (IIIb) is administered into the nasal cavity. In another embodiment of any of the aforementioned embodiments of enhancing tear clearance, at least 100 micrograms of the compound of Formula (I), (II), (IIIa), or (IIIb) is administered into the nasal cavity. In another embodiment of any of the aforementioned embodiments of enhancing tear clearance, at least 250 micrograms of the compound of Formula (I), (II), (IIIa), or (IIIb) is administered into the nasal cavity. In another embodiment of any of the aforementioned embodiments of enhancing tear clearance, at least 500 micrograms of the compound of Formula (I), (II), (IIIa), or (IIIb) is administered into the nasal cavity. In another embodiment of any of the aforementioned embodiments of enhancing tear clearance, at least 750 micrograms of the compound of Formula (I), (II), (IIIa), or (IIIb) is administered into the nasal cavity. In another embodiment of any of the aforementioned embodiments of enhancing tear clearance, at least 1000 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, between 1 microgram and 1000 micrograms of the compound of Formula (I), (II), (IIIa), or (IIIb) is administered into the nasal cavity. In another embodiment of any of the aforementioned embodiments of enhancing tear clearance, between 5 micrograms and 1000 micrograms of the compound of Formula (I), (II), (IIIa), or (IIIb) is administered into the nasal cavity. In another embodiment of any of the aforementioned embodiments of increasing tear clearance, between 10 micrograms and 1000 micrograms of the compound of Formula (I), (II), (IIIa), or (IIIb) is administered into the nasal cavity. In another embodiment of any of the aforementioned embodiments of enhancing tear clearance, between 5 micrograms and 100 micrograms of the compound of Formula (I), (II), (IIIa), or (IIIb) is administered into the nasal cavity. In another embodiment of any of the aforementioned embodiments of enhancing tear clearance, between 5 micrograms and 50 micrograms of the compound of Formula (I), (II), (IIIa), or (IIIb) is administered into the nasal cavity. In another embodiment of any of the aforementioned embodiments of enhancing tear clearance, between 10 micrograms and 50 micrograms of the compound of Formula (I), (II), (IIIa), or (IIIb) is administered into the nasal cavity. In another embodiment of any of the aforementioned embodiments of enhancing tear clearance, between 25 micrograms and 1000 micrograms of the compound of Formula (I), (II), (IIIa), or (IIIb) is administered into the nasal cavity. In another embodiment of any of the aforementioned embodiments of enhancing tear clearance, between 50 micrograms and 1000 micrograms of the compound of Formula (I), (II), (IIIa), or (IIIb) is administered into the nasal cavity. In another embodiment of any of the aforementioned embodiments of enhancing tear clearance, between 100 micrograms and 1000 micrograms of the compound of Formula (I), (II), (IIIa), or (IIIb) is administered into the nasal cavity. In another embodiment of any of the aforementioned embodiments of increasing tear clearance, between 150 micrograms and 1000 micrograms of the compound of Formula (I), (II), (IIIa), or (IIIb) is administered into the nasal cavity. In another embodiment of any of the aforementioned embodiments of enhancing tear clearance, between 100 micrograms and 750 micrograms of the compound of Formula (I), (II), (IIIa), or (IIIb) is administered into the nasal cavity. In another embodiment of any of the aforementioned embodiments of enhancing tear clearance, between 150 micrograms and 750 micrograms of the compound of Formula (I), (II), (IIIa), or (IIIb) is administered into the nasal cavity. In another embodiment of any of the aforementioned embodiments of enhancing tear clearance, between 150 micrograms and 600 micrograms of the compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, less than 100 micrograms of a compound of Formula (I), (II), (IIIa), or (IIIb) is administered into the nasal cavity. In another embodiment of any of the aforementioned embodiments of enhancing tear clearance, less than 75 micrograms of a compound of Formula (I), (II), (IIIa), or (IIIb) is administered into the nasal cavity. In another embodiment of any of the aforementioned embodiments of enhancing tear clearance, less than 50 micrograms of a compound of Formula (I), (II), (IIIa), or (IIIb) is administered into the nasal cavity. In another embodiment of any of the aforementioned embodiments of enhancing tear clearance, less than 25 micrograms of a compound of Formula (I), (II), (IIIa), or (IIIb) is administered into the nasal cavity. In another embodiment of any of the aforementioned embodiments of enhancing tear clearance, less than 15 micrograms of a compound of Formula (I), (II), (IIIa), or (IIIb) is administered into the nasal cavity. In another embodiment of any of the aforementioned embodiments of enhancing tear clearance, about 75 micrograms of a compound of Formula (I), (II), (IIIa), or (IIIb) is administered into the nasal cavity. In another embodiment of any of the aforementioned embodiments of enhancing tear clearance, about 50 micrograms of a compound of Formula (I), (II), (IIIa), or (IIIb) is administered into the nasal cavity. In another embodiment of any of the aforementioned embodiments of enhancing tear clearance, about 25 micrograms of a compound of Formula (I), (II), (IIIa), or (IIIb) is administered into the nasal cavity. In another embodiment of any of the aforementioned embodiments of enhancing tear clearance, about 10 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, between 1 microgram and 100 micrograms of a compound of Formula (I), (II), (IIIa), or (IIIb) is administered into the nasal cavity. In another embodiment of any of the aforementioned embodiments of enhancing tear clearance, between 1 microgram and 75 micrograms of a compound of Formula (I), (II), (IIIa), or (IIIb) is administered into the nasal cavity. In another embodiment of any of the aforementioned embodiments of enhancing tear clearance, between 5 micrograms and 100 micrograms of a compound of Formula (I), (II), (IIIa), or (IIIb) is administered into the nasal cavity. In another embodiment of any of the aforementioned embodiments of enhancing tear clearance, between 5 micrograms and 75 micrograms of a compound of Formula (I), (II), (IIIa), or (IIIb) is administered into the nasal cavity. In another embodiment of any of the aforementioned embodiments of increasing tear clearance, between 15 micrograms and 100 micrograms of a compound of Formula (I), (II), (IIIa), or (IIIb) is administered into the nasal cavity. In another embodiment of any of the aforementioned embodiments of enhancing tear clearance, between 15 micrograms and 75 micrograms of a compound of Formula (I), (II), (IIIa), or (IIIb) is administered into the nasal cavity. In another embodiment of any of the aforementioned embodiments of increasing tear clearance, between 25 micrograms and 100 micrograms of a compound of Formula (I), (II), (IIIa), or (IIIb) is administered into the nasal cavity. In another embodiment of any of the aforementioned embodiments of increasing tear clearance, between 25 micrograms and 75 micrograms of a compound of Formula (I), (II), (IIIa), or (IIIb) is administered into the nasal cavity. In another embodiment of any of the aforementioned embodiments of enhancing tear clearance, between 25 micrograms and 60 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, between 500 micrograms and 10 milligrams of a compound of Formula (I), (I), (IIIa), or (IIIb) is administered into the nasal cavity. In another embodiment of any of the aforementioned embodiments of enhancing tear clearance, between 500 micrograms and 5 milligrams of a compound of Formula (I), (II), (IIIa), or (IIIb) is administered into the nasal cavity. In another embodiment of any of the aforementioned embodiments of increasing tear clearance, between 500 micrograms and 3 milligrams of a compound of Formula (I), (II), (IIIa), or (IIIb) is administered into the nasal cavity. In another embodiment of any of the aforementioned embodiments of increasing tear clearance, between 500 micrograms and 2 milligrams of a compound of Formula (I), (II), (IIIa), or (IIIb) is administered into the nasal cavity. In another embodiment of any of the aforementioned embodiments of enhancing tear clearance, between 1 milligram and 10 milligrams of a compound of Formula (I), (II), (IIIa), or (IIIb) is administered into the nasal cavity. In another embodiment of any of the aforementioned embodiments of enhancing tear clearance, between 1 milligram and 5 milligrams of a compound of Formula (I), (II), (IIIa), or (IIIb) is administered into the nasal cavity. In another embodiment of any of the aforementioned embodiments of enhancing tear clearance, between 1 milligram and 3 milligrams of a compound of Formula (I), (II), (IIIa), or (IIIb) is administered into the nasal cavity. In another embodiment of any of the aforementioned embodiments of enhancing tear clearance, between 1 milligram and 2 milligrams of a compound of Formula (I), (II), (IIIa), or (IIIb) is administered into the nasal cavity. In another embodiment of any of the aforementioned embodiments of enhancing tear clearance, about 500 micrograms of a compound of Formula (I), (II), (IIIa), or (IIIb) is administered into the nasal cavity. In another embodiment of any of the aforementioned embodiments of enhancing tear clearance, about 1 milligram of a compound of Formula (I), (II), (IIIa), or (IIIb) is administered into the nasal cavity. In another embodiment of any of the aforementioned embodiments of enhancing tear clearance, about 1.5 milligrams of a compound of Formula (I), (II), (IIIa), or (IIIb) is administered into the nasal cavity. In another embodiment of any of the aforementioned embodiments of enhancing tear clearance, about 2 milligrams of a compound of Formula (I), (II), (IIIa), or (IIIb) is administered into the nasal cavity. In another embodiment of any of the aforementioned embodiments of enhancing tear clearance, about 2.5 milligrams of a compound of Formula (I), (II), (IIIa), or (IIIb) is administered into the nasal cavity. In another embodiment of any of the aforementioned embodiments of enhancing tear clearance, about 3 milligrams of a compound of Formula (I), (II), (IIIa), or (IIIb) is administered into the nasal cavity. In another embodiment of any of the aforementioned embodiments of enhancing tear clearance, about 4 milligrams of a compound of Formula (I), (II), (IIIa), or (IIIb) is administered into the nasal cavity. In another embodiment of any of the aforementioned embodiments of enhancing tear clearance, about 5 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, between 1 microgram and 10 milligrams of a compound of Formula (I), (II), (IIIa), or (IIIb) is administered into the nasal cavity. In another embodiment of any of the aforementioned embodiments of enhancing tear clearance, between 5 micrograms and 10 milligrams of a compound of Formula (I), (II), (IIIa), or (IIIb) is administered into the nasal cavity. In another embodiment of any of the aforementioned embodiments of enhancing tear clearance, between 10 micrograms and 10 milligrams of a compound of Formula (I), (II), (IIIa), or (IIIb) is administered into the nasal cavity. In another embodiment of any of the aforementioned embodiments of enhancing tear clearance, between 25 micrograms and 10 milligrams of a compound of Formula (I), (II), (IIIa), or (IIIb) is administered into the nasal cavity. In another embodiment of any of the aforementioned embodiments of enhancing tear clearance between 50 micrograms and 10 milligrams of a compound of Formula (I), (II), (IIIa), or (IIIb) is administered into the nasal cavity. In another embodiment of any of the aforementioned embodiments of enhancing tear clearance, between 100 micrograms and 10 milligrams of a compound of Formula (I), (II), (IIIa), or (IIIb) is administered into the nasal cavity. In another embodiment of any of the aforementioned embodiments of enhancing tear clearance, between 150 micrograms and 10 milligrams of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, between 1 microgram and 10 milligrams of a compound of Formula (I), (II), (IIIa), or (IIIb) is administered into the nasal cavity. In another embodiment of any of the aforementioned embodiments of enhancing tear clearance, between 1 microgram and 5 milligrams of a compound of Formula (I), (II), (IIIa), or (IIIb) is administered into the nasal cavity. In another embodiment of any of the aforementioned embodiments of enhancing tear clearance, between 1 microgram and 4 milligrams of a compound of Formula (I), (II), (IIIa), or (IIIb) is administered into the nasal cavity. In another embodiment of any of the aforementioned embodiments of enhancing tear clearance, between 1 microgram and 3 milligrams of a compound of Formula (I), (II), (IIIa), or (IIIb) is administered into the nasal cavity. In another embodiment of any of the aforementioned embodiments of enhancing tear clearance, between 1 microgram and 2 milligrams of a compound of Formula (I), (II), (IIIa), or (IIIb) is administered into the nasal cavity. In another embodiment of any of the aforementioned embodiments of enhancing tear clearance, between 1 microgram and 1 milligrams of a compound of Formula (I), (II), (IIIa), or (IIIb) is administered into the nasal cavity. In another embodiment of any of the aforementioned embodiments of enhancing tear clearance, between 1 microgram and 750 micrograms of a compound of Formula (I), (II), (IIIa), or (IIIb) is administered into the nasal cavity. In another embodiment of any of the aforementioned embodiments of enhancing tear clearance, between 1 microgram and 600 micrograms of a compound of Formula (I), (II), (IIIa), or (IIIb) is administered into the nasal cavity. In another embodiment of any of the aforementioned embodiments of enhancing tear clearance, between 1 microgram and 100 micrograms of a compound of Formula (I), (II), (IIIa), or (IIIb) is administered into the nasal cavity. In another embodiment of any of the aforementioned embodiments of enhancing tear clearance, between 1 microgram and 50 micrograms of a compound of Formula (I), (II), (IIIa), or (IIIb) is administered into the nasal cavity. In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method comprises about 0.1 mg/mL of a compound of Formula (I), (II), (IIIa), or (IIIb). In another embodiment, the pharmaceutical formulation for use in the method comprises about 0.2 mg/mL of a compound of Formula (I), (II), (IIIa), or (IIIb). In another embodiment, the pharmaceutical formulation for use in the method comprises about 0.5 mg/mL, of a compound of Formula (I), (II), (IIIa), or (IIIb). In another embodiment, the pharmaceutical formulation for use in the method comprises about 1 mg/mL of a compound of Formula (I), (II), (IIIa), or (IIIb). In another embodiment, the pharmaceutical formulation for use in the method comprises about 2 mg/mL of a compound of Formula (I), (II), (IIIa), or (IIIb). In another embodiment, the pharmaceutical formulation for use in the method comprises about 3 mg/mL of a compound of Formula (I), (II), (IIIa), or (IIIb). In another embodiment, the pharmaceutical formulation for use in the method comprises about 4 mg/mL of a compound of Formula (I), (II), (IIIa), or (IIIb). In another embodiment, the pharmaceutical formulation for use in the method comprises about 5 mg/mL of a compound of Formula (I), (II), (IIIa), or (IIIb). In another embodiment, the pharmaceutical formulation for use in the method comprises about 6 mg/mL of a compound of Formula (I), (II), (IIIa), or (IIIb). In another embodiment, the pharmaceutical formulation for use in the method comprises about 7 mg/mL of a compound of Formula (I), (II), (IIIa), or (IIIb). In another embodiment, the pharmaceutical formulation for use in the method comprises about 8 mg/mL of a compound of Formula (I), (II), (IIIa), or (IIIb). In another embodiment, the pharmaceutical formulation for use in the method comprises about 9 mg/mL of a compound of Formula (I), (II), (IIIa), or (IIIb). In another embodiment, the pharmaceutical formulation for use in the method comprises about 10 mg/mL of a compound of Formula (I), (II), (IIIa), or (IIIb). In another embodiment, the pharmaceutical formulation for use in the method comprises about 12 mg/mL of a compound of Formula (I), (II), (IIIa), or (IIIb). In another embodiment, the pharmaceutical formulation for use in the method comprises about 15 mg/mL of a compound of Formula (I), (II), (IIIa), or (IIIb). In another embodiment, the pharmaceutical formulation for use in the method comprises about 20 mg/mL of a compound of Formula (I), (II), (IIIa), or (IIIb). In another embodiment, the pharmaceutical formulation for use in the method comprises about 25 mg/mL of a compound of Formula (I), (II), (IIIa), or (IIIb). In another embodiment, the pharmaceutical formulation for use in the method comprises about 30 mg/mL of a compound of Formula (I), (II), (IIIa), or (IIIb). In another embodiment, the pharmaceutical formulation for use in the method comprises about 40 mg/mL of a compound of Formula (I), (II), (IIIa), or (IIIb). In another embodiment, the pharmaceutical formulation for use in the method comprises about 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 5 mg/mL and 200 mg/mL of a compound of Formula (I), (II), (IIIa), or (IIIb). In another embodiment, the pharmaceutical formulation for use in the method comprises between 10 mg/mL and 200 mg/mL of a compound of Formula (I), (II), (IIIa), or (IIIb). In another embodiment, the pharmaceutical formulation for use in the method comprises between 5 mg/mL and 100 mg/mL of a compound of Formula (I), (II), (IIIa), or (IIIb). In another embodiment, the pharmaceutical formulation for use in the method comprises between 10 mg/mL and 75 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 10 mg/mL and 30 mg/mL of a compound of Formula (I), (II), (IIIa), or (IIIb). In another embodiment, the pharmaceutical formulation for use in the method comprises between 5 mg/mL and 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment, the pharmaceutical formulation for use in the method comprises between 10 mg/mL and 25 mg/mL of a compound of Formula (I), (II), (IIIa), or (IIIb). In another embodiment, the pharmaceutical formulation for use in the method comprises between 10 mg/mL and 50 mg/mL of a compound of Formula (I), (II), (IIIa), or (IIIb). In another embodiment, the pharmaceutical formulation for use in the method comprises between 20 mg/mL and 50 mg/mL of a compound of Formula (I), (II), (IIIa), or (IIIb). In another embodiment, the pharmaceutical formulation for use in the method comprises between 30 mg/mL and 75 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In any of the aforementioned embodiments, the pharmaceutical formulation for use in the method is provided at about 10 to 200 µl. In another embodiment, the pharmaceutical formulation for use in the method is provided at about 10 to 150 µl. In another embodiment, the pharmaceutical formulation for use in the method is provided at about 10 to 100 µl. In another embodiment, the pharmaceutical formulation for use in the method is provided at about 50 to 200 µl. In another embodiment, the pharmaceutical formulation for use in the method is provided at about 100 to 200 µl. In another embodiment, the pharmaceutical formulation for use in the method is provided at about 50 to 100 µl. In another embodiment, the pharmaceutical formulation for use in the method is provided at about 10 to 150 µl. In another embodiment, the pharmaceutical formulation for use in the method is provided at about 10, 20, 30, 40, 50, 60, 70, 80, 90, 100, 110, 120, 130, 140, 150, 160, 170, 180, 190, or 200 µl. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, the compound of Formula (I), (II), (IIIa), or (IIIb) is administered once daily. In another embodiment of any of the aforementioned embodiments of enhancing tear clearance, the compound of Formula (I), (II), (IIIa), or (IIIb) is administered at least once daily. In another embodiment of any of the aforementioned embodiments of enhancing tear clearance, the compound of Formula (I), (II), (IIIa), or (IIIb) is administered twice daily. In another embodiment of any of the aforementioned embodiments of enhancing tear clearance, the compound of Formula (I), (II), (IIIa), or (IIIb) is administered at least twice daily. In another embodiment of any of the aforementioned embodiments of enhancing tear clearance, the compound of Formula (I), (II), (IIIa), or (IIIb) is administered three times daily. In another embodiment of any of the aforementioned embodiments of enhancing tear clearance, the compound of Formula (I), (II), (IIIa), or (IIIb) is administered at least three times daily. In another embodiment of any of the aforementioned embodiments of enhancing tear clearance, the compound of Formula (I), (II), (IIIa), or (IIIb) is administered for one day. In another embodiment of any of the aforementioned embodiments of enhancing tear clearance, the compound of Formula (I), (II), (IIIa), or (IIIb) is administered for at least two days. In another embodiment of any of the aforementioned embodiments of enhancing tear clearance, the compound of Formula (I), (II), (IIIa), or (IIIb) is administered for at least three days. In another embodiment of any of the aforementioned embodiments of enhancing tear clearance, the compound of Formula (I), (II), (IIIa), or (IIIb) is administered for at least four days. In another embodiment of any of the aforementioned embodiments of enhancing tear clearance, the compound of Formula (I), (II), (IIIa), or (IIIb) is administered for at least five days. In another embodiment of any of the aforementioned embodiments of enhancing tear clearance, the compound of Formula (I), (II), (IIIa), or (IIIb) is administered for at least seven days. In another embodiment of any of the aforementioned embodiments of enhancing tear clearance, the compound of Formula (I), (II), (IIIa), or (IIIb) is administered for at least ten days. In another embodiment of any of the aforementioned embodiments of enhancing tear clearance, the compound of Formula (I), (II), (IIIa), or (IIIb) is administered for at least fourteen days. In another embodiment of any of the aforementioned embodiments of enhancing tear clearance, the compound of Formula (I), (II), (IIIa), or (IIIb) is administered for at least twenty one days. In another embodiment of any of the aforementioned embodiments of enhancing tear clearance, the compound of Formula (I), (II), (IIIa), or (IIIb) is administered for at least thirty days. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, the compound of Formula (I), (II), (IIIa), or (IIIb) is administered in alternating nostrils. For example, the compound of Formula (I), (II), (IIIa), or (IIIb) is administered in one nostril and then the other nostril after a pre-determined amount of time. In another embodiment, the compound of Formula (I), (II), (IIIa), or (IIIb) is administered in both nostrils. For example, the compound of Formula (I), (II), (IIIa), or (IIIb) is administered in one nostril and then the other nostril at the same time or immediately after the first nostril. In another embodiment, the compound of Formula (I), (II), (IIIa), or (IIIb) is administered in one nostril. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, the compound of Formula (I), (II), (IIIa), or (IIIb) is administered into the nasal cavity as a liquid, suspension, aerosol, gel, ointment, dry powder, cream, paste, lotion, or balm. In another embodiment of any of the aforementioned embodiments of enhancing tear clearance, the compound of Formula (I), (II), (IIIa), or (IIIb) is administered into the nasal cavity as a liquid. In another embodiment of any of the aforementioned embodiments of enhancing tear clearance, the compound of Formula (I), (II), (IIIa), or (IIIb) is administered into the nasal cavity as a suspension. In another embodiment of any of the aforementioned embodiments of enhancing tear clearance, the compound of Formula (I), (II), (IIIa), or (IIIb) is administered into the nasal cavity as an aerosol. In another embodiment of any of the aforementioned embodiments of enhancing tear clearance, the compound of Formula (I), (II), (IIIa), or (IIIb) is administered into the nasal cavity as a gel. In another embodiment of any of the aforementioned embodiments of enhancing tear clearance, the compound of Formula (I), (II), (IIIa), or (IIIb) is administered into the nasal cavity as an ointment. In another embodiment of any of the aforementioned embodiments of enhancing tear clearance, the compound of Formula (I), (II), (IIIa), or (IIIb) is administered into the nasal cavity as a dry powder. In another embodiment of any of the aforementioned embodiments of enhancing tear clearance, the compound of Formula (I), (II), (IIIa), or (IIIb) is administered into the nasal cavity as a cream. In another embodiment of any of the aforementioned embodiments of enhancing tear clearance, the compound of Formula (I). (II), (IIIa), or (IIIb) is administered into the nasal cavity as a paste. In another embodiment of any of the aforementioned embodiments of enhancing tear clearance, the compound of Formula (I), (II), (IIIa), or (IIIb) is administered into the nasal cavity as a lotion. In another embodiment of any of the aforementioned embodiments of enhancing tear clearance, the compound of Formula (I), (II), (IIIa), or (IIIb) is administered into the nasal cavity as a balm. In some embodiments, the compound of Formula (I) is (R)-5-((E)-2-pyrolidin-3-ylvinyl)pyrimidine, or a pharmaceutically acceptable salt thereof.

In another embodiment of any of the aforementioned embodiments of enhancing tear clearance, the compound of Formula (I), (II), (IIIa), or (IIIb) is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of enhancing tear clearance, the compound of Formula (I), (II), (IIIa), or (IIIb) is administered into the nasal cavity by a syringe. In another embodiment of any of the aforementioned embodiments of enhancing tear clearance, the compound of Formula (I). (II), (IIIa), or (IIIb) is administered into the nasal cavity by a dropper. In another embodiment of any of the aforementioned embodiments of enhancing tear clearance, the compound of Formula (I), (II), (IIIa), or (IIIb) is administered into the nasal cavity by a bottle nebulizer. In another embodiment of any of the aforementioned embodiments of enhancing tear clearance, the compound of Formula (I), (II), (IIIa), or (IIIb) is administered into the nasal cavity by an atomization pump. In another embodiment of any of the aforementioned embodiments of enhancing tear clearance, the compound of Formula (I), (II), (IIIa), or (IIIb) is administered into the nasal cavity by an inhaler. In another embodiment of any of the aforementioned embodiments of enhancing tear clearance, the compound of Formula (I), (II), (IIIa), or (IIIb) is administered into the nasal cavity by a powder spray device. In another embodiment of any of the aforementioned embodiments of enhancing tear clearance, the compound of Formula (I), (II), (IIIa), or (IIIb) is administered into the nasal cavity by a vaporizer. In another embodiment of any of the aforementioned embodiments of enhancing tear clearance, the compound of Formula (I), (II), (IIIa), or (IIIb) is administered into the nasal cavity by a patch. In another embodiment of any of the aforementioned embodiments of enhancing tear clearance, the compound of Formula (I), (II), (IIIa), or (IIIb) is administered into the nasal cavity by a medicated stick. In another embodiment of any of the aforementioned embodiments of enhancing tear clearance, the compound of Formula (I), (II), (IIIa), or (IIIb) is administered into the nasal cavity by a pipette. In another embodiment of any of the aforementioned embodiments of enhancing tear clearance, the compound of Formula (I), (II), (IIIa), or (IIIb) is administered into the nasal cavity by a jet of liquid. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned embodiments of enhancing tear clearance, the trigeminal nerve is activated. In a further embodiment of enhancing tear clearance, the anterior ethmoidal nerve is activated. In another embodiment of any of the aforementioned embodiments of enhancing tear clearance, the nasolacrimal reflex is activated.

In another embodiment of any of the aforementioned embodiments of enhancing tear clearance, the condition relieved by enhancing tear clearance is an acute condition. An acute condition refers to a condition with a rapid onset of a health effect that is considered brief, not prolonged. Acute conditions can result from ophthalmologic surgical procedures or other ophthalmologic treatment. In some embodiments, the ophthalmologic surgical procedure is cataract surgery (cataract extraction and lens replacement), refractive lens exchange, glaucoma surgery, lasik surgery (laser eye surgery), vitrectomy, retinal photocoagulation, retinal detachment repair, macular hole repair, retroiris tumor or mass removal, posterior sclerotomy, optic neurotomy, or other treatments that decrease the function of the lacrimal gland. In some embodiments, the ophthalmologic treatment comprises radiation therapy. In some embodiments, the radiation therapy is directed to orbital area, for example, in connection to cancers of head and/or neck. In some embodiments, the compound of Formula (I) is (R)-5-((E)-2-pyrrolidin-3-ylvinyl)pyrimidine, or a pharmaceutically acceptable salt thereof.

Acute Indications

The ocular conditions disclosed herein can be acute conditions. An acute condition refers to a condition with a rapid onset of a health effect that is considered brief, not prolonged. Acute conditions can result from ophthalmologic surgical procedures or other ophthalmologic treatment. The present disclosure provides a method of treating an ocular condition comprising the local administration of a therapeutically effective of an amount of a disclosed compound, wherein the ocular condition is an acute condition. The present disclosure also provides a method of treating an ocular condition comprising the local administration of a therapeutically effective of an amount of a disclosed compound, wherein the ocular condition is a result from an ophthalmologic surgical procedure or an ophthalmologic treatment.

In some embodiments, the ophthalmologic surgical procedure is cataract surgery (cataract extraction and lens replacement), refractive lens exchange, glaucoma surgery, lasik surgery (laser eye surgery), vitrectomy, retinal photocoagulation, retinal detachment repair, macular hole repair, retroiris tumor or mass removal, posterior sclerotomy, optic neurotomy, or other treatments that decrease the function of the lacrimal gland.

In some embodiments, the ophthalmologic treatment comprises radiation therapy. In some embodiments, the radiation therapy is directed to orbital area, for example, in connection to cancers of head and/or neck.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include". "includes," and "included." is not limiting. The section headings used herein are for organizational purposes only and are not to be construed as limiting the subject matter described.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the pharmaceutical formulation comprising a nicotinic acetylcholine receptor agonist compound of Formula (I), (II), (IIIa), or (IIIb) as disclosed herein required to provide a clinically significant decrease in disease symptoms. An appropriate "effective" amount in any individual case may be determined using techniques, such as a dose escalation study.

The terms "individual", "subject", and "patient" encompass mammals and non-mammals. Examples of mammals include, but are not limited to, any member of the Mammalian class humans, non-human primates such as chimpanzees, and other apes and monkey species: farm animals such as cattle, horses, sheep, goats, swine: domestic animals such as rabbits, dogs, and cats; laboratory animals including rodents, such as rats, mice and guinea pigs, and the like. In one embodiment, the mammal is a human.

A "tissue" comprises two or more cells. The two or more cells may have a similar function. The tissue may be a connective tissue, epithelial tissue, muscular tissue, or nervous tissue. Alternatively, the tissue is a bone, tendon (both referred to as musculoskeletal grafts), cornea, skin, heart valve, or vein.

An "organ" comprises two or more tissues. The two or more tissues may perform a specific function or group of functions. In some instances, the organ is a lung, mouth, nose, parathyroid gland, pineal gland, pituitary gland, carotid body, salivary gland, skin, gall bladder, pancreas, small intestine, stomach, spleen, spinal cord, thymus, thyroid gland, trachea, uterus, or vermiform appendix. Alternatively, the organ is an adrenal gland, appendix, brain, bladder, kidney, intestine, large intestine, small intestine, liver, heart, or muscle.

The term "nicotinic acetylcholine receptor agonist" encompasses a full agonist or a partial agonist of the nicotinic acetylcholine receptor. In some embodiments described herein, the nicotinic acetylcholine receptor agonist is a compound of compound of Formula (I), (II), (IIIa), or (IIIb).

The terms "treat," "treating" or "treatment," as used herein, include alleviating, abating or ameliorating at least one symptom of a disease or condition, preventing additional symptoms, preventing progression of the condition, inhibiting the disease or condition, e.g., arresting the development of the disease or condition, relieving the disease or condition, causing regression of the disease or condition, relieving a condition caused by the disease or condition, or stopping the symptoms of the disease or condition. In one embodiment, treatment is prophylactic treatment.

In another embodiment, treatment refers to therapeutic treatment.

The term "does not cross the blood-brain barrier in a pharmacologically relevant concentration" as used herein, refers to an insufficient amount of a nicotinic acetylcholine receptor agonist (i.e., compound of Formula (I), (II), (IIIa), or (IIIb)) as disclosed herein passing through the blood-brain barrier to produce a pharmacological response.

The term "undesired psychoactive side effects" as used herein, refers to unintended effects in the brain including, but not limited to, anxiety, depression, hallucination, euphoria, addiction, sleep disorder/disturbances, insomnia, abnormal dreams, and nightmares.

The term "undesired systemic side effects" as used herein, refers to unintended effects in the body including, but not limited to, abdominal pain, vomiting, nausea, constipation, diarrhea, flatulence, dyspepsia, and dry mouth.

The term "formulated to prevent desensitization" as used herein, refers to a formulation that does not result in tolerance, dependence, withdrawal, or loss of sensitivity to the effect of the nicotinic acetylcholine receptor agonist (i.e., compound of Formula (I), (II), (IIIa), or (IIIb)).

The term "produces a local effect" as used herein, refers to the effect of the nicotinic acetylcholine receptor agonist (i.e., compound of Formula (I), (II), (IIIa), or (IIIb)) on the peripheral nicotinic acetylcholine receptor and not producing a pharmacological response on the central nervous system.

The term "environmentally challenging conditions" as used herein, refers to external conditions including naturally and ran-made conditions. Naturally occurring environmentally challenging conditions include, but are not limited to, exposure to smoke, wind, and dry climates. Man-made environmentally challenging conditions include, but are not limited to, exposure to pollution from automobiles, factories, and airplanes, as well as homes/offices with low humidity, high airflow or poor air quality. In some embodiments, "environmentally challenging conditions" refer to controlled challenge environments commonly used for dry eye clinical trials.

The term "ocular discomfort" includes, but is not limited to, the symptoms of dry eye disease, such as itchiness, dryness, photophobia, blurriness, pain, sticky feeling, burning, stinging, and foreign body sensation. In some embodiments, ocular discomfort is associated with blepharitis, meibomian gland dysfunction, allergic conjunctivitis, ocular surface toxicity and irritation, lacrimal drainage problems, or eyelid disorders.

The term "soft drug" as used herein, refers to a drug substance that is rapidly metabolized into an inactive form immediately after achieving the therapeutic effect.

As used herein, the dose of a given agent can be calculated based on any form of the compound, including free acid, free base, or salt form (e.g., pharmaceutically acceptable salt form). For example, in certain embodiments, the dose or concentration is calculated based on the molecular weight of the free base. Likewise, in some embodiments, the dose or concentration is calculated based on the molecular weight of a salt form (e.g., galactarate, hemi-galactarate, citrate, mono-citrate, etc.) as described herein.

Nicotinic Acetylcholine Receptor Agonists

The methods described herein comprise the local administration of a therapeutically effective amount of a nicotinic acetylcholine receptor agonist into the nasal cavity of an individual in need thereof, wherein the nicotinic acetylcholine receptor agonist is a compound of Formula (I), (II), (IIIa), or (IIIb). In some embodiments of the methods described herein, the compound of Formula (I), (II), (IIIa), or (IIIb) is a full agonist. In some embodiments of the methods described herein, the compound of Formula (I), (II), (IIIa), or (IIIb) is a partial agonist. In some embodiments of the methods described herein, the compound of Formula (I), (II), (IIIa), or (IIIb) is (R)-5-((E)-2-pyrrolidin-3-ylvinyl)pyrimidine (or Compound 1). In some embodiments of the methods described herein, the compound of Formula (I), (II), (IIIa), or (IIIb) is (R)-5-((E)-2-pyrrolidin-3-ylvinyl)pyrimidine, or a pharmaceutically acceptable salt thereof. In some embodiments of the methods described herein, the compound of Formula (I), (II), (IIIa), or (IIIb) is (R)-5-((E)-2-pyrrolidin-3-ylvinyl)pyrimidine as a free base. In some embodiments of the methods described herein, the compound of Formula (I), (II), (IIIa), or (IIIb) is (R)-5-((E)-2-pyrrolidin-3-ylvinyl)pyrimidine citrate salt. In some embodiments of the methods described herein, the compound of Formula (I), (II), (IIIa), or (IIIb) is (R)-5-((E)-2-pyrrolidin-3-ylvinyl)pyrimidine mono citrate salt. In some embodiments of the methods described herein, the compound of Formula (I), (II), (IIIa), or (IIIb) is (R)-5-((E)-2-pyrrolidin-3-ylvinyl)pyrimidine HCl salt. In some embodiments of the methods described herein, the compound of Formula (I), (I), (IIIa), or (IIIb) is (R)-5-((E)-2-pyrrolidin-3-ylvinyl)pyrimidine galactarate salt. In some embodiments of the methods described herein, the compound of Formula (I), (II), (IIIa), or (IIIb) is (R)-5-((E)-2-pyrrolidin-3-ylvinyl)pyrimidine hemigalactarate salt. In some embodiments of the methods described herein, the compound of Formula (I), (II), (IIIa), or (IIIb) is (R)-5-((E)-2-pyrrolidin-3-ylvinyl)pyrimidine hemigalactarate monohydrate. In some embodiments of the described herein, the compound of Formula (I), (II), (IIIa), or (IIIb) is (R)-5-((E)-2-pyrrolidin-3-ylvinyl)pyrimidine hemigalactarate dihydrate. In some embodiments of the methods described herein, the compound of Formula (I), (II), (IIIa), or (IIIb) is N-(5-chlorofuran-2-ylcarbonyl)-3,7-diazabicyclo[3.3.0]octane. In some embodiments of the methods described herein, nicotine is not administered. WO 2010/065443, which is hereby incorporated by reference in its entirety, provides additional description.

In some embodiments of the methods described herein, the compound of Formula (I), (II), (IIIa), or (IIIb) is a soft drug.

In some embodiments of the methods described herein is a compound of Formula (I) having the structure:

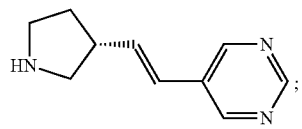 [SMILES: C(=C\[C@H]1CCNC1)/c1cncnc1]

or a pharmaceutically acceptable salt thereof.

In some embodiments of the methods described herein is a compound of Formula (I) having the structure:

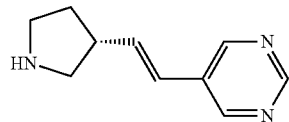

hemigalactarate monohydrate or dihydrate.

In some embodiments of the methods described herein is a compound of Formula (I) having the structure:

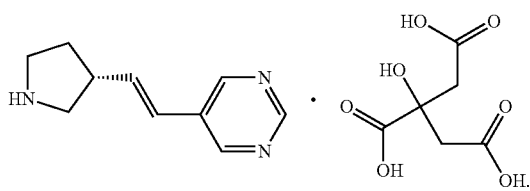 [SMILES: C(=C\[C@H]1CCNC1)/c1cncnc1 ; O=C(O)CC(O)(CC(=O)O)C(=O)O]

In some embodiments of the methods described herein is a compound of Formula (I) having the structure:

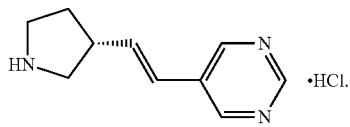 [SMILES: C(=C\[C@H]1CCNC1)/c1cncnc1]

In some embodiments of the methods described herein is a compound of Formula (I) having the structure:

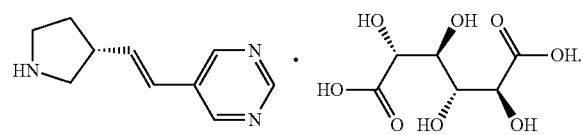 [SMILES: C(=C\[C@H]1CCNC1)/c1cncnc1 ; O=C(O)[C@@H](O)[C@H](O)[C@H](O)[C@@H](O)C(=O)O]

In some embodiments of the methods described herein is a compound of Formula (II) having the structure:

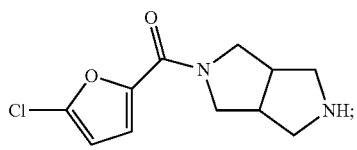 [SMILES: O=C(c1ccc(Cl)o1)N1CC2CNCC2C1]

or a pharmaceutically acceptable salt thereof.

Polymorphs

The compounds of the present disclosure may crystallize in more than one form, a characteristic known as polymorphism, and such polymorphic forms ("polymorphs") are within the scope of the present disclosure. Polymorphism generally can occur as a response to changes in temperature, pressure, or both. Polymorphism can also result from variations in the crystallization process. Polymorphs can be distinguished by various physical characteristics known in the art such as XRPD patterns (diffractograns), solubility in various solvents, and melting point.

The present disclosure includes various polymorphic forms of the salt forms of (R)-5-((E)-2-pyrrolidin-3-ylvinyl) pyrimidine, including hydrates and solvates of the salts. Such polymorphic forms are characterized by their x-ray powder diffraction (XRPD) patterns (diffractograms).

One embodiment of the present disclosure includes a crystalline form of (R)-5-((E)-2-pyrrolidin-3-ylvinyl)pyrimidine mono-citrate. Another embodiment of the present disclosure includes an amorphous form of (R)-5-((E)-2-pyrrolidin-3-ylvinyl)pyrimidine mono-citrate. Another embodiment of the present disclosure includes an amorphous form of (R)-5-((E)-2-pyrrolidin-3-ylvinyl)pyrimidine mono-citrate whose XRPD pattern substantially corresponds to that shown in FIG. 1 of WO 2010/065443, which is hereby incorporated by reference in its entirety.

One embodiment of the present disclosure includes a polymorphic form of (R)-5-((E)-2-pyrrolidin-3-ylvinyl)pyrimidine mono-citrate Form 1 characterized by a XRPD pattern comprising at least one of the following peaks:

| 2θ |
|---|
| 5.27 |
| 10.03 |
| 13.77 |
| 21.73 |

Figure 2:
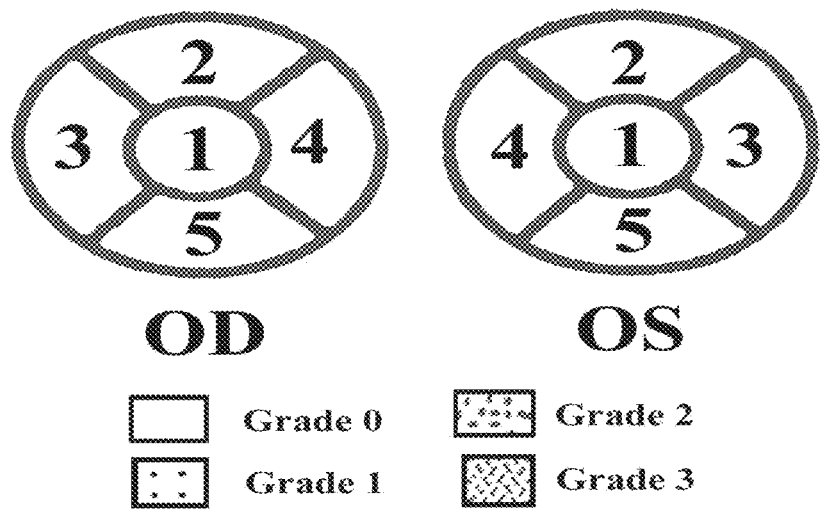
FIG. 2 shows a diagram of the division of the corneal surface for measuring fluorescein uptake.

Another embodiment, the present disclosure includes a polymorphic form of (R)-5-((E)-2-pyrrolidin-3-ylvinyl)pyrimidine mono-citrate Form 1 whose XRPD pattern substantially corresponds to that shown in FIG. 2 of WO 2010/065443, which is hereby incorporated by reference in its entirety.

One embodiment of the present disclosure includes a polymorphic form of (R)-5-((E)-2-pyrrolidin-3-ylvinyl)pyrimidine mono-citrate Form 11 characterized by a powder x-ray diffraction pattern comprising at least one of the following peaks:

| 2θ |
|---|
| 11.02 |
| 20.01 |
| 22.06 |
| 24.66 |
| 32.13 |
| 33.35 |
| 34.61 |
| 35.96 |
| 38.65 |
| 40.23 |

Another embodiment, the present disclosure includes a polymorphic form of (R)-5-((E)-2-pyrrolidin-3-ylvinyl)pyrimidine mono-citrate Form II whose XRPD pattern substantially corresponds to that shown in FIG. 3 of WO 2010/065443, which is hereby incorporated by reference in its entirety.

One embodiment of the present disclosure includes a polymorphic form of (R)-5-((E)-2-pyrrolidin-3-ylvinyl)pyrimidine mono-citrate Form III characterized by a XRPD pattern comprising at least one of the following peaks:

| 2θ |
|---|
| 9.43 |
| 12.24 |
| 16.24 |
| 18.38 |
| 19.18 |
| 19.48 |
| 21.52 |
| 22.89 |
| 23.08 |
| 24.28 |
| 30.77 |
| 31.27 |
| 32.36 |
| 33.09 |
| 34.86 |
| 37.26 |
| 37.63 |
| 39.47 |

Figure 4:
FIG. 4 shows an exemplary visual analog scale (VAS), wherein the subject is instructed to rate the severity of their current "dryness" symptoms by drawing a vertical line on the line indicated.

Another embodiment, the present disclosure includes a polymorphic form of (R)-5-((E)-2-pyrrolidin-3-ylvinyl)pyrimidine mono-citrate Form 111 whose XRPD pattern substantially corresponds to that shown in FIG. 4 of WO 2010/065443, which is hereby incorporated by reference in its entirety.

One embodiment of the present disclosure includes a polymorphic form of (R)-5-((E)-2-pyrrolidin-3-ylvinyl)pyrimidine mono-citrate Form IV characterized by a XRPD pattern comprising at least one of the following peaks:

| 2θ |
|---|
| 5.05 |
| 10.81 |
| 14.06 |
| 15.20 |
| 17.43 |
| 23.57 |
| 24.21 |
| 25.52 |
| 26.95 |

Figure 5:
FIG. 5 shows an exemplary visual analog scale (VAS), wherein the subject is instructed to rate their eye dryness by drawing a vertical line on the horizontal line to indicate the level of discomfort.

Another embodiment, the present disclosure includes a polymorphic form of (R)-5-((E)-2-pyrrolidin-3-ylvinyl)pyrimidine mono-citrate Form IV whose XRPD pattern substantially corresponds to that shown in FIG. 5 of WO 2010/065443, which is hereby incorporated by reference in its entirety.

One embodiment of the present disclosure includes a crystalline form of (R)-5-((E)-2-pyrrolidin-3-ylvinyl)pyrimidine mono-orotate.

One embodiment of the present disclosure includes a polymorphic form of (R)-5-((E)-2-pyrrolidin-3-ylvinyl)pyrimidine mono-orotate Form 1 characterized by a XRPD pattern comprising at least one of the following peaks:

| 2θ |
|---|
| 2.55 |
| 6.54 |
| 8.66 |
| 13.26 |
| 14.56 |
| 15.98 |
| 17.47 |
| 18.53 |
| 19.30 |
| 20.26 |
| 21.05 |
| 22.02 |
| 23.14 |
| 24.32 |
| 25.56 |
| 26.87 |
| 27.84 |
| 28.76 |
| 29.53 |

Another embodiment, the present disclosure includes a polymorphic form of (R)-5-((E)-2-pyrrolidin-3-ylvinyl)pyrimidine mono-orotate Form 1 whose XRPD pattern substantially corresponds to that shown in FIG. 6 of WO 2010/065443, which is hereby incorporated by reference in its entirety.

One embodiment of the present disclosure includes a crystalline form of (R)-5-((E)-2-pyrrolidin-3-ylvinyl)pyrimidine mono-maleate.

One embodiment of the present disclosure includes a polymorphic form of (R)-5-((E)-2-pyrrolidin-3-ylvinyl)pyrimidine mono-maleate Form 1 characterized by a XRPD pattern comprising at least one of the following peaks:

| 2θ |
|---|
| 12.81 |
| 16.09 |
| 18.00 |
| 19.07 |
| 24.49 |
| 26.40 |
| 26.04 |
| 27.88 |

Another embodiment, the present disclosure includes a polymorphic form of (R)-5-((E)-2-pyrrolidin-3-ylvinyl)pyrimidine mono-maleate Form 1 whose XRPD pattern substantially corresponds to that shown in FIG. 7 of WO 2010/065443, which is hereby incorporated by reference in its entirety.

One embodiment of the present disclosure includes a polymorphic form of (R)-5-((E)-2-pyrrolidin-3-ylvinyl)pyrimidine mono-maleate Form II characterized by a XRPD pattern comprising at least one of the following peaks:

| 2θ |
|---|
| 4.31 |
| 16.56 |
| 18.29 |
| 18.78 |
| 19.64 |
| 20.27 |
| 21.02 |
| 21.46 |
| 21.90 |
| 22.43 |
| 22.86 |
| 25.40 |
| 25.73 |
| 26.15 |
| 26.56 |
| 27.40 |
| 28.59 |
| 29.57 |

Another embodiment, the present disclosure includes a polymorphic form of (R)-5-((E)-2-pyrrolidin-3-ylvinyl)pyrimidine mono-maleate Form 11 whose XRPD pattern substantially corresponds to that shown in FIG. 8 of WO 2010/065443, which is hereby incorporated by reference in its entirety.

As noted, the salt forms of (R)-5-((E)-2-pyrrolidin-3-ylvinyl)pyrimidine may exist in solvated, for example hydrated, as well as unsolvated forms. The present disclosure encompasses all such forms.

The present invention also includes isotopically labeled compounds wherein one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine, and chlorine, such as $^2$H, H, $^{13}$C, $^{14}$C, $^{15}$N, $^{18}$O, and $^{17}$O. Such isotopically labeled compounds are useful as research or diagnostic tools.

Intranasal Route of Administration

The methods described herein comprise the local administration of a therapeutically effective amount of a nicotinic acetylcholine receptor agonist into the nasal cavity of an individual in need thereof, in some embodiments, the methods described herein comprise the local administration of a therapeutically effective amount of a nicotinic acetylcholine receptor agonist into the nasal cavity of an individual in need thereof, wherein the nicotinic acetylcholine receptor agonist is a compound of Formula (I), (II), (IIIa), or (IIIb). In some embodiments, the methods described herein comprise the local administration of a therapeutically effective amount of a compound of Formula (I), (II), (IIIa), or (IIIb) into the nasal cavity of an individual in need thereof, wherein the compound of Formula (I), (II), (IIIa), or (IIIb) is administered into the nasal cavity as a liquid, suspension, aerosol, gel, ointment, dry powder, cream, paste, lotion, or balm. In some embodiments of the methods described herein, the compound of Formula (I), (II), (IIIa), or (IIIb) is administered into the nasal cavity as a liquid. In some embodiments of the methods described herein, the compound of Formula (I), (II), (IIIa), or (IIIb) is administered into the nasal cavity as a suspension. In some embodiments of the methods described herein, the compound of Formula (I), (II), (IIIa), or (IIIb) is administered into the nasal cavity as an aerosol. In some embodiments of the methods described herein, the compound of Formula (I), (II), (IIIa), or (IIIb) is administered into the nasal cavity as a gel. In some embodiments of the methods described herein, the compound of Formula (I), (II), (IIIa), or (IIIb) is administered into the nasal cavity as an ointment. In some embodiments of the methods described herein, the compound of Formula (I), (II), (IIIa), or (IIIb) is administered into the nasal cavity as a dry powder. In some embodiments of the methods described herein, the compound of Formula (I), (II), (IIIa), or (IIIb) is administered into the nasal cavity as a cream. In some embodiments of the methods described herein, the compound of Formula (I), (II), (IIIa), or (IIIb) is administered into the nasal cavity as a paste. In some embodiments of the methods described herein, the compound of Formula (I), (II), (IIIa), or (IIIb) is administered into the nasal cavity as a lotion. In some embodiments of the methods described herein, the compound of Formula (I), (II), (IIIa), or (IIIb) is administered into the nasal cavity as a balm. In some embodiments, the compound of Formula (I) is (R)-5-((E)-2-pyrrolidin-3-ylvinyl)pyrimidine, or a pharmaceutically acceptable salt thereof.

In some embodiments, the methods described herein comprise the local administration of a therapeutically effective amount of a compound of Formula (I), (II), (IIIa), or (IIIb) into the nasal cavity of an individual in need thereof, wherein the compound of Formula (I), (II), (IIIa), or (IIIb) is administered into the nasal cavity by a syringe, dropper, bottle nebulizer, atomization pump, inhaler, powder spray device, vaporizer, patch, medicated stick, pipette, or jet of liquid. In some embodiments of the methods described herein, the compound of Formula (I), (II), (IIIa), or (IIIb) is administered into the nasal cavity by a syringe. In some embodiments of the methods described herein, the compound of Formula (I), (II), (IIIa), or (IIIb) is administered into the nasal cavity by a dropper. In some embodiments of the methods described herein, the compound of Formula (I), (II), (IIIa), or (IIIb) is administered into the nasal cavity by a bottle nebulizer. In some embodiments of the methods described herein, the compound of Formula (I), (II), (IIIa), or (IIIb) is administered into the nasal cavity by an atomization pump. In some embodiments of the methods described herein, the compound of Formula (I), (II), (IIIa), or (IIIb) is administered into the nasal cavity by an inhaler. In some embodiments of the methods described herein, the compound of Formula (I), (II), (IIIa), or (IIIb) is administered into the nasal cavity by a powder spray device. In some embodiments of the methods described herein, the compound of Formula (I), (I), (IIIa), or (IIIb) is administered into the nasal cavity by a vaporizer. In some embodiments of the methods described herein, the compound of Formula (I). (II), (IIIa), or (IIIb) is administered into the nasal cavity by a patch. In some embodiments of the methods described herein, the compound of Formula (I), (II), (IIIa), or (IIIb) is administered into the nasal cavity by a medicated stick. In some embodiments of the methods described herein, the compound of Formula (I), (II), (IIIa), or (IIIb) is administered into the nasal cavity by a pipette. In some embodiments of the methods described herein, the compound of Formula (I), (I), (IIIa), or (IIIb) is administered into the nasal cavity by a jet of liquid. In some embodiments, the compound of Formula (I) is (R)-5-((E)-2-pyrrolidin-3-ylvinyl)pyrimidine, or a pharmaceutically acceptable salt thereof.

In another embodiment, the compound of Formula (I), (II), (IIIa), or (IIIb) is administered in alternating nostrils. For example, the compound of Formula (I), (II), (IIIa), or (IIIb) is administered in one nostril and then the other nostril after a pre-determined amount of time. In another embodiment, the compound of Formula (I), (II), (IIIa), or (IIIb) is administered in both nostrils. For example, the compound of Formula (I), (II), (IIIa), or (IIIb) is administered in one nostril and then the other nostril at the same time or immediately after the first nostril. In another embodiment, the compound of Formula (I), (II), (IIIa), or (IIIb) is administered in one nostril. In some embodiments, the compound of Formula (I) is (R)-5-((E)-2-pyrrolidin-3-ylvinyl)pyrimidine, or a pharmaceutically acceptable salt thereof.

In some embodiments, the compound of Formula (I), (II), (IIIa), or (IIIb) is (R)-5-((E)-2-pyrrolidin-3-ylvinyl)pyrimidine (or Compound 1). In some embodiments, the compound of Formula (I), (II), (IIIa), or (IIIb) is (R)-5-((E)-2-pyrrolidin-3-ylvinyl)pyrimidine, or a pharmaceutically acceptable salt thereof. In some embodiments, the compound of Formula (I), (II), (IIIa), or (IIIb) is (R)-5-((E)-2-pyrrolidin-3-ylvinyl)pyrimidine as a free base. In some embodiments, the compound of Formula (I), (II), (IIIa), or (IIIb) is (R)-5-((E)-2-pyrrolidin-3-ylvinyl)pyrimidine citrate salt. In some embodiments, the compound of Formula (I), (II), (IIIa), or (IIIb) is (R)-5-((E)-2-pyrrolidin-3-ylvinyl)pyrimidine mono citrate salt. In some embodiments, the compound of Formula (I), (II), (IIIa), or (IIIb) is (R)-5-((E)-2-pyrrolidin-3-ylvinyl)pyrimidine HCl salt. In some embodiments, the compound of Formula (I), (II), (IIIa), or (IIIb) is (R)-5-((E)-2-pyrrolidin-3-ylvinyl)pyrimidine galactarate salt. In some embodiments, the compound of Formula (I), (II), (IIIa), or (IIIb) is (R)-5-((E)-2-pyrrolidin-3-ylvinyl)pyrimidine hemigalactarate salt. In some embodiments, the compound of Formula (I), (II), (IIIa), or (IIIb) is (R)-5-((E)-2-pyrrolidin-3-ylvinyl)pyrimidine hemigalactarate monohydrate. In some embodiments of the method described herein, the compound of Formula (I), (II), (IIIa), or (IIIb) is (R)-5-((E)-2-pyrrolidin-3-ylvinyl)pyrimidine hemigalactarate dihydrate.

Pharmaceutical Formulations, Methods of Dosing, and Treatment Regimens

Also provided herein are pharmaceutical formulations of nicotinic acetylcholine receptor agonists for local administration into the nasal cavity of an individual, in some embodiments provided herein is a pharmaceutical formulation of a nicotinic acetylcholine receptor agonist for local administration into the nasal cavity of an individual, wherein the nicotinic acetylcholine receptor agonist is a compound of Formula (I), (II), (IIIa), or (IIIb). In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, further comprising one or more substances selected from protein kinase C (PKC) or factors that upregulate or up-modulate PKC, cAMP-dependent protein kinase (PKA) or factors that upregulate or up-modulate PKA, and calcineurin inhibitors. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, further comprising protein kinase C (PKC) or factors that upregulate or up-modulate PKC. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, further comprising cAMP-dependent protein kinase (PKA) or factors that upregulate or up-modulate PKA. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, further comprising a calcineurin inhibitor. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, further comprising a calcineurin inhibitor, wherein the calcineurin inhibitor is selected from cyclosporine, pimecrolimus, and tacrolimus. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, further comprising a calcineurin inhibitor, wherein the calcineurin inhibitor is cyclosporine. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, further comprising a calcineurin inhibitor, wherein the calcineurin inhibitor is pimecrolimus. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, further comprising a calcineurin inhibitor, wherein the calcineurin inhibitor is tacrolimus.

In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) is (R)-5-((E)-2-pyrrolidin-3-ylvinyl)pyrimidine. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) is (R)-5-((E)-2-pyrrolidin-3-ylvinyl)pyrimidine citrate salt. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) is (R)-5-((E)-2-pyrrolidin-3-ylvinyl)pyrimidine mono citrate salt. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) is (R)-5-((E)-2-pyrrolidin-3-ylvinyl)pyrimidine HCl salt. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) is (R)-5-((E)-2-pyrrolidin-3-ylvinyl)pyrimidine galactarate salt. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) is N-(5-chlorofuran-2-ylcarbonyl)-3,7-diazabicyclo[3.3.0]octane. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the pharmaceutical formulation does not contain nicotine in any form. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the pharmaceutical formulation does not contain nicotine free base, a nicotine salt, a nicotine complex, or a nicotine solvate.

In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) selectively binds to at least one of the peripheral nicotinic acetylcholine receptor subtypes selected from alpha3beta4, alpha4beta2, and alpha7. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) selectively binds to the peripheral nicotinic acetylcholine receptor subtype alpha3beta4. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) selectively binds to the peripheral nicotinic acetylcholine receptor subtype alpha4beta2. In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) selectively binds to the peripheral nicotinic acetylcholine receptor subtype alpha7. In some embodiments, the compound of Formula (I) is (R)-5-((E)-2-pyrrolidin-3-ylvinyl)pyrimidine, or a pharmaceutically acceptable salt thereof.

In some embodiments is a pharmaceutical formulation for local administration into the nasal cavity of an individual comprising a compound of Formula (I), (II), (IIIa), or (IIIb) formulated to prevent desensitization and in a dosage amount that is not systemically bioavailable, wherein the compound of Formula (I), (II), (IIIa), or (IIIb) is a soft drug. In some embodiments, the compound of Formula (I) is (R)-5-((E)-2-pyrrolidin-3-ylvinyl)pyrimidine, or a pharmaceutically acceptable salt thereof.

In some embodiments is a pharmaceutical formulation for local administration into the nasal cavity of an individual comprising a compound of Formula (I) formulated to prevent desensitization and in a dosage amount that is not systemically bioavailable, wherein compound of Formula (I) has the structure:

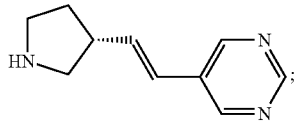

or a pharmaceutically acceptable salt thereof.

In some embodiments is a pharmaceutical formulation for local administration into the nasal cavity of an individual comprising a compound of Formula (I) formulated to prevent desensitization and in a dosage amount that is not systemically bioavailable, wherein compound of Formula (I) has the structure:

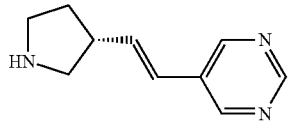

hemigalactarate-monohydrate or dihydrate; or a pharmaceutically acceptable salt thereof.

In some embodiments is a pharmaceutical formulation for local administration into the nasal cavity of an individual comprising a compound of Formula (I) formulated to prevent desensitization and in a dosage amount that is not systemically bioavailable, wherein compound of Formula (I) has the structure:

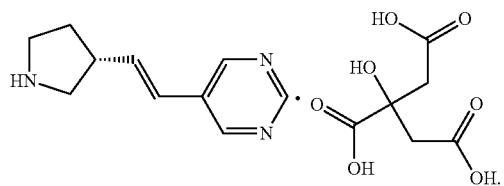

In some embodiments is a pharmaceutical formulation for local administration into the nasal cavity of an individual comprising a compound of Formula (I) formulated to prevent desensitization and in a dosage amount that is not systemically bioavailable, wherein compound of Formula (I) has the structure:

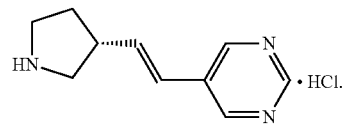 [SMILES: C(=C\[C@H]1CCNC1)/c1cncnc1]

In some embodiments is a pharmaceutical formulation for local administration into the nasal cavity of an individual comprising a compound of Formula (II) formulated to prevent desensitization and in a dosage amount that is not systemically bioavailable, wherein compound of Formula (II) has the structure:

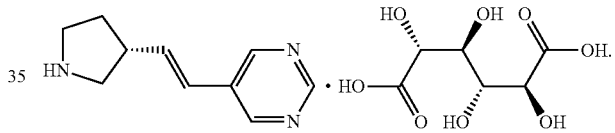

In some embodiments is a pharmaceutical formulation for local administration into the nasal cavity of an individual comprising a compound of Formula (II) formulated to prevent desensitization and in a dosage amount that is not systemically bioavailable, wherein compound of Formula (II) has the structure:

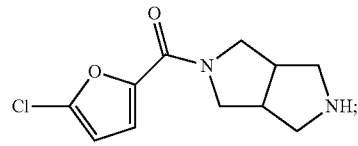 [SMILES: O=C(c1ccc(Cl)o1)N1CC2CNCC2C1]

or a pharmaceutically acceptable salt thereof.

Further described herein, in some embodiments, is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, further comprising one or more substances selected from protein kinase C (PKC) or factors that upregulate or up-modulate PKC, cAMP-dependent protein kinase (PKA) or factors that upregulate or up-modulate PKA, and calcineurin inhibitors. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, further comprising protein kinase C (PKC) or factors that upregulate or up-modulate PKC. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, further comprising cAMP-dependent protein kinase (PKA) or factors that upregulate or up-modulate PKA. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, further comprising a calcineurin inhibitor. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, further comprising a calcineurin inhibitor, wherein the calcineurin inhibitor is selected from cyclosporine, pimecrolimus, and tacrolimus. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, further comprising a calcineurin inhibitor, wherein the calcineurin inhibitor is cyclosporine. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, further comprising a calcineurin inhibitor, wherein the calcineurin inhibitor is pimecrolimus. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, further comprising a calcineurin inhibitor, wherein the calcineurin inhibitor is tacrolimus.

In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, wherein the compound of Formula (I), (II), (IIIa), or (IIIb) is a soft drug. In some embodiments, the compound of Formula (I) is (R)-5-((E)-2-pyrrolidin-3-ylvinyl)pyrimidine, or a pharmaceutically acceptable salt thereof.

In some embodiments is a pharmaceutical formulation for local administration into the nasal cavity of an individual comprising a compound of Formula (I) formulated to prevent desensitization and in a dosage amount that does not result in undesired psychoactive side effects, wherein compound of Formula (I) has the structure:

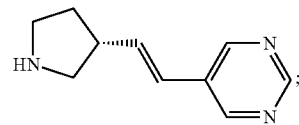 [SMILES: C(=C\[C@H]1CCNC1)/c1cncnc1]

or a pharmaceutically acceptable salt thereof.

In some embodiments is a pharmaceutical formulation for local administration into the nasal cavity of an individual comprising a compound of Formula (I) formulated to prevent desensitization and in a dosage amount that does not result in undesired psychoactive side effects, wherein compound of Formula (I) has the structure:

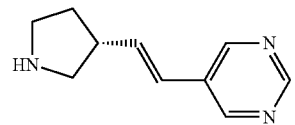

hemigalactarate-monohydrate or dihydrate; or a pharmaceutically acceptable salt thereof.

In some embodiments is a pharmaceutical formulation for local administration into the nasal cavity of an individual comprising a compound of Formula (I) formulated to prevent desensitization and in a dosage amount that does not result in undesired psychoactive side effects wherein compound of Formula (I) has the structure:

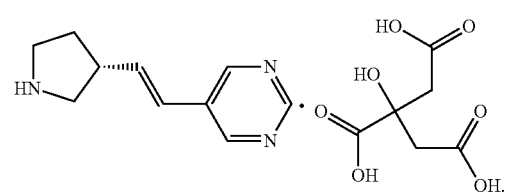

In some embodiments is a pharmaceutical formulation for local administration into the nasal cavity of an individual comprising a compound of Formula (I) formulated to prevent desensitization and in a dosage amount that does not result in undesired psychoactive side effects, wherein compound of Formula (I) has the structure:

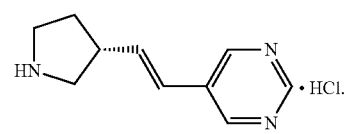 [SMILES: C(=C\[C@H]1CCNC1)/c1cncnc1]

In some embodiments is a pharmaceutical formulation for local administration into the nasal cavity of an individual comprising a compound of Formula (I) formulated to prevent desensitization and in a dosage amount that does not result in undesired psychoactive side effects, wherein compound of Formula (I) has the structure:

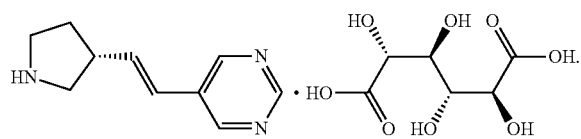

In some embodiments is a pharmaceutical formulation for local administration into the nasal cavity of an individual comprising a compound of Formula (II) formulated to prevent desensitization and in a dosage amount that does not result in undesired psychoactive side effects, wherein compound of Formula (II) has the structure:

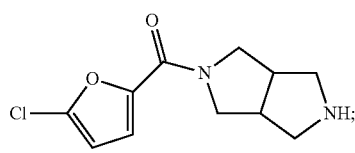 [SMILES: O=C(c1ccc(Cl)o1)N1CC2CNCC2C1]

or a pharmaceutically acceptable salt thereof.

In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, wherein the compound of Formula (I), (II), (IIIa), or (IIIb) selectively binds to at least one of the peripheral nicotinic acetylcholine receptor subtypes selected from alpha3beta4, alpha4beta2, and alpha7. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, wherein the compound of Formula (I), (II), (IIIa), or (IIIb) selectively binds to the peripheral nicotinic acetylcholine receptor subtype alpha3beta4. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, wherein the compound of Formula (I), (II), (IIIa), or (IIIb) selectively binds to the peripheral nicotinic acetylcholine receptor subtype alpha4beta2. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired psychoactive side effects, wherein the compound of Formula (I), (II), (IIIa), or (IIIb) selectively binds to the peripheral nicotinic acetylcholine receptor subtype alpha7. In some embodiments, the compound of Formula (I) is (R)-5-((E)-2-pyrrolidin-3-ylvinyl)pyrimidine, or a pharmaceutically acceptable salt thereof.

Further described herein, in some embodiments, is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, further comprising one or more substances selected from protein kinase C (PKC) or factors that upregulate or up-modulate PKC, cAMP-dependent protein kinase (PKA) or factors that upregulate or up-modulate PKA, and calcineurin inhibitors. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, further comprising protein kinase C (PKC) or factors that upregulate or up-modulate PKC. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, further comprising cAMP-dependent protein kinase (PKA) or factors that upregulate or up-modulate PKA. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, further comprising a calcineurin inhibitor. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, further comprising a calcineurin inhibitor, wherein the calcineurin inhibitor is selected from cyclosporine, pimecrolimus, and tacrolimus. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, further comprising a calcineurin inhibitor, wherein the calcineurin inhibitor is cyclosporine. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, further comprising a calcineurin inhibitor, wherein the calcineurin inhibitor is pimecrolimus. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, further comprising a calcineurin inhibitor, wherein the calcineurin inhibitor is tacrolimus.

In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, wherein the compound of Formula (I), (II), (IIIa), or (IIIb) is a soft drug.

In some embodiments is a pharmaceutical formulation for local administration into the nasal cavity of an individual comprising a compound of Formula (I) formulated to prevent desensitization and in a dosage amount that does not result in undesired systemic side effects, wherein compound of Formula (I) has the structure:

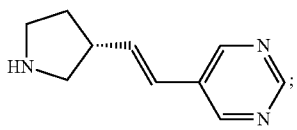 [SMILES: C(=C\[C@H]1CCNC1)/c1cncnc1]

or a pharmaceutically acceptable salt thereof.

In some embodiments is a pharmaceutical formulation for local administration into the nasal cavity of an individual comprising a compound of Formula (I) formulated to prevent desensitization and in a dosage amount that does not result in undesired systemic side effects, wherein compound of Formula (I) has the structure:

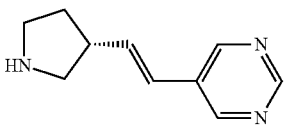 [SMILES: C(=C\[C@H]1CCNC1)/c1cncnc1]

hemigalactarate-monohydrate or dehydrate; or a pharmaceutically acceptable salt thereof.

In some embodiments is a pharmaceutical formulation for local administration into the nasal cavity of an individual comprising a compound of Formula (I) formulated to prevent desensitization and in a dosage amount that does not result in undesired systemic side effects, wherein compound of Formula (I) has the structure:

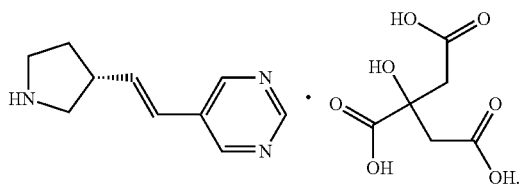

In some embodiments is a pharmaceutical formulation for local administration into the nasal cavity of an individual comprising a compound of Formula (I) formulated to prevent desensitization and in a dosage amount that does not result in undesired systemic side effects, wherein compound of Formula (I) has the structure:

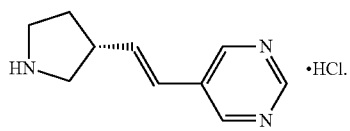 [SMILES: C(=C\[C@H]1CCNC1)/c1cncnc1]

In some embodiments is a pharmaceutical formulation for local administration into the nasal cavity of an individual comprising a compound of Formula (I) formulated to prevent desensitization and in a dosage amount that does not result in undesired systemic side effects, wherein compound of Formula (I) has the structure:

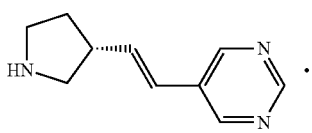

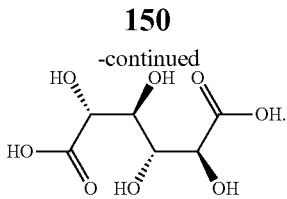

In some embodiments is a pharmaceutical formulation for local administration into the nasal cavity of an individual comprising a compound of Formula (II) formulated to prevent desensitization and in a dosage amount that does not result in undesired systemic side effects, wherein compound of Formula (II) has the structure:

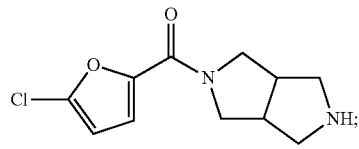 [SMILES: O=C(c1ccc(Cl)o1)N1CC2CNCC2C1]

or a pharmaceutically acceptable salt thereof.

In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, wherein the compound of Formula (I), (II), (IIIa), or (IIIb) selectively binds to at least one of the peripheral nicotinic acetylcholine receptor subtypes selected from alpha3beta4, alpha4beta2, and alpha7. In some embodiments is a pharmaceutical formulation for local administration into the nasal cavity of an individual comprising a compound of Formula (I), (II), (IIIa), or (IIIb) formulated to prevent desensitization and in a, dosage amount that does not result in undesired systemic side effects, wherein the compound of Formula (I), (II), (IIIa), or (IIIb) selectively binds to the peripheral nicotinic acetylcholine receptor subtype alpha3beta4. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, wherein the compound of Formula (I), (II), (IIIa), or (IIIb) selectively binds to the peripheral nicotinic acetylcholine receptor subtype alpha4beta2. In some embodiments is a pharmaceutical formulation for local administration into the nasal cavity of an individual comprising a compound of Formula (I), (II), (IIIa), or (IIIb) formulated to prevent desensitization and in a dosage amount that does not result in undesired systemic side effects, wherein the compound of Formula (I), (II), (IIIa), or (IIIb) selectively binds to the peripheral nicotinic acetylcholine receptor subtype alpha7. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation comprises about 0.1 mg/mL of a compound of Formula (I), (II), (IIIa), or (IIIb). In another embodiment of any of the aforementioned pharmaceutical formulation embodiments, the pharmaceutical formulation comprises about 0.2 mg/m L of a compound of Formula (I), (II), (IIIa), or (IIIb). In another embodiment of any of the aforementioned pharmaceutical formulation embodiments, the pharmaceutical formulation comprises about 0.5 mg/mL of a compound of Formula (I), (II), (IIIa), or (IIIb). In another embodiment of any of the aforementioned pharmaceutical formulation embodiments, the pharmaceutical formulation comprises about 1 mg/mL of a compound of Formula (I), (II), (IIIa), or (IIIb). In another embodiment of any of the aforementioned pharmaceutical formulation embodiments, the pharmaceutical formulation comprises about 2 mg/mL of a compound of Formula (I), (II), (IIIa), or (IIIb). In another embodiment of any of the aforementioned pharmaceutical formulation embodiments, the pharmaceutical formulation comprises about 3 mg/mL of a compound of Formula (I), (II), (IIIa), or (IIIb). In another embodiment of any of the aforementioned pharmaceutical formulation embodiments, the pharmaceutical formulation comprises about 4 mg/mL of a compound of Formula (I), (II), (IIIa), or (IIIb). In another embodiment of any of the aforementioned pharmaceutical formulation embodiments, the pharmaceutical formulation comprises about 5 mg/mL of a compound of Formula (I), (II), (IIIa), or (IIIb). In another embodiment of any of the aforementioned pharmaceutical formulation embodiments, the pharmaceutical formulation comprises about 6 mg/mL of a compound of Formula (I), (II), (IIIa), or (IIIb). In another embodiment of any of the aforementioned pharmaceutical formulation embodiments, the pharmaceutical formulation comprises about 7 mg/mL of a compound of Formula (I), (II), (IIIa), or (IIIb). In another embodiment of any of the aforementioned pharmaceutical formulation embodiments, the pharmaceutical formulation comprises about 8 mg/mL of a compound of Formula (I), (II), (IIIa), or (IIIb). In another embodiment of any of the aforementioned pharmaceutical formulation embodiments, the pharmaceutical formulation comprises about 9 mg/mL of a compound of Formula (I), (II), (IIIa), or (IIIb). In another embodiment of any of the aforementioned pharmaceutical formulation embodiments, the pharmaceutical formulation comprises about 10 mg/mL of a compound of Formula (I), (II), (IIIa), or (IIIb). In another embodiment of any of the aforementioned pharmaceutical formulation comprises about 12 mg/mL of a compound of Formula (I), (II), (IIIa), or (IIIb). In another embodiment of any of the aforementioned pharmaceutical formulation embodiments, the pharmaceutical formulation comprises about 15 mg/mL of a compound of Formula (I), (II), (IIIa), or (IIIb). In another embodiment of any of the aforementioned pharmaceutical formulation embodiments, the pharmaceutical formulation comprises about 20 mg/mL of a compound of Formula (I), (II), (IIIa), or (IIIb). In another embodiment of any of the aforementioned pharmaceutical formulation embodiments, the pharmaceutical formulation comprises about 25 mg/mL of a compound of Formula (I), (II), (IIIa), or (IIIb). In another embodiment of any of the aforementioned pharmaceutical formulation embodiments, the pharmaceutical formulation comprises about 30 mg/mL of a compound of Formula (I), (II), (IIIa), or (IIIb). In another embodiment of any of the aforementioned pharmaceutical formulation comprises about 40 mg/mL of a compound of Formula (I), (II), (IIIa), or (IIIb). In another embodiment of any of the aforementioned pharmaceutical formulation embodiments, the pharmaceutical formulation comprises about 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment of any of any of the aforementioned pharmaceutical formulation embodiments, the pharmaceutical formulation comprises between 5 mg/mL and 200 mg/mL of a compound of Formula (I), (II), (IIIa), or (IIIb). In another embodiment of any of any of the aforementioned pharmaceutical formulation embodiments, the pharmaceutical formulation comprises between 10 mg/mL and 200 mg/mL of a compound of Formula (I), (II), (IIIa), or (IIIb). In another embodiment of any of any of the aforementioned pharmaceutical formulation embodiments, the pharmaceutical formulation comprises between 5 mg/mL and 100 mg/mL of a compound of Formula (I), (II), (IIIa), or (IIIb). In another embodiment of any of any of the aforementioned pharmaceutical formulation embodiments, the pharmaceutical formulation comprises between 10 mg/mL and 75 mg/mL of a compound of Formula (I), (II), (IIIa), or (IIIb). In another embodiment of any of any of the aforementioned pharmaceutical formulation embodiments, the pharmaceutical formulation comprises between 10 mg/mL and 50 mg/mL of a compound of Formula (I), (II), (IIIa), or (IIIb). In another embodiment of any of any of the aforementioned pharmaceutical formulation embodiments, the pharmaceutical formulation comprises between 10 mg/mL and 30 mg/mL of a compound of Formula (I), (II), (IIIa), or (IIIb). In another embodiment of any of any of the aforementioned pharmaceutical formulation embodiments, the pharmaceutical formulation comprises between 5 mg/mL and 50 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation comprises between 10 mg/mL and 25 mg/mL of a compound of Formula (I), (II), (IIIa), or (IIIb). In another embodiment of any of any of the aforementioned pharmaceutical formulation embodiments, the pharmaceutical formulation comprises between 10 mg/mL and 50 mg/mL of a compound of Formula (I), (II), (IIIa), or (IIIb). In another embodiment of any of any of the aforementioned pharmaceutical formulation embodiments, the pharmaceutical formulation comprises between 20 mg/mL and 50 mg/ml, of a compound of Formula (I), (II), (IIIa), or (IIIb). In another embodiment of any of any of the aforementioned pharmaceutical formulation embodiments, the pharmaceutical formulation comprises between 30 mg/mL and 75 mg/mL of a compound of Formula (I), (II), (IIIa), or (IIIb). In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation comprises at least 1 microgram of a compound of Formula (I), (II), (IIIa), or (IIIb) per dose. In another embodiment of any of the aforementioned pharmaceutical formulation embodiments, the pharmaceutical formulation comprises at least 5 micrograms of a compound of Formula (I), (II), (IIIa), or (IIIb) per dose. In another embodiment of any of the aforementioned pharmaceutical formulation embodiments, the pharmaceutical formulation comprises at least 10 micrograms of a compound of Formula (I), (II), (IIIa), or (IIIb) per dose. In another embodiment of any of the aforementioned pharmaceutical formulation embodiments, the pharmaceutical formulation comprises at least 25 micrograms of a compound of Formula (I), (II), (IIIa), or (IIIb) per dose. In another embodiment of any of the aforementioned pharmaceutical formulation embodiments, the pharmaceutical formulation comprises at least 50 micrograms of a compound of Formula (I), (II), (IIIa), or (IIIb) per dose. In another embodiment of any of the aforementioned pharmaceutical formulation embodiments, the pharmaceutical formulation comprises at least 100 micrograms of a compound of Formula (I), (II), (IIIa), or (IIIb) per dose. In another embodiment of any of the aforementioned pharmaceutical formulation embodiments, the pharmaceutical formulation comprises at least 250 micrograms of a compound of Formula (I), (II), (IIIa), or (IIIb) per dose. In another embodiment of any of the aforementioned pharmaceutical formulation embodiments, the pharmaceutical formulation comprises at least 500 micrograms of a compound of Formula (I), (II), (IIIa), or (IIIb) per dose. In another embodiment of any of the aforementioned pharmaceutical formulation embodiments, the pharmaceutical formulation comprises at least 750 micrograms of a compound of Formula (I), (II), (IIIa), or (IIIb) per dose. In another embodiment of any of the aforementioned pharmaceutical formulation embodiments, the pharmaceutical formulation comprises at least 1000 micrograms of a compound of Formula (I), (II), (IIIa), or (IIIb) per dose. In another embodiment of any of the aforementioned pharmaceutical formulation embodiments, the pharmaceutical formulation comprises between 1 microgram and 1000 micrograms of a compound of Formula (I), (II), (IIIa), or (IIIb) per dose. In another embodiment of any of the aforementioned pharmaceutical formulation embodiments, the pharmaceutical formulation comprises between 5 micrograms and 1000 micrograms of a compound of Formula (I), (II), (IIIa), or (IIIb) per dose. In another embodiment of any of the aforementioned pharmaceutical formulation embodiments, the pharmaceutical formulation comprises between 10 micrograms and 1000 micrograms of a compound of Formula (I), (II), (IIIa), or (IIIb) per dose. In another embodiment of any of the aforementioned pharmaceutical formulation embodiments, the pharmaceutical formulation comprises between 5 micrograms and 100 micrograms of a compound of Formula (I), (II), (IIIa), or (IIIb) per dose. In another embodiment of any of any of the aforementioned pharmaceutical formulation embodiments, the pharmaceutical formulation comprises between 5 micrograms and 50 micrograms of a compound of Formula (I), (II), (IIIa), or (IIIb) per dose. In another embodiment of any of the aforementioned pharmaceutical formulation embodiments, the pharmaceutical formulation comprises between 10 micrograms and 50 micrograms of a compound of Formula (I), (II), (IIIa), or (IIIb) per dose. In another embodiment of any of the aforementioned pharmaceutical formulation embodiments, the pharmaceutical formulation comprises between 25 micrograms and 1000 micrograms of a compound of Formula (I), (II), (IIIa), or (IIIb) per dose. In another embodiment of any of the aforementioned pharmaceutical formulation embodiments, the pharmaceutical formulation comprises between 50 micrograms and 1000 micrograms of a compound of Formula (I), (II), (IIIa), or (IIIb) per dose. In another embodiment of any of the aforementioned pharmaceutical formulation embodiments, the pharmaceutical formulation comprises between 100 micrograms and 1000 micrograms of a compound of Formula (I), (II), (IIIa), or (IIIb) is per dose. In another embodiment of any of the aforementioned pharmaceutical formulation embodiments, the pharmaceutical formulation comprises between 150 micrograms and 1000 micrograms of a compound of Formula (I), (II), (IIIa), or (IIIb) per dose. In another embodiment of any of the aforementioned pharmaceutical formulation embodiments, the pharmaceutical formulation comprises between 100 micrograms and 750 micrograms of a compound of Formula (I), (II), (IIIa), or (IIIb) per dose. In another embodiment of any of the aforementioned pharmaceutical formulation embodiments, the pharmaceutical formulation comprises between 150 micrograms and 750 micrograms of a compound of Formula (I), (II), (IIIa), or (IIIb) per dose. In another embodiment of any of the aforementioned pharmaceutical formulation embodiments, the pharmaceutical formulation comprises between 150 micrograms and 600 micrograms of a compound of Formula (I), (II), (IIIa), or (IIIb) per dose. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation comprises less than 100 micrograms of a compound of Formula (I), (II), (IIIa), or (IIIb) per dose. In another embodiment of any of the aforementioned pharmaceutical formulation embodiments, the pharmaceutical formulation comprises less than 75 micrograms of a compound of Formula (I), (II), (IIIa), or (IIIb) per dose. In another embodiment of any of the aforementioned pharmaceutical formulation embodiments, the pharmaceutical formulation comprises less than 50 micrograms of a compound of Formula (I), (II), (IIIa), or (IIIb) per dose. In another embodiment of any of the aforementioned pharmaceutical formulation embodiments, the pharmaceutical formulation comprises less than 25 micrograms of a compound of Formula (I), (II), (IIIa), or (IIIb) per dose. In another embodiment of any of the aforementioned pharmaceutical formulation embodiments, the pharmaceutical formulation comprises less than 15 micrograms of a compound of Formula (I), (II), (IIIa), or (IIIb) per dose. In another embodiment of any of the aforementioned embodiments of enhancing tear clearance, about 75 micrograms of a compound of Formula (I), (II), (IIIa), or (IIIb) is administered into the nasal cavity. In another embodiment of any of the aforementioned pharmaceutical formulation embodiments, the pharmaceutical formulation comprises about 50 micrograms of a compound of Formula (I), (II), (IIIa), or (IIIb) per dose. In another embodiment of any of the aforementioned pharmaceutical formulation embodiments, the pharmaceutical formulation comprises about 25 micrograms of a compound of Formula (I), (II), (IIIa), or (IIIb) per dose. In another embodiment of any of the aforementioned pharmaceutical formulation embodiments, the pharmaceutical formulation comprises about 10 micrograms of a compound of Formula (I), (II), (IIIa), or (IIIb) per dose. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation comprises between 1 microgram and 100 micrograms of a compound of Formula (I), (II), (IIIa), or (IIIb) per dose. In another embodiment of any of the aforementioned pharmaceutical formulation embodiments, the pharmaceutical formulation comprises between 1 microgram and 75 micrograms of a compound of Formula (I), (II), (IIIa), or (IIIb) per dose. In another embodiment of any of the aforementioned pharmaceutical formulation embodiments, the pharmaceutical formulation comprises between 5 micrograms and 100 micrograms of a compound of Formula (I), (II), (IIIa), or (IIIb) per dose. In another embodiment of any of the aforementioned pharmaceutical formulation embodiments, the pharmaceutical formulation comprises between 5 micrograms and 75 micrograms of a compound of Formula (I), (II), (IIIa), or (IIIb) per dose. In another embodiment of any of the aforementioned pharmaceutical formulation embodiments, the pharmaceutical formulation comprises between 15 micrograms and 100 micrograms of a compound of Formula (I), (II), (IIIa), or (IIIb) per dose. In another embodiment of any of the aforementioned pharmaceutical formulation embodiments, the pharmaceutical formulation comprises between 15 micrograms and 75 micrograms of a compound of Formula (I), (II), (IIIa), or (IIIb) per dose. In another embodiment of any of the aforementioned pharmaceutical formulation embodiments, the pharmaceutical formulation comprises between 25 micrograms and 100 micrograms of a compound of Formula (I), (II), (IIIa), or (IIIb) per dose. In another embodiment of any of the aforementioned pharmaceutical formulation embodiments, the pharmaceutical formulation comprises between 25 micrograms and 75 micrograms of a compound of Formula (I), (II), (IIIa), or (IIIb) per dose. In another embodiment of any of the aforementioned pharmaceutical formulation embodiments, the pharmaceutical formulation comprises between 25 micrograms and 60 micrograms of a compound of Formula (I), (II), (IIIa), or (IIIb) per dose. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation comprises between 500 micrograms and 10 milligrams of a compound of Formula (I), (II), (IIIa), or (IIIb) per dose. In another embodiment of any of the aforementioned pharmaceutical formulation embodiments, the pharmaceutical formulation comprises between 500 micrograms and 5 milligrams of a compound of Formula (I), (II), (IIIa), or (IIIb) per dose. In another embodiment of any of the aforementioned pharmaceutical formulation embodiments, the pharmaceutical formulation comprises between 500 micrograms and 3 milligrams of a compound of Formula (I), (II), (IIIa), or (IIIb) per dose. In another embodiment of any of the aforementioned pharmaceutical formulation embodiments, the pharmaceutical formulation comprises between 500 micrograms and 2 milligrams of a compound of Formula (I), (II), (IIIa), or (IIIb) per dose. In another embodiment of any of the aforementioned pharmaceutical formulation embodiments, the pharmaceutical formulation comprises between 1 milligram and 10 milligrams of a compound of Formula (I), (II), (IIIa), or (IIIb) per dose. In another embodiment of any of the aforementioned pharmaceutical formulation embodiments, the pharmaceutical formulation comprises between 1 milligram and 5 milligrams of a compound of Formula (I), (II), (IIIa), or (IIIb) per dose. In another embodiment of any of the aforementioned pharmaceutical formulation embodiments, the pharmaceutical formulation comprises between 1 milligram and 3 milligrams of a compound of Formula (I), (II), (IIIa), or (IIIb) per dose. In another embodiment of any of the aforementioned pharmaceutical formulation embodiments, the pharmaceutical formulation comprises between 1 milligram and 2 milligrams of a compound of Formula (I), (II), (IIIa), or (IIIb) per dose. In another embodiment of any of the aforementioned pharmaceutical formulation embodiments, the pharmaceutical formulation comprises about 500 micrograms of a compound of Formula (I), (II), (IIIa), or (IIIb) per dose. In another embodiment of any of the aforementioned pharmaceutical formulation embodiments, the pharmaceutical formulation comprises about 1 milligram of a compound of Formula (I), (II), (IIIa), or (IIIb) per dose.

In another embodiment of any of the aforementioned pharmaceutical formulation embodiments, the pharmaceutical formulation comprises about 1.5 milligrams of a compound of Formula (I), (II), (IIIa), or (IIIb) per dose. In another embodiment of any of the aforementioned pharmaceutical formulation embodiments, the pharmaceutical formulation comprises about 2 milligrams of a compound of Formula (I), (II), (IIIa), or (IIIb) per dose. In another embodiment of any of the aforementioned pharmaceutical formulation embodiments, the pharmaceutical formulation comprises about 2.5 milligrams of a compound of Formula (I), (II), (IIIa), or (IIIb) per dose. In another embodiment of any of the aforementioned pharmaceutical formulation embodiments, the pharmaceutical formulation comprises about 3 milligrams of a compound of Formula (I), (II), (IIIa), or (IIIb) per dose. In another embodiment of any of the aforementioned pharmaceutical formulation embodiments, the pharmaceutical formulation comprises about 4 milligrams of a compound of Formula (I), (II), (IIIa), or (IIIb) per dose. In another embodiment of any of the aforementioned pharmaceutical formulation embodiments, the pharmaceutical formulation comprises about 5 milligrams of a compound of Formula (I), (II), (IIIa), or (IIIb) per dose. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation comprises between 1 microgram and 10 milligrams of a compound of Formula (I), (II), (IIIa), or (IIIb) per dose. In another embodiment of any of the aforementioned pharmaceutical formulation embodiments, the pharmaceutical formulation comprises between 5 micrograms and 10 milligrams of a compound of Formula (I), (II), (IIIa), or (IIIb) per dose. In another embodiment of any of the aforementioned pharmaceutical formulation embodiments, the pharmaceutical formulation comprises between 10 micrograms and 10 milligrams of a compound of Formula (I), (II), (IIIa), or (IIIb) per dose.

In another embodiment of any of the aforementioned pharmaceutical formulation embodiments, the pharmaceutical formulation comprises between 25 micrograms and 10 milligrams of a compound of Formula (I), (II), (IIIa), or (IIIb) per dose. In another embodiment of any of the aforementioned pharmaceutical formulation embodiments, the pharmaceutical formulation comprises between 50 micrograms and 10 milligrams of a compound of Formula (I), (II), (IIIa), or (IIIb) per dose. In another embodiment of any of the aforementioned pharmaceutical formulation embodiments, the pharmaceutical formulation comprises between 100 micrograms and 10 milligrams of a compound of Formula (I), (II), (IIIa), or (IIIb) per dose. In another embodiment of any of the aforementioned pharmaceutical formulation embodiments, the pharmaceutical formulation comprises between 150 micrograms and 10 milligrams of a compound of Formula (I), (II), (IIIa), or (IIIb) per dose. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation comprises between 1 microgram and 10 milligrams of a compound of Formula (I), (II), (IIIa), or (IIIb) per dose. In another embodiment of any of the aforementioned pharmaceutical formulation embodiments, the pharmaceutical formulation comprises between 1 microgram and 5 milligrams of a compound of Formula (I), (II), (IIIa), or (IIIb) per dose. In another embodiment of any of the aforementioned pharmaceutical formulation embodiments, the pharmaceutical formulation comprises between 1 microgram and 4 milligrams of a compound of Formula (I), (II), (IIIa), or (IIIb) per dose. In another embodiment of any of the aforementioned pharmaceutical formulation embodiments, the pharmaceutical formulation comprises between 1 microgram and 3 milligrams of a compound of Formula (I), (II), (IIIa), or (IIIb) per dose. In another embodiment of any of the aforementioned pharmaceutical formulation embodiments, the pharmaceutical formulation comprises between 1 microgram and 2 milligrams of a compound of Formula (I), (II), (IIIa), or (IIIb) per dose. In another embodiment of any of the aforementioned pharmaceutical formulation embodiments, the pharmaceutical formulation comprises between 1 microgram and 1 milligram of a compound of Formula (I), (II), (IIIa), or (IIIb) per dose. In another embodiment of any of the aforementioned pharmaceutical formulation embodiments, the pharmaceutical formulation comprises between 1 microgram and 750 micrograms of a compound of Formula (I), (II), (IIIa), or (IIIb) per dose. In another embodiment of any of the aforementioned pharmaceutical formulation embodiments, the pharmaceutical formulation comprises between 1 microgram and 600 micrograms of a compound of Formula (I), (II), (IIIa), or (IIIb) per dose. In another embodiment of any of the aforementioned pharmaceutical formulation embodiments, the pharmaceutical formulation comprises between 1 microgram and 100 micrograms of a compound of Formula (I), (II), (IIIa), or (IIIb) per dose. In another embodiment of any of the aforementioned pharmaceutical formulation embodiments, the pharmaceutical formulation comprises between 1 microgram and 50 micrograms of a compound of Formula (I), (II), (IIIa), or (IIIb) per dose. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation is administered once daily. In another embodiment of any of the aforementioned pharmaceutical formulation embodiments, the pharmaceutical formulation is administered at least once daily. In another embodiment of any of the aforementioned pharmaceutical formulation embodiments, the pharmaceutical formulation is administered twice daily. In another embodiment of any of the aforementioned pharmaceutical formulation embodiments, the pharmaceutical formulation is administered at least twice daily. In another embodiment of any of the aforementioned pharmaceutical formulation embodiments, the pharmaceutical formulation is administered three times daily. In another embodiment of any of the aforementioned pharmaceutical formulation embodiments, the pharmaceutical formulation is administered at least three times daily. In another embodiment of any of the aforementioned pharmaceutical formulation embodiments, the pharmaceutical formulation is administered four times daily. In another embodiment of any of the aforementioned pharmaceutical formulation embodiments, the pharmaceutical formulation is administered at least four times daily. In another embodiment of any of the aforementioned pharmaceutical formulation embodiments, the pharmaceutical formulation is administered five times daily. In another embodiment of any of the aforementioned pharmaceutical formulation embodiments, the pharmaceutical formulation is administered at least five times daily. In another embodiment of any of the aforementioned pharmaceutical formulation embodiments, the pharmaceutical formulation is administered six times daily. In another embodiment of any of the aforementioned pharmaceutical formulation embodiments, the pharmaceutical formulation is administered at least six times daily. In another embodiment of any of the aforementioned pharmaceutical formulation embodiments, the pharmaceutical formulation is administered seven times daily. In another embodiment of any of the aforementioned pharmaceutical formulation embodiments, the pharmaceutical formulation is administered at least seven times daily. In another embodiment of any of the aforementioned pharmaceutical formulation embodiments, the pharmaceutical formulation is administered eight times daily. In another embodiment of any of the aforementioned pharmaceutical formulation embodiments, the pharmaceutical formulation is administered at least eight times daily. In another embodiment of any of the aforementioned pharmaceutical formulation embodiments, the pharmaceutical formulation is administered nine times daily. In another embodiment of any of the aforementioned pharmaceutical formulation embodiments, the pharmaceutical formulation is administered at least nine times daily. In another embodiment of any of the aforementioned pharmaceutical formulation embodiments, the pharmaceutical formulation is administered ten times daily. In another embodiment of any of the aforementioned pharmaceutical formulation embodiments, the pharmaceutical formulation is administered at least ten times daily.

In another embodiment of any of the aforementioned pharmaceutical formulation embodiments, the pharmaceutical formulation is administered for one day. In another embodiment of any of the aforementioned pharmaceutical formulation embodiments, the pharmaceutical formulation is administered for at least two days. In another embodiment of any of the aforementioned pharmaceutical formulation embodiments, the pharmaceutical formulation is administered for at least three days. In another embodiment of any of the aforementioned pharmaceutical formulation embodiments, the pharmaceutical formulation is administered for at least four days. In another embodiment of any of the aforementioned pharmaceutical formulation embodiments, the pharmaceutical formulation is administered for at least five days. In another embodiment of any of the aforementioned pharmaceutical formulation embodiments, the pharmaceutical formulation is administered for at least seven days. In another embodiment of any of the aforementioned pharmaceutical formulation embodiments, the pharmaceutical formulation is administered for at least ten days. In another embodiment of any of the aforementioned pharmaceutical formulation embodiments, the pharmaceutical formulation is administered for at least fourteen days. In another embodiment of any of the aforementioned pharmaceutical formulation embodiments, the pharmaceutical formulation is administered for at least twenty one days. In another embodiment of any of the aforementioned pharmaceutical formulation embodiments, the pharmaceutical formulation is administered for at least thirty days. In some embodiments, the compound of Formula (I) is (R)-5-((E)-2-pyrrolidin-3-ylvinyl)pyrimidine, or a pharmaceutically acceptable salt thereof.

In another embodiment of any of the aforementioned pharmaceutical formulation embodiments, the pharmaceutical formulation is administered in alternating nostrils. For example, the pharmaceutical formulation is administered in one nostril and then the other nostril after a pre-determined amount of time. In another embodiment, the pharmaceutical formulation is administered in both nostrils. For example, the pharmaceutical formulation is administered in one nostril and then the other nostril at the same time or immediately after the first nostril. In another embodiment, the pharmaceutical formulation is administered in one nostril. In some embodiments, the compound of Formula (I) is (R)-5-((E)-2-pyrrolidin-3-ylvinyl)pyrimidine, or a pharmaceutically acceptable salt thereof.

In certain embodiments, the pharmaceutical formulations described herein are administered for prophylactic and/or therapeutic treatments. In certain therapeutic applications, the pharmaceutical formulations are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial. In some embodiments, the compound of Formula (I) is (R)-5-((E)-2-pyrrolidin-3-ylvinyl)pyrimidine, or a pharmaceutically acceptable salt thereof.

In prophylactic applications, the pharmaceutical formulations described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments wherein the patient's condition does not improve, upon the doctor's discretion the administration of the pharmaceutical formulations are administered chronically, that is, for an extended period of time, including throughout the duration of the patient's life in order to ameliorate or otherwise control or limit the symptoms of the patient's disease or condition.

In certain embodiments wherein a patient's status does improve, the dose of the pharmaceutical formulation being administered may be temporarily reduced or temporarily suspended for a certain length of time (i.e, a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45/0%, 50%, 55, 60%, 65%, 70%, 75%, 80%, 85%, 90%, 95%, and 100%.

In certain embodiments the dose of the pharmaceutical formulation being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50% 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular pharmaceutical formulation, disease condition and its severity, the identity (e.g., weight, sex) of the subject or host in need of treatment, but can nevertheless be determined according to the particular circumstances surrounding the case, including, e.g., the specific nicotinic acetylcholine receptor agonist (i.e., compound of Formula (I), (II), (IIIa), or (IIIb)) being administered, the condition being treated, and the subject being treated.

A pharmaceutical formulation, as used herein, refers to a mixture of a compound of Formula (I), (II), (IIIa), or (IIIb) as described herein with other chemical components (i.e. pharmaceutically acceptable inactive ingredients), such as carriers, excipients, binders, filling agents, suspending agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. In some embodiments, the pharmaceutical formulations described herein are mixed with other active ingredients, as in combination therapy. In some embodiments, the pharmaceutical formulations include other therapeutically valuable substances. In other embodiments, the pharmaceutical formulations include other medicinal or pharmaceutical agents, carriers, adjuvants, preserving, stabilizing, wetting or emulsifying agents, solution promoters, salts for regulating the osmotic pressure, and/or buffers. In some embodiments, the compound of Formula (I) is (R)-5-((E)-2-pyrrolidin-3-ylvinyl)pyrimidine, or a pharmaceutically acceptable salt thereof.

In some embodiments, the pharmaceutical formulations described herein refer to a mixture of a compound of Formula (I), (II), (IIIa), or (IIIb) and a buffer. In some embodiments, the pharmaceutical formulations described herein refer to a mixture of a compound of Formula (I), (II), (IIIa), or (IIIb) and a phosphate buffer. In some embodiments, the pharmaceutical formulations described herein refer to a mixture of a compound of Formula (I), (II), (IIIa), or (IIIb) and a phosphate buffer, wherein the pH of the phosphate buffer is around 7.0. In some embodiments, the pharmaceutical formulations described herein refer to a mixture of a compound of Formula (I), (II), (IIIa), or (IIIb) and a phosphate-citrate buffer. In some embodiments, the pharmaceutical formulations described herein refer to a mixture of a compound of Formula (I), (II), (IIIa), or (IIIb) and a phosphate-citrate buffer, wherein the pH of the phosphate-citrate buffer is around 6.0. In some embodiments, the pharmaceutical formulations described herein refer to a mixture of a compound of Formula (I), (II), (IIIa), or (IIIb) and a phosphate-citrate buffer. In some embodiments, the pharmaceutical formulations described herein refer to a mixture of a compound of Formula (I), (II), (IIIa), or (IIIb) and a phosphate-citrate buffer, wherein the pH of the phosphate-citrate buffer is around 5.0. In some embodiments, the compound of Formula (I) is (R)-5-((E)-2-pyrrolidin-3-ylvinyl)pyrimidine, or a pharmaceutically acceptable salt thereof.

The pharmaceutical formulation facilitates administration of the compound to an organism. In practicing the methods provided herein, therapeutically effective amounts of a compound of Formula (I), (II), (IIIa), or (IIIb) described herein are administered in a pharmaceutical formulation to a mammal having a disease, disorder, or condition to be treated. In some embodiments, the mammal is a human. A therapeutically effective amount can be widely depending on the severity of the disease, the age and relative health of the subject, the potency of the compound used and other factors. The compound of Formula (I), (II), (IIIa), or (IIIb) can be used singly or in combination with one or more therapeutic agents as components of mixtures. In some embodiments, the compound of Formula (I) is (R)-5-((E)-2-pyrrolidin-3-ylvinyl)pyrimidine, or a pharmaceutically acceptable salt thereof.

The pharmaceutical formulations described herein are administered to the nasal cavity of a subject. The pharmaceutical formulations described herein include, but are not limited to, liquids, suspensions, aerosols, gels, ointments, dry powders, creams, pastes, lotions, or balms. In some embodiments, the compound of Formula (I) is (R)-5-((E)-2-pyrrolidin-3-ylvinyl)pyrimidine, or a pharmaceutically acceptable salt thereof.

Pharmaceutical formulations including a compound of Formula (I), (II), (IIIa), or (IIIb) as described herein are manufactured in a conventional manner. In some embodiments, the compound of Formula (I) is (R)-5-((E)-2-pyrrolidin-3-ylvinyl)pyrimidine, or a pharmaceutically acceptable salt thereof.

The pharmaceutical formulations will include a compound of Formula (I), (II), (IIIa), or (IIIb) as described herein as an active ingredient in free-acid or free-base form, or in a pharmaceutically acceptable salt form. In some embodiments, the compound of Formula (I), (II), (IIIa), or (IIIb) is in the free base form. In some embodiments, the compound of Formula (I), (II), (IIIa), or (IIIb) is in a pharmaceutically acceptable salt form. In some embodiments, the compound of Formula (I), (II), (IIIa), or (IIIb) is in the free base form. In some embodiments, the compound of Formula (I), (II), (IIIa), or (IIIb) is an HCl salt. In some embodiments, the compound of Formula (I), (II), (IIIa), or (IIIb) is a citrate salt. In some embodiments, the compound of Formula (I), (II), (IIIa), or (IIIb) is a mono citrate salt. In some embodiments, the compound of Formula (I), (II), (IIIa), or (IIIb) is a galactarate salt. In some embodiments, the compound of Formula (I), (II), (IIIa), or (IIIb) is a hemigalactarate salt. In some embodiments, the compound of Formula (I), (II), (IIIa), or (IIIb) is a hemigalactarate monohydrate. In addition, the methods and pharmaceutical formulations described herein include the use of N-oxides (if appropriate), crystalline forms, amorphous phases, as well as active metabolites of these compounds of Formula (I), (II), (IIIa), or (IIIb) having the same type of activity. In some embodiments, the compound of Formula (I), (II), (IIIa), or (IIIb) described herein may exist in unsolvated form or in solvated forms with pharmaceutically acceptable solvents such as water, ethanol, and the like. The solvated forms of the compounds of Formula (I), (II), (IIIa), or (IIIb) presented herein are also considered to be disclosed herein. In some embodiments, the compounds may exist as tautomers. All tautomers are included within the scope of the compounds of Formula (I), (II), (IIIa), or (IIIb) presented herein. In some embodiments, the compound of Formula (I) is (R)-5-((E)-2-pyrrolidin-3-ylvinyl)pyrimidine, or a pharmaceutically acceptable salt thereof.

In some embodiments, the compounds of Formula (I), (II), (IIIa), or (IIIb) exist as enantiomers, diasteromers, or other stereoisomeric forms. The compounds of Formula (I), (II), (IIIa), or (IIIb) disclosed herein include all enantiomeric, diastereomeric, and epimeric forms as well as mixtures thereof. In some embodiments, the compound of Formula (I) is (R)-5-((E)-2-pyrrolidin-3-ylvinyl)pyrimidine, or a pharmaceutically acceptable salt thereof.

In certain embodiments, the pharmaceutical formulations provided herein include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, the pharmaceutical formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA. (e) about 0.01% to about 2% w/iv ascorbic acid, (f) 0.003% to about 0.02% w/v polysorbate 80, (g) 0.001% to about 0.05% w/v, polysorbate 20, (h) arginine, (i) heparin. (j) dextran sulfate, (k) cyclodextrins, (l) pentosan polysulfate and other heparinoids, (m) divalent cations such as magnesium and zinc; or (n) combinations thereof.

The pharmaceutical formulations described herein, which include a compound of Formula (I), (II), (IIIa), or (IIIb), are formulated into any suitable dosage form, including but not limited to, liquids, suspensions, aerosols, gels, ointments, dry powders, creams, pastes, lotions, or balms. The pharmaceutical formulations described herein, which include a compound of Formula (I), (II), (IIIa), or (IIIb) are formulated into any suitable dosage form, are administered into the nasal cavity by a syringe, dropper, bottle nebulizer, atomization pump, inhaler, powder spray device, vaporizer, patch, medicated stick, pipette, or jet of liquid. In some embodiments, the compound of Formula (I) is (R)-5-((E)-2-pyrrolidin-3-ylvinyl)pyrimidine, or a pharmaceutically acceptable salt thereof.

Combination Therapy

In certain instances, it is appropriate to administer a compound of Formula (I), (II), (IIIa), or (IIIb) in combination with another therapeutic agent. In some embodiments, the compound of Formula (I) is (R)-5-((E)-2-pyrrolidin-3-ylvinyl)pyrimidine, or a pharmaceutically acceptable salt thereof.

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical formulation or composition, and are, because of different physical and chemical characteristics, administered by different routes. In one embodiment, the initial administration is made according to established protocols, and then, based upon the observed effects, the dosage, modes of administration and times of administration, further modified.

In various embodiments, a compound of Formula (I), (II), (IIIa), or (IIIb), is administered concurrently (e.g., simultaneously, essentially simultaneously or within the same treatment protocol) or sequentially, with other therapeutic reagents that are selected for their particular usefulness against the condition that is being treated. In certain embodiments, the determination of the order of administration, and the number of repetitions of administration of each therapeutic agent during a treatment protocol, is based upon evaluation of the disease being treated and the condition of the patient.

In some embodiments, a compound of Formula (I), (II), (IIIa), or (IIIb), is administered concurrently (e.g., simultaneously, essentially simultaneously or within the same treatment protocol) or sequentially, with another therapeutic reagent for treating dry disease. In some embodiments, a compound of Formula (I), (II), (IIIa), or (IIIb), is administered concurrently (e.g., simultaneously, essentially simultaneously or within the same treatment protocol) or sequentially, with Restasis® eye drops. In some embodiments, a compound of Formula (I), (II), (IIIa), or (IIIb), is administered concurrently (e.g., simultaneously, essentially simultaneously or within the same treatment protocol) or sequentially, with artificial tears. In some embodiments, a compound of Formula (I), (II), (IIIa), or (IIIb), is administered concurrently (e.g., simultaneously, essentially simultaneously or within the same treatment protocol) or sequentially, with ocular steroids.

For combination therapies described herein, dosages of the co-administered compounds vary depending on the type of co-drug employed, on the specific drug employed, on the disease or condition being treated and so forth.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

Administration of a combination of agents, as used herein, includes administration of the agents described in a single composition or in a combination therapy wherein one or more agent is administered separately from at least one other agent.

In some embodiments, a compound of Formula (I), (II), (IIIa), or (IIIb) is administered in combination with the use of a medical device. In some embodiments, a compound of Formula (I), (II), (IIIa), or (IIIb) is administered in combination with the use of punctal plugs.

Exemplary Embodiments

Embodiment I-1

A method of increasing tear production, comprising the local administration of a therapeutically effective amount of a compound of Formula (I) into the nasal cavity of an individual in need thereof, wherein the compound of Formula (I) binds to the peripheral nicotinic acetylcholine receptor and the compound of Formula (I) has the structure:

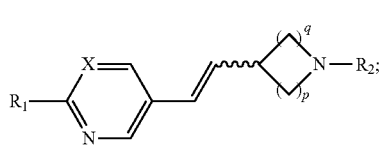

Formula (I)

wherein:
the wavy line represents E or Z geometry about the double bond;
X is N or $CR_3$;
$R_1$ is hydrogen, $C_{1-6}$alkyl, halogen, —$OR_4$, —$SR_4$, or —$NR_5R_6$;
$R_2$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl;
$R_3$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), cycloalkyl, —$OR_7$, —$SR_7$, —$NR_8R_9$, —$SOR_7$, or —$SO_2R_7$, wherein the $C_{1-6}$alkyl, heterocycloalkyl heteroaryl, and aryl groups are optionally substituted with one or more substituents selected from halogen, —CN, —$NO_2$, —$NH_2$, —OH, —$OR_7$, —$CO_2H$, —$C(O)OR_7$, —O—$C(O)R_7$, —$NR_8R_9$, —$NHC(O)R_7$, —$C(O)NR_8R_9$, —$SR_7$, —$S(O)R_7$, —$SO_2R_7$, —$NHSO_2R_7$, —$SO_2NR_8R_9$, —$C(S)NR_8R_9$, —$NHC(S)R_7$, and —O—$SO_2R_7$;
$R_4$, $R_5$, and $R_6$ are independently hydrogen or $C_{1-6}$alkyl; and
$R_7$, $R_8$, and $R_9$ are hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl, wherein the $C_{1-6}$alkyl, heterocycloalkyl, heteroaryl, and aryl groups are optionally substituted one or more substituents selected from the group consisting of F, Cl, Br, I, $R_{10}$, —$NR_{10}R_{11}$, —$CF_3$, —CN, —$NO_2$, —$C_2R_{10}$, —$N_3$, —$SO_2CH_3$, —$OR_{10}$, —$SR_{10}$, —$C(O)NR_{10}R_{11}$, —$NR_{10}C(=O)R_{10}$, —$C(=O)R_{10}$, —$C(=O)OR_{10}$, —$(CH_2)OR_{10}$, —$(CH_2)_2OR_{10}$, —$OC(=O)R_{10}$, —$OC(=O)NR_{10}R_{11}$ and —$NR_{10}C(=O)OR_{10}$;
$R_{10}$ and $R_{11}$ are independently hydrogen, $C_{1-6}$alkyl, pyridyl, quinolinyl, pyrimidinyl, pyrimidinyl, phenyl, or benzyl; or
either $R_8$ and $R_9$ or $R_{10}$ and $R_{11}$ together with the nitrogen to which they are attached, optionally form a heterocycloalkyl ring;
p is 1, 2, 3, or 4; and
q is 1, 2, or 3;
or an enantiomer, diastereomer, tautomer, or pharmaceutically acceptable salt thereof.

Embodiment I-2

A method of treating dry eye, comprising the local administration of a therapeutically effective amount of a compound of Formula (I) into the nasal cavity of an individual in need thereof, wherein the compound of Formula (I) binds to the peripheral nicotinic acetylcholine receptor and the compound of Formula (I) has the structure:

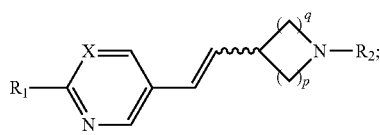

Formula (I)

wherein:

the wavy line represents E or Z geometry about the double bond;

X is N or $CR_3$;

$R_1$ is hydrogen, $C_{1-6}$alkyl, halogen, —$OR_4$, —$SR_4$, or —$NR_5R_6$;

$R_2$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl;

$R_3$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), cycloalkyl, —$OR_7$, —$SR_7$, —$NR_8R_9$, —$SOR_7$, or —$SO_2R_7$ wherein the $C_{1-6}$alkyl, heterocycloalkyl, heteroaryl, and aryl groups are optionally substituted with one or more substituents selected from halogen, —CN, —$NO_2$, —$NH_2$, —OH, —$OR_7$, —$CO_2H$, —C(O)$OR_3$, —O—C(O)$R_7$, —$NR_8R_9$, —NHC(O)$R_7$, —C(O)$NR_8R_9$, —$SR_7$, —S(O)$R_7$, —$SO_2R_7$, —$NHSO_2R_7$, —$SO_2NR_8R_9$, —C(S)$NR_8R_9$, —NHC(S)$R_7$, and —O—$SO_2R_7$;

$R_4$, $R_5$, and $R_6$ are independently hydrogen or $C_{1-6}$alkyl; and $R_7$, $R_8$, and $R_9$ are hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl, wherein the $C_{1-6}$alkyl, heterocycloalkyl, heteroaryl, and aryl groups are optionally substituted one or more substituents selected from the group consisting of F, Cl, Br, I, $R_{10}$, —$NR_{10}R_{11}$, —$CF_3$, —CN, —$NO_2$, —$C_2R_{10}$, —$N_3$, —$SO_2CH_3$, —$OR_{10}$, —$SR_{10}$, —C(O)$NR_{10}R_{11}$, —$NR_{10}$C(=O)$R_{10}$, —C(=O)$R_{10}$, —C(=O)$OR_{10}$, —($CH_2$)$OR_{10}$, —($CH_2$)$_2OR_{10}$, —OC(=O)$R_{10}$, —OC(=O)$NR_{10}R_{11}$ and —$NR_{10}$C(=O)$OR_{10}$;

$R_{10}$ and $R_{11}$ are independently hydrogen, $C_{1-6}$alkyl, pyridyl, quinolinyl, pyrimidinyl, pyrimidinyl, phenyl, or benzyl; or either $R_8$ and $R_9$ or $R_{10}$ and $R_{11}$ together with the nitrogen to which they are attached, optionally form a heterocycloalkyl ring;

p is 1, 2, 3, or 4; and q is 1, 2, or 3;

or an enantiomer, diastereomer, tautomer, or pharmaceutically acceptable salt thereof.

Embodiment I-3

A method of improving ocular discomfort, comprising the local administration of a therapeutically effective amount of a compound of Formula (I) into the nasal cavity of an individual in need thereof, wherein the compound of Formula (I) binds to the peripheral nicotinic acetylcholine receptor and the compound of Formula (I) has the structure:

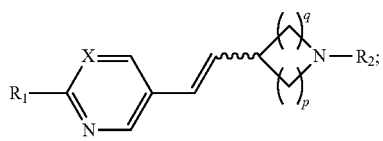

Formula (I)

wherein:

the wavy line represents E or Z geometry about the double bond;

X is N or $CR_3$;

$R_1$ is hydrogen, $C_{1-6}$alkyl, halogen, —$OR_4$, —$SR_4$, or —$NR_5R_6$;

$R_2$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl;

$R_3$ is hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), cycloalkyl, —$OR_7$, —$SR_7$, —$NR_8R_9$, —$SOR_7$, or —$SO_2R_7$, wherein the $C_{1-6}$alkyl, heterocycloalkyl, heteroaryl, and aryl groups are optionally substituted with one or more substituents selected from halogen, —CN, —$NO_2$, —$NH_2$, —OH, —$OR_7$, —$CO_2H$, —C(O)$OR_7$, —O—C(O)$R_7$, —$NR_8R_9$, —NHC(O)$R_7$, —C(O)$NR_8R_9$, —$SR_7$, —S(O)$R_7$, —$SO_2R_7$, —$NHSO_2R_7$, —$SO_2NR_8R_9$, —C(S)$NR_8R_9$, —NHC(S)$R_7$, and —O—$SO_2R_7$;

$R_4$, $R_5$, and $R_6$ are independently hydrogen or $C_{1-6}$alkyl; and $R_7$, $R_8$, and $R_9$ are hydrogen, $C_{1-6}$alkyl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), heterocycloalkyl, —$C_{1-6}$alkyl(heterocycloalkyl), or cycloalkyl, wherein the $C_{1-6}$alkyl, heterocycloalkyl, heteroaryl, and aryl groups are optionally substituted one or more substituents selected from the group consisting of F, Cl, Br, I, $R_{10}$, —$NR_{10}R_{11}$, —$CF_3$, —CN, —$NO_2$, —$C_2R_{10}$, —$N_i$, —$SO_2CH_3$, —$OR_{10}$, —$SR_{10}$, —C(O)$NR_{10}R_{11}$, —$NR_{10}$C(=O)$R_{10}$, —C(=O)$R_{10}$, —C(=O)$OR_{10}$, —($CH_2$)$OR_{10}$, —($CH_2$)$_2OR_{10}$, —OC(=O)$R_{10}$, —OC(=O)$NR_{10}R_{11}$ and —$NR_{10}$C(=O)$OR_{10}$;

$R_{10}$ and $R_{11}$ are independently hydrogen, $C_{1-6}$alkyl, pyridyl, quinolinyl, pyrimidinyl, pyrimidinyl, phenyl, or benzyl; or either $R_8$ and $R_9$ or $R_{10}$ and $R_{11}$ together with the nitrogen to which they are attached, optionally form a heterocycloalkyl ring;

p is 1, 2, 3, or 4; and q is 1, 2, or 3;

or an enantiomer, diastereomer, tautomer, or pharmaceutically acceptable salt thereof.

Embodiment I-4

The method of any one of Embodiments I-1 to I-3, wherein X is N.

Embodiment I-5

The method of any one of Embodiments I-1 to I-4, wherein $R_2$ is hydrogen.

Embodiment I-6

The method of any one of Embodiments I-1 to I-5, wherein $R_1$ is hydrogen, $C_{1-6}$alkyl, —$OR_4$, or —$NR_5R_6$.

Embodiment I-7

The method of any one of Embodiments I-1 to I-5, wherein $R_1$ is hydrogen.

Embodiment I-8

The method of any one of Embodiments I-1 to I-7, wherein q is 1.

Embodiment I-9

The method of any one of Embodiments I-1 to I-7, wherein p is 2.

Embodiment I-10

The method of any one of Embodiments I-1 to I-9, wherein the wavy line represents E geometry about the double bond.

Embodiment I-11

The method of any one of Embodiments I-1 to I-10, wherein the compound of Formula (I) is (R)-5-((E)-2-pyrrolidin-3-ylvinyl)pyrimidine.

Embodiment I-12

The method of any one of Embodiments I-1 to I-10, wherein the compound of Formula (I) is (R)-5-((E)-2-pyrrolidin-3-ylvinyl)pyrimidine mono citrate salt.

Embodiment I-13

A method of increasing tear production, comprising the local administration of a therapeutically effective amount of a compound of Formula (II) into the nasal cavity of an individual in need thereof, wherein the compound of Formula (II) binds to the peripheral nicotinic acetylcholine receptor and the compound of Formula (II) has the structure:

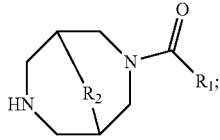

Formula (II)

wherein:
$R_1$ is $C_{1-6}$alkyl, $C_{2-6}$alkenyl, $C_{2-6}$alkynyl, $C_{3-8}$heterocycloalkyl, $C_{3-8}$cycloalkyl, or heteroaryl, optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$NO_2$, —$OR_3$, —$NR_4R_5$, —$CF_3$, —$C_2R_3$, —$SR_3$, —$N_3$, —C(O)$NR_4R_5$, —$NR_4$C(O)$R_3$, —C(O)$R_3$, —C(O)$OR_3$, —OC(O)$R_3$, —OC(O)$NR_4R_5$, —$NR_4$C(O)$OR_3$, —$SO_2R_3$, —$NR_4SO_2R_5$, and —$SO_2NR_4R_5$;
$R_2$ is a bond or —$CH_2$—;
$R_3$ is hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; and
$R_4$ and $R_5$ are independently hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; or $R_4$ and $R_5$ together with the nitrogen to which they are attached, form a heterocycloalkyl ring;
or a pharmaceutically acceptable salt thereof.

Embodiment I-14

A method of treating dry eye, comprising the local administration of a therapeutically effective amount of a compound of Formula (II) into the nasal cavity of an individual in need thereof, wherein the compound of Formula (II) binds to the peripheral nicotinic acetylcholine receptor and the compound of Formula (II) has the structure:

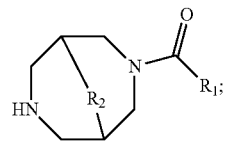

Formula (II)

wherein:
$R_1$ is $C_{1-6}$alkyl, $C_{2-6}$alkenyl, $C_{2-6}$alkynyl, $C_{3-8}$heterocycloalkyl, $C_{3-8}$cycloalkyl, or heteroaryl, optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$NO_2$, —$OR_3$, —$NR_4R_5$, —$CF_3$, —$C_2R_3$, —$SR_3$, —$N_3$, —C(O)$NR_4R_5$, —$NR_4$C(O)$R_3$, —C(O)$R_3$, —C(O)$OR_3$, —OC(O)$R_3$, —OC(O)$NR_4R_5$, —$NR_4$C(O)$OR_3$, —$SO_2R_3$, —$NR_4SO_2R_5$, and —$SO_2NR_4R_5$; $R_2$ is a bond or —$CH_2$—;
$R_3$ is hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; and
$R_4$ and $R_5$ are independently hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; or $R_4$ and $R_5$ together with the nitrogen to which they are attached, form a heterocycloalkyl ring;
or a pharmaceutically acceptable salt thereof.

Embodiment I-15

A method of improving ocular discomfort, comprising the local administration of a therapeutically effective amount of a compound of Formula (II) into the nasal cavity of an individual in need thereof, wherein the compound of Formula (II) binds to the peripheral nicotinic acetylcholine receptor and the compound of Formula (II) has the structure:

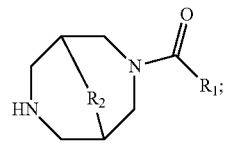

Formula (II)

wherein:
$R_1$ is $C_{1-6}$alkyl, $C_{2-6}$alkenyl, $C_{2-6}$alkynyl, $C_{3-8}$heterocycloalkyl, $C_{3-8}$cycloalkyl, or heteroaryl, optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —C$_{1-6}$alkyl-(aryl), -aryl-(C$_{1-6}$alkyl), heteroaryl, —C$_{1-6}$alkyl-(heteroaryl), -heteroaryl-(C$_{1-6}$alkyl), halogen, —CN, —NO$_2$, —OR$_3$, —NR$_4$R$_5$, —CF$_3$, —C$_2$R$_3$, —SR$_3$, —N$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$;

R$_2$ is a bond or —CH$_2$—;

R$_3$ is hydrogen, C$_{1-6}$alkyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; and R$_4$ and R$_5$ are independently hydrogen, C$_{1-6}$alkyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; or R$_4$ and R$_5$ together with the nitrogen to which they are attached, form a heterocycloalkyl ring;

or a pharmaceutically acceptable salt thereof.

Embodiment I-16

The method of any one of Embodiments I-13 to I-15, wherein R$_1$ is heteroaryl optionally substituted with one to three non-hydrogen substituents independently selected from C$_{1-6}$alkyl, C$_{2-6}$alkenyl, C$_{2-6}$alkynyl, C$_{3-8}$heterocycloalkyl, C$_{3-8}$cycloalkyl, heteroaryl, aryl, —C$_{1-6}$alkyl-(aryl), -aryl-(C$_{1-6}$alkyl), heteroaryl, —C$_{1-6}$alkyl-(heteroaryl), -heteroaryl-(C$_{1-6}$alkyl), halogen, —CN, —OR$_3$, —NR$_4$R$_5$, —CF$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$.

Embodiment I-17

The method of any one of claims 13-16, wherein R$_1$ is 2-furanyl, 3-furanyl, 2-oxazolyl, 4-oxazolyl, 5-oxazolyl, 3-isoxazolyl, 4-isoxazolyl, 5-isoxazolyl, 1,3,4-oxadiazol-2-yl, 1,2,4-oxadiazol-3-yl, 1,2,4-oxadiazol-5-yl, 2-thiazolyl, 4-thiazolyl, 5-thiazolyl, 3-isothiazolyl, 4-isothiazolyl, 5-isothiazolyl, 1,3,4-thiadiazol-2-yl, 1,2,4-thiadiazol-3-yl, 1,2,4-thiadiazol-5-yl or 4-pyridinyl.

Embodiment I-18

The method of any one of Embodiments I-13 to I-17, wherein R$_2$ is a bond.

Embodiment I-19

The method of any one of Embodiments I-13 to I-17, wherein R$_2$ is —CH$_2$—.

Embodiment I-20

The method of any one of Embodiments I-13 to I-17, wherein the compound of Formula (II) is N-(5-chlorofuran-2-ylcarbonyl)-3,7-diazabicyclo[3.3.0]octane.

Embodiment I-21

A method of increasing tear production, comprising the local administration of a therapeutically effective amount of a compound of Formula (IIIa) or (IIIb) into the nasal cavity of an individual in need thereof, wherein the compound of Formula (IIIa) or (IIIb) binds to the peripheral nicotinic acetylcholine receptor and the compound of Formula (IIIa) or (IIIb) has the structure:

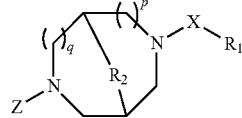
Formula (IIIa)

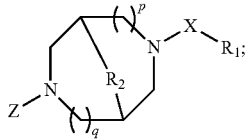
Formula (IIIb)

wherein:

X is C(O), C(S), or S(O)$_n$;

Z is hydrogen, C$_{1-6}$alkyl, or C$_{1-6}$haloalkyl;

n is 1 or 2;

p is 0 or 1;

q is 0 or 1;

when p is 1, then q is 0;

when q is 1, then p is 0;

R$_1$ is —OR$_3$, —NR$_4$R$_5$, C$_{1-6}$alkyl, C$_{2-6}$alkenyl, C$_{2-6}$alkynyl, C$_{3-8}$heterocycloalkyl, C$_{3-8}$cycloalkyl, aryl or heteroaryl, wherein C$_{1-6}$alkyl, C$_{2-6}$alkenyl, C$_{2-6}$alkynyl, C$_{3-8}$heterocycloalkyl, C$_{3-8}$cycloalkyl, aryl or heteroaryl are optionally substituted with one to three non-hydrogen substituents independently selected from C$_{1-6}$alkyl, C$_{2-6}$alkenyl, C$_{2-6}$alkynyl, C$_{3-8}$heterocycloalkyl, C$_{3-8}$cycloalkyl, heteroaryl, aryl, —C$_{1-6}$alkyl-(aryl), -aryl-(C$_{1-6}$alkyl), heteroaryl, —C$_{1-6}$alkyl-(heteroaryl), -heteroaryl-(C$_{1-6}$alkyl), halogen, —CN, —NO$_2$, —OR$_3$, —NR$_4$R$_5$, —CF$_3$, —C$_2$R$_3$, —SR$_3$, —N$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$;

R$_2$ is —CH— or —CH$_2$CH$_2$—;

R$_3$ is hydrogen, C$_{1-6}$alkyl, C$_{2-6}$alkenyl, C$_{2-6}$alkynyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; and R$_4$ and R$_5$ are independently hydrogen, C$_{1-6}$alkyl, C$_{2-6}$alkenyl, C$_{2-6}$alkynyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; or R$_4$ and R$_5$ together with the nitrogen to which they are attached, form a heterocycloalkyl ring;

or a pharmaceutically acceptable salt thereof.

Embodiment I-22

A method of treating dry eye, comprising the local administration of a therapeutically effective amount of a compound of Formula (IIIa) or (IIIb) into the nasal cavity of an individual in need thereof, wherein the compound of Formula (IIIa) or (IIIb) binds to the peripheral nicotinic acetylcholine receptor and the compound of Formula (IIIa) or (IIIb) has the structure:

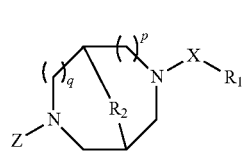
Formula (IIIa)

-continued

Formula (IIIb)

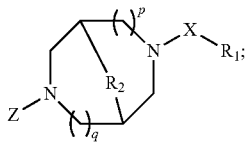

wherein:
X is C(O), C(S), or S(O)$_n$;
Z is hydrogen, C$_{1-6}$alkyl, or C$_{1-6}$haloalkyl;
n is 1 or 2;
p is 0 or 1;
q is 0 or 1;
when p is 1, then q is 0;
when q is 1, then p is 0;
R$_1$ is —OR$_3$, —NR$_4$R$_5$, C$_{1-6}$alkyl, C$_{2-6}$alkenyl, C$_{2-6}$alkynyl, C$_{3-8}$heterocycloalkyl, C$_{3-8}$cycloalkyl, aryl or heteroaryl, wherein C$_{1-6}$alkyl, C$_{2-6}$alkenyl, C$_{2-6}$alkynyl, C$_{3-8}$heterocycloalkyl, C$_{3-8}$cycloalkyl, aryl or heteroaryl are optionally substituted with one to three non-hydrogen substituents independently selected from C$_{1-6}$alkyl, C$_{2-6}$alkenyl, C$_{2-6}$alkynyl, C$_{3-8}$heterocycloalkyl, C$_{3-8}$cycloalkyl, heteroaryl, aryl, —C$_{1-6}$alkyl-(aryl), -aryl-(C$_{1-6}$alkyl), heteroaryl, —C$_{1-6}$alkyl-(heteroaryl), -heteroaryl-(C$_{1-6}$alkyl), halogen, —CN, —NO$_2$, —OR$_3$, —NR$_4$R$_5$, —CF$_3$, —C$_2$R$_5$, —SR$_3$, —N$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$;
R$_2$ is —CH$_2$— or —CH$_2$CH$_2$—;
R$_3$ is hydrogen, C$_{1-6}$alkyl, C$_{2-6}$alkenyl, C$_{2-6}$alkynyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; and
R$_4$ and R$_5$ are independently hydrogen, C$_{1-6}$alkyl, C$_{2-6}$alkenyl, C$_{2-6}$alkynyl, C$_{3-8}$cycloalkyl, C$_{3-8}$heterocycloalkyl, aryl, —C$_{1-6}$alkyl-(aryl), -aryl-(C$_{1-6}$alkyl), or heteroaryl; or R$_4$ and R$_5$ together with the nitrogen to which they are attached, form a heterocycloalkyl ring;
or a pharmaceutically acceptable salt thereof.

Embodiment I-23

A method of improving ocular discomfort, comprising the local administration of a therapeutically effective amount of a compound of Formula (IIIa) or (IIIb) into the nasal cavity of an individual in need thereof, wherein the compound of Formula (IIIa) or (IIIb) binds to the peripheral nicotinic acetylcholine receptor and the compound of Formula (IIIa) or (IIIb) has the structure:

Formula (IIIa)

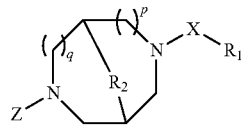

Formula (IIIb)

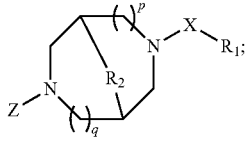

wherein:
X is C(O), C(S), or S(O)$_n$;
Z is hydrogen, C$_{1-6}$alkyl, or C$_{1-6}$haloalkyl;
n is 1 or 2;
p is 0 or 1;
q is 0 or 1;
when p is 1, then q is 0,
when q is 1, then p is 0;
R$_1$ is —OR$_3$, —NR$_4$R$_5$, C$_{1-6}$alkyl, C$_{2-6}$alkenyl, C$_{2-6}$alkynyl, C$_{3-8}$heterocycloalkyl, C$_{3-8}$cycloalkyl, aryl or heteroaryl, wherein C$_{1-6}$alkyl, C$_{2-6}$alkenyl, C$_{2-6}$alkynyl, C$_{3-8}$heterocycloalkyl, C$_{3-8}$cycloalkyl, aryl or heteroaryl are optionally substituted with one to three non-hydrogen substituents independently selected from C$_{1-6}$alkyl, C$_{2-6}$alkenyl, C$_{2-6}$alkynyl, C$_{3-8}$heterocycloalkyl, C$_{3-8}$cycloalkyl, heteroaryl, aryl, —C$_{1-6}$alkyl-(aryl), -aryl-(C$_{1-6}$alkyl), heteroaryl, —C$_{1-6}$alkyl-(heteroaryl), -heteroaryl-(C$_{1-6}$alkyl), halogen, —CN, —NO$_2$, —OR$_3$, —NR$_4$R$_5$, —CF$_3$, —C$_2$R$_5$, —SR$_3$, —N$_3$, —C(O)NR$_4$R$_5$, —NR$_4$C(O)R$_3$, —C(O)R$_3$, —C(O)OR$_3$, —OC(O)R$_3$, —OC(O)NR$_4$R$_5$, —NR$_4$C(O)OR$_3$, —SO$_2$R$_3$, —NR$_4$SO$_2$R$_5$, and —SO$_2$NR$_4$R$_5$;
R$_2$ is —CH$_2$— or —CH$_2$CH$_2$—;
R$_3$ is hydrogen, C$_{1-6}$alkyl, C$_{2-6}$alkenyl, C$_{2-6}$alkynyl, C$_{2-6}$cycloalkyl, C$_{3-8}$heterocycloalkyl, aryl, —C$_{1-6}$alkyl-(aryl), -aryl-(C$_{1-6}$alkyl), or heteroaryl; and
R$_4$ and R$_5$ are independently hydrogen, C$_{1-6}$alkyl, C$_{2-6}$alkenyl, C$_{2-6}$alkynyl, C$_{3-8}$cycloalkyl, C$_{3-8}$ heterocycloalkyl, aryl, —C$_{1-6}$alkyl-(aryl), -aryl-(C$_{1-6}$alkyl), or heteroaryl; or R$_4$ and R$_5$ together with the nitrogen to which they are attached, form a heterocycloalkyl ring;
or a pharmaceutically acceptable salt thereof.

Embodiment I-24

The method of any one of Embodiments I-21 to I-23, wherein p is 1 and q is 0.

Embodiment I-25

The method of any one of Embodiments I-21 to I-23, wherein p is 0 and q is 1.

Embodiment I-26

The method of any one of Embodiments I-21 to I-25, wherein R$_2$ is —CH$_2$—.

Embodiment I-27

The method of any one of Embodiments I-21 to I-25, wherein R$_2$ is —CH$_2$CH$_2$—.

Embodiment I-28

The method of any one of Embodiments I-21 to I-27, wherein Z is hydrogen.

Embodiment I-29

The method of any one of Embodiments I-21 to I-27, wherein Z is C$_{1-6}$alkyl.

Embodiment I-30

The method of any one of Embodiments I-21 to I-29, wherein X is C(O).

Embodiment I-31

The method of any one of Embodiments I-1 to I-30, wherein the compound of Formula (I), (II), (IIIa), or (IIIb) does not cross the blood-brain barrier in a pharmacologically relevant concentration.

Embodiment I-32

The method of any one of Embodiments I-1 to I-31, wherein the compound of Formula (I), (II), (IIIa), or (IIIb) selectively binds to at least one of the peripheral nicotinic acetylcholine receptor subtypes selected from alpha3beta4, alpha4beta2, and alpha7.

Embodiment I-33

The method of any one of Embodiments I-1 to I-32, wherein the compound of Formula (I), (II), (IIIa), or (IIIb) is administered in an amount that is not systemically bioavailable.

Embodiment I-34

The method of any one of Embodiments I-1 to I-33, wherein the compound of Formula (I), (II), (IIIa), or (IIIb) selectively binds to the peripheral nicotinic acetylcholine receptor in an amount that does not result in undesired psychoactive side effects.

Embodiment I-35

The method of any one of Embodiments I-1 to I-34, wherein the compound of Formula (I), (II), (IIIa), or (IIIb) selectively binds to the peripheral nicotinic acetylcholine receptor in an amount that does not result in undesired systemic side effects.

Embodiment I-36

The method of any one of Embodiments I-1 to I-35, further comprising the local administration of one or more substances that prevent the entry or reduce the entry of the nicotinic acetylcholine receptor into the desensitized state, or facilitate the recovery of the nicotinic acetylcholine receptor from the desensitized state.

Embodiment I-37

The method of Embodiment I-36, wherein the one or more substances are selected from protein kinase C (PKC) or factors that upregulate or up-modulate PKC, cAMP-dependent protein kinase (PKA) or factors that upregulate or up-modulate PKA, and calcineurin inhibitors.

Embodiment I-38

The method of Embodiment I-37, wherein the calcineurin inhibitor is selected from cyclosporine, pimecrolimus, and tacrolimus.

Embodiment I-39

The method of any one of Embodiments I-1 to I-38, wherein the compound of Formula (I), (II), (IIIa), or (IIIb) is administered without any form of nicotine.

Embodiment I-40

The method of any one of Embodiments I-1 to I-39, wherein less than 5 milligrams of the compound of Formula (I), (II), (IIIa), or (IIIb) is administered into the nasal cavity.

Embodiment I-41

The method of any one of Embodiments I-1-I-39, wherein between 500 micrograms and 5 milligrams of the compound of Formula (I), (II), (IIIa), or (IIIb) is administered into the nasal cavity.

Embodiment I-42

The method of any one of Embodiments I-1 to I-39, wherein between 1 milligram and 2 milligrams of the compound of Formula (I), (II), (IIIa), or (IIIb) is administered into the nasal cavity.

Embodiment I-43

The method of any one of Embodiments I-1 to I-39, wherein about 1 milligram of the compound of Formula (I), (II), (IIIa), or (IIIb) is administered into the nasal cavity.

Embodiment I-44

The method of any one of Embodiments I-1 to I-39, wherein about 1.5 milligrams of the compound of Formula (I), (II), (IIIa), or (IIIb) is administered into the nasal cavity.

Embodiment I-45

The method of any one of Embodiments I-1 to I-39, wherein about 2 milligrams of the compound of Formula (I), (II), (IIIa), or (IIIb) is administered into the nasal cavity.

Embodiment I-46

The method of any one of Embodiments I-1 to I-45, wherein the compound of Formula (I), (II), (IIIa), or (IIIb) is administered at least once daily.

Embodiment I-47

The method of any one of Embodiments I-1 to I-45, wherein the compound of Formula (I), (II), (IIIa), or (IIIb) is administered at least twice daily.

Embodiment I-48

The method of any one of Embodiments I-1 to I-45, wherein the compound of Formula (I), (II), (IIIa), or (IIIb) is administered at least once weekly.

Embodiment I-49

The method of any one of Embodiments I-1 to I-48, wherein the compound of Formula (I), (II), (IIIa), or (IIIb) is administered into the nasal cavity as a liquid, suspension, aerosol, gel, ointment, dry powder, cream, paste, lotion, or balm.

Embodiment I-50

The method of any one of Embodiments I-1 to I-49, wherein the compound of Formula (I), (II), (IIIa), or (IIIb)

is administered into the nasal cavity by a syringe, dropper, bottle nebulizer, atomization pump, inhaler, powder spray device, vaporizer, patch, medicated stick, pipette, or jet of liquid.

Embodiment I-51

The method of any one of Embodiments I-1 to I-50, wherein the trigeminal nerve is activated.

Embodiment I-52

The method of Embodiment I-51, wherein the anterior ethmoidal nerve is activated.

Embodiment I-53

The method of any one of Embodiments I-1 to I-52, wherein the nasolacrimal reflex is activated.

Embodiment I-54

A pharmaceutical formulation for local administration into the nasal cavity of an individual comprising a compound of Formula (I) formulated (a) for nasal administration and (b) to prevent desensitization of peripheral nicotinic acetylcholine receptors, wherein the compound of Formula (I) has the structure:

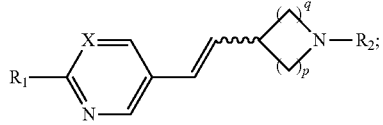

Formula (I)

wherein:
the wavy line represents E or Z geometry about the double bond;
X is N or $CR_3$;
$R_1$ is hydrogen, $C_{1-6}$alkyl, halogen, $-OR_4$, $-SR_4$, or $-NR_5R_6$;
$R_2$ is hydrogen, $C_{1-6}$alkyl, aryl, $-C_{1-6}$alkyl-(aryl), -aryl-($C_{1-6}$alkyl), heteroaryl, $-C_{1-6}$alkyl-(heteroaryl), -heteroaryl-($C_{1-6}$alkyl), heterocycloalkyl, $-C_{1-6}$alkyl(heterocycloalkyl), or cycloalkyl;
$R_3$ is hydrogen, $C_{1-6}$alkyl, aryl, $-C_{1-6}$alkyl-(aryl), -aryl-($C_{1-6}$alkyl), heteroaryl, $-C_{1-6}$alkyl-(heteroaryl), -heteroaryl-($C_{1-6}$alkyl), heterocycloalkyl, $-C_{1-6}$alkyl(heterocycloalkyl), cycloalkyl, $-OR_7$, $-SR_7$, $-NR_8R_9$, $-SOR_7$, or $-SO_2R_7$, wherein the $C_{1-6}$alkyl, heterocycloalkyl, heteroaryl, and aryl groups are optionally substituted with one or more substituents selected from halogen, $-CN$, $-NO_2$, $-NH_2$, $-OH$, $-OR_7$, $-CO_2H$, $-C(O)OR_7$, $-O-C(O)R_7$, $-NR_8R_9$, $-NHC(O)R_7$, $-C(O)NR_8R_9$, $-SR_2$, $-S(O)R_7$, $-SO_2R_7$, $-NHSO_2R_7$, $-SO_2NR_8R_9$, $-C(S)NR_8R_9$, $-NHC(S)R_7$, and $-O-SO_2R_7$;
$R_4$, $R_5$, and $R_6$ are independently hydrogen or $C_{1-6}$alkyl; and
$R_7$, $R_8$, and $R_9$ are hydrogen, $C_{1-6}$alkyl, aryl, $-C_{1-6}$alkyl-(aryl), -aryl-($C_{1-6}$alkyl), heteroaryl, $-C_{1-6}$alkyl-(heteroaryl), -heteroaryl-($C_{1-6}$alkyl), heterocycloalkyl, $-C_{1-6}$alkyl(heterocycloalkyl), or cycloalkyl, wherein the $C_{1-6}$alkyl, heterocycloalkyl, heteroaryl, and aryl groups are optionally substituted one or more substituents selected from the group consisting of F, Cl, Br, I, $R_{10}$, $-NR_{10}R_{11}$, $-CF_3$, $-CN$, $-NO_2$, $-C_2R_{10}$, $-N_3$, $-SO_2CH_3$, $-OR_{10}$, $-SR_{10}$, $-C(O)NR_{10}R_{11}$, $-NR_{10}C(=O)R_{10}$, $-C(=O)R_{10}$, $-C(=O)OR_{10}$, $-(CH_2)OR_{10}$, $-(CH_2)_2OR_{10}$, $-OC(=O)R_{10}$, $-OC(=O)NR_{10}R_{11}$ and $-NR_{10}C(=O)OR_{10}$;
$R_{10}$ and $R_{11}$ are independently hydrogen, $C_{1-6}$alkyl, pyridyl, quinolinyl, pyrimidinyl, pyrimidinyl, phenyl, or benzyl; or either $R_8$ and $R_9$ or $R_{10}$ and $R_{11}$ together with the nitrogen to which they are attached, optionally form a heterocycloalkyl ring;
p is 1, 2, 3, or 4; and
q is 1, 2, or 3;
or an enantiomer, diastereomer, tautomer, or pharmaceutically acceptable salt thereof.

Embodiment I-55

The pharmaceutical formulation of Embodiment I-54, wherein X is N.

Embodiment I-56

The pharmaceutical formulation of Embodiment I-54 or Embodiment I-55, wherein $R_2$ is hydrogen.

Embodiment I-57

The pharmaceutical formulation of any one of Embodiments I-54 to I-56, wherein R is hydrogen, $C_{1-6}$alkyl, $-OR_4$, or $-NR_5R_6$.

Embodiment I-58

The pharmaceutical formulation of any one of Embodiments I-54 to I-56, wherein $R_1$ is hydrogen.

Embodiment I-59

The pharmaceutical formulation of any one of Embodiments I-54 to I-58, wherein q is 1.

Embodiment I-60

The pharmaceutical formulation of any one of Embodiments I-54 to I-59, wherein p is 2.

Embodiment I-61

The pharmaceutical formulation of any one of Embodiments I-54 to I-60, wherein the wavy line represents E geometry about the double bond.

Embodiment I-62

The pharmaceutical formulation of any one of Embodiments I-54 to I-61, wherein the compound of Formula (I) is (R)-5-((E)-2-pyrrolidin-3-ylvinyl)pyrimidine.

Embodiment I-63

The pharmaceutical formulation of any one of Embodiments I-54 to I-61, wherein the compound of Formula (I) is (R)-5-((E)-2-pyrrolidin-3-ylvinyl)pyrimidine mono citrate salt.

Embodiment I-64

A pharmaceutical formulation for local administration into the nasal cavity of an individual comprising a compound of Formula (II) formulated (a) for nasal administration and (b) to prevent desensitization of peripheral nicotinic acetylcholine receptors, wherein the compound of Formula (II) has the structure:

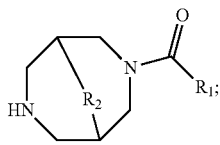

Formula (II)

wherein:
- $R_1$ is $C_{1-6}$alkyl, $C_{2-6}$alkenyl, $C_{2-6}$alkynyl, $C_{3-8}$heterocycloalkyl, $C_{3-8}$cycloalkyl, or heteroaryl, optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$-cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$NO_2$, —$OR_3$, —$NR_4R_5$, —$CF_3$, —$C_2R_3$, —$SR_3$, —$N_3$, —$C(O)NR_4R_5$, —$NR_4C(O)R_3$, —$C(O)R_3$, —$C(O)OR_3$, —$OC(O)R_3$, —$OC(O)NR_4R_5$, —$NR_4C(O)OR_5$, —$SO_2R_3$, —$NR_4SO_2R_5$, and —$SO_2NR_4R_5$;
- $R_2$ is a bond or —$CH_2$—;
- $R_3$ is hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl)k or heteroaryl; and
- $R_4$ and $R_5$ are independently hydrogen, $C_{1-6}$alkyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; or $R_4$ and $R_5$ together with the nitrogen to which they are attached, form a heterocycloalkyl ring;

or a pharmaceutically acceptable salt thereof.

Embodiment I-65

The pharmaceutical formulation of Embodiment I-64, wherein $R_1$ is heteroaryl optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$OR_3$, —$NR_4R_5$, —$CF_3$, —$C(O)NR_4R_5$, —$NR_4C(O)R_3$, —$C(O)R_3$, —$C(O)OR_3$, —$OC(O)R_3$, —$OC(O)NR_4R_5$, —$NR_4C(O)OR_3$, —$SO_2R_3$, —$NR_4SO_2R_3$, and —$SO_2NR_4R_5$.

Embodiment I-66

The pharmaceutical formulation of Embodiment I-64 or Embodiment I-65, wherein $R_1$ is 2-furanyl, 3-furanyl, 2-oxazolyl, 4-oxazolyl, 5-oxazolyl, 3-isoxazolyl, 4-isoxazolyl, 5-isoxazolyl, 1,3,4-oxadiazol-2-yl, 1,2,4-oxadiazol-3-yl, 1,2,4-oxadiazol-5-yl, 2-thiazolyl, 4-thiazolyl, 5-thiazolyl, 3-isothiazolyl, 4-isothiazolyl, 5-isothiazolyl, 1,3,4-thiadiazol-2-yl, 1,2,4-thiadiazol-3-yl, 1,2,4-thiadiazol-5-yl or 4-pyridinyl.

Embodiment I-67

The pharmaceutical formulation of any one of Embodiments I-64 to I-66, wherein $R_2$ is a bond.

Embodiment I-68

The pharmaceutical formulation of any one of Embodiments I-64 to I-66, wherein $R_2$ is —$CH_2$—.

Embodiment I-69

The pharmaceutical formulation of any one of Embodiments I-64 to I-66, wherein the compound of Formula (II) is N-(5-chlorofuran-2-ylcarbonyl)-3,7-diazabicyclo[3.3.0]octane.

Embodiment I-70

A pharmaceutical formulation for local administration into the nasal cavity of an individual comprising a compound of Formula (IIIa) or (IIIb) formulated (a) for nasal administration and (b) to prevent desensitization of peripheral nicotinic acetylcholine receptors, wherein the compound of Formula (IIIa) or (IIIb) has the structure

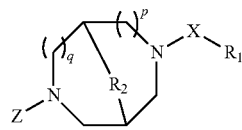

Formula (IIIa)

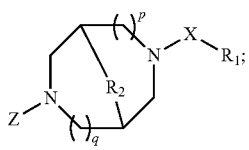

Formula (IIIb)

wherein:
- X is C(O), C(S), or $S(O)_n$;
- Z is hydrogen, $C_{1-6}$alkyl, or $C_{1-6}$haloalkyl;
- n is 1 or 2;
- p is 0 or 1;
- q is 0 or 1;
- when p is 1, then q is 0;
- when q is 1, then p is 0;
- $R_1$ is —$OR_3$, —$NR_4R_5$, $C_{1-6}$alkyl, $C_{2-6}$alkenyl, $C_{2-6}$alkynyl, $C_{3-8}$heterocycloalkyl, $C_{3-8}$cycloalkyl, aryl or heteroaryl, wherein $C_{1-6}$alkyl, $C_{2-6}$alkenyl, $C_{2-6}$alkynyl, $C_{3-8}$heterocycloalkyl, $C_{3-8}$cycloalkyl, aryl or heteroaryl are optionally substituted with one to three non-hydrogen substituents independently selected from $C_{1-6}$alkyl, $C_{2-6}$alkenyl, $C_{2-6}$alkynyl, $C_{3-8}$heterocycloalkyl, $C_{3-8}$cycloalkyl, heteroaryl, aryl, —$C_{1-6}$alkyl-(aryl), -aryl-($C_{1-6}$alkyl), heteroaryl, —$C_{1-6}$alkyl-(heteroaryl), -heteroaryl-($C_{1-6}$alkyl), halogen, —CN, —$NO_2$, —$OR_3$, —$NR_4R_5$, —$CF_3$, —$C_2R_3$, —$SR_3$, —$N_3$, —$C(O)NR_4R_5$, —$NR_4C(O)R_3$, —$C(O)R_3$, —$C(O)OR_3$, —$OC(O)R_3$, —$OC(O)NR_4R_5$, —$NR_4C(O)OR_3$, —$SO_2R_3$, —$NR_4SO_2R_5$, and —$SO_2NR_4R_5$;
- $R_2$ is —$CH_{12}$— or —$CH_2CH_2$—;
- $R_3$ is hydrogen, $C_{1-6}$alkyl, $C_{2-6}$alkenyl, $C_{2-6}$alkynyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; and
- $R_4$ and $R_5$ are independently hydrogen, $C_{1-6}$alkyl, $C_{2-6}$alkenyl, $C_{2-6}$alkynyl, $C_{3-8}$cycloalkyl, $C_{3-8}$heterocycloalkyl, aryl, —$C_{1-6}$alkyl-(aryl), -aryl-($C_{1-6}$alkyl), or heteroaryl; or R₄ and R₅ together with the nitrogen to which they are attached, form a heterocycloalkyl ring; or a pharmaceutically acceptable salt thereof.

Embodiment I-71

The pharmaceutical formulation of Embodiment I-70, wherein p is 1 and q is 0.

Embodiment I-72

The pharmaceutical formulation of Embodiment I-70, wherein p is 0 and q is 1.

Embodiment I-73

The pharmaceutical formulation of any one of Embodiments I-70 to I-72, wherein $R_2$ is —CH₂—.

Embodiment I-74

The pharmaceutical formulation of any one of Embodiments I-70 to I-72, wherein $R_2$ is —CH₂CH₂—.

Embodiment I-75

The pharmaceutical formulation of any one of Embodiments I-70 to I-74, wherein Z is hydrogen.

Embodiment I-76

The pharmaceutical formulation of any one of Embodiments I-70 to I-74, wherein Z is $C_{1-6}$alkyl.

Embodiment I-77

The pharmaceutical formulation of any one of Embodiments I-70 to I-76, wherein X is C(O).

Embodiment I-78

The pharmaceutical formulation of any one of Embodiments T-54 to I-77, wherein the compound of Formula (I), (II), (IIIa), or (IIIb) is formulated in a dosage amount that does not result in undesired psychoactive side effects.

Embodiment I-79

The pharmaceutical formulation of any one of Embodiments I-54 to I-78, wherein the compound of Formula (I), (II), (IIIa), or (IIIb) is formulated in a dosage amount that is not systemically bioavailable.

Embodiment I-80

The pharmaceutical formulation of any one of Embodiments I-54 to I-79, wherein the compound of Formula (I), (II), (IIIa), or (IIIb) is formulated in a dosage amount that does not result in undesired systemic side effects.

Embodiment I-81

The pharmaceutical formulation of any one of Embodiments I-54 to I-80, further comprising one or more substances selected from protein kinase C (PKC) or factors that upregulate or up-modulate PKC, cAMP-dependent protein kinase (PKA) or factors that upregulate or up-modulate PKA, and calcineurin inhibitors.

Embodiment I-82

The pharmaceutical formulation of Embodiment I-81, wherein the calcineurin inhibitor is selected from cyclosporine, pimecrolimus, and tacrolimus.

Embodiment I-83

The pharmaceutical formulation of any one of Embodiments I-54 to I-82, wherein the pharmaceutical formulation does not contain nicotine in any form.

Embodiment I-84

The pharmaceutical formulation of any one of Embodiments I-54 to I-83, wherein the compound of Formula (I), (II), (IIIa), or (IIIb) selectively binds to at least one of the peripheral nicotinic acetylcholine receptor subtypes selected from alpha3beta4, alpha4beta2, and alpha7.

Embodiment I-85

The pharmaceutical formulation of any one of Embodiments I-54 to I-84, wherein the compound of Formula (I), (II), (IIIa), or (IIIb) comprises about 5 mg/mL of the nicotinic acetylcholine receptor agonist.

Embodiment I-86

The pharmaceutical formulation of any one of Embodiments I-54 to I-84, wherein the compound of Formula (I), (II), (IIIa), or (IIIb) comprises about 10 mg/ml of the nicotinic acetylcholine receptor agonist.

Embodiment I-87

The pharmaceutical formulation of any one of Embodiments I-54 to I-84, comprising less than 5 milligrams of the compound of Formula (I), (II), (IIIa), or (IIIb) per dose.

Embodiment I-88

The pharmaceutical formulation of any one of Embodiments I-54 to I-84, comprising between 500 micrograms and 5 milligrams of the compound of Formula (I), (II), (IIIa), or (IIIb) per dose.

Embodiment I-89

The pharmaceutical formulation of any one of Embodiments I-54 to I-84, comprising between 1 milligram and 2 milligrams of the compound of Formula (I), (II), (IIIa), or (IIIb) per dose.

Embodiment I-90

The pharmaceutical formulation of any one of Embodiments I-54 to I-84, comprising about 1 milligram of the compound of Formula (I), (II), (IIIa), or (IIIb) per dose.

Embodiment I-91

The pharmaceutical formulation of any one of Embodiments I-54 to I-84, comprising about 1.5 milligrams of the compound of Formula (I), (II), (IIIa), or (IIIb) per dose.

Embodiment I-92

The pharmaceutical formulation of any one of Embodiments I-54 to I-84, comprising about 2 milligrams of the compound of Formula (I), (II), (IIIa), or (IIIb) per dose.

Embodiment I-93

The pharmaceutical formulation of any one of Embodiments I-54 to I-92, wherein the formulation is administered at least once daily.

Embodiment I-94

The pharmaceutical formulation of any one of Embodiments I-54 to I-92, wherein the formulation is administered at least twice daily.

Embodiment I-95

The pharmaceutical formulation of any one of Embodiments I-54 to I-92, wherein the formulation is administered at least once weekly.

Embodiment I-96

The pharmaceutical formulation of any one of Embodiments I-50 to I-92, wherein the formulation is administered into the nasal cavity as a liquid, suspension, aerosol, gel, ointment, dry powder, cream, paste, lotion, or balm.

Embodiment I-97

The pharmaceutical formulation of any one of Embodiments I-54 to I-96, wherein the formulation is administered into the nasal cavity by a syringe, dropper, bottle nebulizer, atomization pump, inhaler, powder spray device, vaporizer, patch, medicated stick, pipette, or jet of liquid.

Embodiment II-1

A method of increasing tear production, comprising the local administration of a therapeutically effective amount of (R)-5-((E)-2-pyrrolidin-3-ylvinyl)pyrimidine, or a pharmaceutically acceptable salt thereof, into the nasal cavity of an individual in need thereof.

Embodiment II-2

A method of treating dry eye, comprising the local administration of a therapeutically effective amount of (R)-5-((E)-2-pyrrolidin-3-ylvinyl)pyrimidine, or a pharmaceutically acceptable salt thereof; into the nasal cavity of an individual in need thereof.

Embodiment II-3

A method of improving ocular discomfort, comprising the local administration of a therapeutically effective amount of (R)-5-((E)-2-pyrrolidin-3-ylvinyl)pyrimidine, or a pharmaceutically acceptable salt thereof, into the nasal cavity of an individual in need thereof.

Embodiment II-4

The method of any one of Embodiments II-1 to II-3, wherein (R)-5-((E)-2-pyrrolidin-3-ylvinyl)pyrimidine is administered as a free base.

Embodiment II-5

The method of any one of Embodiments II-1 to III-3, wherein (R)-5-((E)-2-pyrrolidin-3-ylvinyl)pyrimidine is administered as a pharmaceutically acceptable salt of (R)-5-((E)-2-pyrrolidin-3-ylvinyl)pyrimidine.

Embodiment II-6

The method Embodiment II-5, wherein the pharmaceutical acceptable salt is a galactarate or citrate salt.

Embodiment II-7

The method of Embodiment II-6, wherein the pharmaceutical acceptable salt is a galactarate salt.

Embodiment II-8

The method of Embodiment II-6, wherein the pharmaceutical acceptable salt is a citrate salt.

Embodiment II-9

The method of Embodiment II-8, wherein the pharmaceutical acceptable salt is (R)-5-((E)-2-pyrrolidin-3-ylvinyl)pyrimidine mono-citrate salt.

Embodiment II-10

The method of any one of Embodiments II-1 to II-3, wherein the dose of (R)-5-((E)-2-pyrrolidin-3-ylvinyl)pyrimidine, or a pharmaceutically acceptable salt thereof, is between 500 micrograms and 10 milligrams per dose.

Embodiment II-11

The method of any one of Embodiments II-1 to II-10, wherein (R)-5-((E)-2-pyrrolidin-3-ylvinyl)pyrimidine, or a pharmaceutically acceptable salt thereof, is administered in an amount that is not systemically bioavailable.

Embodiment II-12

The method of any one of Embodiments II-1 to II-10, wherein (R)-5-((E)-2-pyrrolidin-3-ylvinyl)pyrimidine, or a pharmaceutically acceptable salt thereof, selectively binds to peripheral nicotinic acetylcholine receptors in an amount that does not result in undesired systemic side effects.

Embodiment II-13

The method of any one of Embodiments II-1 to I-12, wherein (R)-5-((E)-2-pyrrolidin-3-ylvinyl)pyrimidine, or a pharmaceutically acceptable salt thereof, selectively binds to peripheral nicotinic acetylcholine receptors in an amount that does not result in undesired psychoactive side effects.

Embodiment II-14

The method of any one of Embodiments II-14 to II-13, further comprising the local administration of one or more substances that prevent the entry or reduce the entry of the nicotinic acetylcholine receptor into the desensitized state, or facilitate the recovery of a peripheral nicotinic acetylcholine receptor from the desensitized state.

Embodiment II-15

The method of Embodiment II-14, wherein the one or more substances are selected from the group consisting of protein kinase C (PKC) or factors that upregulate or up-modulate PKC, cAMP-dependent protein kinase (PKA) or factors that upregulate or up-modulate PKA, and calcineurin inhibitors.

Embodiment II-16

The method of Embodiment II-15, wherein the calcineurin inhibitor is selected from the group consisting of cyclosporine, pimecrolimus, and tacrolimus.

Embodiment II-17

The method of any one of Embodiments II-1 to II-16, wherein (R)-5-((E)-2-pyrrolidin-3-ylvinyl)pyrimidine, or a pharmaceutically acceptable salt thereof, is administered without any form of nicotine.

Embodiment II-18

The method of any one of Embodiments II-1 to II-17, wherein between 500 micrograms and 5 milligrams of (R)-5-((E)-2-pyrrolidin-3-ylvinyl)pyrimidine, or a pharmaceutically acceptable salt thereof, is administered.

Embodiment II-19

The method of Embodiment II-18, wherein less than 5 milligrams of (R)-5-((E)-2-pyrrolidin-3-ylvinyl)pyrimidine, or a pharmaceutically acceptable salt thereof, is administered.

Embodiment II-20

The method of Embodiment II-18, wherein between 1 milligram and 3 milligrams of (R)-5-((E)-2-pyrrolidin-3-ylvinyl)pyrimidine, or a pharmaceutically acceptable salt thereof, is administered.

Embodiment II-21

The method of Embodiment II-18, wherein between 500 micrograms and 5 milligrams of (R)-5-((E)-2-pyrrolidin-3-ylvinyl)pyrimidine, or a pharmaceutically acceptable salt thereof, is administered.

Embodiment II-22

The method of Embodiment I-18, wherein between 1 milligram and 2 milligrams of (R)-5-((E)-2-pyrrolidin-3-ylvinyl)pyrimidine, or a pharmaceutically acceptable salt thereof, is administered.

Embodiment II-23

The method of Embodiment II-18, wherein about 1 milligram of (R)-5-((E)-2-pyrrolidin-3-ylvinyl)pyrimidine, or a pharmaceutically acceptable salt thereof, is administered.

Embodiment II-24

The method of Embodiment II-18, wherein about 1.5 milligrams of (R)-5-((E)-2-pyrrolidin-3-ylvinyl)pyrimidine, or a pharmaceutically acceptable salt thereof, is administered.

Embodiment II-25

The method of Embodiment II-18, wherein about 2 milligrams of (R)-5-((E)-2-pyrrolidin-3-ylvinyl)pyrimidine, or a pharmaceutically acceptable salt thereof, is administered.

Embodiment II-26

The method of any one of Embodiment II-1 to II-25, wherein (R)-5-((E)-2-pyrrolidin-3-ylvinyl)pyrimidine, or a pharmaceutically acceptable salt thereof, is administered as needed in response to symptoms.

Embodiment II-27

The method of any one of Embodiments II-1 to III-26, wherein (R)-5-((E)-2-pyrrolidin-3-ylvinyl)pyrimidine, or a pharmaceutically acceptable salt thereof, is administered at least once daily.

Embodiment II-28

The method of any one of Embodiments II-1 to II-26, wherein (R)-5-((E)-2-pyrrolidin-3-ylvinyl)pyrimidine, or a pharmaceutically acceptable salt thereof is administered at least twice daily.

Embodiment II-29

The method of any one of Embodiments II-1 to II-26, wherein (R)-5-((E)-2-pyrrolidin-3-ylvinyl)pyrimidine, or a pharmaceutically acceptable salt thereof, is administered at least once weekly.

Embodiment II-30

The method of any one of Embodiments II-1 to II-29, wherein (R)-5-((E)-2-pyrrolidin-3-ylvinyl)pyrimidine, or a pharmaceutically acceptable salt thereof, is administered into the nasal cavity as a liquid, suspension, aerosol, gel, ointment, dry powder, cream, paste, lotion, or balm.

Embodiment II-31

The method of any one of Embodiments II-1 to II-30, wherein (R)-5-((E)-2-pyrrolidin-3-ylvinyl)pyrimidine, or a pharmaceutically acceptable salt thereof, is administered into the nasal cavity by a syringe, dropper, bottle nebulizer atomization pump, inhaler, powder spray device, vaporizer, patch, medicated stick, pipette, or jet of liquid.

Embodiment II-32

The method of any one of Embodiments I-1 to III-31, wherein the trigeminal nerve is activated.

Embodiment II-33

The method of Embodiment II-32, wherein the anterior ethmoidal nerve is activated.

Embodiment II-34

The method of any one of Embodiments II-1 to II-33, wherein the nasolacrimal reflex is activated.

Embodiment II-35

The method of any one of Embodiments II-1 to II-34, wherein the (R)-5-((E)-2-pyrrolidin-3-ylvinyl)pyrimidine, or a pharmaceutically acceptable salt thereof, is administered in a pharmaceutical formulation for nasal administration comprising between 5 mg/mL and 200 mg/mL of (R)-5-((E)-2-pyrrolidin-3-ylvinyl)pyrimidine, or a pharmaceutically acceptable salt thereof.

Embodiment II-36

The method of Embodiment II-35, wherein the pharmaceutical formulation for nasal administration comprises between 10 mg/nil, and 75 mg/ml, of (R)-5-((E)-2-pyrrolidin-3-ylvinyl)pyrimidine, or a pharmaceutically acceptable salt thereof.

Embodiment II-37

The method of Embodiment II-36, wherein the pharmaceutical formulation for nasal administration comprises between 10 mg/m- and 50 mg/mL of (R)-5-((E)-2-pyrrolidin-3-ylvinyl)pyrimidine, or a pharmaceutically acceptable salt thereof.

Embodiment II-38

A pharmaceutical formulation for local administration into the nasal cavity of an individual comprising (R)-5-((E)-2-pyrrolidin-3-ylvinyl)pyrimidine, or a pharmaceutically acceptable salt thereof, formulated for nasal administration.

Embodiment II-39

The pharmaceutical formulation of Embodiment II-38, wherein (R)-5-((E)-2-pyrrolidin-3-ylvinyl)pyrimidine is formulated as a free base.

Embodiment II-40

The pharmaceutical formulation of Embodiment II-38, wherein the pharmaceutically acceptable salt is a galactarate or citrate salt.

Embodiment II-41

The pharmaceutical formulation of Embodiment II-40, wherein the pharmaceutically acceptable salt is a galactarate salt.

Embodiment II-42

The pharmaceutical formulation of Embodiment II-40, wherein the pharmaceutically acceptable salt is a citrate salt.

Embodiment II-43

The pharmaceutical formulation of Embodiment II-42, wherein the citrate salt is (R)-5-((E)-2-pyrrolidin-3-ylvinyl) pyrimidine mono-citrate salt.

Embodiment II-44

The pharmaceutical formulation of any one of Embodiments II-38 to II-43 wherein the pharmaceutical formulation is formulated for administration of a dose between 500 micrograms and 10 milligrams per dose.

Embodiment II-45

The pharmaceutical formulation of any one of Embodiments II-38 to III-44 wherein (R)-5-((E)-2-pyrrolidin-3-ylvinyl)pyrimidine, or a pharmaceutically acceptable salt thereof, is formulated in a dosage amount that is not systemically bioavailable.

Embodiment II-46

The pharmaceutical formulation of any one of Embodiments II-38 to II-44, wherein (R)-5-((E)-2-pyrrolidin-3-ylvinyl)pyrimidine, or a pharmaceutically acceptable salt thereof, is formulated in a dosage amount that does not result in undesired systemic side effects.

Embodiment II-47

The pharmaceutical formulation of any one of Embodiments II-38 to II-46, further comprising one or more substances selected from the group consisting of protein kinase C (PKC) or factors that upregulate or up-modulate PKC, cAMP-dependent protein kinase (PKA) or factors that upregulate or up-modulate PKA, and calcineurin inhibitors.

Embodiment II-48

The pharmaceutical formulation of Embodiment II-47, wherein the calcineurin inhibitor is selected from the group consisting of cyclosporine, pimecrolimus, and tacrolimus.

Embodiment II-49

The pharmaceutical formulation of any one of Embodiments II-38 to II-48, wherein the pharmaceutical formulation does not contain nicotine in any form.

Embodiment II-50

The pharmaceutical formulation of any one of Embodiments II-38 to II-49, wherein the pharmaceutical formulation comprises between 5 mg/mL and 200 mg/mL of (R)-5-((E)-2-pyrrolidin-3-ylvinyl)pyrimidine, or a pharmaceutically acceptable salt thereof.

Embodiment II-51

The pharmaceutical formulation of Embodiment II-50, wherein the pharmaceutical formulation comprises between 10 mg/mL and 75 mg/mL of (R)-5-((E)-2-pyrrolidin-3-ylvinyl)pyrimidine, or a pharmaceutically acceptable salt thereof.

Embodiment II-52

The pharmaceutical formulation of Embodiment II-51, wherein the pharmaceutical formulation comprises between 10 mg/mL and 50 mg/mL of (R)-5-((E)-2-pyrrolidin-3-ylvinyl)pyrimidine, or a pharmaceutically acceptable salt thereof.

Embodiment II-53

The pharmaceutical formulation of any one of Embodiments I-38 to II-52, comprising between 500 micrograms and 5 milligrams of (R)-5-((E)-2-pyrrolidin-3-ylvinyl)pyrimidine, or a pharmaceutically acceptable salt thereof, per dose.

Embodiment II-54

The pharmaceutical formulation of any one of Embodiments II-38 to II-52, comprising less than 5 milligrams of (R)-5-((E)-2-pyrrolidin-3-ylvinyl)pyrimidine, or a pharmaceutically acceptable salt thereof, per dose.

Embodiment II-55

The pharmaceutical formulation of any one of Embodiments II-38 to II-52, comprising between 1 milligram and 3 milligrams of (R)-5-((E)-2-pyrrolidin-3-ylvinyl)pyrimidine, or a pharmaceutically acceptable salt thereof, per dose.

Embodiment II-56

The pharmaceutical formulation of any one of Embodiments II-38 to II-52, comprising between 1 milligram and 2 milligrams of (R)-5-((E)-2-pyrrolidin-3-ylvinyl)pyrimidine, or a pharmaceutically acceptable salt thereof, per dose.

Embodiment II-57

The pharmaceutical formulation of any one of Embodiments II-38 to II-52, comprising about 1 milligram of (R)-5-((E)-2-pyrrolidin-3-ylvinyl)pyrimidine, or a pharmaceutically acceptable salt thereof, per dose.

Embodiment II-58

The pharmaceutical formulation of any one of Embodiments II-38 to II-52, comprising about 1.5 milligrams of (R)-5-((E)-2-pyrrolidin-3-ylvinyl)pyrimidine, or a pharmaceutically acceptable salt thereof, per dose.

Embodiment II-59

The pharmaceutical formulation of any one of Embodiments II-38 to II-52, comprising about 2 milligrams of (R)-5-((E)-2-pyrrolidin-3-ylvinyl)pyrimidine, or a pharmaceutically acceptable salt thereof, per dose.

Embodiment II-60

The pharmaceutical formulation of any one of Embodiments II-38 to II-59, wherein the pharmaceutical formulation is formulated for administration as needed in response to symptoms.

Embodiment II-61

The pharmaceutical formulation of any one of Embodiments II-38 to II-59, wherein the pharmaceutical formulation is formulated for administration at least once daily.

Embodiment II-62

The pharmaceutical formulation of any one of Embodiments II-38 to II-59, wherein the pharmaceutical formulation is formulated for administration at least twice daily.

Embodiment II-63

The pharmaceutical formulation of any one of Embodiments II-38 to II-59, wherein the pharmaceutical formulation is formulated for administration at least once weekly.

Embodiment II-64

The pharmaceutical formulation of any one of Embodiments II-38 to II-63, wherein the pharmaceutical formulation is formulated as a liquid, suspension, aerosol, gel, ointment, dry powder, cream, paste, lotion, or balm.

Embodiment II-65

The pharmaceutical formulation of any one of Embodiments II-38 to II-64, wherein the pharmaceutical formulation is formulated for local delivery into the nasal cavity via a syringe, dropper, bottle nebulizer, atomization pump, inhaler, powder spray device, vaporizer, patch, medicated stick, pipette, or jet of liquid.

Embodiment II-66

A method of treating an ocular condition comprising the local administration of a therapeutically effective amount of (R)-5-((E)-2-pyrrolidin-3-ylvinyl)pyrimidine, or a pharmaceutically acceptable salt thereof, into the nasal cavity of an individual in need thereof, wherein the ocular condition is an acute condition.

Embodiment II-67

A method of treating an ocular condition comprising the local administration of a therapeutically effective amount of (R)-5-((E)-2-pyrrolidin-3-ylvinyl)pyrimidine, or a pharmaceutically acceptable salt thereof, into the nasal cavity of an individual in need thereof, wherein the ocular condition is a result from an ophthalmologic surgical procedure or an ophthalmologic treatment.

Embodiment III-1

The compound (R)-5-((E)-2-pyrrolidin-3-ylvinyl)pyrimidine, or a pharmaceutically acceptable salt thereof, for use in the treatment of dry eye or ocular discomfort, which is administered into the nasal cavity of an individual in need thereof.

Embodiment III-2

The compound (R)-5-((E)-2-pyrrolidin-3-ylvinyl)pyrimidine, or a pharmaceutically acceptable salt thereof, for use in the treatment of dry eye or ocular discomfort, which is administered into the nasal cavity of an individual in need thereof, and wherein the ocular condition is a result from an ophthalmologic surgical procedure or an ophthalmologic treatment.

Embodiment III-3

The compound for use according to Embodiment III-1 or III-2 and wherein the dose of (R)-5-((E)-2-pyrrolidin-3-ylvinyl)pyrimidine, or a pharmaceutically acceptable salt thereof, is between 500 micrograms and 10 milligrams per dose.

Embodiment III-4

The compound for use according to any preceding embodiments, wherein (R)-5-((E)-2-pyrrolidin-3-ylvinyl) pyrimidine which is administered as a free base.

Embodiment I-5

The compound for use according any preceding embodiments, wherein the pharmaceutically acceptable salt is a galactarate or citrate salt.

Embodiment III-6

The compound for use according to Embodiment III-5, wherein the pharmaceutically acceptable salt is (R)-5-((E)-2-pyrrolidin-3-ylvinyl)pyrimidine mono-citrate salt.

Embodiment III-7

The compound for use according to any one of Embodiments III-1 to III-6 and which is administered together with one or more substances that prevent the entry or reduce the entry of the nicotinic acetylcholine receptor into the desensitized state, or facilitate the recovery of a peripheral nicotinic acetylcholine receptor from the desensitized state.

Embodiment III-8

The compound for use according to Embodiment III-7, wherein the one or more substances are selected from the group consisting of protein kinase C (PKC) or factors that upregulate or up-modulate PKC, cAMP-dependent protein kinase (PKA) or factors that upregulate or up-modulate PKA, and calcineurin inhibitors.

Embodiment III-9

The compound for use according to Embodiment III-8, wherein the calcineurin inhibitor is selected from the group consisting of cyclosporine, pimecrolimus, and tacrolimus.

Embodiment III-10

The compound for use according to any one of Embodiments III-1 to III-9, which is administered without any form of nicotine.

Embodiment III-11

The compound for use according to any one of Embodiments III-1 to III-10, which is administered in an amount of between 500 micrograms and 5 milligrams.

Embodiment III-12

The compound for use according to any one of Embodiments III-1 to III-11, which is administered in an amount of less than 5 milligrams.

Embodiment II-13

The compound for use according to any one of Embodiments III-1 to III-11, which is administered in an amount of between 1 milligram and 3 milligrams.

Embodiment II-14

The compound for use according to any of Embodiments III-1 to III-11, which is administered in an amount between 500 micrograms and 5 milligrams.

Embodiment III-15

The compound for use according to any of Embodiments III-1 to III-11, which is administered in an amount between 1 milligram and 2 milligrams is administered.

Embodiment III-16

The compound for use according to any of Embodiments III-1 to III-11, which is administered in an amount about 1 milligram.

Embodiment III-17

The compound for use according to any of Embodiments III-1 to III-11, which is administered in an amount of about 1.5 milligrams.

Embodiment II-18

The compound for use according to any of Embodiments III-1 to III-11, which is administered in an amount of about 2 milligrams.

Embodiment III-19

The compound for use according to any one of Embodiments III-1 to III-18, which is administered at least once daily.

Embodiment III-20

The compound for use according to any one of Embodiments III-1 to III-18, which is administered at least twice daily.

Embodiment III-21

The compound for use according to any one of Embodiments III-1 to III-18, which is administered at least once weekly.

Embodiment III-22

The compound for use according to any one of Embodiments III-1 to III-21, which, is administered into the nasal cavity as a liquid, suspension, aerosol, gel, ointment, dry powder, cream, paste, lotion, or balm.

Embodiment III-23

The compound for use according to any one of Embodiments II-1 to III-21, which is administered into the nasal cavity by a syringe, dropper, bottle nebulizer, atomization pump, inhaler, powder spray device, vaporizer, patch, medicated stick, pipette, or jet of liquid.

Embodiment III-24

The compound for use according to any one of Embodiments III-1 to III-23, which is administered in a pharmaceutical formulation for nasal administration comprising an amount between 5 mg/mL and 200 mg/mL of (R)-5-((E)-2-pyrrolidin-3-ylvinyl)pyrimidine, or a pharmaceutically acceptable salt thereof.

Embodiment III-25

The compound for use according to Embodiment III-24, wherein the pharmaceutical formulation for nasal administration comprises between 10 mg/mL and 75 mg/mL of (R)-5-((E)-2-pyrrolidin-3-ylvinyl)pyrimidine, or a pharmaceutically acceptable salt thereof.

Embodiment III-26

The compound for use according Embodiment III-24, wherein the pharmaceutical formulation for nasal administration comprises between 10 mg/mL and 50 mg/mL of (R)-5-((E)-2-pyrrolidin-3-ylvinyl)pyrimidine, or a pharmaceutically acceptable salt thereof.

Embodiment III-27

A pharmaceutical formulation for use in treatment of dry eye or ocular discomfort, the formulation comprising (R)-5-((E)-2-pyrrolidin-3-ylvinyl)pyrimidine, or a pharmaceutically acceptable salt thereof.

Embodiment III-28

A pharmaceutical formulation for use according to Embodiment III-27, wherein the formulation comprises a compound as defined in any one of Embodiments III-1 to III-25.

EXAMPLES

The following specific examples are to be construed as merely illustrative, and not limitative of the remainder of the disclosure in any way whatsoever.

Example 1: Clinical Trial to Evaluate Safety and Efficacy of Nasal Administration of (R)-5-((E)-2-Pyrrolidin-3-ylvinyl)pyrimidine (Compound 1) for Treatment of Dry Eye Disease (DED)

Purpose: This study evaluates the use of Compound 1, 0.1% nasal spray (OC-01) for the treatment of moderate to severe DED in adult patients. This study will investigate the safety and efficacy of using OC-01 to induce aqueous tear production and reduce the symptoms of DED.

Patients: A total of 30 participants with moderate to severe dry eye, meeting the following inclusion and exclusion criteria will be enrolled.

Criteria:
Inclusion:
Males and females ≥18 years of age
Willing to sign the informed consent and deemed capable of complying with the requirements of the study protocol
At screening visit 1, Schirmer tear test (with topical anesthesia) of 10 mm/5 minutes in at least one eye;
At screening visit 1, Schirmer test (with topical anesthesia and nasal stimulation with cotton swab) of at least 7 mm higher than the unstimulated value in at least one eye;
Baseline Ocular Surface Disease Index score of at least 23 with no more than 3 responses of "not applicable" at the first screening visit
Normal lid/lash anatomy, blinking function and closure Exclusion:
Chronic or recurrent epistaxis
Use of tobacco or nicotine products (cigarettes, cigars, electronic cigarettes) within the past 1 year
Coagulation disorders that may lead to increased bleeding such as hemophilia and thrombocytopenia
Lacrimal gland, nasal or sinus neoplasia or significant trauma; prior lacrimal gland, nasal or sinus surgery or ablation leading to denervation of the gland or nasal passages as evidenced by a lack of response with the cotton swab nasal stimulation.
Severe nasal airway obstruction (e.g, severe septal deviation or inferior turbinate hypertrophy)
Ocular surgery (such as refractive or cataract surgery) in either eye within 3 months of the first screening visit.
A systemic condition or disease not stabilized or judged by the investigator to be incompatible with participation in the study (e.g. current systemic infection, uncontrolled autoimmune disease, uncontrolled immunodeficiency disease, history of myocardial infarction, uncontrolled hypertension, etc.) or with the frequent assessments required by the study
The history or presence of any ocular disorder or condition in either eye that would likely interfere with the interpretation of the study results or patient safety such as a significant corneal or conjunctival scarring, pterygium or nodular pinguecula; current ocular infection or inflammation not associated with dry eye; clinically significant anterior (epithelial) basement membrane corneal dystrophy or other clinically significant corneal dystrophy or degeneration; clinically significant blepharitis; ocular herpetic infection, etc.
Known hypersensitivity to any of the procedural agents or materials in the study drug that contact the nasal mucosa.
Active or uncontrolled severe systemic allergy, chronic seasonal allergies, rhinitis or sinusitis requiring treatment (i.e. antihistamines, decongestants, oral or aerosol steroids) at the time of initial screening
Be currently taking any medication known to cause ocular drying (e.g., cyclosporine, antihistamines, tricyclic antidepressants, anxiolytics, antimuscarinics, beta-blocking agents, diuretics, phenothiazines, steroids, etc.) that has not been used on a stable dosing regimen for 30 days prior to the first screening visit
Dissolvable punctal plugs (participants with silicone plugs or permanent occlusion of punctal ducts are eligible)
Active contact lens use unless discontinued at least 7 days prior to the first screening visit and for the duration of the study
Participation in any clinical trial with a new active substance or a new device during the past 3 months
Women w ho are pregnant, planning a pregnancy or nursing at study entry. A urine pregnancy test will be administered to women of childbearing age.
Known allergies or adverse reactions to Compound 1
Any unstable or uncontrolled cardiac, pulmonary, renal, oncology, neurology, metabolic or other systemic condition that, in the opinion of the investigator, would like require the patient to seek emergent medical treatment during the course of this study. This includes but is not limited to cardiac arrhythmias, hypertension, coagulopathies, renal failure and diabetes mellitus.

Inclusion/Exclusion Exceptions:

The Investigator has the right to exclude any patient's participation in the study if he/she deems it in the best interest of the patient.

Minor exceptions to the inclusion/exclusion criteria should be submitted to the sponsor and prospectively approved with the advice of the medical monitor when required.

Major exceptions affecting patient safety/rights or data validity should be reported promptly to the IRB/EC by the investigator.

Primary Outcome: The design of this study will enable the following measurements with respect to OC-01 and tear production:

Change in tear production associated with a single dose of OC-01

Secondary Outcome: The design of this study will enable the following measurements with respect to OC-01 and tear production:

Change in tear production associated with a single dose of vehicle

Change in symptoms associated with a single dose of OC-01

Duration of symptomatic relief associated with a single dose of OC-01

Change in symptoms associated with a single dose of vehicle

Duration of symptomatic relief associated with a single dose of vehicle

Together these comparisons will provide valuable information about the safety and efficacy of OC-01 for increasing tear production in patients with dry eye disease.

The primary safety endpoint of this study is incidence and relatedness of adverse events (AE). Descriptive statistics of adverse events will be provided as will narratives of any serious, unexpected or drug-related AEs. During the study, integrity of the nasal passages will be monitored by a suitably qualified practitioner for patient safety.

Study Design: This study is a prospective, single-arm crossover study to evaluate the safety and efficacy of Compound 1, 0.1% nasal spray in participants with moderate to severe dry eye. Up to 30 participants will be enrolled and followed for a duration of seven days. A 0.1% nasal spray refers to the concentration in a container from which the dose is drawn from.

At the first screening visit, all eligible participants will cease taking their current artificial tears or lubricant drops for the duration of the study and will be provided unit dose unpreserved artificial tears to be taken if their dry eye symptoms become intolerable. Empty unit dose vials will be collected at each study visit and counted. Patients will be instructed not to use artificial tears within 30 minutes of nasal drug administration or within 2 hours of a study visit.

At the second screening visit/Study Day 0, all eligible participants will be tested for their response two nasal formulations: OC-01 and a vehicle control. Tear production will be assessed immediately prior and after delivery of each intranasal dose using the Jones Schirmer Test in both eyes. The order that each patient receives the OC-01 and vehicle formulation will be randomly assigned, and both the patient and examiner will be masked to the identity of the nasal formulation. At least 90 minutes following the tear production assessment, change in symptoms in response to delivery of each of the two nasal formulations will be assessed. The symptom assessment will be performed using a well-established environmental challenge model, the ClimaTears Goggle System manufactured by Biocentric Developments. LLC.

After testing on Day 0, all patients will receive a bottle of OC-01 to take home and self-administer once daily from Day 1 and Day 6. On Day 7, patients will return to the clinic where they will again be assessed for tear production and symptoms with administration of each nasal formulation.

Tear Assessments

The following ocular surface and tear film assessments will be performed in the order shown:

Ocular Surface Staining—Corneal Staining Using Fluorescein

Ocular surface staining using fluorescein and lissamine green will be assessed and recorded in the schematic representation of 5 corneal and 6 conjunctival regions per eye on the case report form using the National Eye Institute grading system. A pictorial and descriptive grading scale (grades 0 to 3) are included on the case report form (CRF).

1. Corneal staining should be assessed using 1.0 mg sodium fluorescein strips.
2. After wetting the end of the strip with a single drop of buffered saline, the excess is shaken into a waste bin with a sharp flick.
3. The lower lid is then pulled down and the flat end of the tip should be gently applied to the inferior tarsal conjunctiva with the intent of instilling a very small volume of dye and not inducing reflex tearing.
4. The patient will be instructed to blink naturally several times without forced closure of the eyelid to distribute the fluorescein.
5. After allowing fluorescein to remain on the eye for at least one minute, the 5 corneal regions will be graded using a yellow (Wratten #12) barrier filter in conjunction with the cobalt (blue) filter to maximize the view of the fluorescence. The upper eyelid is lifted slightly to grade the entire corneal surface. To enhance the contrast, position the yellow barrier filter in the path of the returning light (not in the path of the incident light).

Tear Film Breakup Time (TFBUT)

TFBUT will be assessed using slit lamp biomicroscopy according to the following steps:

1. The slit-lamp will be set to a magnification of approximately 10×.
2. With adequate fluorescein in place (preferably using DET strips), the subject will be asked to stare straight ahead without blinking until told otherwise. The test should be performed in a room with no direct air on the patient's face.
3. A stopwatch will be used to record the time between the last complete blink and the first appearance of a growing micelle indicating tear-film breakup.

Note: If the patient blinks prematurely prior to the development of the breakup of the mires, the examiner should continue to try to obtain a reading.

4. Once TFBUT is observed, instruct patient to blink freely. This test should then be repeated a second time on the same eye.
5. If the difference between the first and second readings differs by more than two seconds, a third measurement should be performed and recorded.
6. This procedure will then be performed in the other eye.
7. It is recommended that TFBUT be performed in a room with a temperature of approximately 18 C with a humidity of approximately 50%.

Ocular Surface Staining—Conjunctival Staining Using Lissamine Green

Ocular surface staining assessment will be completed with lissamine green conjunctival staining.
1. The lissamine green ophthalmic strip should be wetted with buffered saline and applied to the inferior tarsal conjunctiva, Care should be taken to instill adequate dye.
2. After allowing lissamine green to remain on the eye for one minute, the six nasal and temporal conjunctival regions will be graded.
3. To grade the temporal zone, the subject should be instructed to look nasally; to grade the nasal zone, the subject should be instructed to look temporally.
4. This procedure should then be completed in the other eye.

Schirmer Test

At screening visit #1, one basal Jones Schirmer test will be performed followed by a Schirmer test with cotton swab nasal stimulation. The Jones Schirmer test with topical anesthetic will be used to assess tear production using the following steps:
1. Topical anesthetic drops such as 0.5% proparacaine hydrochloride or equivalent (Akorn, Lake Forest, Ill.) should be instilled in both eyes of the patient.
2. The patient will be instructed to keep the eyes gently closed for one minute.
3. After opening the eyes and allowing the eyes to recover for approximately one additional minute, excess moisture in the inferior fornix is gently removed with a cotton-tipped applicator.
4. Schirmer strips (35 mm×5 mm size filter paper strip) will be placed in each eye at the junction of the middle and lateral thirds of the lower eye lid.
5. Under ambient light, the patient will be instructed to look forward and to blink normally during the course of the test. The test should be performed in a room with no direct air on the patient's face.
6. After five minutes, strips will be removed from both eyes and the amount of wetting will be recorded. The strips should be taped to the CRF. Note: Should the Schirmer score reach maximum prior to the 5 minute endpoint, the strip can be removed and the time it took to reach maximum recorded. However, the strip from the contralateral eye should not be removed until it too has reached maximum score prior to the 5 minute endpoint.
7. As multiple Schirmer tests are performed, new anesthetic drops should be added as necessary.

Schirmer Test Using Cotton Swab Nasal Stimulation
1. At screening visit #1, the Schirmer test should be performed using cotton swab nasal stimulation. With new strips in place, the examiner should insert cotton swabs in both participant's nostrils simultaneously and gently probe both nasal middle turbinates for approximately 30 seconds. After this, the examiner can simply hold the swabs in place, applying gentle pressure, and repeat probing intermittently as necessary.
2. Alternatively, the participant can be instructed to hold the cotton swabs and gently probe both nasal turbinates simultaneously, resting intermittently before probing again. The examiner should continuously coach the participant on how to perform this test properly.
3. The Schirmer strips should remain in place until five minutes have elapsed or they have reached maximum score.

Both Schirmer scores will be recorded and verified that they meet the inclusion criteria. As two Schirmer tests are performed, new anesthetic drops should be instilled as necessary.

Schirmer Test with Each of Two Nasal Spray Applications

With each of the two nasal applications, the Jones Schirmer test with topical anesthetic will be used to assess tear production using the following steps:
1. Topical anesthetic drops such as 0.5% proparacaine hydrochloride or equivalent should be instilled in both eyes of the participant for each application.
2. The participant will be instructed to keep the eyes gently closed for one minute.
3. After opening the eyes and allowing the eyes to recover for approximately one additional minute, excess moisture in the inferior fornix is gently removed with a spear.
4. Schirmer strips (35 mm×5 mm size filter paper strip) will be placed in each eye at the junction of the middle and lateral thirds of the lower eye lid.
5. Under ambient light, the participant will be instructed to look forward and to blink normally during the course of the test. The test should be performed in a room with no direct air on the participant's face.
6. After five minutes, strips will be removed from both eyes and the amount of wetting will be recorded. The strips should be taped to the CRF.

Dry Eye Provocation and Symptom Assessment

The ClimaTears Goggle System (Biocentric Developments, LLC) will be used to reduce periocular humidity and induce symptoms of dry eye in patients. This system was designed for the purpose of standardizing testing conditions for clinical studies of dry eye patients.

Patients will wear the ClimaTears Goggles continuously for up to 90 min, with their symptoms recorded via the visual analog scale (VAS) every 5 minutes during the testing period. See FIG. 4. The subject will be asked to rate their dryness symptoms (both eyes simultaneously) by placing a vertical mark on the horizontal line to indicate the level of discomfort, 0 corresponds to "no dryness" and 5 corresponds to "maximal dryness." The assessment line length of the scale will be 100 mm. There are many symptoms of dry eye, including dryness, sticky feeling, burning, foreign body sensation, itching, blurred vision, sensitivity to light, and pain. The subject is instructed: Please rate the severity of your current "dryness" symptoms (and no others) by drawing a vertical line on the line below.

At Day 0, patients will begin wearing the goggles and be monitored until they reach a symptom score of 45 mm or more for two consecutive measurements, at which time they will randomly receive a dose of either OC-01 nasal spray or the control nasal spray (Placebo (OC-01 Vehicle Nasal Spray)), administered 2.5 minutes after the two consecutive 45 mm measurements. Symptoms will be continued to be monitored until the patient again reaches a score of 45 mm or higher for two consecutive measurements, at which time the patient will receive a second nasal dose of which ever test article they did not receive the first time. After the second nasal dose, symptoms will be monitored again until the patient reaches a score of a score of 45 mm or higher for two consecutive measurements. At that time, the goggles will be removed and the test will end. If still ongoing, the test will be terminated after 90 minutes of exposure to the goggles environment. At the end of this period, each patient will be asked to decide which of the nasal sprays made provided more relief of their dry eye symptoms.

At Day 7, patients will begin wearing the goggles and be monitored until they reach a symptom score of 45 mm or more for two consecutive measurements, at which time they will receive a dose of the OC-01 nasal spray. Symptoms will continued to be monitored until the patient again reaches a score of 45 mm or higher for two consecutive measurements, at which time the goggles will be removed and the test will end. If still ongoing, the test will be terminated after 90 minutes of exposure to the goggles environment.

Patients entering with a baseline symptoms score of more than 45 mm will have a treatment threshold equal to this baseline score, and will thus receive treatment after two consecutive symptoms measurements of greater than or equal to this value.

The instructions (in bold above) will be read to the patient before the test begins, and before recording symptoms values immediately following the administration of either nasal spray.

Example 2: OC-01 Formulation

OC-01 contains 0.1% w/v Compound 1 in sterile phosphate buffered saline (PBS) consisting of 137 mM sodium chloride, 2.7 mM potassium chloride and 10 mM phosphate buffer at pH 7.4 without preservatives. The formulation is packaged in a 20 mL opaque polyethylene nasal spray bottle that delivers a unit dose of 50 microliters. The vehicle control is supplied in the identical packaging. Both OC-01 and vehicle are labeled with a code denoting the contents of the package, which will not be known to the participants or masked study personnel.

Example 3: Additional Pharmaceutical Formulations

To prepare pharmaceutical formulations suitable for administration intranasally, 50 mg of a compound of Formula (I), (II), (IIIa), or (IIIb) is dissolved in 10 mL of a specified vehicle. 1 mL of this solution is diluted in 9 mL of vehicle to afford a "0.1× dilution" formulation. Following the first dilution, 1 mL of the "0.1× dilution" formulation is diluted in 9 mL of vehicle to afford a "0.01× dilution" formulation. The three formulations with varying concentrations of the nicotinic acetylcholine receptor agonist are stored at 4° C.

Example 4: Compound 1: An Orally Effective and Selective Alpha4beta2 Neuronal Nicotinic Receptor Agonist with Anti-Allodynic Activity The results reported herein summarize the in-vitro and in-vivo profile of a novel selective alpha4beta2 NNR agonist, Compound 1, which demonstrates a promising overall preclinical drug profile for neuropathic pain management in humans. Compound 1 has a high binding affinity for alpha4beta2 (Ki=27 nM), and exhibits substantially less activity at the alpha7 NNR or the alpha3beta2 or alpha3beta4 nAChRs compared to nicotine. Functionally, Compound 1 was shown to be an agonist at the alpha4beta2 receptor (120%) and in a DA release model ($E_{max}$=114% of nicotine). Furthermore, electrophysiology studies indicate that Compound 1 has agonist activity at both high and low sensitivity alpha4beta2-containing NNR subtypes. It is readily absorbed following oral administration and has favorable pharmacokinetics. Compound 1 is active in promoting anti-allodynia following acute and repeat administration with demonstrated effectiveness in animal models of neuropathic pain. Specifically, Compound 1 significantly reversed tactile allodynia in a model of diabetic neuropathy (STZ-induced) when administered both acutely (0.1 and 1 mg/kg; p.o.) and following repeat administration (0.1-10 mg/kg p.o.). Compound 1 was also efficacious in reversing tactile allodynia in a chemotherapy-induced neuropathy model (paclitaxel-induced; 0.01-1 mg/kg p.o.). Compound 1 exhibits a quicker onset of action (i.e., 30 min) and comparable efficacy and duration of action compared to gabapentin. The compound demonstrated a favorable safety margin in preclinical safety studies, including in vitro and in vivo cardiovascular studies, acute and 14-day repeat dose studies, definitive 90-day studies and a full complement of genotoxicity studies. Overall, results of preliminary studies with Compound 1 provide evidence for a neuronal nicotinic modulator with potential efficacy in controlling neuropathic pain and a superior composite profile compared to previously characterized analgesic compounds acting via nicotinic or other neuronal mechanisms.

Example 5: Compound 1 Properties

Compound 1: α4β2

Compound 1 binds to the human α4β2-containing receptors nAChR with Ki=17 nM.

Compound 1 is a full agonist at the human α4β2-containing nAChR and is more efficacious than nicotine (Emax=120% compared to nicotine, $EC_{50}$=600 nM).

There are two types of α4β2-containing nAChR, depending on which subunit occupies the fifth subunit of the pentaineric complex. There is a high sensitivity subtype, (α4β2)$_2$β2, and a low sensitivity subtype, (α4β2)$_2$α4. Targacept used a rudimentary assay to encourage the expression of one subtype over the other based on incubation temperature. The database summary indicates that Compound 1 is a full agonist (Emax=120%) at both the high and low sensitivity subtypes with similar potencies ($EC_{50}$=3300 for HS and $EC_{50}$=5300 for LS). According to the database summary, Compound 1 fully inhibits the high and low sensitivity subtypes with similar potencies ($IC_{50}$===430 for HS and $IC_{50}$=450 for LS). These data indicate that Compound 1 acts similarly at both the high sensitivity and low sensitivity α4β2 nAChR.

Compound 1: α3β4

Compound 1 binds to the human α3β4-containing receptors nicotinic acetylcholinergic receptor (nAChR) with Ki=600 nM.

Compound 1 is an agonist at the human α3β4-containing nAChR and is less efficacious than nicotine (Emax=60% compared to nicotine and $EC_{50}$=18,000 nM in SH-SY5Y cells; Emax=79% compared to nicotine and $EC_{50}$=22.000 nM in IMR-32 cells).

Compound 1: α7

Compound 1 binds to the human α7 nAChR with Ki=15,000 nM.

Example 6: Testing of a Panel of Compounds with Various Receptor Binding Profiles A panel of twenty compounds with various receptor binding profiles, including other nicotinic acetylcholine receptor (nAchR) agonists were tested. At the onset of the experiment, 50 microliters of a 0.01 mg/mL compound formulation was administered intranasally to three subjects. The dose of each compound was increased logarithmically until an effect on tearing and/or a discomfort response was observed, up to a maximum compound concentration of 10 mg/mL. The effect on tearing and the discomfort response were recorded for each compound, shown in the table below. Compound 1 demonstrated a desired combination of efficacy and tolerability.

| Compound | Target Receptor | Causes Tearing | Discomfort Response |
|---|---|---|---|
| Varenicline | nAchR α7, α3β4 (partial), α4β2 (partial), α6β2 (partial) | Yes | No |
| Nicotine | nAchR: broad spectrum | Yes | Severe |
| Compound 1 | nAchR α4β2, α3β4, α3β2 (partial) | Yes | No |
| TC-6987 | nAchR α7 | No | No |
| Cytisine | nAchR α3β4, α7 and α4β2 (partial) | Partial | Moderate |
| ABT-418 | nAchR α4β2, α3β4, α2β2, α7 | Yes | Moderate |
| PHA-543613 | nAchR α7 | No | No |
| GTS-21 | nAchR α7, α4β2 (partial) | Yes | Severe |
| Denatonium | T2R | No | No |
| Eucaliptol | TrpM8 | No | No |
| Geraniol | TrpM8 | No | No |
| Pulegone | TrpM8 | No | No |
| Menthol | TrpM8/V3 | No | No |
| Capsaicin | TrpV1 | Yes | Severe |
| Benzaldehyde | TrpV1/A1 | No | No |
| Camphor | TrpV1/V2/A1 | No | No |
| Eugenol | TrpV1/V3/A1/M8 | No | No |
| Carvacrol | TrpV2/A1/M7 | Yes | Severe |
| Ethylvanillin | TrpV3 | No | No |
| Betahistine | H1 | No | No | nAchR—nicotinic acetylcholine receptor; T2R—taste receptor type 2; TrpA1—transient receptor potential cation channel, subfamily A, Member 1; TrpM7—transient receptor potential cation channel, subfamily M, Member 7; TrpM8—transient receptor potential cation channel, subfamily M, Member 8; TrpV1—transient receptor potential cation channel, subfamily V, Member 1; TrpV2—transient receptor potential cation channel, subfamily V, Member 2; TrpV3—transient receptor potential cation channel, subfamily V, Member 3; H1—histamine receptor H1.

Example 7: Pharmacology Overview and Pharmacodynamics of Compound 1

The tables below show pharmacological and pharmacodynamics data of Compound 1.

Primary Pharmacodynamics

| Type of Study | Species/Strain | Method of Administration | Noteworthy Findings |
|---|---|---|---|
| RECEPTOR BINDING | | | |
| Receptor Binding - α4β2 [Inhibition of [³H]-(S)-Nicotine binding to the α4β2 nicotinic acetylcholine receptor by Compound 1 | Rat/brain membrane preparations | in vitro dissolution | Binding to α4β2 (rat) Potently inhibits [³H]-S-nicotine binding to the α4β2 in rat brain cortical membranes (Ki = 27 nM). Nicotine displaces [³H]-S-nicotine in rat cortical membranes with a Ki = 2 nM. |
| Receptor Binding - α4β2 | Human/Recombinant receptors - cells | in vitro dissolution | Binding to α4β2 (human) Potently inhibits[³H]-S-nicoline binding to human α4β2 expressed in SH-EP1 cells (Ki = 17 nM) |
| Receptor Binding - α3β2 | Human/Recombinant receptors - cells | in vitro dissolution | Binding to α3β2 (human) Potently inhibits[³H]-S-nicoline binding to human α3β2 expressed in HEK cells (Ki = 27 nM) |
| Receptor Binding - α7 Inhibition of [³H]-Methyllycaconitine ([³H]MLA) binding to the α7 nicotinic acetylcholine receptor by Compound 1 | Rat/brain membrane preparations | in vitro dissolution | Binding to α7 (rat) Poor inhibitor of [³H]-MLA binding to the α7 in rat brain hippocampal membrane preparations (Ki = 5,500 nM). Nicotine displaces [³H]-MLA in rat cortical membranes with a Ki = 1000 nM. |
| Receptor Binding - α7 | Human/Recombinant receptors - cells | in vitro dissolution | Binding to α7 (human) Poor inhibitor of [³H]-epibatidine binding to human α7 expressed in HEK cells (Ki = 15000 nM) |
| Receptor Binding - muscle receptor (α1β1δγ) | Human/Native human receptors - cells | in vitro dissolution | Binding to α1β1δγ (human) Inhibited the binding of [³H]-epibatidine to receptors in TE-671 membranes with a Ki of 36 μM |
| Receptor Binding - ganglionic receptor (α3β4) | Human/Native human receptor - cells | in vitro dissolution | Binding to α3β4 (human) Inhibited binding of [³H]-epibatidine to receptors in SH-SY5Y membranes with a Ki of 620 nM |
| RECEPTOR FUNCTION | | | |
| Receptor Function - α4β2 | Human/Recombinant human receptor - cells | in vitro dissolution | Function α4β2 (human) - In SH-EP1 cells expressing human α4β2, Compound 1 evoked Ca++ flux with an Emax of 120% of nicotine and an EC50 of 5300 nM. |
| Receptor Function - Dopamine release | Rat brain striatum membranes | in vitro dissolution | Function α4β2 (rat) - Compound 1 induced [³H]-DA release from rat striatal synaptosomes with an Emax of 114% of nicotine and an EC50 of 3932 nM. Compound 1 is a full agonist at the α4β2 subtype. |

-continued

| Type of Study | Species/Strain | Method of Administration | Noteworthy Findings |
|---|---|---|---|
| Receptor Function - ganglionic receptors (rat) | Human/ Recombinant human receptor - cells | in vitro dissolution | Function α3β4 (rat) -Activity at rat ganglion receptors in PC-12 cells was low (19%). |
| Receptor Function - ganglionic receptors (human) | Human ganglion cells | in vitro dissolution | Function α3β4 (human) - In human ganglion (SH-SY5Y cells) activity was low (average Emax = 60% vs. nicotine and EC50 was 18 μM). In human ganglion (IMR-32 cells) activity was higher (average Emax = 79% vs. nicotine) but potency was also low, with an EC50 of 22 μM. |
| Receptor Function - muscle receptor (α1β1δγ) | Human/ Recombinant human receptor - cells | in vitro dissolution | Function muscle receptor (α1β1δγ) Compound 1 produced minimal activation of human muscle receptors in TE671 cells (Emax = 42% of nicotine and EC50 = 15 μM) The reduced potency at muscle and ganglion NNRs suggests a lower potential for side effects with Compound 1 as compared to nicotine. |

20

Secondary Pharmacodynamics

| Type of Study | Species/ Strain | Method of Administration | Doses (mg/kg) | Gender and No. per Group | Noteworthy Findings |
|---|---|---|---|---|---|
| IN VITRO BINDING (OFF-TARGET RECEPTORS) | | | | | |
| In vitro binding | Variable/ 10 μM | Solution at $10^{-2}$ M in DMSO then diluted in $H_2O$ | N/A | N/A | Besides high affinity for neuronal nicotinic receptors (100%), the only other binding affinity that Compound 1 (hemigalactarate salt) demonstrated was to the muscarinic (non-selective) sites (51%). In a follow-up assay (CEREP No. 9920133), dose response assessments of these interactions showed that the Ki for the muscarinic M4 was 5.8 μM. Ki values for the remaining muscarinic subtypes were >10 μM. |
| IN VIVO | | | | | |
| Analgesic effects of Compound 1 (hot plate test) | Mouse: NMRI | po | (single doses) 0.01 0.1 1.0 mg/kg | 10 M | Compound 1 (hemigalactarate salt) (0.01, 0.1 and 1 mg/kg po) did not affect the foot-licking latency as compared to vehicle control. Morphine (64 mg/kg, po) significantly increased (+57%) the foot-licking latency when compared to vehicle control group. Compound 1 (hemigalactarate salt) failed to elicit analgesicactivity at the dose levels tested. |
| Analgesic effects of Compound 1 (formalin test) | Mouse: CD-1 | po | (Dosed once daily for 7 days) 0.1 1.0 10.0 | 10 M | On Day 1, Compound 1 (hemigalactarate salt) (0.1, 1 and 10 mg/kg) and Aspirin at 100 mg/kg failed to cause any significant analgesic effects during the 35-minute period after formalin injection. Morphine (30 mg/kg, po) produced a significant analgesic activity relative to the vehicle control group during the early phase (05 minutes) and late phase (15-25 minutes) after the formalin injection at 1 hour post-dosing. On Day 7, Compound 1 (0.1, 1 and 10 mg/kg), Aspirin (100 mg/kg) failed to produce any analgesic activity. Analgesic effects of morphine (30 mg/kg) persisted on Day 7. |
| Reversing symptoms of paclitaxel-induced neuropathy | Rat: Dawley | po | Once daily for 28 days 0.01, 0.1, 1.0 mg/kg Gabapentin 100 mg/kg | 10 M | Allodynia at 3 and 4 weeks post-paclitaxel dosing were significantly reduced from baseline levels in the vehicle group, indicating onset of neuropathic pain. A two-way ANOVA for all the data indicated a treatment |

| Type of Study | Species/ Strain | Method of Administration | Doses (mg/kg) | Gender and No. per Group | Noteworthy Findings |
|---|---|---|---|---|---|
| | | | (ip) | | effect, an effect of time, and an interaction (all p < 0.001). Gabapentin at 100 mg/kg, was effective at reversing allodynia observed in the vehicle-treated groups when delivered 90 min before testing (p < 0.001; Bonferroni post-hoc test) at both Weeks 3 and 4. Chronically administered Compound 1 at all doses significantly reduced allodynia as compared with the vehicle-treated group at 4 weeks post-paclitaxel dosing but at 3 weeks post-dosing, only the 0.1 mg/kg dose was significantly different from vehicle. |
| Effects of Compound 1 onmechanical allodynia (STZ rat model of diabetic neuropathy) | Rat: Sprague-Dawley | po | Acute 0.01, 0.1, 1 mg/kg Gabapentin 100 mg/kg (ip) Once daily for 6 weeks 0.1, 1, 10 mg/kg | 12 M | Acute Dosing - Compound 1 reversed allodynia at 0.5 and 2 hr post-dosing in the 0.1 and 1 mg/kg acute dosing group. Gabapentin (100 mg/kg) was also effective at reducing allodynia at 0.5 and 2 hr post dosing when compared to the vehicle treated group. Compound 1 closely resembled the levels of allodynia and time course of effectiveness of Gabapentin. Repeat Dosing - Chronically administered Compound 1 at all dosessignificantly reduced allodynia as compared with the vehicle-treated group at 6 weeks post-STZ dosing but at 4 weeks post-dosing, no dose levels produced reversal of mechanical allodynia. No changes in blood glucose levels occurred in the animals treated with Compound 1. The insulin-treated group showed reduced blood glucose levels but no significant improvement in pain sensitivity. |

40

Safety Pharmacology

| Organ Systems Evaluated | Species/ Strain | Method of Admin | Doses (mg/kg) | Gender and No. per Group | Noteworthy Findings |
|---|---|---|---|---|---|
| CNS | Rat: Sprague-Dawley | po | 15 50 150 | 5 M | Compound 1 had no effect on general behavior (Irwin profile) with a NOEL greater than 150 mg/kg. |
| CNS | Rat: Sprague-Dawley | po | 10 30 100 | 8 M | Compound 1 had no effect on general behavior (Irwin profile) at doses up to and including 100 mg/kg. |
| CNS | Rat: Sprague-Dawley | po | 3 10 30 | 8 M | Compound 1 at all dose levels tested was not associated with behavioral sensitization as assessed by motor activity in rats. Nicotine administration resulted in marked behavioral sensitization. Acute challenge with nicotine in rats treated with Compound 1 for 15 days and administering Compound 1 at 30 mg/kg to rats after they had been dosed with nicotine daily for 15 days indicated no interaction between Compound 1 and nicotine in terms of behavioral sensitization. |
| CNS | Rat: Sprague-Dawley | po | 10 30 100 | 8 M | Compound 1 in combination with a subconvulsant dose of pentylenetetrazole did not did not induce convulsions. D-amphetamine sulphate in combination with pentylenetetrazole induced convulsions in 6 |

| Organ Systems Evaluated | Species/ Strain | Method of Admin | Doses (mg/kg) | Gender and No. per Group | Noteworthy Findings |
|---|---|---|---|---|---|
| | | | | | out of 8 rats.<br>Compound 1 given orally at doses of 10, 30, or 100 mg/kg in combination with pentylenetetrazole did not elicit convulsant properties.<br>The NOEL was 100 mg/kg. |
| CNS | Rat: Sprague-Dawley | po | 10<br>30<br>100 | 8 M | Compound 1 had no effect on body temperature at doses up to and including 100 mg/kg. |
| Cardiovascular | hERG channel | in vitro | 30 μM<br>100 μM<br>300 μM | N/A | Compound 1 caused noteworthy inhibition of hERG dose-dependently with an IC50 value of 285 uM. |
| Cardiovascular | Rabbit Purkinje fibers | in vitro | 3 μM<br>10 μM<br>30 μM<br>100 μM | N/A | Compound 1 induced a concentration dependent lengthening of the action potential directly at 30 and 100 μM, but had no effect on resting membrane potential, action potential amplitude, and Vmax at any concentration. |
| Cardiovascular | Rabbit Purkinje fibers | in vitro | 3 μM<br>10 μM<br>30 μM<br>100 μM | N/A | Compound 1 induced a concentration-dependent lengthening of the action potential duration at 30 and 100 μM (and had no effect at 3 and 10 μM). It had no noticeable effects on resting membrane potential, action potential amplitude, or maximum rate of rise of the action potential at any concentration tested. |
| Cardiovascular | Guinea Pig | iv | 0.1<br>0.3<br>1<br>3<br>10 | 4 M | At 0.1 and 0.3 mg/kg, blood pressure and heart rate were unchanged.<br>At 1, 3, and 10 mg/kg, the peak increase in diastolic blood pressure was 41 mmHg; the peak increase in systolic blood pressure was 58 mmHg; and the peak increase in heart rate was 41 beats per minute.<br>At 1 and 3 mg/kg, the effects resolved in 3 minutes.<br>10 mg/kg was lethal.<br>Compound 1 caused no effects on ECGs at doses up to 0.3 mg/kg, mild and reversible effects on QTc at 1 mg/kg, and severe effects at 3 and 10 mg/kg.<br>The intravenous dose of 0.3 mg/kg is the MTD. |
| Cardiovascular | Dog: Beagle | po | 5<br>10<br>20 | 2 M & 2 F | Compound 1 produced a transient and slight increase in blood pressure and bursts of sinus tachycardia in all dogs.<br>5 mg/kg produced no other findings.<br>10 mg/kg was associated with 1 ventricular extrasystole 10 to 25 minutes after dosing.<br>20 mg/kg was associated with 1 ventricular extrasystole 10 to 25 minutes after dosing. In addition, slight lengthening of the QT interval and emesis were noted at 20 mg/kg.<br>TK determination revealed a terminal half-life of 1.3 to 4.2 hours, variable absorption, and low exposure at the highest dose of 20 |
| Cardiovascular | Dog: Beagle | po | 2.5<br>5<br>10<br>Once daily for 5 days | 3 M & 3 F | PD: Oral administration of Compound 1 was associated with increased arterial blood pressure (mainly diastolic), marked tachycardia, and decreased PQ interval. These effects were similar after a single dose and after 5 days of dosing, and they were not dose-dependent.<br>There were no changes in the QRS duration, QT interval, or body temperature.<br>TK: There were no proportional increases in Cmax and AUC on either sampling day. There were no differences between the sexes. No accumulation was observed after repeat dosing. |

-continued

| Organ Systems Evaluated | Species/ Strain | Method of Admin | Doses (mg/kg) | Gender and No. per Group | Noteworthy Findings |
|---|---|---|---|---|---|
| Cardiovascular | Monkey: Cynomologous | po | 3 10 30 | 3 M & 3 F | Single oral doses (3, 10, and 30 mg/kg) of TC6499 to conscious telemetered monkeys did not induce notable effects on arterial pressure, heart rate, ECG parameters, and body temperature. |
| Respiratory | Rat: Sprague-Dawley | po | 10 30 100 | 9 M | 10 and 30 mg/kg did not cause changes in respiratory parameters. 100 mg/kg produced a moderate and shortlasting increase in respiratory rate, minute volume, and peak inspiratory flow and a decrease in inspiration time. There were no changes in tidal volume and index of airway resistance during the 5 hour observation period. The NOEL was 30 mg/kg. |

Example 8: In Vitro Data and Summary Report of Compound 1

The table below shows in vitro data and summary report of Compound 1.

| Species | Subtype | Ki (nM) | Assay type | Tissue Type |
|---|---|---|---|---|
| Human | a4b2 | 17 | [$^3$H] Nicotine | α4β2 Transfected SH-EP1 cells |
| Rat | a4b2 | 34 | | |
| Rat | a4b2 | 27 | [$^3$H] Nicotine | Rat cortical membranes |
| Human | a3b2 | 27 | [$^3$H] Nicotine | α3β2 Transfected HEK cells |
| Human | a6/a3b2b3 | 240 | | |
| Human | a4b4 | 680 | | |
| Human | a6b3b4a5 | 1100 | | |
| Human | a7 | 15000 | [$^3$H] mla | α7 Transfected HEK cells |
| Rat | a7 | 3500 | | |
| Rat | a7 | 5533 | [$^3$H] MLA | Rat hippocampal membranes |
| Human | Ganglion-type (a3b4*) | 620 | [$^3$H]Epibatidine | SHSY5Y cell line membranes |
| Human | Ganglion-type (a3b4*) | 8800 | | |
| Human | Muscle-type | 36000 | [$^3$H]Epibatidine | TE671 cell line membranes |

| Species | Subtype | EC50 | Emax | Assay Type | Tissue Type |
|---|---|---|---|---|---|
| Rat | a4b2*/a6b2* | 3900 | 110 | [$^3$H] DA release | Rat Striatal Synaptosomes |
| | | 3932 | 114 | | |
| Rat | a4b2*/a6b2* | 0.55 DA Release ratio | | [$^3$H] DA release | Rat Striatal Synaptosomes |
| Human | a4b2 | 600 | 120 | Ca++ Flux | α4β2 Transfected SH-EP1 cells |
| Human | a4b2 | 5300 | 120 | Ca++ Flux | |
| Human | a4b2 HS 29° C. | 3300 | 120 | Ca++ Flux | |
| Human | a4b2 LS 37° C. | 5300 | 120 | Ca++ Flux | |

| | | (IC50) | (Imax) | | |
|---|---|---|---|---|---|
| Human | a4b2 HS 29° C. | 430 | 98 | Ca++ Flux | |

| | | (DC50) | (Dmax) | | |
|---|---|---|---|---|---|
| Human | a4b2 LS 37° C. | 450 | 98 | Ca++ Flux | |
| Human | a3b2 | 8700 | 66 | Ca++ Flux | |
| Human | a6/a3b2b3 | 470 | 92 | Ca++ Flux | |

| | | (IC50) | (Imax) | | |
|---|---|---|---|---|---|
| Human | a6/a3b2b3 | 2800 | 49 | | |

| | | (DC50) | (Dmax) | | |
|---|---|---|---|---|---|
| Human | a6/a3b2b3 | 31 | 99 | Ca++ Flux | |
| Human | a4b4 | 4300 | 98 | Ca++ Flux | |
| Human | Ganglion-type (a3b4*) | 13000 | 150 | Ca++ Flux | |
| Human | Ganglion-type (a3b4*) | 18000 | 60 | Rb+ Flux | SHSY5Y cells |
| Human | Ganglion-type (a3b4*) | 22000 | 79 | Rb+ Flux | IMR cells |
| Rat | Ganglion-type (a3b4*) | 53000 | 35 | Ca++ Flux | |
| Rat | Ganglion-type (a3b4*) | | 19 | Rb+ Flux, single point | |
| Human | Muscle-type | 15000 | 42 | Ca++ Flux | |
| Human | Muscle-type | | 12 | Rb+ Flux, single point | |

Example 9: Pre-Clinical Data of Compound 1 (5-2-[(R)-Pyrrolidin-3-Yl]-Vinyl)-Pyrimidine, Hemi-Galactarate, Dihydrate)

Preclinical data of Compound 1 (5-2-[(R)-Pyrrolidin-3-yl]-vinyl)-pyrimidine, hemi-galactarate, dihydrate) is presented below.

Chemical Name and Structure

| | |
|---|---|
| Name | 5-2-[(R)-Pyrrolidin-3-yl]-vinyl)-pyrimidine, hemi-galactarate, dihydrate (Compound 1) |
| Structural Formula | 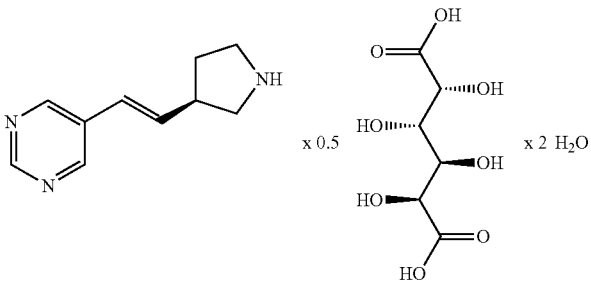 [SMILES: C(=C\[C@H]1CCNC1)/c1cncnc1 ; O=C(O)[C@@H](O)[C@H](O)[C@H](O)[C@@H](O)C(=O)O ; O] |
| Molecular Formula | $C_{10}H_{13}N_3 \cdot 0.5\ C_6H_{10}O_8 \cdot 2\ H_2O$ |
| Molecular Weight | 175.24 (free base)<br>316.34 (hemi-galactarate salt) |

Dosage Form, Route of Administration and Dosing Regimen

| | |
|---|---|
| Dosage Form | Nasal Spray |
| Routee of Administration | Intra-nasal |
| Dosing Regimen | For Phase 2 clinical study, subjects will receive a low dose, medium dose, or high dose (not to exceed 3.3%, i.e. 33.2 μg/μL of Compound 1-free base) of Compound 1, nasal formulation (5-2-[(R)-Pyrrolidin-3-yl]-vinyl)-pyrimidine, hemi-galactarate, dehydrate) at 2 study visits. |

Chemistry Manufacturing and Controls Summary

A batch of drug substance was manufactured under cGMP conditions and assigned a 36-month expiry based upon ICH stability conducted on previous batches of drug substance. This batch will be used to manufacture the clinical supplies for a clinical study. The batch has been stored under controlled ambient conditions since its manufacture and has exceeded the 36 month expiry. Therefore, it will be tested to confirm that the material continues to meet the initial release specifications and will then be placed on stability under ICH real time conditions in order to monitor its stability through the course of the proposed study. The drug product intranasal formulation will be compounded and used within several weeks so any long term degradation of drug substance stability will present minimal risk.

Drug Substance

The drug substance for Compound 1 nasal spray was previously used in clinical trials as an oral formulation. In clinical studies, Compound 1 was considered safe but failed to reach efficacy endpoints. Compound 1 is re-formulated as a nasal spray.

Below summarizes the general properties and stability of Compound 1.

General Properties

| Property | Result |
|---|---|
| Physical Form | Off-white to yellow powder |
| Solubility | The solubility of Compound 1 was tested in several aqueous solutions. The results of which are depicted below. |

| Solvent | Solubility (mg/mL as base equivalents) |
|---|---|
| 0.1N HCl | >10 |
| 0.1M citrate buffer (pH 4.0) | >10 |
| Water (pH 5.9) | >10 |
| 0.1M phosphate buffer (pH 6.8) | >10 |

| Property | Result |
|---|---|
| Polymorphism | Four morphic forms have been identified and have been denoted A, B, C, and D. Form A is a dihydrate form and is physically unaltered from 50 to 85% RH. Forms B, C and D are anhydrous forms of the product. The anhydrous forms convert to Form A when exposed to RH above 50%. Form A will convert to Forms B and C when exposed to severe dehydrating conditions; but will back-transform to Form A when exposed to RH above 50%. Using powder x-ray diffraction (PXRD) to establish and verify the preferred morphic form (Form A) of the drug substance, a differential scanning calorimetry (DSC) scan that is specific to Form A of the drug substance was established. DSC testing is performed as an in-process control at the final step of the |

| | |
|---|---|
| | synthesis to confirm that Form A has been obtained. |
| Optical Isomerism | Compound 1, free-base has one chiral center. The chiral centers are generated during the synthesis. The chirality of the compound is controlled by a resolution/purification step in the synthesis. |
| Optical Rotation | $[\alpha]_D^{20} = -7.5 \pm 0.5$ (c = 0.5, water) |
| pKa Data | pKa(1): 1.73<br>pKa(2): 10.3 |
| Partitioning Coefficient | log P (predicted): 0.29 |
| Distribution Coefficient | Log D (pH 7.4): <1 |
| Melting Point | 180-183° C. |

Description of Manufacturing Process

The proposed clinical batch of drug substance was manufactured. A manufacturing process is described in WO2010/065443, which is herein incorporated by reference in its entirety.

Specifications

The drug substance was released following manufacture against the specifications described in Table 1. These specifications will be applied to the retest of the batch executing those tests that are stability indicating: Appearance, Assay, Related Substances, Chiral Purity and Water Content. These stability indicating tests and specifications will also be used to monitor the stability of the drug substance throughout the course of the proposed study.

TABLE 1

Specifications for Compound 1

| Test | Acceptance Criteria | Analytical Method |
|---|---|---|
| Appearance[1] | Off-white to yellow solid | Visual |
| Identification | | |
| FTIR | Spectrum of the sample is consistent with that of a reference standard similarly prepared. | FTIR |
| HPLC | The retention time of the principal peak corresponds to the retention time of the principal peak in the reference standard. | HPLC - UV |
| Assay[1] | Weight percent assay is 98-102% compared to a reference standard, on a volatile and moisture free basis. | HPLC - UV |
| Related Substances[1] | Reporting level >0.05% | HPLC-UV |
| Unspecified individual impurities | NMT 1% (a/a) | |
| Amide[2] | NMT 1% (a/a) | |
| cis-Isomer[3] | NMT 1% (a/a) | |
| Total specified and unspecified impurities | NMT 2% (a/a) | |
| Chiral Purity[1] | NMT 2% (a/a) of (S) enantiomer | Chiral HPLC - UV |
| Residual Solvents and Process Volatile Impurities (Methods A and B) Ethanol | NMT 5000 ppm | GC-FID |
| Ethyl acetate | NMT 3000 ppm | |
| Heptane | NMT 5000 ppm | |
| MTBE | NMT 5000 ppm | |
| 2-propanol (IPA) | NMT 5000 ppm | |
| Chloroform | NMT 5000 ppm | |
| Dimethoxyethane | NMT 600 ppm | |
| Dimethylacetamide | NMT 1090 ppm | |
| N-Methylpyrrolidone | NMT 530 ppm | |
| Tetrahydrofuran | NMT 720 ppm | |
| Toluene | NMT 890 pm | |
| Residue on Ignition | NMT 0.5% (w/w) | cUSP<281> |
| Heavy Metals | NMT 20 ppm | cUSP<231> |
| Palladium | NMT 20 ppm | ICP-OES |
| Galactaric Acid Content | 35.5% to 39.5% | Titrimetric assay |
| Water Content[1] | Report results | Karl Fischer cUSP<921> |

[1]Testing Performed on stability
[2]Amide is 2,3,4,5-tetrahydroxy-6-oxo-6-[(3R)-(2-pyrimidine-5-yl-vinyl)-pyrrolidine-1-yl]-hexanoic acid
[3]cis-Isomer is 5-{(Z)-2-[3-pyrrolidin-3-yl]vinyl}pyrimidine Batch Release A batch was tested and released against the specifications described herein and the following results were obtained as shown in Table 2.

TABLE 2

Batch Analysis for Compound 1 Drug Substance

| Test | Acceptance Criteria | Result |
| --- | --- | --- |
| Appearance | Off-white to yellow solid | Off-white solid |
| Identification | | |
| FTIR | Spectrum of the sample is consistent with that of a reference standard similarly prepared. | Conforms |
| HPLC | The retention time of the principal peak corresponds to the retention time of the principal peak in the reference standard. | Conforms |
| Assay | Weight percent assay is 98-102% compared to a reference standard, on a volatile and moisture free basis. | 100.1% (w/w) |
| Related Substances | Reporting level >0.05% | |
| Unspecified individual | NMT 1% (a/a) | NR[3] |
| Amide[1] | NMT 1% (a/a) | ND[4] |
| cis-Isomer[2] | NMT 1% (a/a) | ND[4] |
| Total specified and unspecified impurities | NMT 2% (a/a) | NR[3] |
| Chiral Purity | NMT 2% (a/a) of (S) enantiomer | ND[4] |
| Residual Solvents and Process Volatile Impurities | NMT 5000 ppm | 461 ppm |
| Ethanol | | |
| Ethyl acetate | NMT 3000 ppm | ND[4] |
| Heptane | NMT 5000 ppm | ND[4] |
| MTBE | NMT 5000 ppm | ND[4] |
| 2-propanol (IPA) | NMT 5000 ppm | ND[4] |
| Chloroform | NMT 5000 ppm | ND[4] |
| Dimethoxyethane | NMT 600 ppm | ND[4] |
| Dimethylacetamide | NMT 1090 ppm | 100 ppm |
| N-Methylpyrrolidone | NMT 530 ppm | ND[4] |
| Tetrahydrofuran | NMT 720 ppm | ND[4] |
| Toluene | NMT 890 ppm | ND[4] |
| Residue on Ignition | NMT 0.5% (w/w) | 0.0% |
| Heavy Metals | NMT 20 ppm | ≤20 ppm |
| Palladium | NMT 20 ppm | ≤20 ppm |
| Galactaric Acid Content | 35.5% to 39.5% | 38.3% w/w |
| Water Content | Report results | 11.4% w/w |

[1]Amide is 2,3,4,5-tetrahydroxy-6-oxo-6[(3R)-2-pyrimidine-5-yl-vinyl)-pyrrolidin-1-yl]-hexanoic acid
[2]cis-Isomer is 5-{(Z)-2-[3-pyrrolidin-3-yl]vinyl}pyrimidine (synthesis impurity and major UV degradation product).
[3]None reported
[4]None detected Stability A previous cGMP lot of Compound 1 was manufactured. The 3-year stability study protocol for Compound 1 is provided in Table 3 below.

TABLE 3

Protocol for Stability Testing of Compound 1

| | Month | | | | | | | | |
| --- | --- | --- | --- | --- | --- | --- | --- | --- | --- |
| Conditions | 0 | 1 | 3 | 6 | 9 | 12 | 18 | 24 | 36 |
| 25° C./60% RH | A | B | B | B | B | A | B | A | A |
| 30° C./65% RH | | B | B | B | B | — | — | — | — |
| 40° C./75% RH | | B | B | A | — | — | — | — | — |

A = tests: Appearance, Assay, Related substances, Water content, Chiral Purity, Powder X-ray
B = tests: Appearance, Assay, Related substances, Water content Stability data generated at 25° C./60% RH through 36 months indicates that the drug substance undergoes minimal change and is stable through the time period evaluated. There was a slight decrease in assay value below the 98% specification at 6 month 40° C./75% RH and 9 month 30° C./65% RH. However, based on the minimal change at accelerated conditions and the stability of the real time data, the drug substance is currently considered to be stable for at least 36 months. These data are summarized in Table 4.

TABLE 4

Stability Test Results for Compound 1, 25° C./60% RH

| Attributes | Procedure | Specifications | Initial | 1 M | 3 M | 6 M | 9 M | 12 M | 18 M | 24 M | 36 M |
|---|---|---|---|---|---|---|---|---|---|---|---|
| Appearance | Visual | Off white to yellow solid | Off-white solid | Pale yellow solid | Pale yellow solid | Pale yellow solid | Pale yellow solid | Pale yellow solid | Pale yellow solid | Pale yellow solid | Pale yellow solid |
| Assay | HPLC-UV | 98-102% | 100.9 | 102.4 | 100.2 | 98.9 | 99.7 | 101.2 | 100.4 | 100.0 | 99.7 |
| Chiral Purity (% ee) | Chiral HPLC-UV | NMT 2% (a/a) | 100 | NA | NA | NA | NA | 100 | NA | 100 | 100 |
| Related Substances (% w/w)* | HPLC-UV | | | | | Each individual NMT 1% | | | | | |
| | | RRT = 0.18 | ND | ND | ND | ND | ND | 0.10 | ND | ND | ND |
| | | RRT = 0.26 | 0.05 | 0.09 | 0.09 | ND | 0.09 | ND | 0.07 | 0.05 | 0.04 |
| | | RRT = 0.88 | ND | ND | ND | ND | ND | 0.05 | ND | ND | ND |
| Total Related Substances | HPLC-UV | NMT 2% (a/a) | 0.05 | 0.09 | 0.09 | 0.05 | 0.12 | 0.16 | 0.07 | 0.05 | 0.04 |
| Water Content (% w/w) | Karl Fischer | Report results | 11.36 | 12.10 | 12.25 | 12.04 | 11.52 | 11.52 | 11.50 | 11.42 | 11.53 |

Drug Product

Previous drug product formulations of Compound 1 used for alternate clinical indications comprised an excipient blend in a two piece hard shell capsule for oral dosing. An aqueous based formulation comprising the drug substance in a phosphate buffered saline based solution is being formulated for clinical studies. This solution will be packaged in a clear glass vial and sealed with a rubber stopper. A filter needle will be used at the clinical site to remove the indicated quantity of solution from the vial in order to deliver it into the nasal cavity via an atomizer.

Release of the clinical material will be performed via the specification shown in Table 5.

A short term stability study (approximately 2 weeks) will be conducted during formulation development in order to demonstrate that the assay, achiral impurities and pH of the solution remain within specification for a time frame suitable to support the release and dosing of the material.

TABLE 5

Specifications for Solution of Compound 1

| Test | Acceptance Criteria | Method |
|---|---|---|
| Appearance Description | Clear colorless solution | Visual Inspection |
| Identification | The retention time of the active peak in the sample should match the retention time of the active peak in the standard preparation. | HPLC-UV |
| Assay | 90-110% Label Claim | HPLC-UV |
| Degradation Products | | HPLC-UV |
| Amide | NMT 1% (a/a) | |
| Cis Isomer | NMT 1% (a/a) | |
| Unspecified individual impurities | NMT 1% (a/a) | |
| Total specified and unspecified impurities | NMT 2% (a/a) | |

Pre-Clinical Studies

Nonclinical studies have been conducted with the oral formulation of Compound 1, and comprise pharmacology, safety pharmacology, pharmacokinetics/drug metabolism, toxicokinetics (TK), toxicology and genotoxicity studies. To date, no carcinogenic or reproductive toxicity studies have been conducted with Compound 1. Pivotal studies contributing to the systemic safety of Compound 1 are briefly summarized below.

Primary Pharmacology nAChRs are a class of neurotransmitter receptors that respond to the natural product nicotine, derived from tobacco. They are a large family of receptors that are comprised of combinations of $\alpha$ and $\beta$ subunits. Compound 1 was shown to be a full agonist at the $\alpha 4\beta 2$ and $\alpha 3\beta 4$ nicotine receptor subtypes and a partial agonist at the $\alpha 3\beta 2$ subtype. Nicotinic pharmacological effects mediated by $\alpha 4\beta 2$ receptors have been described in neurons that project from the dorsal motor vagal nucleus; the $\alpha 3\beta 4$ receptor subtype is present within ganglionic synapses of the autonomic nervous system.

Safety Pharmacology

Consistent with recommendations in ICH S7, "Safety Pharmacology Studies for Human Pharmaceuticals", the effects of Compound 1 on the cardiovascular, respiratory, and CNS systems were evaluated. Compound 1 showed no noteworthy changes in behavioral sensitization, locomotor activity, general behavior, body temperature or pro-convulsant properties in a battery of safety pharmacology studies conducted in rats. Transient adverse effects in respiratory rate were noted at 100 mg/kg.

In vitro study results indicated a hERG $IC_{50}$ of 285 µM; and, in a rabbit Purkinje fiber study, there was lengthening of action potential duration at concentrations of 30 and 100 µM (7 and 20%, respectively), but there was no effect on resting membrane potential and action potential amplitude at any concentration.

Results from a telemetry study conducted in conscious dogs indicated a non-dose dependent increase in systolic and diastolic blood pressure and heart rate at oral doses up to 10 mg/kg. Findings were similar at a 20 mg/kg dose, except that there was a slight lengthening of the QT interval at that dose level. Dogs exhibited emesis at all doses shortly after dosing, concurrent with maximal cardiovascular changes.

Previous general toxicology studies have demonstrated that dogs appear to be the most sensitive species to Compound 1 (as well as other nicotinic agonists), exhibiting severe gastric distress/emesis on dosing.

There were no noteworthy changes in a telemetry study conducted in monkeys at oral doses up to 30 mg/kg.

Pharmacokinetics and Product Metabolism in Animals

Studies evaluating the pharmacokinetics of Compound 1 have been conducted in mice, rats, and monkeys. Compound 1 has also been investigated in a number of nm vitro and in vivo studies designed to determine tissue distribution, drug metabolism, excretion pattern, and plasma protein binding. The results from these studies are summarized below. Of note, one study assessing the absorption of Compound 1 by the nasal route of administration has been conducted, the results of which are presented herein.

Absorption

Oral Administration

In single dose pharmacokinetics studies, Compound 1 was rapidly absorbed into the general circulation with time to reach maximum concentration ($T_{max}$) between 0.167 and 2.25 hours in mouse, rat and monkey. Dosed orally at 1 mg/kg in mouse, the terminal elimination half-life was around 0.5 hours and brain exposure represented about 30% of plasma exposure. In a study using male Sprague-Dawley rats dosed orally at 0.3 or 3 mg/kg, maximum plasma concentration ($C_{max}$) and area under the plasma concentration-time curve from zero to 24 hours ($AUC_{0-24}$) were higher than dose-proportional in the 3 mg/kg group. Plasma and brain concentrations decreased rapidly with a half-life of 1.4 hours; brain exposure represented about 15% of plasma exposure. In a monkey study, [$^{14}$C]-Compound 1 was given at 10 mg/kg orally or 5 mg/kg by iv infusion. Oral bioavailability in this study was about 30%. For unchanged parent, $C_{max}$ and $AUC_{inf}$ were 254 ng/mL and 969 ng*h/mL, respectively, in the orally dosed group; half-life was 1.9 hours. In the iv infusion group, $C_{max}$ and $AUC_{inf}$ were 2032 ng/mL and 1532 ng*h/mL, respectively.

The pharmacokinetic parameters of Compound 1 after oral or intravenous administration to mice, rats or monkeys are summarized in Table 6.

TABLE 6

Pharmacokinetic Parameters after Oral and Intravenous Adminstration of Compound 1 in Mouse, Rat and Monkey

| Species | Dose (mg/kg) | $C_{max}$ (ng/mL) | $T_{max}$ (h) | $t_{1/2}$ (h) | $AUC_{0-1}$ (ng*h/mL) | $F^e$ (%) |
|---|---|---|---|---|---|---|
| Oral Administration | | | | | | |
| Swiss mouse | 1.0$^a$ | 15 | 0.167 | 0.5 | 10.1$^c$ | — |
| S-D rat | 0.3$^a$ | 6.51 | 0.5 | 1.4 | 13.5$^c$ | — |
| S-D rat | 3$^a$ | 169 | 0.167 | 1.4 | 211$^c$ | — |
| S-D rat | 30$^b$ | 1707 | 0.25 | 1.2 | 3307$^d$ | — |
| Cyno monkey | 10$^b$ | 254 | 2.25 | 1.9 | 942$^d$ | 31.1 |
| 20-Minute Intravenous Administration | | | | | | |
| Cyno monkey | 5$^b$ | 2032 | 0.333 | 2.1 | 1530$^d$ | — | a: dose = Compound 1
b: dose = [$^{14}$C]-Compound 1
c: t = 25 h
d: t = 168 h
e: F = oral bioavailability In 2-week and 13-week repeated dose TK studies in rat, animals were dosed orally at 30, 100 or 200 mg/kg/day (2-week study) or at 30, 100 or 300 mg/kg/day (13-week study). In both studies Compound 1 was rapidly absorbed, with a $T_{max}$ of 0.5 to 2 hours. Exposure parameters ($C_{max}$ and $AUC_{0-24}$) increased roughly in proportion to dose on Days 1 and 15 in the 2-week study and on Days 1, 29 and 91 in the 13-week study. In the 2-week study, there was a 1.2 to 2.2-fold increase in exposure from Day 1 to 15. In the 13-week study, there was a general increase from Day 1 to 29 and roughly equivalent exposure from Day 29 to 91. Exposure in females was generally higher than in males in both studies, particularly in the 200 mg/kg/day dose group in the 2-week study.

In 2-week and 13-week repeated dose TK studies in monkey, animals were dosed orally at 10, 30 or 100 mg/kg/day (2-week study) or at 10, 30 or 60 mg/kg/day (13-week study). In both studies Compound 1 was rapidly absorbed, with a $T_{max}$ of 0.5 to 6 hours, and rapidly cleared. In the 2-week study, exposure increased roughly proportional to dose from 10 to 30 mg/kg/day on Days 1 and 14 and less than proportionally from 30 to 100 mg/kg/day on Days 1 and 14; emesis in the 100 mg/kg/day dose group, 6/6 animals on Day 1 and 5/6 animals on Day 14, may have contributed to this. There was little accumulation in any dose group from Day 1 to Day 14. In the 13-week study, exposure increased less than proportionally from 10 to 30 mg/kg/day and generally did not increase from 30 to 60 mg/kg/day. Little to no accumulation was observed in either study and no gender effect was observed in either study.

Intranasal Administration

The absorption of Compound 1 by the nasal route of administration in a 7-day pilot intranasal toxicity and toxicokinetics study in the rat is presented herein.

Distribution

Binding of Compound 1 and [$^{14}$C]-Compound 1 showed low (<13%) plasma protein binding in mouse, rat, guinea pig, dog, monkey and human plasma at concentrations up to about 113 μM. Binding of Compound 1 to red blood cells was 28 to 54% directly after spiking and 41 to 63% at 0.5 and 1 hour after spiking. The blood/plasma ratios ranged from 0.78 to 1.26 and were broadly species and concentration independent.

The distribution studies conducted in male Long Evans rat (1 mg/kg, po) and male and female Sprague-Dawley rat (30 mg/kg, po) showed that [$^{14}$C]-Compound 1 was rapidly absorbed from the GI tract and distributed throughout the body, with highest radioactive concentrations generally observed in 0.5 to 1 hour. In the male Long Evans rat, a first phase of elimination occurred between 1 and 24 hours, with a slow second phase of elimination occurring between 24 and 168 hours in all tissues with most exhibiting radioactivity above LLOQ (9 ng-eq/g) at 168 hours. The adrenal medulla showed the highest concentration of radioactivity at the final sampling time of 168 hours; other tissues with relatively high AUC values included uveal tract, kidney corticomedullar junction, spleen, liver, prostate, kidney pelvis, kidney as a whole and small intestine wall. In male and female Sprague-Dawley rats, tissue distribution appeared similar to that of the Long Evans rat. Tissues with relatively high AUC values included organs of elimination, salivary submaxillary gland, adrenal medulla and prostate (males), adrenal medulla showed the highest concentration of radioactivity at the final sampling time of 24 hours.

Metabolism

Metabolism In Vitro

Studies in human liver microsomes, heat-treated human liver microsomes and human S9 fractions indicated Compound 1 was relatively stable in all test systems, suggesting that Cytochrome P450s, Flavin-containing monooxygenases, and monoamine oxidases do not play a major role in metabolism of the compound. In a 24-hour incubation, cryopreserved hepatocytes from rat, dog, monkey and human, [$^{14}$C]-Compound 1 was slightly to moderately metabolized depending on the species with ranking as follows: rat>monkey>human>dog. In human and monkey, the primary route of metabolism was through oxidation of the pyrrolidine ring (metabolite M02) before further metabolism via dioxidation to M1 or M3. In humans, parent accounted for 37% of extracellular radioactivity, M02 was 13.9%.M1 was 4.1% and M3 was 1.1%. In monkey, parent accounted for 14.2%, M02 was 5.0%, M1 was 5.8% and M3 was 29.4%. In the rat, the primary metabolite is an N-oxide-pyrimidine derivative (M9); it accounted for 71.9% of extracellular radioactivity while parent represented only 1.4%.

Metabolism In Vivo

Following a single po dose of [$^{14}$C]-Compound 1 in rats (30 mg/kg), the parent was extensively metabolized. The main metabolite in plasma and urine was M9; in plasma from 6 to 24 hours post-dose an unknown polar metabolite (M13) accounted for a significant portion of total radioactivity. In plasma, parent accounted for 11.7% of AUC0-24 total radioactivity, M9 accounted for 20.9% and M13 accounted for 15.9%. In urine (the primary route of elimination) over a 24 hours period, parent accounted for 17.8% of total radioactivity, M9 accounted for 37.7% and M13 accounted for 0.7%.

Excretion

The route and extent of excretion of [$^{14}$C]-Compound 1 radioactivity was studied in the Sprague-Dawley rat following a single po dose of 30 mg/kg and in monkey following a single po dose of 10 mg/kg and a single iv infusion of 5 mg/kg. In the rat, nearly all recovered radioactivity in the excreta was eliminated within 24 hours. An average of 91.2% of the administered dose was recovered in the 168 hour period post-dose (77.6% in urine, 10.9% in feces, 2.2% in expired $CO_2$). In the monkey, nearly all the recovered radioactivity in the excreta was eliminated within 24 (iv) or 48 (po) hours. For oral dosing, an average of 90.3% of the administered radioactive dose was recovered in the 168-hour period post-dose (60.7% in urine, 12.8% in feces, 10.2% in cage wash, and 6.6% in diet debris). For iv dosing, an average of 93.0% of the administered radioactive dose was recovered in the 168-hour period post-dose (70.7% in urine, 7.6% in feces, 7.6% in cage wash, and 6.9% in diet debris).

Toxicology

The nonclinical toxicology program for Compound 1 comprised the following: single-dose general toxicity studies in the rat, dog, and monkey; repeat-dose general toxicity studies in the rat and monkey in duration of up to 13-weeks; and genotoxicity studies that included Ames, micronucleus, and chromosome aberration tests. Findings from the 13-week repeat-dose studies and genetic toxicology studies are summarized below.

13-Week Repeat-Dose Toxicity in Rats

Compound 1 was given to rats once daily for at least 13 weeks via oral gavage at doses of 30, 100, or 300 mg/kg/day. Two of 15 females receiving 300 mg/kg/day died. Clinical signs in males and females in this high-dose group included; reduced food consumption, anogenital staining, lacrimation, chromodacryorrhea, and tremors. Laboratory results included marginally lower RBC mass that correlated with elevated reticulocyte counts with recovery; elevated liver enzymes and bilirubin throughout the dosing period, with evidence of resolution during recovery urinary changes, including increased urine volume, elevated urinary protein, and higher bilirubin and urobilinogen, with resolution during recovery. Rats receiving doses of 100 mg/kg/day and higher had clinical signs that included excessive salivation, tan brown muzzle, closed or partially closed eyelids, and reduced body weight. Laboratory results included elevated WBC (lymphocytes and neutrophils), with recovery; elevated bilirubin; and a slight decrease in total serum protein (globulins and albumin). Gross and histological examination of tissues showed marginally elevated liver weights. At doses ≥100 mg/kg/day, microscopic findings of centrilobular hepatocellular hypertrophy, medullary adrenal gland cell hypertrophy, mucosal epithelial cell hyperplasia of the small intestine, and increased extramedullary hematopoiesis and hemosiderin deposits in the red pulp of the spleen were observed. At a dose of 300 mg/kg/day, gross and histological examination of tissues revealed elevated spleen weights with hemosiderin deposits in the red pulp of the spleen and in Kupffer cells of the liver. The low dose of 30 mg/kg/day was well tolerated except for minimal hepatocellular hypertrophy that was observed in 7 of 10 males, but not in females. Accordingly, the NOAEL was considered to be 30 mg/kg/day. Compound 1 was rapidly absorbed with a $T_{max}$ of 0.5 to 2 hours after dosing and was detected in the plasma up to 24 hours after dosing. AUC and $C_{max}$ increased between Day 1 and Day 29. The AUC remained constant between Day 29 and Day 91, suggesting that steady state was reached by Day 29. At the NOAEL, $C_{max}$ values ranged from 2570 ng/mL for males to 3150 ng/mL for females. AUC values ranged from 12100 ng*hr/mL for males to 10200 ng*hr/mL for females.

13-Week Repeat-Dose Toxicity in Monkeys

Compound 1 was given to Cynomolgus monkeys once daily for at least 13 weeks via oral gavage at doses of 10, 30, or 60 mg/kg/day. At the end of the dosing period, 2 monkeys per sex in the high-dose and control dose groups were selected for a recovery of 4 weeks. One monkey that received 60 mg/kg/day was sacrificed during the fourth week because of marked deterioration, including body weight loss (−22% vs. Day 1 value), decreased motor activity, hyperactivity, hypothermia, and noteworthy clinical chemistry alterations (increased urea nitrogen and creatinine, low sodium and potassium and decreased chloride) suggesting renal impairment, which were associated with microscopic findings of moderate tubulointerstitial nephritis characterized by neutrophilic and mononuclear interstitial inflammation, intratubular neutrophilic inflammation, tubular epithelial degeneration and regeneration, and tubular casts, mineralization and dilation. In the surviving monkeys at 60 mg/kg/day, clinical observations included emesis, decreased motor activity, body weight loss, slight increases in QT (up to +16%), QTcB (up to +9.2%), and QTcF (up to +11%) intervals that were associated with slight decreases in heart rate. These findings had resolved by the end of the 4-week recovery period. Importantly, no noteworthy changes in ECG measurements were identified in clinical studies with Compound 1 to date. Microscopic evaluations in the 60 mg/kg group revealed mild interstitial vacuolization in the heart in 1 of 2 males and 2 of 3 females. At 30 mg/kg, all animals had emesis, but they had fewer episodes of emesis than the animals dosed at 60 mg/kg. The dose of 30 mg/kg was well tolerated and was considered the NOAEL, $C_{max}$ and AUC increased less than proportionally at doses between 10 and 30 mg/kg. No dose effect was observed at doses between 30 and 60 mg/kg, suggesting a saturation of absorption; inter-individual variability of the plasma concentrations was high. At the NOAEL, $C_{max}$ values ranged from 382 ng/mL for males to 696 ng/mL for females. AUC values ranged from 1670 ng*hr/mL for males to 2440 ng*nr/mL for females.

Genotoxicity Studies

Compound 1 was negative for mutagenicity in both in vitro bioassays—including an Ames test, a micronucleus test in mouse lymphoma cells, and a chromosome aberration assay using cultured human peripheral blood lymphocytes—and an in vivo rat bone marrow micronucleus test.

Intranasal Toxicology Studies

Intranasal administration studies can be performed in rodents (rats and mice), rabbits, and larger species, including dogs and non-human primates, though experimental techniques (e.g., dose volume per nostril, delivery device) for administration of test article may differ across species. The use of rats and dogs or monkey are most common for evaluation of intranasal drug products in rodents and non-rodents, respectively. However, rabbits are also used, and methods for the histopathological evaluation of the rabbit nasal cavity in safety assessment studies have been developed by Pereira et al. (Pereira M E, Macri N P, Creasy D M. Evaluation of the rabbit nasal cavity in inhalation studies and a comparison with other common laboratory species and man. Toxicologic Pathology, 2011. 39:893-900.)

Although systemic toxicity was previously evaluated in the rat and monkey in GLP oral administration studies up to 13 weeks in duration, the rat and rabbit (New Zealand) were selected for evaluation of Compound 1 in intranasal toxicity studies. The primary focus of intranasal toxicity studies in the rat and rabbit is the assessment of local toxicity using clinically relevant dose concentrations of Compound 1, up to 6% (based on the hemi-galacterate salt). Since the rabbit was not previous evaluated in systemic toxicity studies with Compound 1, a complete systemic evaluation will also be conducted in the ongoing GLP 28-day study.

Completed Toxicology Studies

A 7-Day Pilot Study of Compound 1 by Intranasal Administration in Rats

The potential toxicity and TK of Compound 1 was assessed in a 7-day intranasal administration study in rats. The study design was as follows:

TABLE 7

Experimental Design of 7-Day Pilot Study of Compound 1-A by Intranasal Administration in Rats

| | | Dose | Dise | | Number of Animals | | | |
|---|---|---|---|---|---|---|---|---|
| | | Volume | Volume | Dose | Main Study | | Toxicokinetic Study | |
| Group No. | Test Material | (μL/animal dose)[a] | (μL/animal/ day)[a] | Concentration (%)[c] | Males | Females | Males | Females |
| 1 | Control Article[b] | 60 | 180 | 0 | 5 | 5 | — | — |
| 2 | Compd 1 | 60 | 180 | 0.5 | 5 | 5 | 9 | 9 |
| 3 | Compd 1 | 60 | 180 | 2 | 5 | 5 | 9 | 9 |
| 4 | Compd 1 | 60 | 180 | 6 | 5 | 5 | 9 | 9 |

— = not applicable.
[a]The dose volume was administered to each animal, with the total volume administered split equally between each nostril (30 μL per nostril per dose), 3 times daily.
[b]Phosphate Buffered Saline (PBS).
[c]Based on the hemi-galacterate salt.

The following parameters and end points were evaluated in this study; clinical signs, body weights, body weight gain, food consumption, ophthalmology, toxicokinetic parameters, gross necropsy findings, organ weights, and histopathologic examination of select tissues, including nasal cavity at levels I-IV and detailed ocular histopathology for all dose groups: histopathology for brain, pharynx, larynx, trachea, lung, and select target tissues (i.e., adrenal gland, liver, and spleen) that were identified in a GLP 13-week oral toxicity study in rats (DSE 2004-0356) in group 1 and 4 animals, and gross lesions.

The toxicokinetics of Compound 1 systemic exposure are presented below (FIG. 1 and Table 8). Blood samples were collected for plasma Compound 1 concentration analysis from 3 rats/sex/group/time point prior to dosing and at 0.083, 2, 5, 6.083 (5 minutes following the second daily dose), 8,11,12,083 (5 minutes following the third daily dose), and 24 hours following the first daily dose on Day 1 and Day 7.

TABLE 8

Toxicokinetic Parameters of Compound 1 after TID Administration in the Rat on Day 1 and Day 7

| Gender | Day | Dose Level[a] (mg/day) | AUC$_{0-t}$ (ng*h/mL) | DN AUC$_{0-t}$[b] | C$_{max}$[c] (ng/mL) | T$_{max}$[c] (h) | C1[d] (ng/mL) | C2[d] (ng/mL) | C3[d] (ng/mL) |
|---|---|---|---|---|---|---|---|---|---|
| Male | 1 | 0.9 | NR | NR | 54.2 | 12.083 | 51.9 | 36.3 | 54.2 |
|  |  | 3.6 | 829 | 230 | 343 | 6.083 | 86.4 | 343 | 134 |
|  |  | 10.8 | 1700 | 157 | 924 | 12.083 | 208 | 332 | 924 |
| Female | 1 | 0.9 | 138 | 154 | 34.9 | 12.083 | 26.1 | 34.8 | 34.9 |
|  |  | 3.6 | 626 | 174 | 278 | 12.083 | 50.2 | 119 | 278 |
|  |  | 10.8 | 4170 | 386 | 481 | 6.083 | 326 | 481 | 329 |
| Male | 7 | 0.9 | NR | NR | 33.7 | 12.083 | 12.4 | 28.0 | 33.7 |
|  |  | 3.6 | 298 | 82.7 | 110 | 0.083 | 110 | 53.8 | 25.5 |
|  |  | 10.8 | 878 | 81.3 | 225 | 12.083 | 166 | 209 | 225 |
| Female | 7 | 0.9 | 148 | 164 | 37.5 | 12.083 | 20.3 | 16.3 | 37.5 |
|  |  | 3.6 | 336 | 93.5 | 79.9 | 6.083 | 68.0 | 79.9 | 76.0 |
|  |  | 10.8 | 1480 | 137 | 224 | 6.083 | 218 | 224 | 210 |

[a]Dose concentrations 0.5%, 2%, and 6% are equivalent to 0.9, 3.6, and 10.8 mg/day of the hemi-galacterate salt, respectively.
[b]Units for dose-normalized (DN) AUC$_{0-t}$ are (ng*h/mL)/(mg)
[c]C$_{max}$ is the maximum concentration and T$_{max}$ is the time of peak concentration over the total blood collection time span
[d]C1, C2, and C3 are peak concentrations following the 1$^{st}$, 2$^{nd}$, and 3$^{rd}$ instillation
NR = Not reportable due to <3 consecutive concentrations used to determine AUC0-t Compound 1 was rapidly absorbed after intranasal administration and demonstrated increasing systemic exposure in males and females with increasing dose. The peak systemic exposure of Compound 1 after each instillation was observed at the 5 minute post administration time point. The T ax that correlated with maximum observed exposure, C$_{max}$, was usually after the second or third instillation, with one exception (Group 3 Male Day 7). Based on the TK data, derived from limited sampling, that indicates rapid absorption and a half-life of 1.4 hours, it is not possible to accurately determine if there is systemic accumulation of Compound 1 or induction of clearance over 7 days when Compound 1 is administered TID in rat.

Intranasal administration of 60 L Compound 1 at dose concentrations of 0%, 0.5%, 2%, and 6% to rats 3 times per day for 7 days resulted in survival of all animals to scheduled euthanasia. There were isolated body weight, food consumption, and organ weight values that were statistically different from their respective controls; however, there were no patterns, trends, or correlating data to suggest these values were toxicologically relevant. The clinical observations, ocular, gross and microscopic findings observed were considered incidental, of the nature commonly observed in this strain and age of rats, and/or were of similar incidence in control and treated animals and, therefore, were considered unrelated to administration of Compound 1-A. As a result, the no-observed-adverse-effect-level (NOAEL) was considered to be 180 μL 6% Compound 1 per animal per day.

Single-Dose Tolerability and PK in Rabbits

The potential toxicity and TK of Compound 1 nasal spray was assessed following a single spray (100 μL) of either 2% or 5% Compound 1 in the right nostril of male New Zealand White rabbits (N=36). Phosphate buffered solution (PBS) served as the control and was sprayed (100 μL) in the left nostril. Bioanalytical and histopathological analyses were conducted at 1, 3, 6, 9, and 24 h post-treatment. Prior to sacrifice, the intranasal/nasal area of each animal was assessed using the Draize Classification System for Scoring Skin Irritation.

No clinical signs were observed in any animals during the study and no signs of erythema, edema, eschar formation or discharge were observed in the intranasal/nasal assessments. Histopathologically, there were no macroscopic or microscopic findings related to the test article application of 2% or 5% Compound 1 in the nasal cavity.

Ongoing Toxicology Studies

Studies evaluating the toxicity of Compound 1 nasal spray that will be ongoing and the following studies are to be conducted:
 28-Day Repeat-Dose Intranasal Toxicity Study in Rats;
 7-Day Repeat-Dose Tolerability and PK in Rabbits;
 28-Day Repeat-Dose Intranasal Toxicity Study in Rabbits.

Pivotal toxicity studies intended to support clinical trials are being conducted in full compliance with good laboratory practice (GLP) regulations. A brief synopsis of the protocol for each study is provided below.

GLP 28-Day Repeat-Dose Toxicology Study of Compound 1 Administered Intranasally to Rats with a 4-Week Recovery Period

| Objective | To evaluate the potential toxicity and toxicokinetics of intranasally administered Compound 1-A |
|---|---|
| GLP | GLP 21 CFR Part 58 compliant |
| Test Article | Compound 1-A |
| Test System | Sprague Dawley rats, 80/sex, 160 total |
| Experimental Design | 28-day dosing plus 4-week recovery |

| | Safety Evaluation | | Recovery | | Toxicokinetics | |
|---|---|---|---|---|---|---|
| Group | Male | Female | Male | Female | Male | Female |
| Vehicle | 10 | 10 | 5 | 5 | 3 | 3 |
| Compound 1 | 10 | 10 | — | — | 9 | 9 |

-continued

|  |  |  |  |  |  |  |
|---|---|---|---|---|---|---|
| 0.5% Compound 1 2% | 10 | 10 | — | — | 9 | 9 |
| Compound 1 6% | 10 | 10 | 5 | 5 | 9 | 9 |

| | |
|---|---|
| Route/Frequency of Dosing | Intranasal instillation via micropipette, 30 μL / nostril, 3× daily. |
| Safety Endpoints | Cage-side observations: 2× daily; mortality/moribundity<br>Clinical observations: Weekly<br>Functional observational battery: Prior to study and at Day 14 (30 min post-dose)<br>Body weights: Pre-study, Day 1 (before dosing), weekly thereafter, and prior to termination at end of dosing and recovery periods<br>Food consumption: Weekly; quantitative assessment<br>Ophthalmic Exams (slit lamp and indirect): Pre-study, first day of dosing (Day 1), midway through dosing (Day 15), and at the end of the treatment and recovery periods. |
| Clinical Pathology | Clinical chemistry, hematology, and coagulation parameters: prior to treatment and at the end of the treatment and recovery periods. |
| Toxicokinetics | Blood samples will be collected from all animals prior to and following the first and last dose of the study. |
| Necropsy | Complete with full tissue collection and organ weights (liver, lungs, heart, kidneys, brain, adrenal glands, testes, thyroid, pituitary, spleen, and thymus). |
| Histopathology | Histopathology of control and high dose (Compound 1 6%) groups, including full ocular and respiratory tract histopathology, as well as histopathology of rat select target tissues (adrenal gland, liver, spleen), and brain. In addition, detailed nasal histopathology will be performed on all groups. Gross lesions will also be examined. |

25

7-Day Repeat Dose Tolerability and PK in Rabbits

| | |
|---|---|
| Objective | To evaluate the potential toxicity and toxicokinetics of intranasally administered Compound 1-A |
| GLP | No |
| Test Article | Compound 1-A |
| Test System | New Zealand White rabbits, 24 total (male) |
| Experimental Design | 7-day dosing |

| Group | Dosing Frequency | Number of Animals |
|---|---|---|
| Vehicle (PBS) | 2× Daily | 6 |
| Compound 1 1% | 1× Daily | 6 |
| Compound 1 2.5% | 1× Daily | 6 |
| Compound 1 2.5% | 2× Daily | 6 |

| | |
|---|---|
| Route | Intranasal instillation via micropipette, 100 μL/nostril |
| Safety Endpoints | Clinical Observations<br>Intranasal Assessment: Intranasal irritation will be performed using a Draize scoring scale<br>Body Weights |
| Toxicokinetics | Blood samples will be collected from all animals after the first dose (1 hr post-dose) and at termination (24 h post-dose). |
| Necropsy | Complete with full tissue collection and organ weights (liver, lungs, heart, kidneys, brain, adrenal glands, testes, thyroid, pituitary, spleen, and thymus). |
| Histopathology | Histopathological assessment of the nasal cavity (right and left nostrils) and respiratory tissues (pharynx, larynx, mediastinal lymph nodes, and trachea with lung lobes) will be performed on 3 animals per group. Right nasal meatus mucosa and front lobe of the brain will be harvested for tissue PK from the remaining 3 animals per group. |

GLP 28-Day Repeat-Dose Toxicity Study of Compound 1 Administered by Intranasal Spray to New Zealand White Rabbits with a 4-Week Recovery Period

| | | | | | |
|---|---|---|---|---|---|
| Objective | To evaluate the potential toxicity of toxicokinetics of Compound 1 Nasal Spray | | | | |
| GLP | GLP 21 CFR Part 58 compliant | | | | |
| Test Article | Compound 1 Nasal Spray | | | | |
| Test System | New Zealand White Rabbits, 18/sex, 36 total | | | | |
| xperimental Design | 28-day dosing plus 4-week recovery | | | | |
| | Group | Terminal | | Recovery | |
| | | Male | Female | Male | Female |
| | Vehicle | 3 | 3 | 3 | 3 |
| | Compound 1 0.5% | 3 | 3 | — | — |
| | Compound 1 2% | 3 | 3 | — | — |
| | Compound 1 6% | 3 | 3 | 3 | 3 |
| Route/Frequency of Dosing | Intranasal spray, 100 µL/nostril, 2x daily. | | | | |
| Safety Endpoints | Cage-side observations: 2x daily; mortality/moribundity<br>Clinical observations: Weekly<br>Body weights: Pre-study, weekly (before dosing), and prior to termination<br>Food consumption: Weekly; qualitative assessment<br>Intranasal/Nasal Assessment: Pre-study and at the end of the treatment and recovery periods; assessment will be performed using an otoscope, and intranasal irritation will be performed using a Draize scoring scale<br>Ophthalmic Exams (slit lamp and indirect): Pre-study, first day of dosing (Day 1), midway through dosing (Day 15), and at the end of the treatment and recovery periods.<br>Schirmer tear test: First day of dosing (Day 1), midway through dosing (Day 15), and at the end of the treatment and recovery periods. | | | | |
| Clinical Pathology | Clinical chemistry, hematology, and coagulation parameters: prior to treatment; midway through dosing (Day 15); and at the end of the treatment and recovery periods. | | | | |
| Toxicokinetics | Blood samples will be collected from all animals prior to and following the first and last dose of the study. | | | | |
| Necropsy | Complete with full tissue collection and organ weights (liver, heart, kidneys, brain, adrenal glands, testes, thyroid, pituitary, spleen, and thymus). | | | | |
| Histopathology | Full histopathology of control and high dose (Compound 1 6%) groups. In addition, detailed nasal histopathology will be performed on all groups. Gross lesions will also be examined. | | | | |

Pre-Clinical Summary

Oral repeat-dose toxicity studies of Compound 1 were conducted in rats and monkeys for up to 13 weeks. Compound 1 was well-tolerated in both species at a dose of 30 mg/kg. Significant toxicity findings in the 13-week study in rats included deaths at the high dose of 300 mg/kg and histopathology findings (adrenal gland, liver, small intestine, and spleen) at 100 mg/kg. In the 13-week study in monkeys, kidney toxicity was observed in one monkey at 60 mg/kg that was sacrificed in moribund condition during study week 4, and mild interstitial vacuolization was observed in the heart of 3 monkeys at 60 mg/kg. NOAELs of 13-week rat and monkey studies were considered to be 30 mg/kg for both studies.

The rat and rabbit mw ere selected for evaluation of Compound 1 in intranasal toxicity studies. Since systemic toxicity was previously evaluated in two species, as summarized above, the primary focus of intranasal toxicity studies in the rat and rabbit is the assessment of local toxicity using clinically relevant close concentrations of Compound 1-A, up to 6%. The dose levels for pivotal GLP studies were selected to allow evaluation of anticipated clinical dose concentrations, in the range of 0.5% to 6%. In addition, dosing frequencies (i.e., three times per day in rats and two times per day in rabbits) were planned to exceed the highest planned clinical dosing frequency in the proposed clinical study.

Compound 1 doses for the ongoing GLP 28-day rat and rabbit intranasal toxicology studies are summarized in Table 9, expressed on a mg/day, mg/kg/day, and mg/cm² basis.

TABLE 9

Compound 1 doses in ongoing GLP 28-day rat and rabbit intranasal toxicology studies

| Group | Dose volume (µL/animal/day) | Dose concentration (%)$^{a,b}$ | mg/day$^b$ | mg/kg/day$^{b,c}$ | mg/cm$^{2(b,d)}$ |
|---|---|---|---|---|---|
| Rat 28-day toxicology study | | | | | |
| 2 | 180 | 0.5 | 0.9 | 3.6 | 0.06 |
| 3 | 180 | 2 | 3.6 | 14.4 | 0.26 |
| 4 | 180 | 6 | 10.8 | 43.2 | 0.77 |

TABLE 9-continued

Compound 1 doses in ongoing GLP 28-day rat and rabbit intranasal toxicology studies

| Group | Dose volume (μL/animal/day) | Dose concentration (%)$^{a,b}$ | mg/day$^b$ | mg/kg/day$^{b,c}$ | mg/cm$^{2(b,d)}$ |
|---|---|---|---|---|---|
| Rabbit 28-day toxicology study | | | | | |
| 2 | 400 | 0.5 | 2 | 0.8 | 0.03 |
| 3 | 400 | 2 | 8 | 3.2 | 0.13 |
| 4 | 400 | 6 | 24 | 9.6 | 0.39 |

$^a$0.5% = 5 μg/μL; 2% = 20 μg/μL; 6% = 60 μg/μL
$^b$Based on the hemi-galactarate salt
$^c$Weight assumptions: 0.25 kg rat; 2.5 kg rabbit
$^d$Nasal surface area assumptions: 14 cm$^2$ (both nares), rat; 61 cm$^2$ (both nares), rabbit; 180 cm$^2$ (both nares), human

TABLE 10

Compound 1 Free Base Equivalent Doses in Ongoing GLP 28-day rat and rabbit intranasal toxicology studies

| Group | Dose volume (μL/animal/day) | Dose concentration (%)$^{a,b}$ | mg/day$^b$ | mg/kg/day$^{b,c}$ | mg/cm$^{2(b,d)}$ |
|---|---|---|---|---|---|
| Rat 28-day toxicology study | | | | | |
| 2 | 180 | 0.28 | 0.5 | 2 | 0.04 |
| 3 | 180 | 1.1 | 2 | 8 | 0.14 |
| 4 | 180 | 3.3 | 6 | 24 | 0.43 |
| Rabbit 28-day toxicology study | | | | | |
| 2 | 400 | 0.28 | 1.1 | 0.4 | 0.02 |
| 3 | 400 | 1.1 | 4.4 | 1.8 | 0.07 |
| 4 | 400 | 3.3 | 13.3 | 5.3 | 0.22 |

$^a$0.28% = 2.8 μg/μL; 1.1% = 11.1 μg/μL; 3.3% = 33.2 μg/μL
$^b$Free base; Correction factor from hemi-galactarate salt to free base = 0.554
$^c$Weight assumptions: 0.25 kg rat; 2.5 kg rabbit
$^d$Nasal surface area assumptions: 14 cm$^2$ (both nares), rat; 61 cm$^2$ (both nares), rabbit; 180 cm$^2$ (both nares), human Intranasal doses for humans typically range from 50-100 μL per spray. As an example, assuming two sprays (100 μL per spray per nostril for a total of 200 μL; equivalent to 6.6 mg/day or 0.11 mg/kg for a 60 kg patient) of a 3.3% (33.2 μg/μL) Compound 1 nasal spray (free base) in proposed clinical study, the animal-to-human exposure margins at the high dose of rat and rabbit 28-day repeat dose studies would be 10.8- and 5.5-fold, respectively. On a mg/m$^2$ basis, safety margins would be much greater, 218- and 48.2-fold for rats and rabbits, respectively. Ongoing pivotal rat and rabbit studies are anticipated to provide adequate safety margin (at least 2-3-fold on a mg/cm$^2$ basis) for the maximum clinical close (to-be-determined) in the proposed clinical study.

Clinical Studies

The oral form of Compound 1-A, Compound 1, has been studied in several clinical trials. A total of 108 human subjects have received Compound 1: 69 healthy volunteers in Phase 1 studies, 23 subjects in a Phase 1b gastroparesis study, and 16 subjects with constipation predominant irritable bowel syndrome (IBS-C) in a Phase 2a study. Subjects were exposed to doses of Compound 1 ranging from 5 mg through and including 200 mg. No clinical noteworthy changes in physical exam, blood or urine laboratory measurements or ECG measurements were identified. Adverse events reported in all studies were typically GI-related and included nausea, abdominal pain, vomiting and diarrhea.

Example 10: Proposed Phase 2 Clinical Study on Compound 1 (5-2-[(R)-Pyrrolidin-3-yl]-vinyl)-pyrimidine, Hemi-Galactarate, Dihydrate)

The synopsis for the proposed phase 2 study is presented below.

| | |
|---|---|
| Protocol Title: | Multicenter, Randomized, Controlled, Double-Masked Clinical Trial to Evaluate the Efficacy of Compound 1 Nasal Spray on Signs and Symptoms of Dry Eye Disease |
| Investigational Product: | Compound 1 Nasal Spray |
| Study Objective: | The objective of this study is to evaluate the safety and effectiveness of Compound 1 Nasal Spray as compared to placebo on signs and symptoms of dry eye disease |
| | Overall Study Design |
| Structure: | A Phase 2, multicenter, randomized, controlled, double-masked study |

-continued

| | |
|---|---|
| Duration: | Two study visits over approximately two weeks |
| Controls: | Placebo (Compound 1 Vehicle Nasal Spray) |
| Dosing Regimen: | Treatment at Visit 1 and Visit 2 |
| Summary of Visit Schedule: | Visit 1 = Day 1, Screening and Treatment (Schirmer's Test Evaluation) |
| | Visit 2 = Day 15 + 4, Treatment (Eye Dryness Score Evaluation) |
| Measures Taken to Reduce Bias: | This is a randomized, double-masked study |

Study Population Characteristics

| | |
|---|---|
| Number of Subjects: | Approximately 200 (50 per arm) |
| Condition/Disease: | Dry Eye Disease |
| Inclusion Criteria: | Subjects must: |
| | 1. Be at least 22 years of age at the Screening Visit |
| | 2. Have used and/or desired to us an artificial tear substitute for dry eye symptoms within 6 months prior to Visit 1 |
| | 3. Have an OSDI © score of ≥23 with ≤3 responses of "N/A" at the Screening Visit |
| | 4. Have ALL of the following in the study eye at the Screening Visit: |
| | A corneal fluorescein staining score of ≥2 in at least one corneal region OR have a sum of >4 for all corneal regions |
| | A baseline Schirmer's Test (with topical anesthesia) score of ≤10 mm/5 minutes with a cotton swab nasal stimulation Schirmer's Test score at least 7 mm greater in the same eye |
| | The study eye will be defined as the eye that meets all inclusion criteria; if both eyes qualify then the eye with the greatest increase in tear production with stimulation by a cotton swab at the Screening Visit or, if there is no difference in stimulated tear production, the eye with the lower basal Schirmer's score at screening. If there is no difference for either measure, the right eye will be used as the study eye. |
| | 5. Best corrected visual acuity (BCVA) of 0.7 logMAR or better (logMAR <0.7; Snellen equivalent score of 20/100 or better) in each eye at the Screening Visit |
| | 6. Have normal lid/lash anatomy, blinking function and closure as determined by the Investigator |
| | 7. Not be familiar with (e.g., know the study drug is used to stimulate tear production) or have previously used the study drug |
| | 8. Be literate, able to speak English, and able to complete questionnaires independently |
| | 9. Be able to participate in the study for approximately four consecutive hours on Day 15 |
| | 10. Be able and willing to use the study drug and participate in all study assessments and visits |
| | 11. Have provided verbal and written informed consent |
| | 12. If a female of childbearing potential, have a negative urine pregnancy test on Day 1 |
| Exclusion Criteria: | Subjects must not: |
| | 1. Have clinically significant corneal epithelial defects at Study Day 1 prior to performing Schirmer's Test |
| | 2. Have chronic or recurrent epistaxis, coagulation disorders or other conditions that, in the opinion of the Investigator, may lead to clinically significant risk of increased bleeding |
| | 3. Have had nasal or sinus surgery (including history of application of nasal cautery) or significant trauma to these areas |
| | 4. Have a vascularized polyp, severely deviated septum, chronic recurrent nosebleeds, or severe nasal airway obstruction as confirmed by intranasal examination performed prior to Day 1 |
| | 5. Be currently treated with nasal continuous positive airway pressure (CPAP) |
| | 6. Have had any intraocular surgery (such as cataract surgery), extraocular surgery (such as blepharoplasty) in either eye within three months or refractive surgery (e.g. LASIK, LASEK, PRK or corneal implant) within twelve months of Visit 1 |
| | 7. Have had a corneal transplant in either or both eyes |

| | |
|---|---|
| | 8. Have used contact lenses within 7 days prior to Visit 1 or anticipate the use of contact lenses during the study period<br>9. Have a punctal or intracanalicular plug present in any eyelid (participants with permanent occlusion of punctal ducts are eligible)<br>10. Have a history or presence of any ocular disorder or condition in either eye that would, in the opinion of the Investigator, likely interfere with the interpretation of the study results or participant safety such as significant corneal or conjunctival scarring; pterygium or nodular pinguecula; current ocular infection, conjunctivitis, or inflammation not associated with dry eye; anterior (epithelial) basement membrane corneal dystrophy or other clinically significant corneal dystrophy or degeneration; ocular herpetic infection; evidence of keratoconus; etc. Blepharitis not requiring treatment and mild meibomian gland disease that are typically associated with dry eye disease are allowed<br>11. Have a systemic condition or disease not stabilized or judged by the Investigator to be incompatible with participation in the study or with the lengthier assessments required by the study (e.g., current systemic infection, uncontrolled autoimmune disease, uncontrolled immunodeficiency disease, history of myocardial infarction or heart disease, etc.)<br>12. Have a known hypersensitivity to any of the procedural agents or study drug components<br>13. Have current concomitant use of snuff, chewing tobacco, or cigarettes/cigars during the study or within the previous 30 days<br>14. Have current concomitant use of a nicotinic acetylcholine receptor agonist [Nicoderm ®, Nicorette ®, Nicotrol NS ® (nicotine), Tabex ®, Desmoxan ® (cytisine), and Chantix ® (varenicline)] or within the previous 30 days<br>15. Have active or uncontrolled, severe:<br>Systemic allergy<br>Chronic seasonal allergies at risk of being active during the study<br>Rhinitis or sinusitis requiring treatment such as antihistamines, decongestants, oral or aerosol steroids at the Screening Visit<br>Untreated nasal infection at Visit 1<br>16. Have any condition or history that, in the opinion of the investigator, may interfere with study compliance, outcome measures, safety parameters, and/or the general medical condition of the subject<br>17. Be a female who is pregnant, nursing an infant, or planning a pregnancy at Visit 1<br>18. Be currently enrolled in an investigational drug or device study or have used an investigational drug or device within 30 days prior to Visit 1 |
| Study Formulations: | Compound 1 Nasal Spray<br>Placebo (Compound 1 Vehicle Nasal Spray)<br>Evaluation Criteria |
| Efficacy Measures: | Primary Efficacy Measures:<br>Schirmer's Test at Visit 1<br>Eye Dryness Score (EDS) at Visit 2 |
| Safety Measures: | Adverse Event (AE) Query |
| Other Measures: | Ora Calibra ™ Ocular Discomfort Scale<br>Urine pregnancy test |

General Statistical Methods and Types of Analyses
Analysis Populations:
Intent-to-Treat Population - The intent-to-treat (ITT) population includes all randomized subjects. Subjects in the ITT population will be analyzed as randomized.
Per Protocol Population - The per protocol (PP) population includes subjects in the ITT population who do not have significant protocol deviations and who complete the study. Protocol deviations will be assessed prior to database lock and unmasking. Subjects in the PP population will be analyzed as treated, randomized.
Safety Population - The safety population includes all subjects who have received at least one dose of the investigational product. Subjects in the Safety population will be analyzed as treated.
Sample Size:
The sample size for this study is not based on statistical power considerations. It is expected that approximately 50 subjects will be enrolled in each of the four treatment arms, for a total of approximately 200 randomized subjects. Assuming a 5% drop out rate, approximately 47

-continued subjects per group are expected to complete the study.
Multiplicity Consideration:
Adjustments for multiple testing will not be implemented for this early phase study.
Primary Efficacy Analyses:
Schirmer's Test and Eye Dryness scores will be summarized by visit, time point (where appropriate) and treatment with descriptive statistics (n, mean, median, standard deviation, minimum and maximum).
An ANCOVA model will be used to compare results from Schirmer's Test concurrent with treatment between each dose of Compound 1 Nasal Spray and placebo treatment groups. The ANCOVA model will include baseline Schirmer's Test (captured at Screening), treatment and study site as covariates. Least Squares Means (LS Means) for each treatment, the corresponding 95% confidence intervals (CIs), and the estimated treatment differences between each dose of Compound 1 Nasal Spray and placebo will be calculated from this ANCOVA model. In addition, the study site by treatment interaction will be explored in a separate model to evaluate how the treatment effect may differ across study sites.
The change in EDS from pre- to post-treatment will be analyzed using an ANCOVA model with pre-treatment EDS as a covariate and with treatment and time point as fixed effects (accounting for repeated measures). LS means for each treatment, the corresponding 95% Cis, and the estimated treatment difference between each dose of Compound 1 Nasal Spray and placebo will be calculated from this ANCOVA model. A study site by treatment interaction will also be explored in a separate model to evaluate how the treatment effect may differ across study sites.
The primary analyses will be performed on the ITT population on observed data. Two-sample t-tests and non-parametric Wilcoxon rank sum tests will be used to compare treatments as unadjusted sensitivity analyses. Sensitivity analyses will also be performed on the ITT population with multiple imputation (MI) to impute missing data, as well as the PP population with observed data only.
Other Efficacy Analyses:
Change from pre to post-treatment in EDS will also be analyzed at each individual time point in a manner similar to the primary analysis for Schirmer's Test. These ANCOVA models will include pre-treatment EDS, treatment and study site as covariates.
Change from pre-to post-treatment in Ora Calibra Ocular Discomfort Scale results will be summarized by visit, time point (where appropriate) and treatment with quantitative descriptive statistics and will be analyzed at each individual time point in a manner similar to EDS.
The analyses will be performed for observed data only for the ITT and PP populations.
Safety Variables:
Adverse events will be coded using the MedDRA dictionary. Frequencies and percentages of subjects with treatment-emergent adverse events (TEAEs), serious TEAEs, and TEAEs causing premature discontinuation will be provided by treatment group. An AE is treatment emergent if it occurs or worsens after the first dose of study treatment. Furthermore, frequencies will be given of subjects with TEAEs by system organ class, by system organ class and preferred term, by system organ class, preferred term and maximal severity, by system organ class, preferred term and strongest relationship, and by system organ class, preferred term, maximal severity, and strongest relationship. Separate analyses will be performed for ocular specific and all AEs (including systemic).
Other safety endpoints including visual acuity, slit-lamp biomicroscopy and intranasal endoscopic examination will be summarized by treatment group and visit using descriptive statistics. Changes or shifts from baseline will also be summarized where appropriate. For assessments performed by eye, study eye and fellow eye will be summarized separately. In addition, shifts from baseline to worst on-treatment value for ocular safety assessments will be summarized.
Summary of Known and Potential Risks and Benefits to Human Subjects
There are no known risks with the instillation of Compound 1 Nasal Spray.

LIST OF ABBREVIATIONS

| | |
|---|---|
| AE | Adverse event |
| BCVA | Best corrected visual acuity |
| CAE<sup>SM</sup> | Controlled adverse environment |
| CFR | Code of Federal Regulations |
| CI | Confidence interval |
| DED | Dry eye disease |
| CRF | Case report form |
| FDA | Food and Drug Administration |
| GCP | Good clinical practice |
| HIPAA | Health Information Portability and Accountability Act |
| ICF | Informed consent form |
| ICH | International Conference on Harmonisation |
| IRB | Institutional/independent review board |
| logMAR | Logarithm of the minimum angle of resolution |
| mm | Millimeter |
| OSDI © | Ocular Surface Disease Index © |
| OTC | Over-the-counter |

-continued

LIST OF ABBREVIATIONS

| | |
|---|---|
| SAE | Serious adverse event |
| TENS | Transcutaneous electrical nerve stimulation |
| US | United States |

1. Introduction

Dry eye is a multifactoral, age-related disorder of the ocular surface resulting in severe pain, visual impairment, tear film hyperosmolarity and instability, inflammation, and corneal wounding. While the prevalence of dry eye is difficult to report due to varying definitions and diagnostic criteria, it is estimated that between 5% and 35% of the world's population over 50 years old suffers from this condition[1]. In the United States, it is estimated that as many as 3.2 million women and 1.7 million men over the age of 50 have dry eye, with a projected 40% increase in the number of patients affected by 2030.

Compound 1 nasal spray is being developed for the treatment of dry eye through the targeting of the nasolacrimal reflex pathway. The nasolacrimal reflex is a well-established pathway by which nasal stimuli promote both resting basal and bolus Lear secretion. The reflex plays a functional role in expelling foreign bodies or irritants from the nose by secreting tears into the nasal cavity via the nasolacrimal duct upon stimulation by the irritant. Reflex activation of the lacrimal glands is also one of the body's primary compensatory mechanisms for addressing ocular surface dryness. Unfortunately, over time, an arid environment and resulting inflammation results in damage to the afferent nerves innervating the cornea, compromising the reflex response and ultimately leading to an even drier ocular surface.

Compound 1 serves as a nasal stimulus through activation of nicotinic acetylcholine receptors (nAchRs). It is well established that nAchRs can mediate afferent signals within the trigeminal nerve, including response to nicotinic nasal stimuli. These afferent signals form the basis for the nasolacrimal reflex which results in tear production. Indeed, nicotine-containing nasal sprays, developed for smoking cessation, are known to increase tearing as a side effect of treatment. Thus, nAchRs are a logical target for activating the tear reflex for treatment of dry eye.

This study will utilize the Controlled Adverse Environment (CAES$^{SM}$) model to assess symptoms of dry eye. The CAE is a room that standardizes environmental conditions by regulating humidity, temperature, airflow, lighting conditions and visual tasking. Dry eye patients are exposed to the CAE for up to two hours, during which subjective and objective parameters can be evaluated before, during and after exposure. The CAE represents everyday situations that dry eye patients encounter such as forced air heating systems, airplane travel and computer use and allows for the standardization of these influential factors.

2. Study Objectives

The objective of this study is to evaluate the safety and effectiveness of Compound 1 Nasal Spray as compared to placebo on signs and symptoms of dry eye disease (DED).

3. Clinical Hypotheses

The clinical hypothesis for this study is that Compound 1 nasal spray is superior to placebo in treating the signs and symptoms of DED.

4. Overall Study Design

This is a Phase 2, multicenter, randomized, double-masked, placebo controlled study designed to evaluate the safety and efficacy of Compound 1 nasal spray in adult participants with DED. Approximately 200 subjects at least 22 years of age with a subject-reported history of dry eye and meeting all other study eligibility criteria will be randomized to receive an application of Compound 1 or placebo at Visit 1 and Visit 2.

| | Screening |
|---|---|
| Screening & Treatment (Schirmer's Evaluation) | Informed Consent<br>Demographics, Medical/Medication & Ocular History<br>Eligibility Criteria<br>Dry Eye Questionnaires |
| Visit 1 (Day 1) | Best Corrected Visual Acuity<br>Slit Lamp Biomicroscopy<br>corneal Fluorescein Staining<br>Schirmer's Test<br>Schirmer's Test with Nasal Stimulation (Cotton Swab)<br>Intranasal Examination<br>Urine Pregnancy Test (if applicable)<br>Concomitant Medications<br>Adverse Events<br>Treatment (Schirmer's Test Evaluations)<br>Randomization<br>Treatment and concurrent Schirmer's Test<br>Best Corrected Visual Acuity<br>Slit Lamp Biomicroscopy<br>Intranasal Endoscopic Examination<br>Concomitant Medications<br>Adverse Events<br>Scheduling of Participants for Visit 2<br>↓ |
| Visit 2 (Day 15 + 4) CAE | Medical/Medication & Ocular History Update<br>Pre-CAE Symptoms<br>CAE Exposure, Symptom Assessment and Treatment<br>Best Corrected Visual Acuity<br>Slit Lamp Biomicroscopy<br>Intranasal Endoscopic Examination<br>Concomitant Medications<br>Adverse Events<br>Study Exit |

Participants who terminate early during the application period will be asked to complete safety assessments (if the participants agree) prior to study exit. Participants who are terminated early from the study will not be replaced.

5. Study Population 5.1. Number of Subjects

It is estimated that approximately 200 participants (approximately 50 per sequence arm) will be enrolled at up to 3 sites in the US. Subjects will be randomized to receive a Low Dose. Medium Dose, High Dose (not to exceed 3.3%, i.e. 33.2 µg/µL of Compound 1 free base), or placebo at Visit 1 and Visit 2.

5.2. Study Population Characteristics

All subjects must be at least 22 years of age, of either gender, and of any race, and must meet all inclusion criteria and none of the exclusion criteria.

5.3. Inclusion Criteria

Subjects must:
1. Be at least 22 years of age at the Screening Visit
2. Have used and/or desired to us an artificial tear substitute for dry eye symptoms within 6 months prior to Visit 1
3. Have an OSDI© score of ≥23 with ≥3 responses of "N/A" at the Screening Visit
4. Have ALL of the following in the study eye at the Screening Visit:
   A corneal fluorescein staining score of ≥2 in at least one corneal region OR have a sum of ≥4 for all corneal regions
   A baseline Schirmer's Test (with topical anesthesia) score of ≤10 mm/5 minutes with a cotton swab nasal stimulation Schirmer's Test score at least 7 mm greater in the same eye
   The study eye will be defined as the eye that meets all inclusion criteria; if both eyes qualify then the eye with the greatest increase in tear production with stimulation by a cotton swab at the Screening Visit or, if there is no difference in stimulated tear production, the eye with the lower basal Schirmer's score at screening. If there is no difference for either measure, the right eye will be used as the study eye.
5. Best corrected visual acuity (BCVA) of 0.7 log MAR or better (log MAR<0.7; Snellen equivalent score of 20/100 or better) in each eye at the Screening Visit 6. Have normal lid/lash anatomy, blinking function and closure as determined by the Investigator
7. Not be familiar with (e.g., know the study drug is used to stimulate tear production) or have previously used the study drug
8. Be literate, able to speak English, and able to complete questionnaires independently
9. Be able to participate in the study for approximately four consecutive hours on Day 15
10. Be able and willing to use the study drug and participate in all study assessments and visits
11. Have provided verbal and written informed consent
12. If a female of childbearing potential, have a negative urine pregnancy test on Day 1

5.4. Exclusion Criteria

Subjects must not:
1. Have clinically significant corneal epithelial defects at Study Day 1 prior to performing Schirmer's Test
2. Have chronic or recurrent epistaxis, coagulation disorders or other conditions that, in the opinion of the Investigator, may lead to clinically significant risk of increased bleeding
3. Have had nasal or sinus surgery (including history of application of nasal cautery) or significant trauma to these areas
4. Have a vascularized polyp, severely deviated septum, chronic recurrent nosebleeds, or severe nasal airway obstruction as confirmed by intranasal examination performed prior to Day 1
5. Be currently treated with nasal continuous positive airway pressure (CPAP)
6. Have had any intraocular surgery (such as cataract surgery), extraocular surgery (such as blepharoplasty) in either eye within three months or refractive surgery (e.g. LASIK, LASEK, PRK or corneal implant) within twelve months of Visit 1
7. Have had a corneal transplant in either or both eyes
8. Have used contact lenses within 7 days prior to Visit 1 or anticipate the use of contact lenses during the study period
9. Have a punctal or intracanalicular plug present in any eyelid (participants with permanent occlusion of punctal ducts are eligible)
10. Have a history or presence of any ocular disorder or condition in either eye that would, in the opinion of the Investigator, likely interfere with the interpretation of the study results or participant safety such as significant corneal or conjunctival scarring; pterygium or nodular pinguecula; current ocular infection, conjunctivitis, or inflammation not associated with dry eye; anterior (epithelial) basement membrane corneal dystrophy or other clinically significant corneal dystrophy or degeneration; ocular herpetic infection; evidence of keratoconus; etc. Blepharitis not requiring treatment and mild meibomian gland disease that are typically associated with dry eye disease are allowed
11. Have a systemic condition or disease not stabilized or judged by the Investigator to be incompatible with participation in the study or with the lengthier assessments required by the study (e.g., current systemic infection, uncontrolled autoimmune disease, uncontrolled immunodeficiency disease, history of myocardial infarction or heart disease, etc.)
12. Have a known hypersensitivity to any of the procedural agents or study drug components
13. Have current concomitant use of snuff, chewing tobacco, or cigarettes/cigars during the study or within the previous 30 clays
14. Have current concomitant use of a nicotinic acetylcholine receptor agonist [Nicodem®, Nicorette®, Nicotrol NS® (nicotine), Tabex®, Desmoxan® (cytisine), and Chantix® (varencline)] or within the previous 30 days
15. Have active or uncontrolled, severe:
   Systemic allergy
   Chronic seasonal allergies at risk of being active during the study
   Rhinitis or sinusitis requiring treatment such as antihistamines, decongestants, oral or aerosol steroids at the Screening Visit
   Untreated nasal infection at Visit 1
16. Have any condition or history that, in the opinion of the investigator, may interfere with study compliance, outcome measures, safety parameters, and/or the general medical condition of the subject
17. Be a female who is pregnant, nursing an infant, or planning a pregnancy at Visit 1
18. Be currently enrolled in an investigational drug or device study or have used an investigational drug or device within 30 days prior to Visit 1

5.5. Withdrawal Criteria (if Applicable)

If at any time during the study the Investigator determines that a subject's safety has been compromised, the subject may be withdrawn from the study.

Subjects may withdraw consent from the study at any time.

Sponsor and/or Investigator may discontinue any subject for non-compliance or any valid medical reason during the course of the study (see Section 8.6.2).

6. Study Parameters 6.1 Efficacy Measures 6.11. Primary Efficacy Measures

The following primary endpoints will be tested:
Schirmer's Test at Visit 1
Eye Dryness Score (EDS) at Visit 2

6.2. Safety Measure
Adverse Events 6.3. Other Measures
Ora Calibra™ Ocular Discomfort Scale
Urine pregnancy test (Day 1)

7. Study Materials 7.1. Study Drug(s)

7.1.1. Formulations
Compound 1 Nasal Spray
Placebo (Compound 1 Vehicle Nasal Spray)

7.1.2. Dispensation Schedule
At Visit 1, qualified subjects will be randomized and the first dose of study drug will be administered in office.
At Visit 2, subjects will receive their second dose of study drug during CAE™ exposure.

7.1.3. Instructions for Use
Compound 1 (and Placebo) will be formulated at the desired concentration depending upon dose group assignment in phosphate buffered saline as a sterile aqueous solution, and presented in single-use glass vials sealed with a rubber stopper.

The product is preservative free and intended for intranasal use only. The product should not be used if cloudy or if particles are present.

Compound 1 solution will be administered without dilution.

The drug solution will be removed from the glass vial via a 5-micron filter needle.

The 5-micron filter needle will then be discarded and Compound 1 will be administered using the supplied single-use syringe and single-use intranasal atomizer.

7.2. Other Study Supplies

Urine pregnancy test kits

Fluorescein sodium solution or fluorescein strips

Schirmer's test strips

Proparacaine

8. Study Methods and Procedures 8.1. Participant Entry Procedures 8.1.1. Overview Participants as defined by the criteria in section 5.2, 5.3, and 5.4 will be considered for entry into this study.

8.1.2. Informed Consent

Prior to a participant's participation in the trial (i.e., prior to study-related procedures), the study will be discussed with each potential participant and participants wishing to participate must be administered and provide written informed consent using an IRB approved informed consent form (ICF). The ICF must be the most recent version that has received approval by a properly constituted Institutional Review Board.

8.1.3. Washout Intervals

Prohibited medications, treatments, and activities are outlined in the Exclusion Criteria (Section 5.4).

8.1.4. Procedures for Final Study Entry

Subjects must meet all inclusion criteria and none of the exclusion criteria.

8.1.5. Methods for Assignment to Treatment Groups

Each subject who qualifies will be assigned a screening number. All screening numbers will be assigned in strict numerical sequence at a site and no numbers will be skipped or omitted. If all inclusion and exclusion criteria are met at Visit 1, each qualifying subject will then be assigned a randomization number.

A randomization schedule will be provided to each investigational site. The randomization schedule will be stratified by site, such that there will be an approximate equal number of subjects assigned to each of the four treatment arms at each site. The site staff will dispense to the patient the study kit labeled with the corresponding randomization number. The randomization number will be recorded on the patient's source document and eCRF. The Sponsor, Investigators, and study staff will be masked during the randomization process and throughout the study.

8.2. Concurrent Therapies

The use of any concurrent medication, prescription or over-the-counter, is to be recorded on the subjects source document and corresponding electronic case report form (eCRF) along with the reason the medication was taken.

Concurrent enrollment in another investigational drug or device study is not permitted.

8.2.1. Prohibited Medications/Treatments

Disallowed medications/treatments during the study are outlined in the Exclusion Criteria (Section 5.4)

8.2.2. Escape Medications

No escape medications are required for this study.

8.2.3. Special Diet or Activities

No special diets or activities are required for this study.

8.3. Examination Procedures 8.3.1. Procedures to be Performed at Each Study Visit with Regard to Study Objectives(s)

The following procedures will be performed:

Visit 1 (Day 1): Screening and Schirmer's Test Evaluation

Screening

Informed consent/Health Information Portability and Accountability Act (HIPAA) consent Demographic data, medical/medication, and ocular history Eligibility Criteria

OSDI

EDS (visual analog scale)

Ora Calibra™ Ocular Discomfort Scale

Best Corrected Visual acuity

Slit lamp biomicroscopy

Corneal fluorescein staining

Schirmer's Test

Schirmer's Test with nasal stimulation (cotton swab)

Intranasal examination

Urine Pregnancy Test (if applicable)

Concomitant Medications

Adverse events

Treatment (Schirmer's Test Evaluation)

Pre-Treatment Procedures:

Randomization: Qualified participants will be treated with a Low Dose, Medium Dose, or High Dose (not to exceed not to exceed 3.3%, i.e. 33.2 µg/µL of Compound 1 free base), or placebo.

Treatment Procedures:

Instruct subjects on investigational drug/placebo administration

Treatment with concurrent Schirmer's test

Investigational drug/placebo administration

Post-Treatment Procedures

Best Corrected Visual Acuity (BCVA)

Slit lamp biomicroscopy

Intranasal endoscopic examination

Concomitant Medications

Adverse Events

Schedule participant for Visit 2

Visit 2 (Day 15+4): CAE

Medical/medication and ocular history updates

Eye Dryness Scale (EDS, visual analog scale)

Ora Calibra™ Ocular Discomfort Scale

Approximately 120 minutes of $CAE^{SM}$ Exposure

EDS collected upon entering the $CAE^{SM}$ and every 5 minutes thereafter.

Ora Calibra™ Ocular Discomfort Scale upon entering the $CAE^{SM}$ and every 5 minutes thereafter.

Qualified participants will be treated with a Low Dose, Medium Dose, or High Dose (not to exceed not to exceed 3.3%, i.e. 33.2 µg/µL of Compound 1 free base), or placebo.

Treatment with Investigational drug/placebo will be administered upon participant reporting an Ocular Discomfort score ≥3 at two or more consecutive time points in at least one eye during $CAE^{SM}$ exposure (if a participant has an Ocular Discomfort rating of 3 at time=0 for an eye, s/he must report an Ocular Discomfort rating of 4 for two consecutive measurements for that eye) using the Ora Calibra™ Scale. Participant will resume symptom assessments 1 minute after the application ends every 5 minutes.

Best Corrected Visual acuity

Slit lamp biomicroscopy

Intranasal Endoscopic Examination

Urine Pregnancy Test (if applicable)

Concomitant Medications

Adverse Events

Study exit

8.4. Schedule of Visits, Measurements and Dosing

8.4.1. Scheduled Visits

Refer to section herein for a schedule of visits and measurements.

8.4.2. Unscheduled Visits

These visits may be performed in order to ensure subject safety

Evaluations that may be conducted at an Unscheduled Visit include:
- Slit-lamp Biomicroscopy;
- Visual Acuity;
- Intranasal Endoscopic Examination;
- Urine Pregnancy Test;
- Assessment of Adverse Events;
- Assessment of concurrent medications and/or treatments; and
- Any other assessments needed in the judgment of the investigator.

8.5. Compliance with Protocol

Subjects will be instructed on how study drug will be administered at Visits 1 and 2 and provided detailed written instructions to review.

Dosing compliance will be based on used/unused study drug at Visits 1 and 2.

8.6. Subject Disposition

8.6.1. Completed Subjects

A completed subject is one who has not be discontinued from the study.

8.6.2. Discontinued Subjects

Subjects may be discontinued at any time prior to their completion of the study due to:
- adverse events;
- unmasking when medically necessary;
- protocol violations;
- administrative reasons (e.g., inability to continue, lost to follow up);
- sponsor termination of study;
- subject choice (e.g., withdrawal of consent); and
- other Note: In addition, any subject may be discontinued for any sound medical reason at the discretion of the investigator (after consultation with the Sponsor) or Sponsor.

Notification of a subject discontinuation and the reason for discontinuation will be clearly documented.

Discontinued subjects will not be replaced.

8.7. Study Termination

The study may be stopped at any time with appropriate notification.

8.8. Study Duration

An individual subject's participation will involve 2 visits over approximately 2-weeks (14 days)

8.9. Monitoring and Quality Assurance

During the course of the study a monitor, or designee, will make routine site visits to review protocol compliance, assess study drug accountability, subject safety, and ensure the study is being conducted according to the pertinent regulatory requirements. The review of the subjects' medical records will be performed in a manner that adequately maintains subject confidentiality. Further details of the study monitoring will be outlined in a monitoring plan.

9. Adverse Events

9.1. Adverse Event

An adverse event is defined as any untoward medical occurrence associated with the use of a drug in humans, whether or not the event is considered drug-related. An adverse event can therefore be any unfavorable and unintended sign (e.g., an abnormal laboratory finding), symptom, or disease occurring after the subject started dosing with the study drug, without any judgment about causality. Any pre-existing medical condition that worsens after administration of the study drug will also be considered a new adverse event.

Study drug includes the investigational drug under evaluation and placebo.

Documentation regarding the adverse event should be made as to the nature, date of onset, end date, severity, relationship to study drug, action(s) taken, seriousness, and outcome of any sign or symptom observed by the Investigator or reported by the subject upon indirect questioning.

9.1.1. Severity

Severity of an adverse event is defined as a qualitative assessment of the degree of intensity of an adverse event as determined by the investigator or reported to him/her by the patient/subject. The assessment of severity is made irrespective of relationship to study drug or seriousness of the event and should be evaluated according to the following scale:

- Mild: Event is noticeable to the subject, but is easily tolerated and does not interfere with the subject's daily activities.
- Moderate: Event is bothersome, possibly requiring additional therapy, and may interfere with the subject's daily activities.
- Severe: Event is intolerable, necessitates additional therapy or alteration of therapy, and interferes with the subject's daily activities.

9.1.2. Relationship to Study Drug

The relationship of each AE to the investigational product should be determined by the investigator (in a blinded manner) using these explanations:

- Definite: When there are good reason and sufficient documentation to demonstrate a direct causal relationship between investigational product and AE;
- Probable. When there are good reasons and sufficient documentation to assume a causal relationship in the sense of plausible, conceivable, likely but not necessarily highly probable.
- Possible: When there is sufficient information to accept the possibility of a causal relationship in the sense of not impossible and not unlikely, although the connection is uncertain or doubtful, for example; due to missing data or insufficient evidence.
- None: When there is sufficient information to accept a lack of a causal relationship, in the sense of impossible and improbable.
- Unclassified: When the causal relationship is not assessable for whatever reason due to insufficient evidence, conflicting data or poor documentation.

9.1.3. Expectedness

The expectedness of an adverse event should be determined based upon existing safety information about the study drug using these explanations:

- Unexpected: An adverse event that is not listed in the Investigator's brochure or is not listed at the specificity or severity that has been observed.
- Expected: An adverse event that is listed in the Investigator's brochure at the specificity and severity that has been observed.
- Not Applicable: Any adverse event that is unrelated to the study drug.

Adverse events that are mentioned in the Investigator's brochure as occurring with a class of drugs or as anticipated from the pharmacological properties of the drug, but are not specifically mentioned as occurring with the particular drug under investigation are to be considered unexpected.

The investigator should initially classify the expectedness of an adverse event, but the final classification is subject to the Medical Monitor's determination.

9.2. Serious Adverse Events

An adverse event is considered serious if, in the view of either the investigator or Sponsor, it results in any of the following outcomes:

Death;

A life-threatening adverse event;
- Note: An adverse event is considered "life-threatening" if, in the view of either the investigator or Sponsor, its occurrence places the patient or subject at immediate risk of death. It does not include an adverse event that, had it occurred in a more severe form, might have caused death.

Inpatient hospitalization or prolongation of existing hospitalization;
- Note: The term "inpatient hospitalization" refers to any inpatient admission (even if less than 24 hours). For chronic or long-term inpatients, inpatient admission includes transfer within the hospital to an acute/intensive care inpatient unit. Inpatient hospitalization does not include: emergency room visits; outpatient/same-day/ambulatory procedures; observation/short stay units; rehabilitation facilities; hospice facilities; nursing homes; or clinical research/phase 1 units.
- Note: The term "prolongation of existing hospitalization" refers to any extension of an inpatient hospitalization beyond the stay anticipated or required for the reason for the initial admission as determined by the investigator or treating physician.

A persistent or significant incapacity or substantial disruption of the ability to conduct normal life functions;
- Note: A serious adverse event specifically related to visual threat would be interpreted as any potential impairment or damage to the subject's eyes (e.g., hemorrhage, retinal detachment, central corneal ulcer or damage to the optic nerve).

A congenital anomaly/birth defect.

Important medical events that may not result in death, are life-threatening, or require hospitalization may be considered serious when, based upon appropriate medical judgment, they may jeopardize the patient or subject and may require medical or surgical intervention to prevent one of the outcomes listed in this definition.

9.3. Procedures for Reporting Adverse Events

All adverse events and their outcomes must be reported and recorded.

9.3.1. Reporting a Suspected Unexpected Adverse Reaction

All adverse events that are 'suspected' and 'unexpected' are to be reported.

9.3.2. Reporting a Serious Adverse Event

To ensure subject safety, all serious adverse events, regardless of relationship to the study drug, must be immediately reported. All information relevant to the serious adverse event must be recorded on the appropriate case report forms. All subjects experiencing a serious adverse event must be followed up and the outcome reported.

In the event of a serious adverse event, the investigator must notify the Sponsor immediately; obtain and maintain in his/her files all pertinent medical records, information, and medical judgments from colleagues who assisted in the treatment and follow-up of the subject; provide the Sponsor with a complete case history.

9.3 Procedures for Unmasking of Study Drug

All subjects, investigators, and study personnel involved with the conduct of the study will be masked with regard to treatment assignments. When medically necessary, the investigator may need to determine what treatment arm has been assigned to a subject. The unmasked subject will be discontinued from the study.

9.5 Type and Duration of the Follow-Up of Subjects after Adverse Events

The investigator will follow unresolved AEs to resolution until the subject is lost to follow-up or until the AE is otherwise classified. Resolution means the subject has returned to baseline state of health or the Investigator does not expect any further improvement or worsening of the AE. If the patient is lost to follow-up, the Investigator should make 3 reasonable attempts to contact the patient via telephone, post, or certified mail. All follow-up will be documented in the subject's source document.

If the Investigator becomes aware of any new information regarding an existing SAE (i.e., resolution, change in condition, or new treatment), a new SAE/Unanticipated Report Form must be completed. The original SAE form is not to be altered. The report should describe whether the event has resolved or continues and how the event was treated.

10. Statistical Hypotheses and Methods of Analyses 10.1. Analysis Populations

The following analysis populations will be considered:

Intent-to-Treat Population—The intent-to-treat (ITT) population includes all randomized subjects. Subjects in the ITT population will be analyzed as randomized.

Per Protocol Population—The per protocol (PP) population includes subjects in the ITT population who do not have significant protocol deviations and who complete the study. Protocol deviations will be assessed prior to database lock and unmasking. Subjects in the PP population will be analyzed as treated.

Safety Population—The safety population includes all subjects who have received at least one dose of the investigational product. Subjects in the Safety population will be analyzed as treated.

The statistical analysis of safety data will be performed for the safety population. The analysis of baseline and efficacy data will be performed for the ITT population. Efficacy analyses will also be performed for the PP population as sensitivity analyses.

10.2. Statistical Hypotheses $H_{01}$: There is no difference between Compound 1 Nasal Spray (Low Dose, Medium Dose, or High Dose), and placebo in the change from baseline in Schirmer's Test results.

$H_{11}$: There is a difference between Compound 1 Nasal Spray (Low Dose, Medium Dose, or High Dose) and placebo in the change from baseline in Schirmer's Test results.

$H_{02}$: There is no difference between Compound 1 Nasal Spray (Low Dose, Medium Dose, or High Dose) and placebo in the change from pre- to post-treatment in EDS.

$H_{12}$: There is a difference between Compound 1 Nasal Spray (Low Dose, Medium Dose, or High Dose) and placebo in the change from pre- to post-treatment in EDS.

A successful outcome will be one that rejects both null hypotheses ($H_{01}$ and $H_{02}$).

10.3. Sample Size

The sample size for this study is not based on statistical power considerations. It is expected that approximately 50 subjects will be enrolled in each of the four treatment arms, for a total of approximately 200 randomized subjects. Assuming a 5% drop out rate, approximately 47 subjects per group are expected to complete the study.

10.4. Statistical Analysis 10.4.1. General Considerations

Quantitative variables will be summarized using number of subjects (n), mean, median, standard deviation, minimum and maximum. Qualitative variables will be summarized using counts and percentages.

All summaries will be presented by treatment group. Summaries will be provided for demographics, medical history, concomitant medications, and subject disposition.

For the purpose of summarization, medical history, concomitant medications, and adverse events will be coded to MedDRA and WHO Drug dictionaries, as appropriate.

Baseline measures are defined as the last measure prior to the initiation of study treatment, usually at Visit 1 screening.

10.4.2. Unit of Analysis

Safety endpoints will be analyzed for both eyes. For efficacy endpoints, the unit of analysis will be the study eye as defined by the following:

The study eye is defined as the eye that meets all inclusion/exclusion criteria; if both eyes qualify then the eye with the greatest increase in tear production with stimulation by a cotton swab at the Screening Visit or, if there is no difference in stimulated tear production, the eye with the lower basal Schirmer's score at screening. If there is no difference for either measure, the right eye will be used as the study eye.

10.4.3. Missing Data

The primary analyses will be performed using observed data (without imputing missing data). Sensitivity analyses for the primary efficacy analysis will be performed using Markov Chain Monte Carlo (MCMC) multiple imputation methodology to impute missing data. The rate of missing data is expected to be low; however, if the missing data rate exceeds 5%, additional missing data imputation methods (such as tipping point analyses) will be employed to understand the potential impact of missing data on the primary outcomes.

Other efficacy analyses will be performed using observed data only.

10.4.4. Multiplicity Consideration

Adjustments for multiple testing will not be implemented for this early phase study.

10.4.5. Primary Efficacy Analyses

Primary efficacy analyses will be conducted on the following endpoints:

Schirmer's Test at Visit 1

Eye Dryness Score during CAE at Visit 2

Schirmer's Test and Eye Dryness Score will be summarized by visit, time point (where appropriate) and treatment with quantitative descriptive statistics (n, mean, median, standard deviation, minimum and maximum).

An ANCOVA model will be used to compare results from Schirmer's Test concurrent with treatment between each dose of Compound 1 Nasal Spray and placebo treatment groups. The ANCOVA model will include baseline Schirmer's Test (captured at Screening), treatment and study site as covariates. Least Squares Means (LS Means) for each treatment, the corresponding 95% confidence intervals (CIs), and the estimated treatment differences between each dose of Compound 1 Nasal Spray and placebo will be calculated from this ANCOVA model. In addition, the study site by treatment interaction will be explored in a separate model to evaluate how the treatment effect may differ across study sites.

The change in EDS from pre- to post-treatment will be analyzed using an ANCOVA model with pre-treatment EDS as a covariate and with treatment and time point as fixed effects (accounting for repeated measures). LS means for each treatment, the corresponding 95% CIs, and the estimated treatment difference between each dose of Compound 1 Nasal Spray and placebo will be calculated from this ANCOVA model. The study site by treatment interaction will also be explored in a separate model to evaluate how the treatment effect may differ across study sites.

The primary analyses will be performed on the ITT population on observed data. Two-sample t-tests and non-parametric Wilcoxon rank sum tests will be used to compare treatments as unadjusted sensitivity analyses. Sensitivity analyses will also be performed on the ITT population with multiple imputation (MI) to impute missing data, as well as the PP population with observed data only.

10.4.6. Other Efficacy Analyses

Change from pre- to post-treatment in EDS will also be analyzed at each individual time point in a manner similar to the primary analysis for Schirmer's Test. These ANCOVA models will include pre-treatment EDS, treatment and study site as covariates.

Change from pre- to post-treatment in Ora Calibra Ocular Discomfort Scale results will be summarized by visit, time point (where appropriate) and treatment with quantitative descriptive statistics and will be analyzed at each individual time point in a manner similar to EDS.

The analyses will be performed for observed data only for the ITT and PP populations.

10.4.7. Safety Variables

Adverse events will be coded using the MedDRA dictionary. Frequencies and percentages of subjects with treatment-emergent adverse events (TEAEs), serious TEAEs, and TEAEs causing premature discontinuation will be provided by treatment group. An AE is treatment emergent if it occurs or worsens after the first dose of study treatment. Furthermore, frequencies will be given of subjects with TEAEs by system organ class, by system organ class and preferred term, by system organ class, preferred term and maximal severity, by system organ class, preferred term and strongest relationship, and by system organ class, preferred term, maximal severity, and strongest relationship. Separate analyses will be performed for ocular specific and all AEs (including systemic).

Other safety endpoints including visual acuity, slit-lamp biomicroscopy and intranasal endoscopic examination will be summarized by treatment group and visit using descriptive statistics. Changes or shifts from baseline will also be summarized where appropriate. For assessments performed by eye, study eye and fellow eye will be summarized separately. In addition, shifts from baseline to worst on-treatment value for ocular safety assessments will be summarized.

10.4.8. Interim Analyses

No interim analyses are planned for this study.

11. Compliance with Good Clinical Practices, Ethical Considerations, and Administrative Issues This study will be conducted in compliance with the protocol, Good Clinical Practices (GCPs), including the International Conference on Harmonization (ICH) Guidelines, and in general, consistent with the Declaration of Helsinki. In addition, all applicable local, state, and federal requirements relevant to the use of study drugs in the countries involved will be adhered to.

11.1. Protection of Human Subjects

11.1.1. Subject Informed Consent

Informed consent/assent must take place before any study specific procedures are initiated. Signed and dated written informed consent must be obtained from each subject and/or from the subject's parent or legal guardian prior to enrollment into the study. If the subject is under the legal age of consent, the consent form must be signed by a legal guardian or as required by state and/or local laws and regulations.

All informed consent/assent forms must be approved for use by the Sponsor and receive approval/favorable opinion from an IRB/IEC prior to their use. If the consent form requires revision (e.g., due to a protocol amendment or significant new safety information), it is the investigator's responsibility to ensure that the amended informed consent is reviewed and approved by Ora prior to submission to the governing IRB/IEC and that it is read, signed and dated by all subjects subsequently enrolled in the study as well as those currently enrolled in the study.

11.1.2. Institutional Review Board (IRB) Approval

This study is to be conducted in accordance with Institutional Review Board regulations (U.S. 21 CFR Part 56.103). The investigator must obtain appropriate IRB approval before initiating the study and re-approval at least annually.

Only an IRB/ERC approved version of the informed consent form will be used.

11.2. Ethical Conduct of Study

This study will be conducted in accordance with the ethical principles that originated with the Declaration of Helsinki.

11.3. Subject Confidentiality

All personal study subject data collected and processed for the purposes of this study should be maintained by the investigator and his/her staff with adequate precautions as to ensure that the confidentiality of the data in accordance with local, state, and federal laws and regulations.

A report of the results of this study may be published or sent to the appropriate health authorities in any country in which the study drug may ultimately be marketed, but the subject's identity will not be disclosed in these documents.

11.4. Documentation

Source documents may include a subject's medical records, hospital charts, clinic charts, the investigator's study subject files, as well as the results of diagnostic tests such as X-rays, laboratory tests, and EKGs. The investigator's copy of the Case Report Forms serves as the investigator's record of a subject's study-related data.

11.4.1. Retention of Documentation

All study related correspondence, subject records, consent forms, record of the distribution and use of all study drug and copies of case report forms should be maintained on file for at least two years after the last approval of a marketing application in an ICH region and until there are no pending or contemplated marketing applications in an ICH region; or until at least two years have elapsed since the formal discontinuation of clinical development of the study drug. These documents will be retained for a longer period if required by the applicable regulatory requirements or by an agreement with the Sponsor. It is the responsibility of the Sponsor to inform the investigator/institution as to when these documents no longer need to be retained.

If the responsible investigator retires, relocates, or for other reasons withdraws from the responsibility of keeping study records, custody must be transferred to a person who will accept the responsibility. The Sponsor must be notified in writing of the name and address of the new custodian.

11.5. Labeling, Packaging, Storage, Accountability, and Return or Disposal of Study Drug

11.5.1. Labeling/Packaging

Investigational drug will be provided in single-use vials and assigned prior to each treatment at Visit 1 and Visit 2.

11.5.2. Storage of Investigational Drug/Placebo

The investigational drug/placebo must be stored in a secure area accessible only to the investigator and his/her designee(s). Study drug(s) must be refrigerated (2-8° C. Do Not Freeze), protected from light, and secured at the investigational site in a locked container.

11.5.3. Accountability of Study Drug

The investigational drug/placebo is only prescribed by the principal investigator or his/her named sub investigator (s), and is to only be used in accordance with this protocol. The study drugs must only be distributed to subjects properly qualified under this protocol to receive study drug. The investigator must keep an accurate accounting of the study drugs by maintaining a detailed inventory. This includes the amount of study drugs received by the site, amount dispensed to subjects, amount returned to the site by the subjects, and the amount returned to the Sponsor upon the completion of the study.

11.5.4. Return or Disposal of Study Drug

All study drugs will be returned to the Sponsor or their designee for destruction.

11.6. Recording of Data on Source Documents and Electronic Case Reports Forms (eCRFs)

All subject data will be captured in the subject source documents which will be transcribed in the cCRFs. The investigator is responsible for ensuring that study data is completely and accurately recorded on each subject's eCRF, source documents, and all study-related materials. All study data should also be attributable, legible, contemporaneous, and original. Recorded datum should only be corrected in a manner that does not obliterate, destroy, or render illegible the previous entry (e.g., by drawing a single line through the incorrect entry and writing the revision next to the corrected data). An individual who has corrected a data entry should make clear who made the correction and when, by adding to the correction his/her initials as well as the date of the correction.

Data entry of all enrolled and randomized subjects will use software that conforms to 21 CFR Part 11 requirements, and will be performed only by staff who have been trained on the system and have access to the system. Data will not be entered for screen failure subjects. An audit trail will be maintained within the electronic system to capture all changes made within the eCRF database. After the end of the study and database lock, compact discs (CDs) containing copies of all applicable subjects' eCRFs will be provided to each Investigator Site to be maintained on file by the Investigator.

11.7. Handling of Biological Specimens

Not applicable.

11.8. Publications

The study will be documented in a final report, which will contain appropriate statistical analysis and medical overview.

12. References
 1. The epidemiology of dry eye disease; report of the Epidemiology Subcommittee of the International Dry Eye WorkShop (2007). The ocular surface 5, 93-107 (2007).
 2. Schaumberg, D. A, Dana. R, Buring. J. E. & Sullivan, D. A. Prevalence of dry eye disease among US men: estimates from the Physicians' Health Studies. Archives of ophthalmology 127, 763-768, doi:10.1001/archophthalmol.2009.103 (2009).
 3. Schaumberg, D. A, Sullivan, D. A, Buring. J. E. & Dana. M. R. Prevalence of dry eye syndrome among US women. American journal of ophthalmology 136, 318-326 (2003).
 4. Schaumberg, D. A, Sullivan, D. A. & Dana, M. R. Epidemiology of dry eye syndrome. Advances in experimental medicine and biology 506, 989-998 (2002).
 5. Albrecht J, Kopictz R, Linn J. Sakar V, Anzinger A. Schreder T, et al. Activation of olfactory and trigeminal cortical areas following stimulation of the nasal mucosa with low concentrations of S(−)-nicotine vapor-An fMRI study on chemosensory perception. Hum. Brain Mapp. Wiley Subscription Services. Inc, A Wiley Company: 2009 Mar. 30(3):699-710.
 6. Alimohamnmadi H, Silver W L. Evidence for nicotinic acetylcholine receptors on nasal trigeminal nerve endings of the rat. Chem. Senses. 2000 Feb. 25(1):61-6.
 7. Flores C M, DeCamp R M, Kilo S, Rogers S W, Hargreaves K M. Neuronal nicotinic receptor expression in sensory neurons of the rat trigeminal ganglion: demonstration of alpha3beta4, a novel subtype in the mammalian nervous system. J. Neurosci. 1996 Dec. 15:16(24):7892-901.
 8. Prescribing Information—Nicotrol N S (nicotine nasal spray). Pfizer, Inc: 2010.
 9. DEWS. Design and conduct of clinical trials: report of the Clinical Trials Subcommittee of the International Dry Eye WorkShop Ocul Surf 2007:5:158.
 10. Abelson R. Lane K J, Rodriguez J, et al. A single-center study evaluating the effect of the controlled adverse environment (CAE(SM)) model on tear film stability. Clin Ophthalmol 2012:6:1865-72.
 11. Meerovitch K. Torkildsen G, Lonsdale J, et al. Safety and efficacy of MIM-D3 ophthalmic solutions in a randomized, placebo-controlled Phase 2 clinical trial in patients with dry eye. Clin Ophthalmol 2013; 7:1275-85.
 12. Mundorf T. Wilcox K A, Ousler G W, 3rd. Welch D, Abelson M B. Evaluation of the comfort of Alphagan P compared with Alphagan in irritated eyes. Advances in therapy 2003.20:329-36.
 13. Ousler G W, 3rd, Abelson M B, Nally L A, Welch D. Casavant J S. Evaluation of the time to "natural compensation" in normal and dry eye subject populations during exposure to a controlled adverse environment. Advances in experimental medicine and biology 2002; 506:1057-63.
 14. Patane M A, Cohen A, From S, Torkildsen G, Welch D, Ousler G W, 3rd. Ocular iontophoresis of EGP-437 (dexamethasone phosphate) in dry eye patients: results of a randomized clinical trial. Clin Ophthalmol 2011; 5:633-43.
 15. Petrov A, Perekhvatova N. Skulachev M. Stein L, Ousler G. SkQ1 Ophthalmic Solution for Dry Eye Treatment: Results of a Phase 2 Safety and Efficacy Clinical Study in the Environment and During Challenge in the Controlled Adverse Environment Model. Advances in therapy 2016; 33:96-115.
 16. Semba C P, Torkildsen G L, Lonsdale J D, et al. A phase 2 randomized, double-masked, placebo-controlled study of a novel integrin antagonist (SAR 1118) for the treatment of dry eye. Am J Ophthalmol 2012; 153:1050-60 e1.
 17. Sosne G, Ousler G W. Thymosin beta 4 ophthalmic solution for dry eye: a randomized, placebo-controlled, Phase II clinical trial conducted using the controlled adverse environment (CAE) model. Clin Ophthalmol 2015:9:877-84.
 18. Ousler G W, Gomes P J, Welch D, Abelson M B. Methodologies for the study of ocular surface disease. Ocul Surf 2005; 3: 143-54.

Schedule of Visits and Measurements

|  | Visit 1 (Day 1) | | Visit 2 (Day 15 + 4) | |
| --- | --- | --- | --- | --- |
| Procedure | Screening | Schirmer's Test Evaluation | Pre-CAE$^{SM}$ | Post-CAE$^{SM}$ |
| Informed consent/HIPAA | X | | | |
| Demographics | X | | | |
| Medical/Medication, ocular history and updates | X | | X | |
| Eligibility criteria | X | | | |
| Urine pregnancy test | $X_3$ | | $X_3$ | |
| OSDI © questionnaire | X | | | |
| Eye Dryness Score (EDS) | X | | X4 | X4 |
| Ora Calibra ™ Ocular Discomfort Scale | X | | X4 | X4 |
| Best Corrected Visual acuity | X | $X_1$ | | X5 |
| Slit lamp biomicroscopy | X | $X_1$ | | X5 |
| Corneal fluorescein staining | X | | | |
| Schirmer's test | X | X | | |
| Schirmer's test with cotton swab stimulation | X | | | |
| Intranasal examination | X | $X_1$ | | X |
| Concomitant medications | X | $X_1$ | | X |
| Randomization | | X | | |

-continued

| | Visit 1 (Day 1) | | | |
|---|---|---|---|---|
| | | Schirmer's Test | Visit 2 (Day 15 + 4) | |
| Procedure | Screening | Evaluation | Pre-CAE$^{SM}$ | Post-CAE$^{SM}$ |
| Administer investigational drug/placebo | | X2 | X | |
| Adverse event query | X | X$_1$ | X | X |
| Exit from study | | | | X |

X$_1$ = Post-treatment procedures;
X2 = Concurrent with Schirmer's Test;
X$_3$ = For females of childbearing potential;
X4 = Procedure started at time 0 and then conducted every 5 minutes thereafter during the 120 minute CAE $^{SM}$ exposure;
X5 = Procedure may be performed after CAE $^{SM}$ exit at the Investigator's discretion as needed Examination Procedures, Tests, Equipment, and Techniques The following examination procedures, tests, equipment and techniques are listed in this section:

Visual Acuity Procedures

Log MAR visual acuity must be assessed using an ETDRS chart. The procedure used will be consistent with the recommendations provided for using the ETDRS eye chart. Visual acuity should be evaluated at the beginning of each visit in the study (i.e., prior to slit lamp examination). Participants should use the most recent correction to attain their corrected distance visual acuity (CDVA); if they forget their spectacles, this prescription can be placed in atrial frame.

Equipment

The visual acuity chart to be used is the ETDRS chart. If smaller reproduction (18" by 18", e.g., from Prevent Blindness) wall charts are used, the participant viewing distance should be exactly 10 feet (or as specified by the manufacturer). In ALL cases, for purposes of standardizing the testing conditions during the study, all sites must use only ETDRS Series 2000 Chart 1 & 2, and the right eye should be tested first. For reflectance (wall) charts, the chart should be placed frontally and be well illuminated.

Measurement Technique

The chart should be at a comfortable viewing angle. The right eye should be tested first. The participant should attempt to read each letter, line-by-line, left to right, beginning with line 1 at the top of the chart. The participant should be told that the chart has letters only, no numbers. If the participant reads a number, s/he should be reminded that the chart contains no numbers, and the examiner should then request a letter in lieu of the number.

The participant should be asked to read slowly, so as to achieve the best identification of each letter. S/he is not to proceed to the next letter until s/he has given a definite response.

If the participant changes a response (e.g., 'that was a "C" not an "O"') before s/he has read aloud the next letter, then the change must be accepted. If the participant changes a response having read the next letter, then the change is not accepted. The examiner should never point to the chart or to specific letters on the chart during the test.

A maximum effort should be made to identify each letter on the chart. When the participant says s/he cannot read a letter, s/he should be encouraged to guess. If the participant identifies a letter as one of two letters, s/he should be asked to choose one letter and, if necessary, to guess. When it becomes evident that no further meaningful readings can be made, despite encouragement to read or guess, the examiner should stop the test for that eye. However, all letters on the last line should be attempted as letter difficulties vary and the last may be the only one read correctly. The number of letters missed or read incorrectly should be noted.

Log MAR Visual Acuity Calculations

The last line in which a letter is read correctly will be taken as the base log MAR reading. To this value will be added the number "N×0.02" where 'N' represents the total number of letters missed up to and including the last line read. This total sum represents the log MAR visual acuity for that eye.

Example: Participant correctly reads 4 of 5 letters on the 0.2 line, and 2 of 5 letters on the 0.1 line.

| | |
|---|---|
| Base logMAR | =0.1 |
| N (total number of letters incorrect on line 0.2 as well as 0.1) | =4 |
| N × T (T = 0.02) | =0.08 |
| Base logMAR + (N × T) | =0.1 + 0.08 |
| logMAR visual acuity | =0.18 |

Repeat the procedure for the left eye.

In order to provide standardized and well-controlled assessments of visual acuity during the study, all visual acuity assessments at a single site must be consistently done using the same lighting conditions and same correction if possible during the entire study. If the same correction cannot be used (i.e., a participant broke his/her glasses), the reason for the change in correction should be documented.

Note: A clinically significant visual acuity decrease (defined as an increase of 0.22 or greater in log MAR score) from the Screening Visit (Visit 1) should be evaluated by the Investigator as a potential A E.

Slit Lamp Biomicroscopy

Slit lamp biomicroscopy will be performed during the study. Observations will be graded as Normal or Abnormal. Abnormal findings, which are clinically significant, will be described. The following will be examined at each visit:

Cornea
Conjunctiva
Anterior Chamber
Lid

Corneal Fluorescein Staining

The examiner should instill 5 μL of 2%4, preservative-free sodium fluorescein solution into the inferior conjunctival cul-de-sac of each eye. Alternatively, corneal staining can be assessed using 1.0 mg sodium fluorescein strips. After moistening the tip of the strip with sterile buffered saline, the excess is shaken into a waste bin with a sharp flick. The lower lid is then pulled down and the flat end of the tip should be gently applied to the inferior tarsal conjunctiva with the intent of not inducing reflex tearing and instilling a very small volume of dye.

The participant will be instructed to blink naturally several times without forced closure of the eyelid to distribute the fluorescein. In order to achieve maximum fluorescence, the examiner should wait at least two minutes after instillation before evaluating corneal fluorescein staining. A Wratten #12 yellow filter will be used to enhance the ability to grade fluorescein staining. The staining will be graded with the NEI Scale. The upper eyelid is lifted slightly to grade the entire corneal surface. Digital images of fluorescein staining may be taken for digital analysis.

NEI/Industry Workshop Scale

Score each of five areas on the cornea of each eye with a grading system shown in FIG. 2. FIG. 2 shows a diagram of the division of the corneal surface for measuring fluorescein uptake. A standardized grading system of 0-3 is used for each of the five areas on each cornea. Grade 0 will be specified when no staining is present. The maximum score is 15.

Intranasal Examination

Qualified participants for the study must undergo a nasal endoscopy exam to make the final eligibility determination (e.g. severe nasal airway obstruction such as, severe septal deviation or inferior turbinate hypertrophy, or vascularized polyp seen on examination are reasons for exclusion). To monitor nasal mucosal integrity during the study for participant safety, an examination of the nasal cavities via an endoscopic camera will be performed at the Screening Visit (after all other screening procedures have been completed). This examination will be performed by an Ear Nose and Throat (ENT) specialist, otolaryngologist or other suitably qualified medical practitioner (i.e, one who has been trained to perform nasal endoscopy). Still images or video may be captured. Participants should be instructed not to perform nasal stimulation on the day nasal endoscopy will be performed.

Schirmer's Test with Topical Anesthesia

At the Screening Visit, one basal Schirmer's test will be performed followed by a Schirmer's test with cotton swab nasal stimulation. The Schirmer's test with topical anesthetic will be used to assess tear production using the following steps:
1. Topical anesthetic drops such as 0.5% proparacaine hydrochloride or equivalent should be instilled in both eyes of the participant.
2. The participant will be instructed to keep the eyes gently closed for one minute.
3. After opening the eyes and allowing the eyes to recover for approximately one additional minute, excess moisture in the inferior formix is gently removed with a spear.
4. Schirmer's strips (35 mm×5 mm size filter paper strip) will be placed in each eye at the junction of the middle and lateral thirds of the lower eye lid.
5. Under ambient light, the participant will be instructed to look forward and to blink normally during the course of the test. The test should be performed in a room with no direct air on the participant's face.
6. The Schirmer's strips should remain in place until five minutes have elapsed or both strips have reached maximum score.
7. After five minutes, strips will be removed from both eyes and the amount of wetting will be recorded. The strips should be taped to the CRF.

Schirmer's Test Using Cotton Swab Nasal Stimulation

At the Screening Visit, the Schirmer's test should be performed using cotton swab nasal stimulation. New anesthetic drops should be instilled following the same procedure specified in steps #1 to 3 above.
1. With new strips in place, the examiner should insert cotton swabs in the participant's two nostrils simultaneously and gently probe both nasal middle turbinates for approximately 30 seconds. After this, the examiner can simply hold the swabs in place, applying gentle pressure, and repeat probing intermittently as necessary.
2. Alternatively, the participant can be instructed to hold the cotton swabs and gently probe both nasal turbinates simultaneously, resting intermittently before probing again. The examiner should continuously coach the participant on how to perform this test properly.
3. The Schirmer's strips should remain in place until five minutes have elapsed or both strips have reached maximum score.

Both Schirmer's scores will be recorded and verified that they meet the inclusion criteria.

Ocular Surface Disease Index© (OSDI©)

To minimize bias, participants will be asked to complete the OSDI questionnaire independently and in private after instructions have been provided by site personnel.

The OSDI is a 12-item questionnaire generated by the Outcomes Research Group at Allergan (Irvine, Calif.),[22] which asks participants to describe the severity and the nature of their irritation symptoms. The participant will answer the 12 questions by circling the number that best represents each answer: 4 (all of the time), 3 (most of the time), 2 (half of the time), 1 (some of the time), or 0 (none of the time). The final score for the questionnaire is calculated as follows:

Add subotals from Sections I, II, and III=A
Determine total number of questions answered from Sections I, II, and III (do not include N/A)=B
Final OSDI score=A×25 divided by B
An example of the questionnaire is shown in FIG. 3.

Eye Dryness Score (EDS) Using a Visual Analog Scale (VAS)

Participants will be asked the following question regarding eye dryness every 5 minutes during CAE$^{SM}$ exposure.

The participant will be asked to rate their ocular symptoms (both eyes simultaneously) due to eye dryness by placing a vertical mark on the horizontal line to indicate the level of discomfort; 0 corresponds to "no discomfort" and 100 corresponds to "maximal discomfort." The assessment line length of the scale will be 100 mm. See FIG. 5. The subject is instructed: Please rate your current eye dryness by drawing a vertical line on the line below.

The EDS is an instrument that has been used in other studies.[23,24] Ora Calibra™ Ocular Discomfort Scale Ocular discomfort scores will be subjectively graded by the participants according to the following scale, rating each eye separately.
0=No discomfort
1: Intermittent awareness
2=Constant awareness
3=Intermittent discomfort
4=Constant discomfort While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating dry eye, comprising the local administration of a therapeutically effective amount of (R)-5-((E)-2-pyrrolidin-3-ylvinyl)pyrimidine, or a pharmaceutically acceptable salt thereof, in alternating nostrils of an individual in need thereof.

2. The method of claim 1, wherein the pharmaceutically acceptable salt is a galactarate or citrate salt of (R)-5-((E)-2-pyrrolidin-3-ylvinyl)pyrimidine.

3. The method of claim 1, wherein the pharmaceutically acceptable salt is (R)-5-((E)-2-pyrrolidin-3-ylvinyl)pyrimidine mono-citrate.

4. The method of claim 1, wherein the pharmaceutically acceptable salt is (R)-5-((E)-2-pyrrolidin-3-ylvinyl)pyrimidine hemigalactarate.

5. The method of claim 1, wherein the pharmaceutically acceptable salt is (R)-5-((E)-2-pyrrolidin-3-ylvinyl)pyrimidine hemigalactarate dihydrate or (R)-5-((E)-2-pyrrolidin-3-ylvinyl)pyrimidine hemigalactarate monohydrate.

6. The method of claim 1, comprising administering between 1 microgram and 5 milligrams of (R)-5-((E)-2-pyrrolidin-3-ylvinyl)pyrimidine, or a pharmaceutically acceptable salt thereof, in alternating nostrils of the individual in need thereof.

7. The method of claim 1, comprising administering between 1 microgram and 2 milligrams of (R)-5-((E)-2-pyrrolidin-3-ylvinyl)pyrimidine, or a pharmaceutically acceptable salt thereof, in alternating nostrils of the individual in need thereof.

8. The method of claim 1, comprising administering between 100 micrograms and 1000 micrograms of (R)-5-((E)-2-pyrrolidin-3-ylvinyl)pyrimidine, or a pharmaceutically acceptable salt thereof, in alternating nostrils of the individual in need thereof.

9. The method of claim 1, further comprising the local administration of one or more substances that prevent the entry or reduce the entry of the nicotinic acetylcholine receptor into the desensitized state, or facilitate the recovery of a peripheral nicotinic acetylcholine receptor from the desensitized state.

10. The method of claim 9, wherein the one or more substances are selected from the group consisting of protein kinase C (PKC) or factors that upregulate or up-modulate PKC, cAMP-dependent protein kinase (PKA) or factors that upregulate or up-modulate PKA, and calcineurin inhibitors.

11. The method of claim 10, wherein the calcineurin inhibitor is selected from the group consisting of cyclosporine, pimecrolimus, and tacrolimus.

12. The method of claim 1, wherein (R)-5-((E)-2-pyrrolidin-3-ylvinyl)pyrimidine, or a pharmaceutically acceptable salt thereof, is administered at least once daily.

13. The method of claim 1, wherein (R)-5-((E)-2-pyrrolidin-3-ylvinyl)pyrimidine, or a pharmaceutically acceptable salt thereof, is administered at least twice daily.

14. The method of claim 1, wherein (R)-5-((E)-2-pyrrolidin-3-ylvinyl)pyrimidine, or a pharmaceutically acceptable salt thereof, is administered as a liquid, suspension, aerosol, gel, ointment, dry powder, cream, paste, lotion, or balm.

15. The method of claim 1, wherein (R)-5-((E)-2-pyrrolidin-3-ylvinyl)pyrimidine, or a pharmaceutically acceptable salt thereof, is administered by a syringe, dropper, bottle nebulizer, atomization pump, inhaler, powder spray device, vaporizer, patch, medicated stick, pipette, or jet of liquid.

16. The method of claim 1, wherein the (R)-5-((E)-2-pyrrolidin-3-ylvinyl)pyrimidine, or a pharmaceutically acceptable salt thereof, is administered in a pharmaceutical formulation for nasal administration comprising between 10 mg/mL and 25 mg/mL of (R)-5-((E)-2-pyrrolidin-3-ylvinyl)pyrimidine, or a pharmaceutically acceptable salt thereof.

17. The method of claim 1, wherein the (R)-5-((E)-2-pyrrolidin-3-ylvinyl)pyrimidine, or a pharmaceutically acceptable salt thereof, is administered in a pharmaceutical formulation for nasal administration comprising between 5 mg/mL and 50 mg/mL of (R)-5-((E)-2-pyrrolidin-3-ylvinyl)pyrimidine, or a pharmaceutically acceptable salt thereof.

18. The method of claim 1, wherein the (R)-5-((E)-2-pyrrolidin-3-ylvinyl)pyrimidine, or a pharmaceutically acceptable salt thereof, is administered in a pharmaceutical formulation for nasal administration comprising about 5 mg/mL of (R)-5-((E)-2-pyrrolidin-3-ylvinyl)pyrimidine, or a pharmaceutically acceptable salt thereof.

19. The method of claim 1, wherein the (R)-5-((E)-2-pyrrolidin-3-ylvinyl)pyrimidine, or a pharmaceutically acceptable salt thereof, is administered in a pharmaceutical formulation for nasal administration comprising about 10 mg/mL of (R)-5-((E)-2-pyrrolidin-3-ylvinyl)pyrimidine, or a pharmaceutically acceptable salt thereof.

20. The method of claim 1, wherein the (R)-5-((E)-2-pyrrolidin-3-ylvinyl)pyrimidine, or a pharmaceutically acceptable salt thereof, is administered prior to or after LASIK eye surgery.

21. A method of treating ocular discomfort, comprising the local administration of a therapeutically effective amount of (R)-5-((E)-2-pyrrolidin-3-ylvinyl)pyrimidine, or a pharmaceutically acceptable salt thereof, in alternating nostrils of an individual in need thereof.

22. The method of claim 21, wherein the pharmaceutically acceptable salt is a galactarate or citrate salt of (R)-5-((E)-2-pyrrolidin-3-ylvinyl)pyrimidine.

23. The method of claim 21, wherein the pharmaceutically acceptable salt is (R)-5-((E)-2-pyrrolidin-3-ylvinyl)pyrimidine mono-citrate.

24. The method of claim 21, wherein the pharmaceutically acceptable salt is (R)-5-((E)-2-pyrrolidin-3-ylvinyl)pyrimidine hemigalactarate.

25. The method of claim 21, wherein the pharmaceutically acceptable salt is (R)-5-((E)-2-pyrrolidin-3-ylvinyl)pyrimidine hemigalactarate dihydrate or (R)-5-((E)-2-pyrrolidin-3-ylvinyl)pyrimidine hemigalactarate monohydrate.

26. The method of claim 21, comprising administering between 1 microgram and 5 milligrams of (R)-5-((E)-2-pyrrolidin-3-ylvinyl)pyrimidine, or a pharmaceutically acceptable salt thereof, in alternating nostrils of the individual in need thereof.

27. The method of claim 21, comprising administering between 1 microgram and 2 milligrams of (R)-5-((E)-2-pyrrolidin-3-ylvinyl)pyrimidine, or a pharmaceutically acceptable salt thereof, in alternating nostrils of the individual in need thereof.

28. The method of claim 21, comprising administering between 100 micrograms and 1000 micrograms of (R)-5-((E)-2-pyrrolidin-3-ylvinyl)pyrimidine, or a pharmaceutically acceptable salt thereof, in alternating nostrils of the individual in need thereof.

29. The method of claim 21, further comprising the local administration of one or more substances that prevent the entry or reduce the entry of the nicotinic acetylcholine receptor into the desensitized state, or facilitate the recovery of a peripheral nicotinic acetylcholine receptor from the desensitized state.

30. The method of claim 29, wherein the one or more substances are selected from the group consisting of protein kinase C (PKC) or factors that upregulate or up-modulate PKC, cAMP-dependent protein kinase (PKA) or factors that upregulate or up-modulate PKA, and calcineurin inhibitors.

31. The method of claim 30, wherein the calcineurin inhibitor is selected from the group consisting of cyclosporine, pimecrolimus, and tacrolimus.

32. The method of claim 21, wherein (R)-5-((E)-2-pyrrolidin-3-ylvinyl)pyrimidine, or a pharmaceutically acceptable salt thereof, is administered at least once daily.

33. The method of claim 21, wherein (R)-5-((E)-2-pyrrolidin-3-ylvinyl)pyrimidine, or a pharmaceutically acceptable salt thereof, is administered at least twice daily.

34. The method of claim 21, wherein (R)-5-((E)-2-pyrrolidin-3-ylvinyl)pyrimidine, or a pharmaceutically acceptable salt thereof, is administered as a liquid, suspension, aerosol, gel, ointment, dry powder, cream, paste, lotion, or balm.

35. The method of claim 21, wherein (R)-5-((E)-2-pyrrolidin-3-ylvinyl)pyrimidine, or a pharmaceutically acceptable salt thereof, is administered by a syringe, dropper, bottle nebulizer, atomization pump, inhaler, powder spray device, vaporizer, patch, medicated stick, pipette, or jet of liquid.

36. The method of claim 21, wherein the (R)-5-((E)-2-pyrrolidin-3-ylvinyl)pyrimidine, or a pharmaceutically acceptable salt thereof, is administered in a pharmaceutical formulation for nasal administration comprising between 10 mg/mL and 25 mg/mL of (R)-5-((E)-2-pyrrolidin-3-ylvinyl)pyrimidine, or a pharmaceutically acceptable salt thereof.

37. The method of claim 21, wherein the (R)-5-((E)-2-pyrrolidin-3-ylvinyl)pyrimidine, or a pharmaceutically acceptable salt thereof, is administered in a pharmaceutical formulation for nasal administration comprising between 5 mg/mL and 50 mg/mL of (R)-5-((E)-2-pyrrolidin-3-ylvinyl)pyrimidine, or a pharmaceutically acceptable salt thereof.

38. The method of claim 21, wherein the (R)-5-((E)-2-pyrrolidin-3-ylvinyl)pyrimidine, or a pharmaceutically acceptable salt thereof, is administered in a pharmaceutical formulation for nasal administration comprising about 5 mg/mL of (R)-5-((E)-2-pyrrolidin-3-ylvinyl)pyrimidine, or a pharmaceutically acceptable salt thereof.

39. The method of claim 21, wherein the (R)-5-((E)-2-pyrrolidin-3-ylvinyl)pyrimidine, or a pharmaceutically acceptable salt thereof, is administered in a pharmaceutical formulation for nasal administration comprising about 10 mg/mL of (R)-5-((E)-2-pyrrolidin-3-ylvinyl)pyrimidine, or a pharmaceutically acceptable salt thereof.

40. The method of claim 21, wherein the (R)-5-((E)-2-pyrrolidin-3-ylvinyl)pyrimidine, or a pharmaceutically acceptable salt thereof, is administered prior to or after LASIK eye surgery.

41. A method of increasing tear production, comprising the local administration of a therapeutically effective amount of (R)-5-((E)-2-pyrrolidin-3-ylvinyl)pyrimidine, or a pharmaceutically acceptable salt thereof, in alternating nostrils of an individual in need thereof.

42. The method of claim 41, wherein the pharmaceutically acceptable salt is a galactarate or citrate salt of (R)-5-((E)-2-pyrrolidin-3-ylvinyl)pyrimidine.

43. The method of claim 41, wherein the pharmaceutically acceptable salt is (R)-5-((E)-2-pyrrolidin-3-ylvinyl)pyrimidine mono-citrate.

44. The method of claim 41, wherein the pharmaceutically acceptable salt is (R)-5-((E)-2-pyrrolidin-3-ylvinyl)pyrimidine hemigalactarate.

45. The method of claim 41, wherein the pharmaceutically acceptable salt is (R)-5-((E)-2-pyrrolidin-3-ylvinyl)pyrimidine hemigalactarate dihydrate or (R)-5-((E)-2-pyrrolidin-3-ylvinyl)pyrimidine hemigalactarate monohydrate.

46. The method of claim 41, comprising administering between 1 microgram and 5 milligrams of (R)-5-((E)-2-pyrrolidin-3-ylvinyl)pyrimidine, or a pharmaceutically acceptable salt thereof, in alternating nostrils of the individual in need thereof.

47. The method of claim 41, comprising administering between 1 microgram and 2 milligrams of (R)-5-((E)-2-pyrrolidin-3-ylvinyl)pyrimidine, or a pharmaceutically acceptable salt thereof, in alternating nostrils of the individual in need thereof.

48. The method of claim 41, comprising administering between 100 micrograms and 1000 micrograms of (R)-5-((E)-2-pyrrolidin-3-ylvinyl)pyrimidine, or a pharmaceutically acceptable salt thereof, in alternating nostrils of the individual in need thereof.

49. The method of claim 41, further comprising the local administration of one or more substances that prevent the entry or reduce the entry of the nicotinic acetylcholine receptor into the desensitized state, or facilitate the recovery of a peripheral nicotinic acetylcholine receptor from the desensitized state.

50. The method of claim 49, wherein the one or more substances are selected from the group consisting of protein kinase C (PKC) or factors that upregulate or up-modulate PKC, cAMP-dependent protein kinase (PKA) or factors that upregulate or up-modulate PKA, and calcineurin inhibitors.

51. The method of claim 50, wherein the calcineurin inhibitor is selected from the group consisting of cyclosporine, pimecrolimus, and tacrolimus.

52. The method of claim 41, wherein (R)-5-((E)-2-pyrrolidin-3-ylvinyl)pyrimidine, or a pharmaceutically acceptable salt thereof, is administered at least once daily.

53. The method of claim 41, wherein (R)-5-((E)-2-pyrrolidin-3-ylvinyl)pyrimidine, or a pharmaceutically acceptable salt thereof, is administered at least twice daily.

54. The method of claim 41, wherein (R)-5-((E)-2-pyrrolidin-3-ylvinyl)pyrimidine, or a pharmaceutically acceptable salt thereof, is administered as a liquid, suspension, aerosol, gel, ointment, dry powder, cream, paste, lotion, or balm.

55. The method of claim 41, wherein (R)-5-((E)-2-pyrrolidin-3-ylvinyl)pyrimidine, or a pharmaceutically acceptable salt thereof, is administered by a syringe, dropper, bottle nebulizer, atomization pump, inhaler, powder spray device, vaporizer, patch, medicated stick, pipette, or jet of liquid.

56. The method of claim 41, wherein the (R)-5-((E)-2-pyrrolidin-3-ylvinyl)pyrimidine, or a pharmaceutically acceptable salt thereof, is administered in a pharmaceutical formulation for nasal administration comprising between 10 mg/mL and 25 mg/mL of (R)-5-((E)-2-pyrrolidin-3-ylvinyl)pyrimidine, or a pharmaceutically acceptable salt thereof.

57. The method of claim 41, wherein the (R)-5-((E)-2-pyrrolidin-3-ylvinyl)pyrimidine, or a pharmaceutically acceptable salt thereof, is administered in a pharmaceutical formulation for nasal administration comprising between 5 mg/mL and 50 mg/mL of (R)-5-((E)-2-pyrrolidin-3-ylvinyl)pyrimidine, or a pharmaceutically acceptable salt thereof.

58. The method of claim 41, wherein the (R)-5-((E)-2-pyrrolidin-3-ylvinyl)pyrimidine, or a pharmaceutically acceptable salt thereof, is administered in a pharmaceutical formulation for nasal administration comprising about 5 mg/mL of (R)-5-((E)-2-pyrrolidin-3-ylvinyl)pyrimidine, or a pharmaceutically acceptable salt thereof.

59. The method of claim 41, wherein the (R)-5-((E)-2-pyrrolidin-3-ylvinyl)pyrimidine, or a pharmaceutically acceptable salt thereof, is administered in a pharmaceutical formulation for nasal administration comprising about 10 mg/mL of (R)-5-((E)-2-pyrrolidin-3-ylvinyl)pyrimidine, or a pharmaceutically acceptable salt thereof.

60. The method of claim 41, wherein the (R)-5-((E)-2-pyrrolidin-3-ylvinyl)pyrimidine, or a pharmaceutically acceptable salt thereof, is administered prior to or after LASIK eye surgery.

61. The method according to claim 1, wherein (R)-5-((E)-2-pyrrolidin-3-ylvinyl)pyrimidine, or a pharmaceutically acceptable salt thereof, is administered with a medical device.

62. The method according to claim 21, wherein (R)-5-((E)-2-pyrrolidin-3-ylvinyl)pyrimidine, or a pharmaceutically acceptable salt thereof, is administered with a medical device.

63. The method according to claim 41, wherein (R)-5-((E)-2-pyrrolidin-3-ylvinyl)pyrimidine, or a pharmaceutically acceptable salt thereof, is administered with a medical device.

64. The method according to claim 1, wherein (R)-5-((E)-2-pyrrolidin-3-ylvinyl)pyrimidine, or a pharmaceutically acceptable salt thereof, is administered in a pharmaceutical formulation for nasal administration comprising about 1 mg/mL of (R)-5-((E)-2-pyrrolidin-3-ylvinyl)pyrimidine, or a pharmaceutically acceptable salt thereof.

65. The method according to claim 21, wherein (R)-5-((E)-2-pyrrolidin-3-ylvinyl)pyrimidine, or a pharmaceutically acceptable salt thereof, is administered in a pharmaceutical formulation for nasal administration comprising about 1 mg/mL of (R)-5-((E)-2-pyrrolidin-3-ylvinyl)pyrimidine, or a pharmaceutically acceptable salt thereof.

66. The method according to claim 41, wherein (R)-5-((E)-2-pyrrolidin-3-ylvinyl)pyrimidine, or a pharmaceutically acceptable salt thereof, is administered in a pharmaceutical formulation for nasal administration comprising about 1 mg/mL of (R)-5-((E)-2-pyrrolidin-3-ylvinyl)pyrimidine, or a pharmaceutically acceptable salt thereof.

67. The method according to claim 1, wherein (R)-5-((E)-2-pyrrolidin-3-ylvinyl)pyrimidine, or a pharmaceutically acceptable salt thereof, is administered in a pharmaceutical formulation for nasal administration comprising about 6 mg/mL of (R)-5-((E)-2-pyrrolidin-3-ylvinyl)pyrimidine, or a pharmaceutically acceptable salt thereof.

68. The method according to claim 21, wherein (R)-5-((E)-2-pyrrolidin-3-ylvinyl)pyrimidine, or a pharmaceutically acceptable salt thereof, is administered in a pharmaceutical formulation for nasal administration comprising about 6 mg/mL of (R)-5-((E)-2-pyrrolidin-3-ylvinyl)pyrimidine, or a pharmaceutically acceptable salt thereof.

69. The method according to claim 41, wherein (R)-5-((E)-2-pyrrolidin-3-ylvinyl)pyrimidine, or a pharmaceutically acceptable salt thereof, is administered in a pharmaceutical formulation for nasal administration comprising about 6 mg/mL of (R)-5-((E)-2-pyrrolidin-3-ylvinyl)pyrimidine, or a pharmaceutically acceptable salt thereof.

70. The method according to claim 1, wherein the (R)-5-((E)-2-pyrrolidin-3-ylvinyl)pyrimidine, or a pharmaceutically acceptable salt thereof, is administered prior to or after an ophthalmologic surgical procedure.

71. The method according to claim 21, wherein the (R)-5-((E)-2-pyrrolidin-3-ylvinyl)pyrimidine, or a pharmaceutically acceptable salt thereof, is administered prior to or after an ophthalmologic surgical procedure.

72. The method according to claim 41, wherein the (R)-5-((E)-2-pyrrolidin-3-ylvinyl)pyrimidine, or a pharmaceutically acceptable salt thereof, is administered prior to or after an ophthalmologic surgical procedure.

\* \* \* \* \*

UNITED STATES PATENT AND TRADEMARK OFFICE
CERTIFICATE OF CORRECTION

PATENT NO. : 10,709,707 B2
APPLICATION NO. : 16/091830
DATED : July 14, 2020
INVENTOR(S) : Douglas Michael Ackermann et al.

It is certified that error appears in the above-identified patent and that said Letters Patent is hereby corrected as shown below:

In the Specification

At Column 1, Line number 36:
"The present disclosure provides a method of treating d y eye"
Should read:
--The present disclosure provides a method of treating dry eye--.

At Column 3, Line number 19:
"(R)-5-((E)-2-pyrrolidin-3-ylvinyl)pyridine"
Should read:
--(R)-5-((E)-2-pyrrolidin-3-ylvinyl)pyrimidine--.

At Column 5, Line number 4:
"X is N or $CR_1$"
Should read:
--X is N or $CR_3$--;

At Column 5, Line number 32:
"—$CR_{10}$"
Should read:
-- —$C_2R_{10}$--.

At Column 10, Line number 47:
"—$N_5R_6$"
Should read:
-- —$NR_5R_6$--.

At Column 28, Line number 15:
"Formula (I) formulated (a) for nasal administration"
Should read:

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*

--Formula (II) formulated (a) for nasal administration--.

At Column 72, Line number 6:
"(R)-5-((E)-2-pyrolidin-3-ylvinyl)pyrimidine"
Should read:
--(R)-5-((E)-2-pyrrolidin-3-ylvinyl)pyrimidine--.

At Column 73, Line number 38:
"Formula (II) (II), (IIIa), or (IIIb)"
Should read:
--Formula (I), (II), (IIIa), or (IIIb)--.

At Column 74, Line number 45:
"Formula (I), (II), (IIIa), or (lib)"
Should read:
--Formula (I), (II), (IIIa), or (IIIb)--.

At Column 77, Line number 2:
"(R)-5-((E)-2-pyrolidin-3-ylvinyl)pyrimidine"
Should read:
--(R)-5-((E)-2-pyrrolidin-3-ylvinyl)pyrimidine--.

At Column 88, Line number 9:
"Formula (I), (II), (IIIa), or (Tub)"
Should read:
--Formula (I), (II), (IIIa), or (IIIb)--.

At Column 90, Line number 16:
"(R)-5-((E)-2-pyrrolidin-3-ylvinyl-3-ylvinyl)pyrimidine"
Should read:
--(R)-5-((E)-2-pyrrolidin-3-ylvinyl)pyrimidine--.

At Column 130, Line number 13:
"(R)-5-((E)-2-pyrolidin-3-ylvinyl)pyrimidine"
Should read:
--(R)-5-((E)-2-pyrrolidin-3-ylvinyl)pyrimidine--.

At Column 133, Line number 24:
"ran-made conditions"
Should read:
--man-made conditions--.

At Column 135, Line number 51:
"XRPD patterns (diffractograns)"
Should read:
--XRPD patterns (diffractograms)--.

At Column 149, Line number 22:
"hemigalactarate-monohydrate or dehydrate"
Should read:
--hemigalactarate-monohydrate or dihydrate--.

At Column 159, Line number 50:
"40%, 45/0%, 50%"
Should read:
--40%, 45%, 50%--.

At Column 161, Line number 5:
"effective amount can be widely"
Should read:
--effective amount can vary widely--;

At Column 161, Line number 65:
"exist as enantiomers, diasteromers"
Should read:
--exist as enantiomers, diastereomers--.

At Column 172, Line number 20:
"—$C_2R_5$"
Should read:
-- —$C_2R_3$--.

At Column 176, Line number 29:
"wherein R is hydrogen"
Should read:
--wherein $R_1$ is hydrogen--.

At Column 177, Line number 51:
"—$NR_4SO_2R_3$"
Should read:
-- —$NR_4SO_2R_5$--.

At Column 178, Line number 61:
"$R_2$ is —$CH_{12}$"
Should read:
--$R_2$ is —$CH_2$--.

At Column 182, Line number 9:
"Embodiments II-1 to III-3"
Should read:
--Embodiments II-1 to II-3--.

At Column 183, Line number 58:

"Embodiment I-18"
Should read:
--Embodiment II-18--.

At Column 184, Line number 24:
"Embodiments II-1 to III-26"
Should read:
--Embodiments II-1 to II-26--;

At Column 184, Line number 61:
"Embodiments I-1 to III-31"
Should read:
--Embodiments II-1 to II-31--.

At Column 186, Line number 6:
"Embodiments II-38 to III-44"
Should read:
--Embodiments II-38 to II-44--;

At Column 186, Line number 66:
"Embodiments I-38 to II-52"
Should read:
--Embodiments II-38 to II-52--.

At Column 189, Line number 6:
"Embodiment I-5"
Should read:
--Embodiment III-5--;

At Column 189, Line number 61:
"Embodiment II-13"
Should read:
--Embodiment III-13--.

At Column 190, Line number 1:
"Embodiment II-14"
Should read:
--Embodiment III-14--;

At Column 190, Line number 25:
"Embodiment II-18"
Should read:
--Embodiment III-18--;

At Column 190, Line number 58:
"Embodiments II-1 to III-21"

Should read:
--Embodiments III-1 to III-21--.

At Column 198, Line number 31:
"the pentaineric complex"
Should read:
--the pentameric complex--.

At Column 236, Line number 57:
"Dry eye is a multifactoral"
Should read:
--Dry eye is a multifactorial--.

At Column 237, Line number 5:
"basal and bolus Lear secretion"
Should read:
--basal and bolus tear secretion--.

At Column 240, Line number 3:
"the previous 30 clays"
Should read:
--the previous 30 days--;

At Column 240, Line number 7:
"Chantix® (varencline)"
Should read:
--Chantix® (varenicline)--.